United States Patent [19]

Wexler

[11] Patent Number: 4,778,512
[45] Date of Patent: Oct. 18, 1988

[54] HERBICIDAL HETEROCYCLIC SULFONAMIDES

[75] Inventor: Barry A. Wexler, Wilmington, Del.

[73] Assignee: E. I. Du Pont de Nemours and Company, Wilmington, Del.

[21] Appl. No.: 93,416

[22] Filed: Sep. 4, 1987

Related U.S. Application Data

[63] Continuation-in-part of Ser. No. 29,434, Mar. 30, 1987, which is a continuation-in-part of Ser. No. 874,307, Jun. 13, 1986, abandoned.

[51] Int. Cl.$^4$ ............... C07D 401/12; C07D 491/052; A01N 43/54; A01N 43/90

[52] U.S. Cl. .......................................... 71/92; 71/90; 544/116; 544/117; 544/278; 544/253
[58] Field of Search ............... 544/122, 123, 278, 253, 544/116, 117; 71/92, 90

[56] References Cited

U.S. PATENT DOCUMENTS 4,481,029 11/1984 Levitt ....................................... 71/93
4,661,147 4/1987 Dumas ................................ 544/253
4,666,506 5/1987 Hillemann ........................... 544/253

Primary Examiner—John M. Ford

[57] ABSTRACT

This invention relates to certain heterocyclic sulfonylurea herbicidal compounds, agriculturally suitable compositions thereof and a method of their use.

36 Claims, No Drawings

HERBICIDAL HETEROCYCLIC SULFONAMIDES

RELATED APPLICATIONS

This is a continuation-in-part of U.S. Ser. No. 29,434 filed Mar. 30, 1987 which is a continuation-in-part of U.S. Ser. No. 874,307 filed June 13, 1986, now abandoned.

BACKGROUND OF THE INVENTION

This invention relates to novel ketone pyrazole, thiophene, and pyridine sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel shortage tanks, ammunition depots and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within the class of herbicides, but they generally consist of a sulfonylurea bridge, —$SO_2NHCONH$—, linking two aromatic or heteroaromatic rings.

EP-A No. 95,925 which was published Dec. 7, 1983 discloses herbicidal sulfonylureas of formula

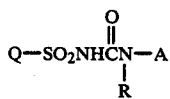

wherein
Q is, in part,

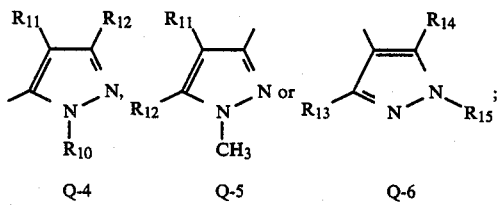

$R_{10}$ is H, $C_1$–$C_4$ alkyl, $C_3$–$C_4$ alkenyl, $C_3$–$C_4$ alkynyl, $CO_2R_{24}$, $SO_2NR_{20}R_{21}$ or $SO_2R_{22}$;
$R_{11}$ is H, $C_1$–$C_3$ alkyl, F, Cl, Br, $NO_2$, $OR_{16}$, $CO_2R_{24}$, $S(O)_mR_{25}$ or $SO_2NR_{20}R_{21}$;
provided that when $R_{10}$ is other than $C_1$–$C_3$ alkyl, then $R_{11}$ is H, Cl, $OCH_3$, $NO_2$, or $CH_3$;
$R_{12}$ is H or $CH_3$;
$R_{13}$ and $R_{14}$ are independently H, $C_1$–$C_3$ alkyl, $OR_{16}$, F, Cl, Br, $NO_2$, $CO_2R_{24}$, $S(O)_mR_{25}$ or $SO_2NR_{20}R_{21}$;
provided that, when either of $R_{13}$ or $R_{14}$ is $CO_2R_{24}$, $S(O)_mR_{25}$ or $SO_2NR_{20}R_{21}$, then the other is H, Cl, $CH_3$, $OCH_3$ or $NO_2$; and
$R_{15}$ is H or $CH_3$.

EP-A No. 87,780 (published Sept. 7, 1983) discloses herbicidal sulfonylureas of formula

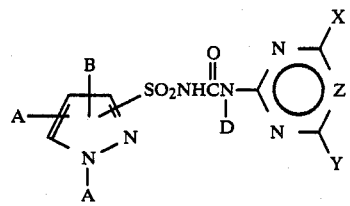

wherein
A is H, $C_1$–$C_8$ alkyl or optionally substituted phenyl;
B and C are independently H, halogen, $NO_2$, $C_1$–$C_8$ alkyl, arylalkyl, $C_1$–$C_8$ alkoxy, haloalkyl, $CO_2R$, $CONR_1R_2$, $S(O)_nR_3$, $SO_2NR_4R_5$, or optionally substituted phenyl.

ZA No. 83/3850 (published Nov. 28, 1983) discloses compounds of formula

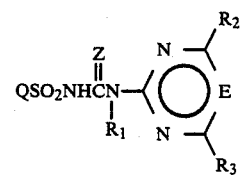

wherein
Q is a five-membered, heterocyclic radical which is bound by way of a carbon atom and contains 2 or 3 heteroatoms and which may be optionally substituted by halogen, pseudohalogen, nitro, alkyl, hydroxyl, haloalkyl, alkoxy, alkylthio, haloalkoxy, haloalkylthio, amino, alkylamino, dialkylamino, alkylcarbonylamino, alkylcarbonyl, alkoxycarbonyl, alkoxyalkyl, alkylthiocarbonyl, carbamoyl, alkylaminocarbonyl, dialkylaminocarbonyl, alkylsulfinyl, alkylsulfonyl, alkenyloxy or alkynyloxy; and groups such as phenyl, phenoxy or phenylthio, which are unsubstituted or substituted by halogen, nitro, cyano, alkyl, alkoxy, haloalkyl, alkylcarbonyl, alkoxycarbonyl or haloalkoxy; and also benzyl unsubstituted or substituted by halogen and/or alkyl.

U.S. Pat. No. 4,127,405 and U.S. Pat. No. 4,169,719 disclose herbicidal thiophenesulfonamides, wherein the thiophene ring may be optionally substituted with $CH_3$, Cl or Br.

U.S. Pat. No. 4,398,939 discloses herbicidal thiophenesulfonamides, wherein the thiophene ring is substituted with substituent groups selected from $C_1$–$C_4$ alkyl, $C_3$ alkenyl, $OCH_3$, $NO_2$, Cl, Br, $SO_2N(C_1$–$C_3$ alkyl$)_2$ or $SO_2N(OCH_3)CH_3$.

U.S. Pat. No. 4,481,029 discloses herbicidal thiophenesulfonamides, wherein the thiophene ring is substituted with carboxylic acid, carboxylic ester and alkylcarbonyl groups or derivatives thereof.

U.S. Pat. No. 4,441,910 discloses herbicidal thiophenesulfonamides, wherein the thiophene ring is substituted with the group represented by $R_6S(O)_n$ wherein $R_6$ is $C_1$–$C_4$ alkyl, $C_3$–$C_4$ alkenyl, cyclopentyl or cyclopropylmethyl.

European Publication No. 13,480 (published July 23, 1980) discloses herbicidal pyridine-2-, -3- and -4-sulfonylureas, wherein the pyridine ring may be substituted by Cl, Br, F, $C_1$–$C_4$ alkyl, $C_1$–$C_4$ alkoxy, $C_1$–$C_4$ alkylthio, $NO_2$ or a carboxylic ester group.

U.S. Pat. No. 4,456,469 (issued June 29, 1984) discloses herbicidal pyridine-3-sulfonylureas substituted by $C_1$–$C_6$ alkyl-, $C_3$–$C_6$ alkenyl-, $C_2$–$C_4$ alkoxyalkyl- and $C_5$–$C_6$ cycloalkylsulfonyl groups.

U.S. Pat. No. 4,518,776 (Swiss priority July 19, 1982) discloses, in part, a process for the preparation of compounds of formula

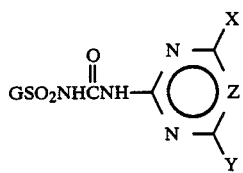

wherein
G is

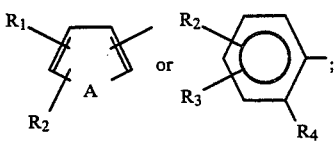

$R_1$ is H, $C_1$–$C_4$ alkyl, halogen, $NO_2$, CN, $NH_2$, $S(O)_n$-$C_1$–$C_4$ alkyl, $SO_2C_1$–$C_4$ alkoxy, $SO_2$-di-$C_1$–$C_4$ alkylamino, CHO, $CONH_2$, $DC_3$–$C_5$ alkynyl, $CODC_3$–$C_5$ alkynyl, $DC_1$–$C_4$ alkyl, $DC_3$–$C_5$ alkenyl, $COC_1$–$C_4$ alkyl, $CODC_1$–$C_4$ alkyl or $CODC_3$–$C_5$ alkenyl;

n is 1 or 2;

D is O, S, NH or $NC_1$–$C_4$ alkyl;

$R_2$ is H, halogen, $CF_3$, $NO_2$, $C_1$–$C_4$ alkyl or $C_1$–$C_4$ alkoxy; and A is O, S, $NR_5$ or —C=N—.

U.S. Pat. No. 4,521,597 discloses, in part, a process for the preparation of compounds of formula

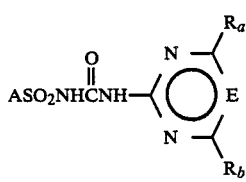

wherein
A is

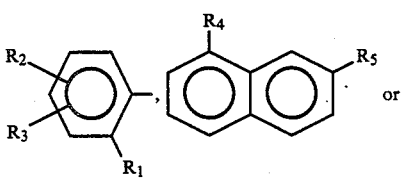

-continued

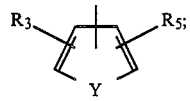

$R_3$ is H, halogen, $NO_2$, $OCH_3$ or $CF_3$;

$R_5$ is H, F, Cl, Br, $NO_2$, $C_1$–$C_5$ alkyl, $C_1$–$C_5$ alkoxy, $CF_3$, $S(O)_mC_1$–$C_5$ alkyl, $COR_7$ or $SO_2NR_8R_9$;

Y is O, S or $C(R_6)$=N; and $R_7$ is H, $C_1$–$C_5$ alkyl, $C_1$–$C_5$ haloalkyl, $C_1$–$C_5$ alkoxy, $C_1$–$C_5$ haloalkoxy, $C_2$–$C_{10}$ alkoxyalkoxy, $C_3$–$C_5$ alkenyloxy, $C_3$–$C_5$ alkynyloxy, phenoxy, benzyloxy, $C_1$–$C_5$ alkylthio or $NR_8R_9$.

U.S. Pat. No. 4,549,898 discloses herbicidal sulfonylureas of formula

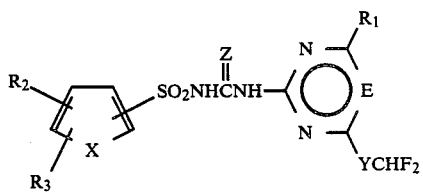

wherein
X is O, S, $NR_4$ or $C(R_5)$=N;

Y is O or S;

Z is O or S;

E is N or CH;

$R_1$ is H, $C_1$–$C_4$ alkyl, $C_1$–$C_4$ haloalkyl, $C_1$–$C_4$ haloalkoxy, $C_1$–$C_4$ alkoxy, halogen, $C_1$–$C_4$ alkylthio, $NR_6R_7$ or alkoxyalkyl containing not more than 4 carbon atoms;

$R_2$ is H, $C_1$–$C_3$ alkyl, $C_1$–$C_3$ haloalkyl, halogen, $NO_2$, $C_1$–$C_3$ alkoxy, $C(W)R_8$, $SO_2NR_6R_7$, $S(O)_nC_1$–$C_3$ alkyl or $COR_9$;

$R_3$ is H, halogen, $C_1$–$C_3$ alkyl, $OCH_3$ or $CF_3$;

$R_5$ is H, $NO_2$, F, Cl, Br, $CH_3$, $CF_3$, $S(O)_nC_1$–$C_3$ alkyl, $COC_1$–$C_4$ alkoxy or $C_1$–$C_3$ alkoxy;

$R_8$ is H, $C_1$–$C_6$ alkyl, $C_1$–$C_4$ haloalkyl, $C_3$–$C_6$ cycloalkyl, $C_4$–$C_7$ cycloalkylalkyl or alkoxyalkyl containing not more than 4 carbon atoms; and W is O or $NOR_{10}$.

Japanese patent application No. 58-70407 (SHO 59-219,218, laid open Dec. 10, 1984) discloses pyrazole-5-sulfonylureas of formula

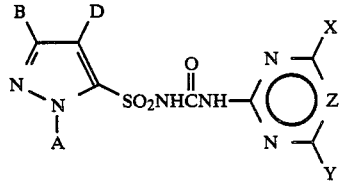

wherein
A is H, lower alkyl or phenyl;

B is H or lower alkyl;

D is H, $CO_2R$ or COAr, halogen, $NO_2$ or $SO_2NR^1R^2$; and

Ar is phenyl optionally substituted with halogen.

U.S. Pat. No. 4,370,480 discloses herbicidal sulfonylureas of formula

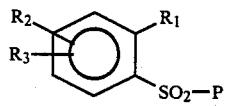

wherein
R₁ is

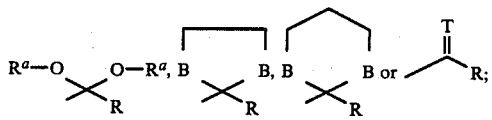

R is H, $C_1-C_2$ alkyl, $C_2-C_6$ alkenyl, $C_2-C_6$ alkynyl; $C_1-C_4$ alkyl substituted with one to four substituents selected from 0–3F, 0–3Cl, 0–3Br, 0–2OCH₃, 0–1 cyano, 0–1CO₂R₁' where R₁' is $C_1-C_3$ alkyl, CO₂R₁', $C_2-C_4$ alkenyl substituted with 1–3Cl, $C_3-C_6$ cycloalkyl, $C_5-C_6$ cycloalkenyl, $C_5-C_6$ cycloalkyl substituted with substituents selected from 1–3CH₃ or one of CH₃CH₂, Cl, OCH₃, $C_4-C_7$ cycloalkylalkyl,

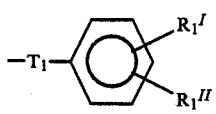

where T₁ is

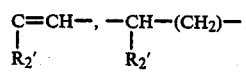

or a single bond; and
T is O or NOR₁ᴵᴵᴵ.

Japanese patent application No. 84-273152 (Sho 86-151188, laid open July 9, 1986) discloses the following compound

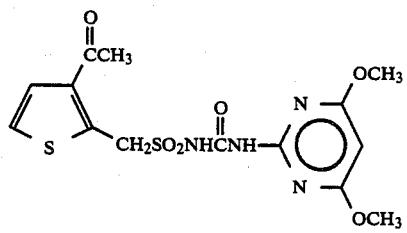

SUMMARY OF THE INVENTION

This invention relates to novel compounds of Formula I, agriculturally suitable compositions containing them, and their method-of-use as general preemergence and/or postemergence herbicides or plant growth regulants.

$$\text{JSO}_2\text{NHCNR}_1\text{A} \quad\quad \text{I}$$
(with W above C)

wherein
J is

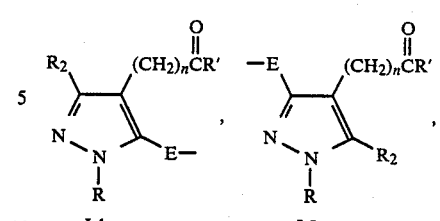

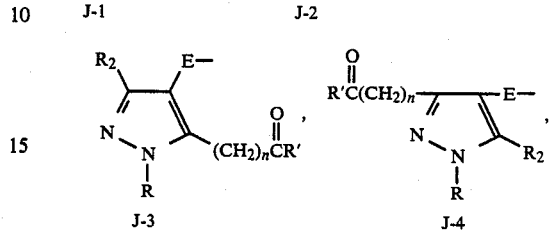

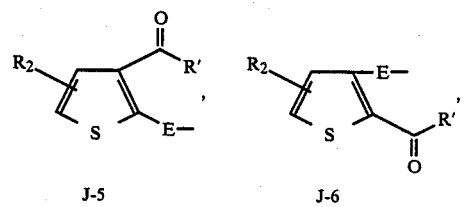

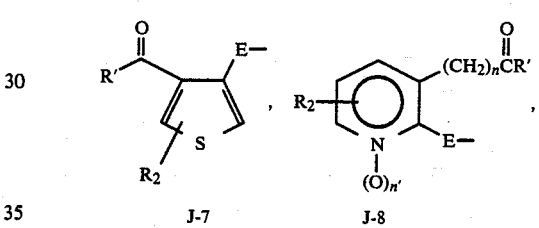

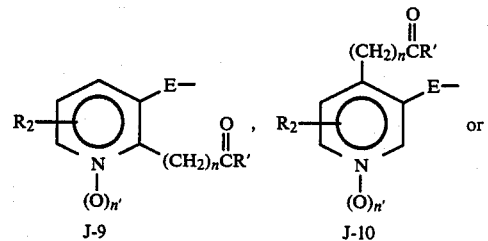

R is H, $C_1-C_3$ alkyl, phenyl, SO₂NR$_a$R$_b$, $C_1-C_2$ haloalkyl, $C_2-C_4$ alkoxyalkyl, $C_2-C_3$ cyanoalkyl, $C_2-C_4$ alkylthioalkyl, $C_2-C_4$ alkylsulfinylalkyl, $C_2-C_4$ alkylsulfonylalkyl, CO₂$C_1-C_2$ alkyl, $C_1-C_4$ alkylcarbonyl, $C_1-C_2$ alkylsulfonyl, $C_3-C_4$ alkenyl, $C_3-C_4$ alkynyl or $C_1-C_2$ alkyl substituted with CO₂$C_1-C_2$ alkyl;

R₁ is H or CH₃;

R₂ is H, $C_1-C_3$ alkyl, $C_1-C_3$ haloalkyl, halogen, nitro, $C_1-C_3$ alkoxy, SO₂NR$_c$R$_d$, $C_1-C_3$ alkylthio, $C_1-C_3$ alkylsulfinyl, $C_1-C_3$ alkylsulfonyl, CN, CO₂R$_e$, $C_1-C_3$ haloalkoxy, $C_1-C_3$ haloalkylthio, amino, $C_1-C_2$ alkylamino, di($C_1-C_3$ alkyl)amino or $C_1-C_2$ alkyl substituted with $C_1$-$C_2$ alkoxy, $C_1$-$C_2$ haloalkoxy, $C_1$-$C_2$ alkylthio, $C_1$-$C_2$ haloalkylthio, CN, OH or SH;

$R_a$ and $R_b$ are independently $C_1$-$C_2$ alkyl;

$R_c$ is H, $C_1$-$C_4$ alkyl, $C_2$-$C_3$ cyanoalkyl, methoxy or ethoxy;

$R_d$ is H, $C_1$-$C_4$ alkyl or $C_3$-$C_4$ alkenyl; or $R_c$ and $R_d$ may be taken together as —($CH_2$)$_3$—, —($CH_2$)$_4$—, —($CH_2$)$_5$— or —$CH_2CH_2OCH_2CH_2$—;

$R_e$ is $C_1$-$C_4$ alkyl, $C_3$-$C_4$ alkenyl, $C_3$-$C_4$ alkynyl, $C_2$-$C_4$ haloalkyl, $C_1$-$C_2$ cyanoalkyl, $C_5$-$C_6$ cycloalkyl, $C_4$-$C_7$ cycloalkylalkyl or $C_2$-$C_4$ alkoxyalkyl;

R' is $C_1$-$C_5$ alkyl, $C_1$-$C_5$ haloalkyl, $C_1$-$C_5$ alkyl substituted with one or two $R_3$ groups, $C_2$-$C_5$ alkenyl, $C_2$-$C_5$ haloalkenyl, $C_3$-$C_5$ alkenyl substituted with one or two $R_3$ groups, $C_3$-$C_5$ alkynyl, $C_3$-$C_5$ haloalkynyl, $C_3$-$C_5$ alkynyl substituted with one or two $R_3$ groups, $C_3$-$C_5$ cycloalkyl, $C_3$-$C_5$ halocycloalkyl, $C_3$-$C_5$ cycloalkyl substituted with one or two $R_4$ groups, $C_4$-$C_7$ cycloalkylalkyl, $C_4$-$C_7$ halocycloalkylalkyl, $C_4$-$C_7$ cycloalkylalkyl substituted with one or two $R_4$ groups, phenyl or benzyl;

$R_3$ is $C_1$-$C_3$ alkoxy, $C_1$-$C_3$ alkylthio, $C_1$-$C_3$ haloalkoxy, $C_1$-$C_3$ alkylsulfinyl, $C_1$-$C_3$ alkylsulfonyl, CN, $NO_2$, OH, $OR_5$ or di-($C_1$-$C_3$ alkyl)amino;

$R_4$ is $C_1$-$C_3$ alkyl, $C_1$-$C_3$ alkoxy, $C_1$-$C_3$ haloalkoxy, CN, $NO_2$, OH, $OR_5$ or di-($C_1$-$C_3$ alkyl)amino;

$R_5$ is $SO_2CH_3$, $Si(CH_3)_3$, $C_2$-$C_3$ alkylcarbonyl or $CO_2C_1$-$C_2$ alkyl;

E is a single bond or $CH_2$;

W is O or S;

n is 0 or 1;

n' is 0 or 1;

A is

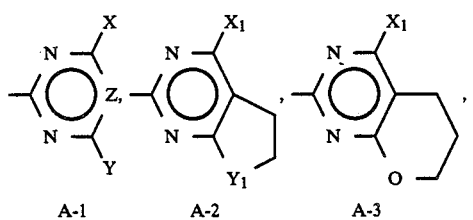

A-1 A-2 A-3

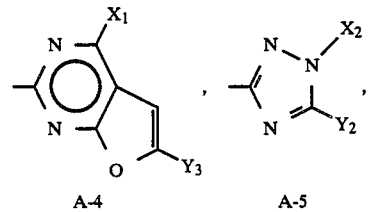

A-4 A-5

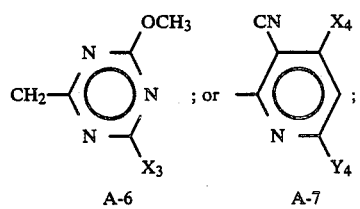

A-6 A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl,

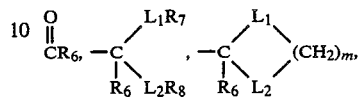

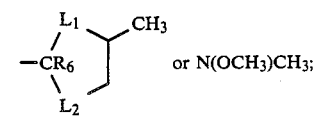

m is 2 or 3;

$L_1$ and $L_2$ are independently O or S;

$R_6$ is H or $C_1$-$C_3$ alkyl;

$R_7$ and $R_8$ are independently $C_1$-$C_3$ alkyl;

Z is CH or N;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$X_4$ is $CH_3$, $OCH_3$, $OC_2H_5$, $CH_2OCH_3$ or Cl; and $Y_4$ is $CH_3$, $OCH_3$, $OC_2H_5$ or Cl;

and their agriculturally suitable salts; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when X or Y is $C_1$ haloalkoxy, then Z is CH;

(c) $X_4$ and $Y_4$ are not simultaneously Cl;

(d) when W is S, then $R_1$ is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(e) when the total number of carbons of X and Y is greater than four, then the number of carbons of R must be less than or equal to two;

(f) when J is J-1, J-2, J-3 or J-4 then R' is other than $C_3$-$C_5$ cycloalkyl or phenyl;

(g) when J is J-5, J-6 or J-7 wherein E is a single bond, then R' is other than $C_1$-$C_5$ alkyl, $C_3$-$C_5$ alkenyl, phenyl, benzyl, cyclopentyl or $C_4$-$C_7$ cycloalkylalkyl;

(h) when either or both of X and Y are $OCF_2H$ then J is J-1, J-2, J-3, J-4, J-8, J-9, J-10 or J-11; and (i) when the total number of carbon atoms of X and Y is greater than four, then the total number of carbon atoms of $R_2$ and R' must be less than or equal to 7.

In the above definitions, the term "alkyl", used either alone or in compound words such as "alkylthio" or "haloalkyl", denotes straight chain or branched alkyl, e.g. methyl, ethyl, n-propyl, isopropyl or the different butyl and pentyl isomers.

Alkoxy denotes methoxy, ethoxy, n-propyloxy, isopropyloxy and the different butyl isomers.

Alkenyl denotes straight chain or branched alkenes, e.g., 1-propenyl, 2-propenyl, 3-propenyl and the different butenyl and pentenyl isomers.

Alkynyl denotes straight chain or branched alkynes, e.g. ethynyl, 1-propynyl, 2-propynyl and the different butynyl and pentynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 7. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

Compounds preferred for reasons of increased ease of synthesis and/or greater herbicidal efficacy are:

1. Compounds of Formula I wherein
   J is $J_1$ to $J_{10}$ and E is a single bond; or
   J is $J_1$ to $J_4$ or $J_8$ to $J_{10}$ and E is $CH_2$; or
   J is $J_5$ to $J_7$, E is $CH_2$ and
   R' is $C_1$-$C_5$ haloalkyl, $C_1$-$C_5$ alkyl substituted with one or two $R_3$ groups, $C_2$-$C_5$ alkenyl, $C_2$-$C_5$ haloalkenyl, $C_3$-$C_5$ alkenyl substituted with one or two $R_3$ groups, $C_3$-$C_5$ alkynyl, $C_3$-$C_5$ haloalkynyl, $C_3$-$C_5$ alkynyl substituted with one or two $R_3$ groups, $C_3$-$C_5$ cycloalkyl, $C_3$-$C_5$ halocycloalkyl, $C_3$-$C_5$ cycloalkyl substituted with one or two $R_4$ groups, $C_4$-$C_7$ cycloalkylalkyl, $C_4$-$C_7$ halocycloalkylalkyl, $C_4$-$C_7$ cycloalkylalkyl substituted with one or two $R_4$ groups, phenyl or benzyl;
   The scope of compounds within these that are most preferred can be also defined by adding the following proviso to the above described geneva scope as proviso (j) when J is J-5, J-6 or J-7 and E is $CH_2$, then R' is other than $C_1$-$C_5$ alkyl.

2. Compounds of Formula I wherein the scope is further limited by proviso (k) when J is J-8, n is O, n' is O, $R_1$ is H, $R_2$ is H, R' is $C_1$-$C_4$ alkyl, A is A-1, W is O, E is a single bond and X is halogen, $CH_3$, $OCH_3$ or $OCH_2CH_3$, then Y is other than $CH_3$, $OCH_3$ or $OCH_2CH_3$.

3. Compounds of Preferred 1 further defined in the proviso (k) when J is J-8, n is O, n' is O, $R_1$ is H, $R_2$ is H, R' is $C_1$-$C_4$ alkyl, A is A-1, W is O, E is a single bond and X is halogen, $CH_3$, $OCH_3$ or $OCH_2CH_3$, then Y is other than $CH_3$, $OCH_3$ or $OCH_2CH_3$.

4. Compounds of Preferred 3 where E is a single bond; and W is O.

5. Compounds of Preferred 3 where E is $CH_2$; and W is O.

6. Compounds of Preferred 4 where $R_2$ is H,
   $C_1$-$C_3$ alkyl, halogen, $C_1$-$C_3$ alkyl substituted with 1 to 3 halogen atoms selected from 1 to 3 Cl, 1 to 3 F or 1 Br, $OCH_3$, $SO_2NHCH_3$, $SO_2N(CH_3)_2$, $S(O)_nCH_3$, $CO_2CH_3$, $CO_2CH_2CH_3$, $OCF_2H$, $CH_2OCH_3$ or $CH_2CN$;
   R is H, $C_1$-$C_3$ alkyl, phenyl, $CH_2CF_3$ or $CH_2CH=CH_2$;

X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

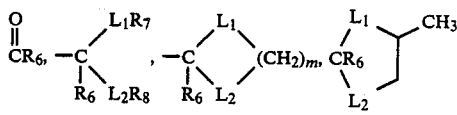

$OCF_2H$, $OCF_2Br$, $SCF_2H$, cyclopropyl, $C\equiv CH$ or $C\equiv CCH_3$.

7. Compounds of Preferred 6 where
   R' is $C_1$-$C_4$ alkyl, $C_1$-$C_3$ alkyl substituted with 1 to 3 halogen atoms selected from 1 to 3 Cl, 1 to 3 F or 1 Br, $C_2$-$C_4$ alkoxyalkyl, $C_2$-$C_4$ alkylthioalkyl, $C_2$-$C_4$ cyanoalkyl, $C_2$-$C_4$ alkenyl, $C_2$-$C_3$ alkenyl substituted with 1 to 3 halogen atoms selected from 1 to 3 Cl, 1 to 3 F or 1 Br, $C_3$-$C_4$ alkynyl, $C_3$-$C_5$ cycloalkyl, $C_3$-$C_5$ cycloalkyl substituted with 1 to 3 halogen atoms selected from 1 to 3 Cl, 1 to 3 F or 1 Br or cyclopropylmethyl.

8. Compounds of Preferred 7 where
   A is A-1;
   n is O;
   X is $CH_3$, $OCH_3$, $OCH_2CH_3$, Cl or $OCF_2H$; and
   Y is $CH_3$, $OCH_3$, $C_2H_5$, $CH_2OCH_3$, $NHCH_3$, $CH(OCH_3)_2$ or cyclopropyl.

9. Compounds of Preferred 8 where
   $R_1$ is H;
   $R_2$ is H, Cl, Br, $OCH_3$ or $CH_3$; and
   R' is $C_1$-$C_3$ alkyl, $C_1$-$C_3$ alkyl substituted with 1 to 3 F, $C_2$-$C_3$ alkoxyalkyl, $C_2$-$C_3$ alkylthioalkyl, $C_2$-$C_3$ cyanoalkyl, $C_2$-$C_3$ alkenyl, propargyl, $C_3$-$C_5$ cycloalkyl or cyclopropylmethyl.

10. Compounds of Preferred 9 where J is J-1.
11. Compounds of Preferred 9 where J is J-2.
12. Compounds of Preferred 9 where J is J-3.
13. Compounds of Preferred 9 where J is J-4.
14. Compounds of Preferred 9 where J is J-5.
15. Compounds of Preferred 9 where J is J-6.
16. Compounds of Preferred 9 where J is J-7.
17. Compounds of Preferred 9 where J is J-8.
18. Compounds of Preferred 9 where J is J-9.
19. Compounds of Preferred 9 where J is J-10.
20. Compounds of Preferred 9 where J is J-11.
21. Compounds of Preferred 10 where
    R' is $C_1$-$C_3$ alkyl.
22. Compounds of Preferred 10 where
    R' is $C_1$-$C_3$ alkyl substituted with 1 to 3 F, $C_2$-$C_3$ alkoxyalkyl, $C_2$-$C_3$ alkylthioalkyl, $C_2$-$C_3$ cyanoalkyl, $C_2$-$C_3$ alkenyl, propargyl, $C_3$-$C_5$ cycloalkyl or cyclopropylmethyl.
23. Compounds of Preferred 5 where
    R is H, $C_1$-$C_3$ alkyl, phenyl, $CH_2CF_3$ or $CH_2CH=CH_2$;
    $R_2$ is H, Cl, Br, $OCH_3$ or $CH_3$;
    R' is $C_1$-$C_3$ alkyl, $C_1$-$C_3$ alkyl substituted with 1 to 3 F, $C_2$-$C_3$ alkoxyalkyl, $C_2$-$C_3$ alkylthioalkyl, $C_2$-$C_3$ cyanoalkyl, $C_2$-$C_3$ alkenyl, propargyl, $C_3$-$C_5$ cycloalkyl or cyclopropylmethyl.
    n is O;
    A is A-1;
    X is $CH_3$, $OCH_3$, $OCH_2CH_3$, Cl or $OCF_2H$; and Y is $CH_3$, $OCH_3$, $C_2H_5$, $CH_2OCH_3$, $NHCH_3$, $CH(OCH_3)_2$ or cyclopropyl.

24. Compounds of Preferred 3 where
   J is J-1, J-2, J-3 or J-4; and
   R' is $C_1$–$C_5$ haloalkyl, $C_1$–$C_5$ alkyl substituted with one or two $R_3$ groups, $C_2$–$C_5$ alkenyl, $C_2$–$C_5$ haloalkenyl, $C_3$–$C_5$ alkenyl substituted with one or two $R_3$ groups, $C_3$–$C_5$ alkynyl, $C_3$–$C_5$ haloalkynyl, $C_3$–$C_5$ alkynyl substituted with one or two $R_3$ groups, $C_3$–$C_5$ cycloalkyl, $C_3$–$C_5$ halocycloalkyl, $C_3$–$C_5$ cycloalkyl substituted with one or two $R_4$ groups, $C_4$–$C_7$ cycloalkylalkyl substituted with one or two $R_4$ groups, phenyl or benzyl.

25. Compounds of Preferred 3 where
   J is J-5, J-6 or J-7.

26. Compounds of Preferred 3 where
   J is J-8, J-9, J-10 or J-11; and both of X and Y are other than $C_1$ haloalkoxy.

27. Compounds of Formula I wherein
   J is J-5, J-6 or J-7;
   E is $CH_2$; and
   R' is $C_1$–$C_5$ alkyl.

28. Compounds of Preferred 27 where
   when J is J-5, $R_1$ is H, $R_2$ is H, E is $CH_2$,
   A is A-1, X is $OCH_3$, Y is $OCH_3$ and Z is CH, then R' is other than $CH_3$.

29. Compounds of Preferred 27 where
   R' is $C_2$–$C_5$ alkyl.

Specifically preferred for reasons of greatest ease of synthesis and/or greatest herbicidal efficacy are:
4-(1-oxopropyl)-N-[(4,6-dimethoxypyrimidin-2-yl)aminocarbonyl]-1-methyl-1H-pyrazole-5-sulfonamide, m.p. 189°–192° C.(d), and
2-(cyclopropylcarbonyl)-N-[(4,6-dimethoxypyrimidin-2-yl)aminocarbonyl]-3-thiophenesulfonamide, m.p. 165°–168° C.

DETAILED DESCRIPTION OF THE INVENTION

Synthesis

Compounds of Formula I can be prepared by one or more of the procedures shown in Equations 1, 4, and 5. J, $R_1$, and A are as previously defined.

$$JSO_2N{=}C{=}W + H\underset{\underset{R_1}{|}}{N}A \longrightarrow I \quad \text{Equation 1}$$
$$\text{II} \qquad \text{III}$$

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocayanates (II, W is O) are known in the art and are prepared from the corresponding sulfonamides (IV) by one of the following two general methods.

$$JSO_2NH_2 \xrightarrow[COCl_2, \text{cat.}]{CH_3(CH_2)_3NCO} \text{II, W is O} \quad \text{Equation 2}$$
$$\text{IV}$$

The sulfonamide IV is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]bicyclooctane (DABCO). The reaction mixture is heated to 135°–140° C. and held at that temperature for 5–60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g, $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (IV) is high melting and has low solubility in the phosgenation solvent.

Sulfonyl isocyanates (II, W is O) can also be prepared by the following method.

$$\text{(a) IV} \xrightarrow{SOCl_2} \underset{V}{JSO_2NSO} \quad \text{Equation 3}$$

$$\text{(b) V} \xrightarrow[\text{pyridine cat.}]{COCl_2,} \text{II, W is O}$$

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2–3 equivalents) of phosgene. A catalytic amount of pyridine (typically 0.1 equivalent) is added, and the mixture is heated to about 60°–140° C., with 80°–100° C. preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Many of the compounds of Formula I can be prepared by the procedure shown in Equation 4.

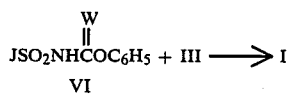

Equation 4

The reaction of Equation 4 is carried out by contacting phenylcarbamates or phenylthiocarbamates of Formula VI with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art, in U.S. Pat. No. 4,443,243.

Alternatively, many of the compounds of Formula I can be prepared by the method described in Equation 5.

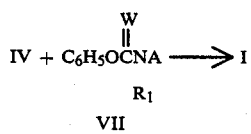

Equation 5

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African patent application No. 83/0441. The phenylcarbamates and phenylthiocarbamates of Formula VII can be prepared by methods, or modifications thereof known to those skilled in the art, described in South African patent application No. 82/5671 and South African patent application No. 82/5045.

The sulfonamides IV of this invention may be prepared in a variety of ways some of which are described in Equations 6 through 22.

For example, the 4-keto-5-sulfonamide isomer 1 may be prepared as outlined in Equation 6.

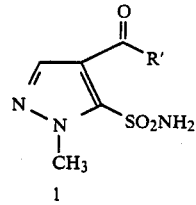

1

Preparation of the intermediates such as bromide 2 may be found in EPA No. 95,925. Exposure of bromide 2 to n-butyllithium (n-BuLi) followed by addition of the resulting anion to an acid chloride affords the protected sulfonamide. Deprotection of the sulfonamide affords the desired sulfonamide 1.

Introduction of various R and $R_2$ groups to sulfonamides such as 1 may be accomplished in several ways. For example, the sequence in Equation 6 could also be performed on 3-chloro-1-methylpyrazole of 1,3-dimethylpyrazole affording 3 and 4 respectively. Chloride 3 may then be used to further elaborate

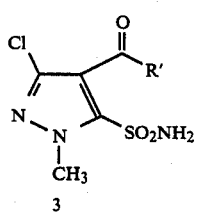   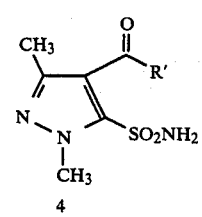

3                       4

$R_2$ as outlined in Equation 7.

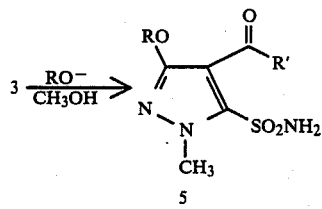

Equation 7

The N-substituent of compounds such as 1, 3, 4 and 5 may also be varied by applying the same sequence of reactions as outlined in Equation 6 to various N-substituent pyrazoles. For example, pyrazole may be alkylated with dimethylsulfamoylchloride to afford pyrazole 6. Pyrazole 6 is then converted to sulfonamide 7 as outlined in Equation 8.

Equation 6

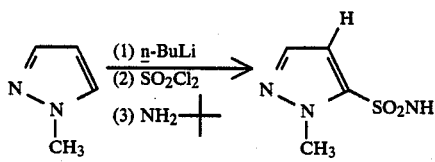

Br₂

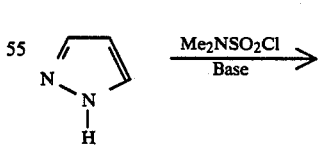

Equation 8

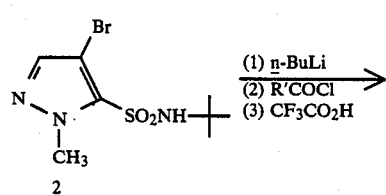

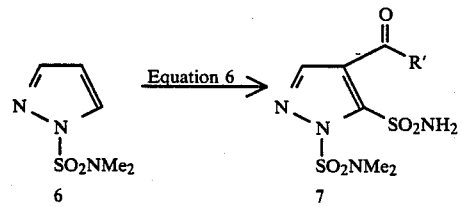

In the case where either R or $R_2$ are sensitive to n-BuLi (i.e. $R_2$ is $CO_2CH_3$ or Br) then the lithiating reagent of choice is lithium diisopropylamide (LDA). Utilizing the same sequence as outlined in Equation 6 but substituted LDA for n-BuLi affords sulfonamides such as 8. This is outlined in Equation 9.

Equation 9

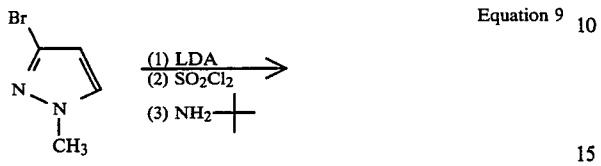

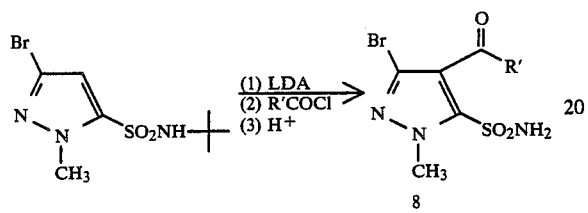

The isomeric 5-keto-4-sulfonamide pyrazoles may be prepared as outlined in Equations 10 and 11.

Equation 10

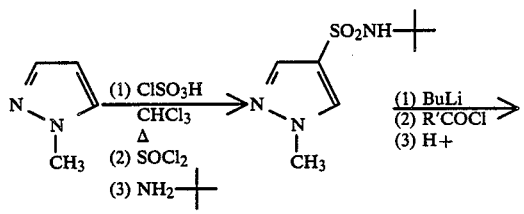

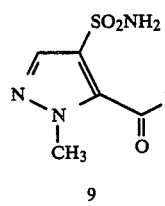

In Equation 10 the sequential order of group introduction is reversed to that of Equation 6. The introduction of various R and $R_2$ groups may be accomplished in the same manor as previously described for the 4-ketoisomer in Equations 7, 8 and 9.

An alternate synthesis of sulfonamides such as 9 is outlined in Equation 11.

Equation 11

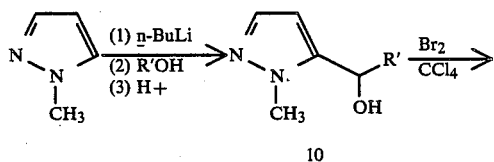

-continued
Equation 11

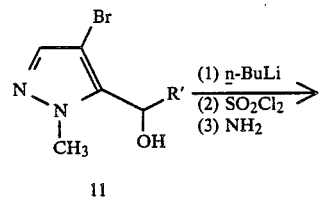

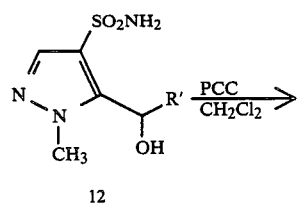

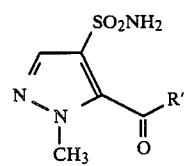

Oxidations of alcohols to ketones such as 12 to 9 are well known in the art. For further discussion pertaining to the oxidation of alcohols to ketones, see R. H. Cornforth, J. W. Cornforth and G. Popjak, *Tetrahedron*, 18, 1351 (1962).

The isomeric 3-keto-4-sulfonamide such as 13 may be prepared as outlined in Equation 12.

Equation 12

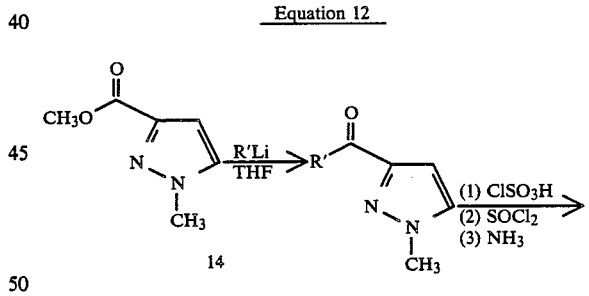

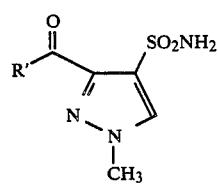

In the above example of Equation 12, as before, minor variations of starting material allows for the introduction of different R and $R_2$ groups. The starting pyrazoles 14 or 15 may be prepared via the condensation of a hydrazine with a triketo species as outlined in Equation 13.

Equation 13

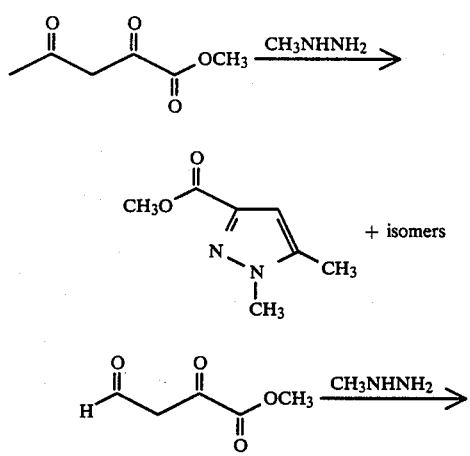

The final pyrazole isomer of the invention such as sulfonamide 16 may be prepared as outlined in Equation 14.

Equation 14

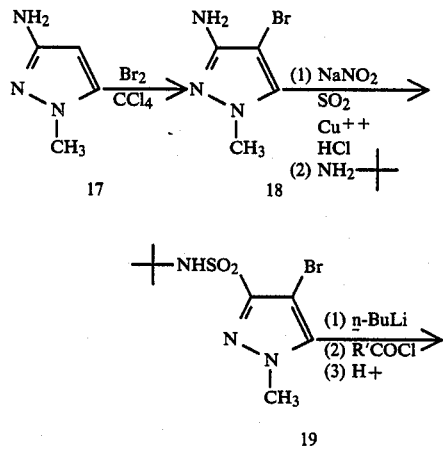

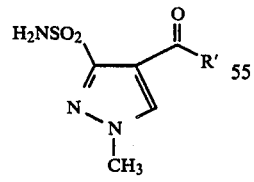

Again, as described previously, alteration of the starting material allows for the preparation of compounds such as 16 where R and/or $R_2$ may be varied. For example, utilizing phenylhydrazine and a chloronitrile results in pyrazole 20 and subsequently sulfonamide, 21. This is outlined in Equation 15.

Equation 15

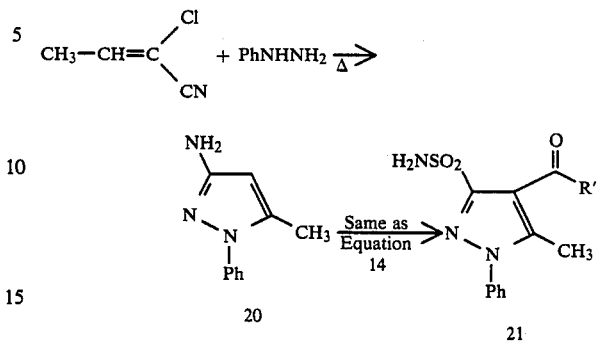

Examples of sulfonamides which can be prepared according to Equations 6-15 are compounds 22, 23, 24, 25 and 26.

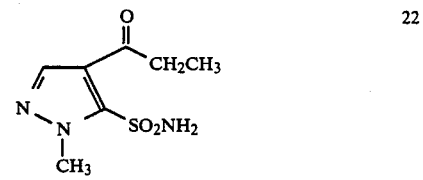

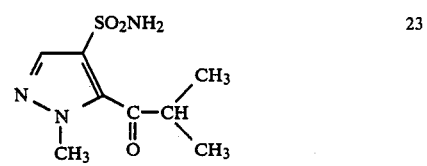

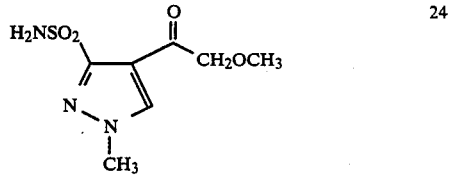

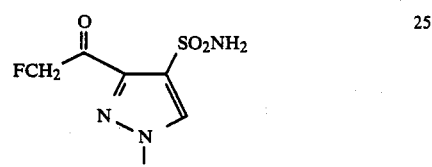

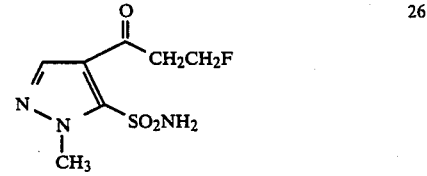

For further details pertaining to the synthesis of pyrazoles see EP-A No. 87,780, South African patent application No. 833,350, EP-A No. 95,925 and T. L. Jacobs, "Heterocyclic Compounds", R. C. Elderfield, ed., Vol. 5, pp. 45-161, Wiley, New York, 1957.

For further details pertaining to carbanions see J. Stowell, "Carbanions in Organic Synthesis", Wiley-Interscience, New York, 1979.

Thiophene sulfonamides such as 27 may be prepared as outlined in Equation 16.

Equation 16

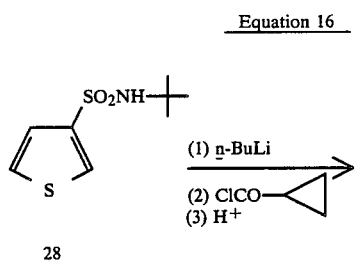

Introduction of various $R_2$ groups on the thiophene ring may be accomplished in several ways. For example, the sequence in Equation 16 may also be performed on the 4-substituted analogs resulting in the corresponding sulfonamides such as 29 and 30.

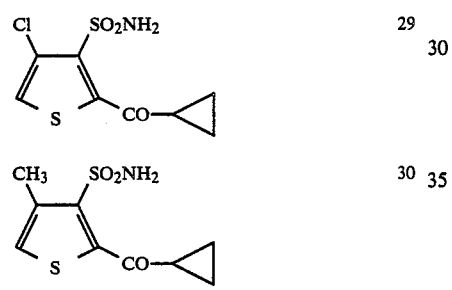

The isomeric 2-thiophenesulfonamide such as 31 may be prepared as outlined in Equation 17.

Equation 17

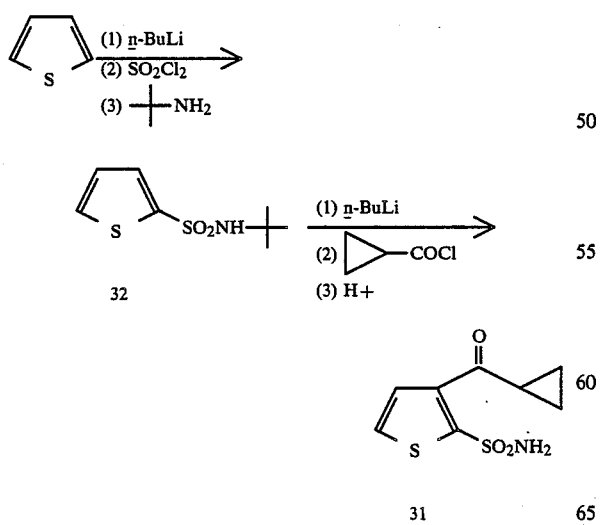

An alternate synthesis of sulfonamides such as 31 is outlined in Equation 18.

Equation 18

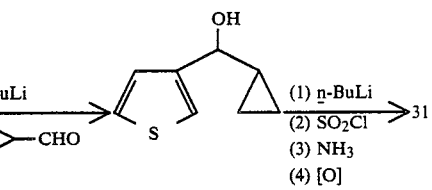

The isomeric 3-thiophenesulfonamide such as 33 may be prepared as outlined in Equation 19.

Equation 19

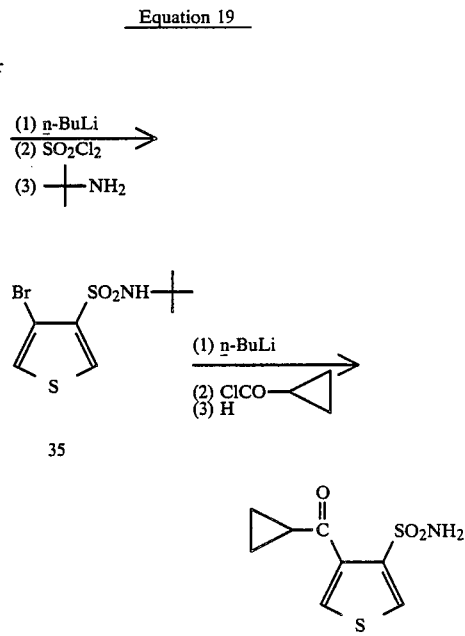

Introduction of various $R_2$ groups onto the thiophene ring may be accomplished by varying the starting material as previously described.

Further details pertaining to the preparation and functional group manipulation of thiophenes may be found in U.S. Pat. No. 4,481,029.

Preparation of the pyridinesulfonamides of this invention, such as pyridine 36 may be carried out in a variety of ways. For example, Meerwein reaction of 37 followed by ortho lithiation affords sulfonamides such as 36, as outlined in Equation 20.

Equation 20

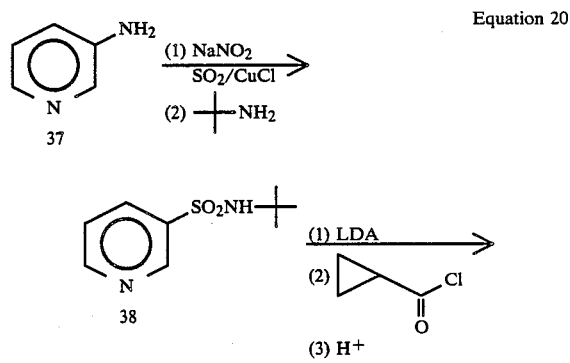

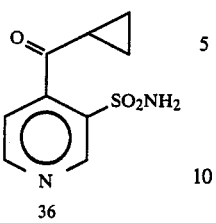

36

40

Prior to removal of the tert-butyl group it may be necessary to protect the ketone functionality as the ethylene ketal which may then be removed subsequently at a later time.

The isomeric sulfonamide, 39, may be prepared as outlined in Equation 21.

Equation 21

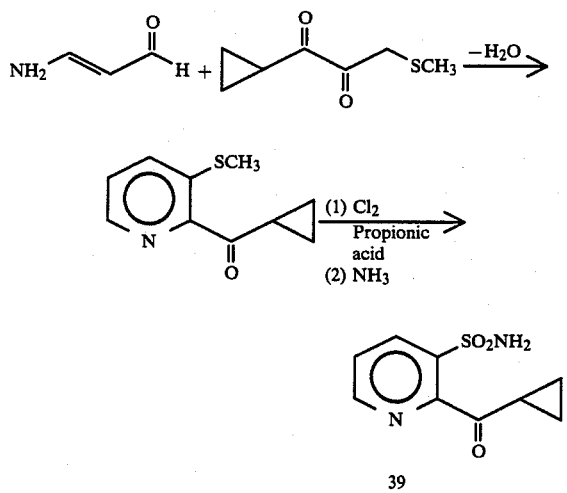

39

The isomeric sulfonamide 40 may be prepared as outlined in Equation 22.

Equation 22

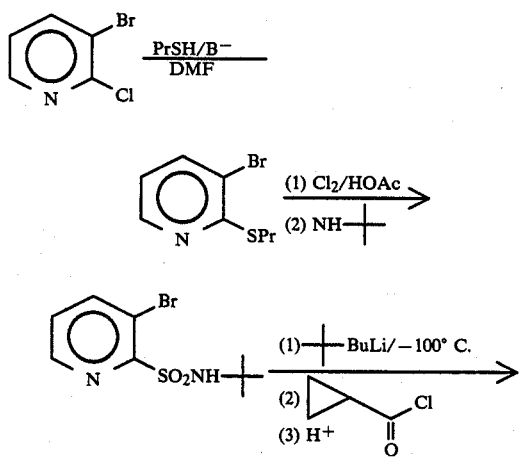

Introduction of various substituents on the pyridine ring system as well as variation of R' may be accomplished as described previously for the pyrazole system.

For further details pertaining to the synthesis of pyridines see, E. Beritmaier, S. Gassenmann and E. Bayer, *Tetrahedron* 26, 5907 (1970); B. Blank et al., *J. Med. Chem.*, 17, 1065 (1974); M. Mallet and G. Queguiner, *Tetrahedron*, 41, 3433 (1985) and J. Delarge and C. L. Lapier, *Annales Pharm. France*, 36, 369 (1978).

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyrimidines of Formula III, where A is A-1 and Y is cyclopropyl or OCF$_2$H can be synthesized according to the methods taught in U.S. Pat. No. 4,515,626 and U.S. Pat. No. 4,540,782, respectively.

Compounds of Formula III, where A is A-2 or A-3, can be prepared by procedures disclosed in U.S. Pat. No. 4,339,267.

Compounds of Formula III, where A is A-4, can be prepared by methods taught in U.S. Pat. No. 4,487,626.

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in the U.S. Pat. No. 4,496,392.

Compounds of Formula III, where A is A-7 can be prepared by methods taught in EP-A-No. 125,864.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

Preparation of 4-Acetyl-1-methyl-1H-pyrazole-5-sulfonamide

To a stirring solution of n-BuLi (3.7 g, 57.2 mmol) in 350 mL of tetrahydrofuran cooled to −95° C. is added 4-bromo-1-methyl-1H-pyrazole-5-t-butylsulfonamide (7.5 g, 25.4 mmol). The solution is cannulated into a stirring solution of acetyl chloride (76.2 mmol) cooled to −78° C. The reaction is stirred for ½ hour at −78° C. then quenched with saturated sodium chloride. The organic layer is separated, dried and concentrated. The resulting crude oil was added to $CF_3CO_2H$ and allowed to stir for 24 hours. The acid was removed under vacuum and the resulting oil was flash chromatographed. The resulting solid, m.p. 153°–162° C., was mostly the closed hemiaminal, which was used directly in the next reaction.

EXAMPLE 2

Preparation of 4-Acetyl-N-[(4,6-dimethoxy-2-pyrimidin-yl)aminocarbonyl]-1-methyl-1H-pyrazole-5-sulfonamide To a mixture of the hemiaminal from Example 1 (200 mg, 0.98 mmol), the phenyl carbamate of 4,6-dimethoxy-2-aminopyrimidine (271 mg, 0.98 mmol) 3 mL of acetonitrile, and DBU (212 mg, 0.98 mmol) was added. The reaction was diluted with 3 mL of water and 3 mL of 5% hydrochloric acid. The resulting solids were collected to afford 200 mg of a white solid, m.p. 179°–182° C.; NMR (200 MHz, $CDCl_3$) δ2.46 (s, 3H), 4.06 (s, 6H), 4.37 (s, 3H), 5.81 (s, 1H), 7.4 (br.s, 1H), 7.9 (s, 1H) and 13.0 (br.s, 1H); IR (KBr) 1730 cm$^{-1}$.

EXAMPLE 3

Preparation of N-(1,1-Dimethylethyl)-1-methyl-4-(1-oxobutyl)-1H-pyrazole-5-sulfonamide To a solution of n-BuLi (2.1 g, 33.7 mmol) cooled to −78° C. in 250 mL of tetrahydrofuran is added the t-butyl protected 4-bromo-1-methyl-5-pyrazolesulfonamide (4.5 g, 15.2 mmol). The solution is then added to butyric anhydride (2.9 g, 18.2 mmol) at −78° C. Standard work-up afforded 4.4 g of an oil which was a mixture of the desired product and debrominated starting material. This material was not purified, but used as is in the next reaction.

EXAMPLE 4

Preparation of 1-Methyl-4-(1-oxobutyl)-1H-pyrazole-5-sulfonamide

The mixture from the previous Example 3 (3.9 g) was added to $CF_3CO_2H$ (TFA) and stirred for 4.5 hours. Removal of the TFA afforded a brown oil. Flash chromatography (15:85 EtOAC:hexane (v/v)) yielded 1.0 g of a white solid, m.p. 97°–99° C. NMR (200 MHz, $CDCl_3$) δ0.97 (t, 3H), 1.67 (m, 2H), 2.83 (t, 3H), 4.19 (s, 3H), 6.40 (br.s, 2H) and 7.91 (s, 1H).

EXAMPLE 5

Preparation of N-[(4-Methoxy-6-methyl-1,3,5-triazin-2-yl)aminocarbonyl]-1-methyl-4-(1-oxobutyl)-1H-pyrazole-5-sulfonamide To a mixture of sulfonamide (150 mg, 0.61 mmol) and the phenyl carbamate of 4-methyl-6-methoxy-2-aminotriazine (158 mg, 0.61 mmol) in 3 mL of acetonitrile is added DBU (93 mg, 0.61 mmol). The solution is diluted with 3 mL of $H_2O$ and 3 mL of 5% HCl, and the resulting solids are collected, m.p. 174°–176° C. NMR (200 MHz, $CDCl_3$) δ0.88 (s, 3H), 1.68 (m, 2H), 2.7 (s, 3H), 2.79 (t, 2H), 4.19 (s, 3H), 4.33 (s, 3H), 7.7 (br.s, 1H), 7.9 (s, 1H) and 12.9 (br.s, 1H).

EXAMPLE 6

Preparation of 2-(cyclopropylcarbonyl)-N-(1-1-dimethylethyl)-3-thiophenesulfonamide To a stirring solution of n-BuLi (6.6 g, 102 mmol) in 300 ml of tetrahydrofuran is added the t-butyl protected 3-thiophenesulfonamide (10.0 g, 45.7 mmol). The solution was warmed to −30° C. and then recooled to −78° C. The solution was cannulated into a mixture of cyclopropane carbonylic acid chloride (5.7 g, 51.7 mmol) in 50 ml of tetrahydrofuran @ −78° C. The reaction was quenched with brine, separated and dryed over magnesium sulfate, concentration of the organic in vaccuo afforded 17 g of anvil. Flash chromatography (25:75 EtCAC/hexane (v/v)) afforded 44 g of the desired product. NMR (200 MHz, $CDC_3$) δ1.26 (m, 13H), 2.5 (m, 1H), 6.5 (br. S, 1H), 7.5 (d, 1H), 7.67 (d, 1H):

EXAMPLE 7

Preparation of 2-(cyclopropylcarbonyl)-N-[(4,6-dimethoxy-1,3,5-triazin-2-yl)aminocarbonyl]-3-thiophenesulfonamide To a stirring solution of sulfonamide (300 mg, 1.3 mmol), the phenylcarbamate of 4,6-dimethoxy-2-aminotriazine (358 mg, 1.3 mmol) in 5 ml of acetonitrile was added DBU (197 mg, 1.3 mmol). The same work up as in example 5 afforded 390 mg of the desired product. m.p. 146°–148° C., NMR (200 mHz, $CDCl_3$), δ, 1.1 (m, 2H), 1.3 (m, 2H), 2.5 (m, 1H), 4.1 (S, 6H), 7.5 hr, s, 1H), 7.6 (d, 1H), 7.9 (d, 1H), 12.3 (s, 1H):

Using the procedures from Equations 1 to 22 and Examples 1 to 7 the compounds of Tables I to XIII can be prepared.
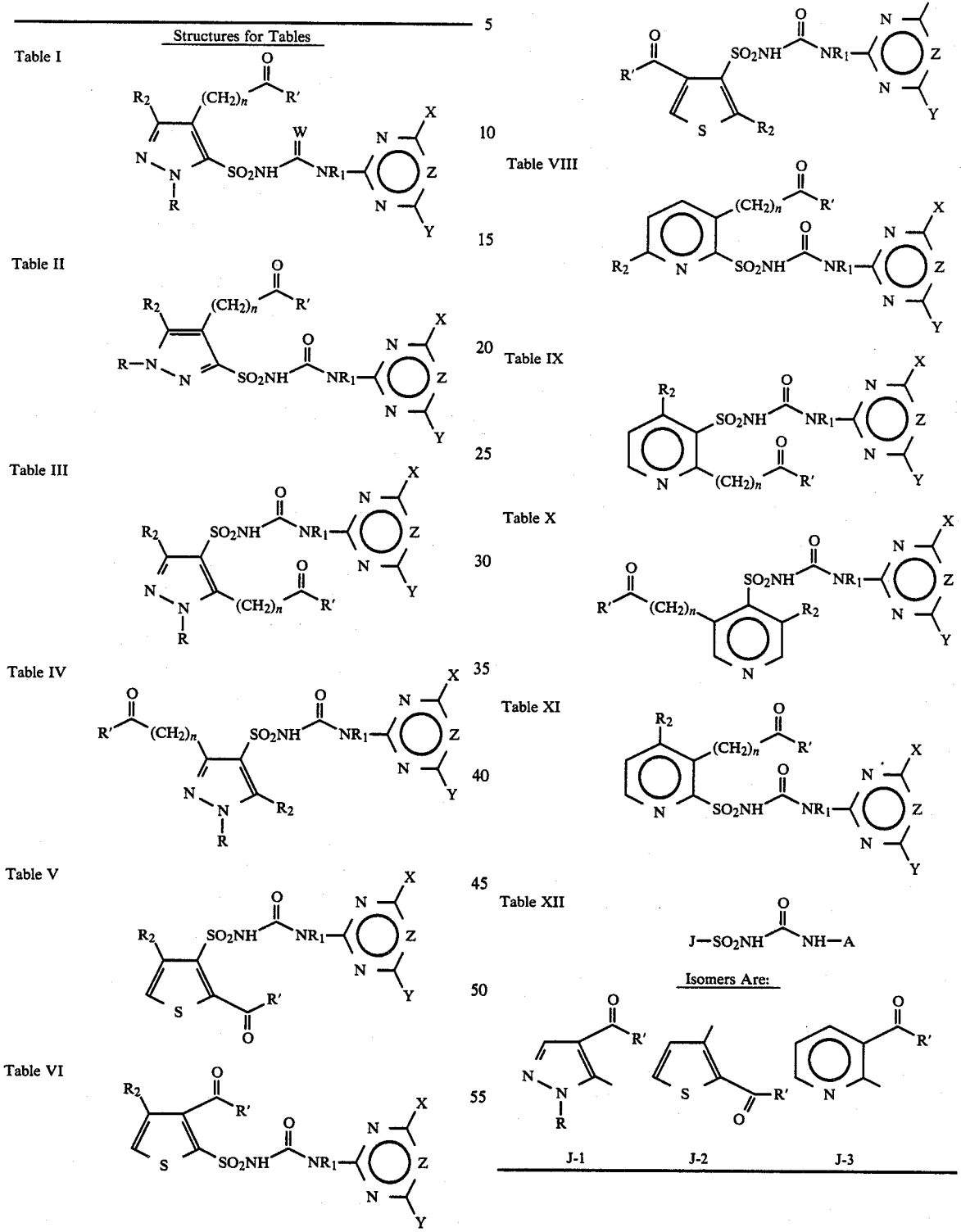
| R | R$_1$ | n | R$_2$ | R' | X | Y | Z | m.p. (°C.) |
|---|---|---|---|---|---|---|---|---|
| | | | | W = O | | | | |
| CH$_3$ | H | 0 | H | CH$_3$ | CH$_3$ | CH$_3$ | CH | 185–188 |
| CH$_3$ | H | 0 | H | CH$_3$ | CH$_3$ | OCH$_3$ | CH | 180–183 |
| CH$_3$ | H | 0 | H | CH$_3$ | OCH$_3$ | OCH$_3$ | CH | 179–182 |

TABLE 1-continued

| R | R₁ | n | R₂ | R' | X | Y | Z | m.p. (°C.) |
|---|---|---|---|---|---|---|---|---|
| CH₃ | H | 0 | H | CH₃ | CH₃ | CH₃ | N | |
| CH₃ | H | 0 | H | CH₃ | CH₃ | OCH₃ | N | 110–112 |
| CH₃ | H | 0 | H | CH₃ | OCH₃ | OCH₃ | N | 163–165 |
| CH₃ | H | 0 | H | CH₃ | Cl | OCH₃ | CH | 199–201 |
| CH₃ | H | 0 | H | CH₂CH₃ | CH₃ | CH₃ | CH | 157–161 |
| CH₃ | H | 0 | H | CH₂CH₃ | CH₃ | OCH₃ | CH | 151–154 |
| CH₃ | H | 0 | H | CH₂CH₃ | OCH₃ | OCH₃ | CH | 143–146 |
| CH₃ | H | 0 | H | CH₂CH₃ | CH₃ | CH₃ | N | |
| CH₃ | H | 0 | H | CH₂CH₃ | CH₃ | OCH₃ | N | 145–147 |
| CH₃ | H | 0 | H | CH₂CH₃ | OCH₃ | OCH₃ | N | 122–137 |
| CH₃ | H | 0 | H | CH₂CH₃ | Cl | OCH₃ | CH | 180–182 |
| CH₃ | H | 0 | H | CH₂CH₂CH₃ | CH₃ | CH₃ | CH | 163–165 |
| CH₃ | H | 0 | H | CH₂CH₂CH₃ | CH₃ | OCH₃ | CH | 173–175 |
| CH₃ | H | 0 | H | CH₂CH₂CH₃ | OCH₃ | OCH₃ | CH | 180–184 |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | 174–176 |
| CH₃ | H | 0 | H | CH₂CH₂CH₃ | OCH₃ | OCH₃ | N | 154–156 |
| CH₃ | H | 0 | H | CH₂CH₂CH₃ | Cl | OCH₃ | CH | 203–205 |
| CH₃ | H | 0 | H | CH₂CH₂CH₂CH₃ | CH₃ | CH₃ | CH | |
| CH₃ | H | 0 | H | CH₂CH₂CH₂CH₃ | CH₃ | OCH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |
| CH₃ | H | 0 | H | CH₂CH₂CH₂CH₂CH₃ | CH₃ | CH₃ | CH | |
| CH₃ | H | 0 | H | CH₂CH₂CH₂CH₂CH₃ | CH₃ | OCH₃ | CH | |
| CH₃ | H | 0 | H | CH₂CH₂CH₂CH₂CH₃ | OCH₃ | OCH₃ | CH | |
| CH₃ | H | 0 | H | CH₂CH₂CH₂CH₂CH₃ | CH₃ | CH₃ | N | |
| CH₃ | H | 0 | H | CH₂CH₂CH₂CH₂CH₃ | CH₃ | OCH₃ | N | |
| CH₃ | H | 0 | H | CH₂CH₂CH₂CH₂CH₃ | OCH₃ | OCH₃ | N | |
| CH₃ | H | 0 | H | CH₂CH₂CH₂CH₂CH₃ | Cl | OCH₃ | CH | |
| CH₃ | H | 0 | H | CH(CH₃)₂ | CH₃ | CH₃ | CH | 148–150 |
| CH₃ | H | 0 | H | CH(CH₃)₂ | CH₃ | OCH₃ | CH | 178–180 |
| CH₃ | H | 0 | H | CH(CH₃)₂ | OCH₃ | OCH₃ | CH | 181–183 |
| CH₃ | H | 0 | H | CH(CH₃)₂ | CH₃ | CH₃ | N | |
| CH₃ | H | 0 | H | CH(CH₃)₂ | CH₃ | OCH₃ | N | 152–154 |
| CH₃ | H | 0 | H | CH(CH₃)₂ | OCH₃ | OCH₃ | N | 159–161 |
| CH₃ | H | 0 | H | CH(CH₃)₂ | Cl | OCH₃ | CH | 194–196 |
| CH₃ | H | 0 | H | CH₂CH(CH₃)₂ | CH₃ | CH₃ | CH | |
| CH₃ | H | 0 | H | CH₂CH(CH₃)₂ | CH₃ | OCH₃ | CH | |
| CH₃ | H | 0 | H | CH₂CH(CH₃)₂ | OCH₃ | OCH₃ | CH | |
| CH₃ | H | 0 | H | CH₂CH(CH₃)₂ | CH₃ | CH₃ | N | |
| CH₃ | H | 0 | H | CH₂CH(CH₃)₂ | CH₃ | OCH₃ | N | |
| CH₃ | H | 0 | H | CH₂CH(CH₃)₂ | OCH₃ | OCH₃ | N | |
| CH₃ | H | 0 | H | CH₂CH(CH₃)₂ | Cl | OCH₃ | CH | |
| CH₃ | H | 0 | H | CH(CH₃)CH₂CH₃ | CH₃ | CH₃ | CH | |
| CH₃ | H | 0 | H | CH(CH₃)CH₂CH₃ | CH₃ | OCH₃ | CH | |
| CH₃ | H | 0 | H | CH(CH₃)CH₂CH₃ | OCH₃ | OCH₃ | CH | |
| CH₃ | H | 0 | H | CH₂CH₂CH(CH₃)₂ | CH₃ | CH₃ | N | |
| CH₃ | H | 0 | H | CH₂CH₂CH(CH₃)₂ | CH₃ | OCH₃ | N | |
| CH₃ | H | 0 | H | CH₂CH₂CH(CH₃)₂ | OCH₃ | OCH₃ | N | |
| CH₃ | H | 0 | H | CH₂CH₂CH(CH₃)₂ | Cl | OCH₃ | CH | |
| CH₃ | H | 0 | H | CH₂F | CH₃ | CH₃ | CH | |
| CH₃ | H | 0 | H | CH₂F | CH₃ | OCH₃ | CH | |
| CH₃ | H | 0 | H | CH₂F | OCH₃ | OCH₃ | CH | |
| CH₃ | H | 0 | H | CH₂F | CH₃ | CH₃ | N | |
| CH₃ | H | 0 | H | CH₂F | CH₃ | OCH₃ | N | |
| CH₃ | H | 0 | H | CH₂F | OCH₃ | OCH₃ | N | |
| CH₃ | H | 0 | H | CH₂F | Cl | OCH₃ | CH | |
| CH₃ | H | 0 | H | CH₂CH₂F | CH₃ | CH₃ | CH | |
| CH₃ | H | 0 | H | CH₂CH₂F | CH₃ | OCH₃ | CH | |
| CH₃ | H | 0 | H | CH₂CH₂F | OCH₃ | OCH₃ | CH | |
| CH₃ | H | 0 | H | CH₂CH₂F | CH₃ | CH₃ | N | |
| CH₃ | H | 0 | H | CH₂CH₂F | CH₃ | OCH₃ | N | |
| CH₃ | H | 0 | H | CH₂CH₂F | OCH₃ | OCH₃ | N | |
| CH₃ | H | 0 | H | CH₂CH₂F | Cl | OCH₃ | CH | |
| CH₃ | H | 0 | H | CHF₂ | CH₃ | CH₃ | CH | |
| CH₃ | H | 0 | H | CHF₂ | CH₃ | OCH₃ | CH | |
| CH₃ | H | 0 | H | CHF₂ | OCH₃ | OCH₃ | CH | |
| CH₃ | H | 0 | H | CHF₂ | CH₃ | CH₃ | N | |
| CH₃ | H | 0 | H | CHF₂ | CH₃ | OCH₃ | N | |
| CH₃ | H | 0 | H | CHF₂ | OCH₃ | OCH₃ | N | |
| CH₃ | H | 0 | H | CHF₂ | Cl | OCH₃ | CH | |
| CH₃ | H | 0 | H | CH₂CF₃ | CH₃ | CH₃ | CH | |
| CH₃ | H | 0 | H | CH₂CF₃ | CH₃ | OCH₃ | CH | |
| CH₃ | H | 0 | H | CH₂CF₃ | OCH₃ | OCH₃ | CH | |
| CH₃ | H | 0 | H | CH₂Cl | CH₃ | CH₃ | N | |
| CH₃ | H | 0 | H | CH₂Cl | CH₃ | OCH₃ | N | |
| CH₃ | H | 0 | H | CH₂Cl | OCH₃ | OCH₃ | N | |
| CH₃ | H | 0 | H | CH₂Cl | Cl | OCH₃ | CH | |

TABLE 1-continued

| R | R₁ | n | R₂ | R' | X | Y | Z | m.p. (°C.) |
|---|---|---|---|---|---|---|---|---|
| CH₃ | H | 0 | H | CH₂Br | CH₃ | CH₃ | CH | |
| CH₃ | H | 0 | H | CH₂Br | CH₃ | OCH₃ | CH | |
| CH₃ | H | 0 | H | CH₂Br | OCH₃ | OCH₃ | CH | |
| CH₃ | H | 0 | H | CH₂Br | CH₃ | CH₃ | N | |
| CH₃ | H | 0 | H | CH₂CH₂Br | CH₃ | OCH₃ | N | |
| CH₃ | H | 0 | H | CH₂CH₂Br | OCH₃ | OCH₃ | N | |
| CH₃ | H | 0 | H | CH₂CH₂Br | Cl | OCH₃ | CH | |
| CH₃ | H | 0 | H | CH(CH₃)CH₂F | CH₃ | CH₃ | CH | |
| CH₃ | H | 0 | H | CH(CH₃)CH₂F | CH₃ | OCH₃ | CH | |
| CH₃ | H | 0 | H | CH(CH₃)CH₂F | OCH₃ | OCH₃ | CH | |
| CH₃ | H | 0 | H | CH(CH₃)CH₂F | CH₃ | CH₃ | N | |
| CH₃ | H | 0 | H | CH(CH₃)CH₂F | CH₃ | OCH₃ | N | |
| CH₃ | H | 0 | H | CH(CH₃)CH₂F | OCH₃ | OCH₃ | N | |
| CH₃ | H | 0 | H | CH(CH₃)CH₂F | Cl | OCH₃ | CH | |
| CH₃ | H | 0 | H | CH(CH₂F)₂ | CH₃ | CH₃ | CH | |
| CH₃ | H | 0 | H | CH(CH₂F)₂ | CH₃ | OCH₃ | CH | |
| CH₃ | H | 0 | H | CH(CH₂F)₂ | OCH₃ | OCH₃ | CH | |
| CH₃ | H | 0 | H | CH(CH₂F)₂ | CH₃ | CH₃ | N | |
| CH₃ | H | 0 | H | CH(CH₂F)₂ | CH₃ | OCH₃ | N | |
| CH₃ | H | 0 | H | CH(CH₂F)₂ | OCH₃ | OCH₃ | N | |
| CH₃ | H | 0 | H | CH(CH₂F)₂ | Cl | OCH₃ | CH | |
| CH₃ | H | 0 | H | CH₂I | CH₃ | CH₃ | CH | |
| CH₃ | H | 0 | H | CH₂I | CH₃ | OCH₃ | CH | |
| CH₃ | H | 0 | H | CH₂I | OCH₃ | OCH₃ | CH | |
| CH₃ | H | 0 | H | CH₂I | CH₃ | CH₃ | N | |
| CH₃ | H | 0 | H | CH₂CH₂CH₂F | CH₃ | OCH₃ | N | |
| CH₃ | H | 0 | H | CH₂CH₂CH₂F | OCH₃ | OCH₃ | N | |
| CH₃ | H | 0 | H | CH₂CH₂CH₂F | Cl | OCH₃ | CH | |
| CH₃ | H | 0 | H | CH₂OCH₃ | CH₃ | CH₃ | CH | |
| CH₃ | H | 0 | H | CH₂OCH₃ | CH₃ | OCH₃ | CH | |
| CH₃ | H | 0 | H | CH₂OCH₃ | OCH₃ | OCH₃ | CH | |
| CH₃ | H | 0 | H | CH₂OCH₃ | CH₃ | CH₃ | N | |
| CH₃ | H | 0 | H | CH₂OCH₃ | CH₃ | OCH₃ | N | |
| CH₃ | H | 0 | H | CH₂OCH₃ | OCH₃ | OCH₃ | N | |
| CH₃ | H | 0 | H | CH₂OCH₃ | Cl | OCH₃ | CH | |
| CH₃ | H | 0 | H | CH₂OCH₂CH₃ | CH₃ | CH₃ | CH | |
| CH₃ | H | 0 | H | CH₂OCH₂CH₃ | CH₃ | OCH₃ | CH | |
| CH₃ | H | 0 | H | CH₂OCH₂CH₃ | OCH₃ | OCH₃ | CH | |
| CH₃ | H | 0 | H | CH₂OCH₂CH₃ | CH₃ | CH₃ | N | |
| CH₃ | H | 0 | H | CH₂CH₂OCH₃ | CH₃ | OCH₃ | N | |
| CH₃ | H | 0 | H | CH₂CH₂OCH₃ | OCH₃ | OCH₃ | N | |
| CH₃ | H | 0 | H | CH₂CH₂OCH₃ | Cl | OCH₃ | CH | |
| CH₃ | H | 0 | H | CH₂CH₂OCH₃ | CH₃ | CH₃ | CH | |
| CH₃ | H | 0 | H | CH₂CH₂OCH₃ | CH₃ | OCH₃ | CH | |
| CH₃ | H | 0 | H | CH₂CH₂OCH₃ | OCH₃ | OCH₃ | CH | |
| CH₃ | H | 0 | H | CH₂CH₂OCH₃ | CH₃ | CH₃ | N | |
| CH₃ | H | 0 | H | CH(OCH₃)₂ | CH₃ | OCH₃ | N | |
| CH₃ | H | 0 | H | CH(OCH₃)₂ | OCH₃ | OCH₃ | N | |
| CH₃ | H | 0 | H | CH(OCH₃)₂ | Cl | OCH₃ | CH | |
| CH₃ | H | 0 | H | CH₂SCH₃ | CH₃ | CH₃ | CH | |
| CH₃ | H | 0 | H | CH₂SCH₃ | CH₃ | OCH₃ | CH | |
| CH₃ | H | 0 | H | CH₂SCH₃ | OCH₃ | OCH₃ | CH | |
| CH₃ | H | 0 | H | CH₂SCH₃ | CH₃ | CH₃ | N | |
| CH₃ | H | 0 | H | CH₂SCH₃ | CH₃ | OCH₃ | N | |
| CH₃ | H | 0 | H | CH₂SCH₃ | OCH₃ | OCH₃ | N | |
| CH₃ | H | 0 | H | CH₂SCH₃ | Cl | OCH₃ | CH | |
| CH₃ | H | 0 | H | CH₂OCH₂F | CH₃ | CH₃ | CH | |
| CH₃ | H | 0 | H | CH₂OCH₂F | CH₃ | OCH₃ | CH | |
| CH₃ | H | 0 | H | CH₂OCH₂F | OCH₃ | OCH₃ | CH | |
| CH₃ | H | 0 | H | CH₂OCH₂F | CH₃ | CH₃ | N | |
| CH₃ | H | 0 | H | CH₂OCH₂F | CH₃ | OCH₃ | N | |
| CH₃ | H | 0 | H | CH₂OCH₂F | OCH₃ | OCH₃ | N | |
| CH₃ | H | 0 | H | CH₂OCH₂F | Cl | OCH₃ | CH | |
| CH₃ | H | 0 | H | CH₂SOCH₃ | CH₃ | CH₃ | CH | |
| CH₃ | H | 0 | H | CH₂SOCH₃ | CH₃ | OCH₃ | CH | |
| CH₃ | H | 0 | H | CH₂SOCH₃ | OCH₃ | OCH₃ | CH | |
| CH₃ | H | 0 | H | CH₂SOCH₃ | CH₃ | CH₃ | N | |
| CH₃ | H | 0 | H | CH₂SOCH₃ | CH₃ | OCH₃ | N | |
| CH₃ | H | 0 | H | CH₂SOCH₃ | OCH₃ | OCH₃ | N | |
| CH₃ | H | 0 | H | CH₂SOCH₃ | Cl | OCH₃ | CH | |
| CH₃ | H | 0 | H | CH₂SO₂CH₃ | CH₃ | CH₃ | CH | |
| CH₃ | H | 0 | H | CH₂SO₂CH₃ | CH₃ | OCH₃ | CH | |
| CH₃ | H | 0 | H | CH₂SO₂CH₃ | OCH₃ | OCH₃ | CH | |
| CH₃ | H | 0 | H | CH₂SO₂CH₃ | CH₃ | CH₃ | N | |
| CH₃ | H | 0 | H | CH₂SO₂CH₃ | CH₃ | OCH₃ | N | |
| CH₃ | H | 0 | H | CH₂SO₂CH₃ | OCH₃ | OCH₃ | N | |
| CH₃ | H | 0 | H | CH₂SO₂CH₃ | Cl | OCH₃ | CH | |
| CH₃ | H | 0 | H | CH₂CN | CH₃ | CH₃ | CH | |
| CH₃ | H | 0 | H | CH₂CH₂CN | CH₃ | OCH₃ | CH | |
| CH₃ | H | 0 | H | CH(CH₃)CN | OCH₃ | OCH₃ | CH | |
| CH₃ | H | 0 | H | CH₂NO₂ | CH₃ | CH₃ | N | |

TABLE 1-continued

| R | R₁ | n | R₂ | R' | X | Y | Z | m.p. (°C.) |
|---|---|---|---|---|---|---|---|---|
| CH₃ | H | 0 | H | CH₂CH₂NO₂ | CH₃ | OCH₃ | N | |
| CH₃ | H | 0 | H | CH₂CN | OCH₃ | OCH₃ | N | |
| CH₃ | H | 0 | H | CH₂CN | Cl | OCH₃ | CH | |
| CH₃ | H | 0 | H | CH₂OH | CH₃ | CH₃ | CH | |
| CH₃ | H | 0 | H | CH₂OH | CH₃ | OCH₃ | CH | |
| CH₃ | H | 0 | H | CH₂OH | OCH₃ | OCH₃ | CH | |
| CH₃ | H | 0 | H | CH₂OH | CH₃ | CH₃ | N | |
| CH₃ | H | 0 | H | CH₂OH | CH₃ | OCH₃ | N | |
| CH₃ | H | 0 | H | CH₂OH | OCH₃ | OCH₃ | N | |
| CH₃ | H | 0 | H | CH₂OH | Cl | OCH₃ | CH | |
| CH₃ | H | 0 | H | CH(CH₃)OH | CH₃ | CH₃ | CH | |
| CH₃ | H | 0 | H | CH(CH₃)OH | CH₃ | OCH₃ | CH | |
| CH₃ | H | 0 | H | CH(CH₃)OH | OCH₃ | OCH₃ | CH | |
| CH₃ | H | 0 | H | CH(CH₃)OH | CH₃ | CH₃ | N | |
| CH₃ | H | 0 | H | CH(CH₃)OH | CH₃ | OCH₃ | N | |
| CH₃ | H | 0 | H | CH(CH₃)OH | OCH₃ | OCH₃ | N | |
| CH₃ | H | 0 | H | CH(CH₃)OH | Cl | OCH₃ | CH | |
| CH₃ | H | 0 | H | CH₂OSi(CH₃)₃ | CH₃ | CH₃ | CH | |
| CH₃ | H | 0 | H | CH₂OSi(CH₃)₃ | CH₃ | OCH₃ | CH | |
| CH₃ | H | 0 | H | CH₂OSi(CH₃)₃ | OCH₃ | OCH₃ | CH | |
| CH₃ | H | 0 | H | CH₂OSi(CH₃)₃ | CH₃ | CH₃ | N | |
| CH₃ | H | 0 | H | CH₂OSi(CH₃)₃ | CH₃ | OCH₃ | N | |
| CH₃ | H | 0 | H | CH₂OSi(CH₃)₃ | OCH₃ | OCH₃ | N | |
| CH₃ | H | 0 | H | CH₂OSi(CH₃)₃ | Cl | OCH₃ | CH | |
| CH₃ | H | 0 | H | CH₂COCH₃ | CH₃ | CH₃ | CH | |
| CH₃ | H | 0 | H | CH₂COCH₃ | CH₃ | OCH₃ | CH | |
| CH₃ | H | 0 | H | CH₂COCH₃ | OCH₃ | OCH₃ | CH | |
| CH₃ | H | 0 | H | CH₂COCH₃ | CH₃ | CH₃ | N | |
| CH₃ | H | 0 | H | CH₂COCH₃ | CH₃ | OCH₃ | N | |
| CH₃ | H | 0 | H | CH₂CO₂CH₃ | OCH₃ | OCH₃ | N | |
| CH₃ | H | 0 | H | CH₂CO₂CH₃ | Cl | OCH₃ | CH | |
| CH₃ | H | 0 | H | CH₂N(CH₃)₂ | CH₃ | CH₃ | CH | |
| CH₃ | H | 0 | H | CH₂N(CH₃)₂ | CH₃ | OCH₃ | CH | |
| CH₃ | H | 0 | H | CH₂N(CH₃)₂ | OCH₃ | OCH₃ | CH | |
| CH₃ | H | 0 | H | CH₂N(CH₃)₂ | CH₃ | CH₃ | N | |
| CH₃ | H | 0 | H | CH₂N(CH₃)₂ | CH₃ | OCH₃ | N | |
| CH₃ | H | 0 | H | CH₂N(CH₃)₂ | OCH₃ | OCH₃ | N | |
| CH₃ | H | 0 | H | CH₂N(CH₃)₂ | Cl | OCH₃ | CH | |
| CH₃ | H | 0 | H | CH₂CH₂N(CH₃)₂ | CH₃ | CH₃ | CH | |
| CH₃ | H | 0 | H | CH₂CH₂N(CH₃)₂ | CH₃ | OCH₃ | CH | |
| CH₃ | H | 0 | H | CH₂CH₂N(CH₃)₂ | OCH₃ | OCH₃ | CH | |
| CH₃ | H | 0 | H | CH₂CH₂N(CH₃)₂ | CH₃ | CH₃ | N | |
| CH₃ | H | 0 | H | CH₂CH₂N(CH₃)₂ | CH₃ | OCH₃ | N | |
| CH₃ | H | 0 | H | CH₂CH₂N(CH₃)₂ | OCH₃ | OCH₃ | N | |
| CH₃ | H | 0 | H | CH₂CH₂N(CH₃)₂ | Cl | OCH₃ | N | |
| CH₃ | H | 0 | H | CH₂CH=CH₂ | CH₃ | CH₃ | CH | |
| CH₃ | H | 0 | H | CH₂CH=CH₂ | CH₃ | OCH₃ | CH | |
| CH₃ | H | 0 | H | CH₂CH=CH₂ | OCH₃ | OCH₃ | CH | |
| CH₃ | H | 0 | H | CH₂CH=CH₂ | CH₃ | CH₃ | N | |
| CH₃ | H | 0 | H | CH₂CH=CH₂ | CH₃ | OCH₃ | N | |
| CH₃ | H | 0 | H | CH₂CH=CH₂ | OCH₃ | OCH₃ | N | |
| CH₃ | H | 0 | H | CH₂CH=CH₂ | Cl | OCH₃ | CH | |
| CH₃ | H | 0 | H | CH=CH₂ | CH₃ | CH₃ | CH | |
| CH₃ | H | 0 | H | CH=CH₂ | CH₃ | OCH₃ | CH | |
| CH₃ | H | 0 | H | CH=CH₂ | OCH₃ | OCH₃ | CH | |
| CH₃ | H | 0 | H | CH=CH₂ | CH₃ | CH₃ | N | |
| CH₃ | H | 0 | H | CH=CH₂ | CH₃ | OCH₃ | N | |
| CH₃ | H | 0 | H | CH=CH₂ | OCH₃ | OCH₃ | N | |
| CH₃ | H | 0 | H | CH=CH₂ | Cl | OCH₃ | CH | |
| CH₃ | H | 0 | CH₃ | CH₃ | CH₃ | CH₃ | CH | |
| CH₃ | H | 0 | CH₃ | CH₃ | CH₃ | OCH₃ | CH | |
| CH₃ | H | 0 | CH₃ | CH₃ | OCH₃ | OCH₃ | CH | |
| CH₃ | H | 0 | CH₃ | CH₃ | CH₃ | CH₃ | N | |
| CH₃ | H | 0 | CH₃ | CH₃ | CH₃ | OCH₃ | N | |
| CH₃ | H | 0 | CH₃ | CH₃ | OCH₃ | OCH₃ | N | |
| CH₃ | H | 0 | CH₃ | CH₃ | Cl | OCH₃ | CH | |
| CH₃ | H | 0 | CH₃ | CH₂CH₃ | CH₃ | CH₃ | CH | |
| CH₃ | H | 0 | CH₃ | CH₂CH₃ | CH₃ | OCH₃ | CH | |
| CH₃ | H | 0 | CH₃ | CH₂CH₃ | OCH₃ | OCH₃ | CH | |
| CH₃ | H | 0 | CH₃ | CH₂CH₃ | CH₃ | CH₃ | N | |
| CH₃ | H | 0 | CH₃ | CH₂CH₃ | CH₃ | OCH₃ | N | |
| CH₃ | H | 0 | CH₃ | CH₂CH₃ | OCH₃ | OCH₃ | N | |
| CH₃ | H | 0 | CH₃ | CH₂CH₃ | Cl | OCH₃ | CH | |
| CH₃ | H | 0 | CH₃ | CH₂CH₂CH₃ | CH₃ | CH₃ | CH | |
| CH₃ | H | 0 | CH₃ | CH₂CH₂CH₃ | CH₃ | OCH₃ | CH | |
| CH₃ | H | 0 | CH₃ | CH₂CH₂CH₃ | OCH₃ | OCH₃ | CH | |
| CH₃ | H | 0 | CH₃ | CH₂CH₂CH₃ | CH₃ | CH₃ | N | |
| CH₃ | H | 0 | CH₃ | CH₂CH₂CH₃ | CH₃ | OCH₃ | N | |
| CH₃ | H | 0 | CH₃ | CH₂CH₂CH₃ | OCH₃ | OCH₃ | N | |
| CH₃ | H | 0 | CH₃ | CH₂CH₂CH₃ | Cl | OCH₃ | CH | |
| CH₃ | H | 0 | CH₃ | CH₂CH₂CH₂CH₃ | CH₃ | CH₃ | CH | |

TABLE 1-continued

| R | R₁ | n | R₂ | R' | X | Y | Z | m.p. (°C.) |
|---|---|---|---|---|---|---|---|---|
| CH₃ | H | 0 | CH₃ | CH₂CH₂CH₂CH₃ | CH₃ | OCH₃ | CH | |
| CH₃ | H | 0 | CH₃ | CH₂CH₂CH₂CH₃ | OCH₃ | OCH₃ | CH | |
| CH₃ | H | 0 | CH₃ | CH₂CH₂CH₂CH₃ | CH₃ | CH₃ | N | |
| CH₃ | H | 0 | CH₃ | CH₂CH₂CH₂CH₃ | CH₃ | OCH₃ | N | |
| CH₃ | H | 0 | CH₃ | CH₂CH₂CH₂CH₃ | OCH₃ | OCH₃ | N | |
| CH₃ | H | 0 | CH₃ | CH₂CH₂CH₂CH₃ | Cl | OCH₃ | CH | |
| CH₃ | H | 0 | CH₃ | CH₂F | CH₃ | CH₃ | CH | |
| CH₃ | H | 0 | CH₃ | CH₂F | CH₃ | OCH₃ | CH | |
| CH₃ | H | 0 | CH₃ | CH₂F | OCH₃ | OCH₃ | CH | |
| CH₃ | H | 0 | CH₃ | CH₂F | CH₃ | CH₃ | N | |
| CH₃ | H | 0 | CH₃ | CH₂F | CH₃ | OCH₃ | N | |
| CH₃ | H | 0 | CH₃ | CH₂F | OCH₃ | OCH₃ | N | |
| CH₃ | H | 0 | CH₃ | CH₂F | Cl | OCH₃ | CH | |
| CH₃ | H | 0 | CH₃ | CH₂CH₂F | CH₃ | CH₃ | CH | |
| CH₃ | H | 0 | CH₃ | CH₂CH₂F | CH₃ | OCH₃ | CH | |
| CH₃ | H | 0 | CH₃ | CH₂CH₂F | OCH₃ | OCH₃ | CH | |
| CH₃ | H | 0 | CH₃ | CH₂CH₂F | CH₃ | CH₃ | N | |
| CH₃ | H | 0 | CH₃ | CH₂CH₂F | CH₃ | OCH₃ | N | |
| CH₃ | H | 0 | CH₃ | CH₂CH₂F | OCH₃ | OCH₃ | N | |
| CH₃ | H | 0 | CH₃ | CH₂CH₂F | Cl | OCH₃ | CH | |
| CH₃ | H | 0 | CH₃ | CHF₂ | CH₃ | CH₃ | CH | |
| CH₃ | H | 0 | CH₃ | CHF₂ | CH₃ | OCH₃ | CH | |
| CH₃ | H | 0 | CH₃ | CHF₂ | OCH₃ | OCH₃ | CH | |
| CH₃ | H | 0 | CH₃ | CHF₂ | CH₃ | CH₃ | N | |
| CH₃ | H | 0 | CH₃ | CHF₂ | CH₃ | OCH₃ | N | |
| CH₃ | H | 0 | CH₃ | CHF₂ | OCH₃ | OCH₃ | N | |
| CH₃ | H | 0 | CH₃ | CHF₂ | Cl | OCH₃ | CH | |
| CH₃ | H | 0 | CH₃ | CH₂CF₃ | CH₃ | CH₃ | CH | |
| CH₃ | H | 0 | CH₃ | CH₂CF₃ | CH₃ | OCH₃ | CH | |
| CH₃ | H | 0 | CH₃ | CH₂CF₃ | OCH₃ | OCH₃ | CH | |
| CH₃ | H | 0 | CH₃ | CH₂Cl | CH₃ | CH₃ | N | |
| CH₃ | H | 0 | CH₃ | CH₂Cl | CH₃ | OCH₃ | N | |
| CH₃ | H | 0 | CH₃ | CH₂Cl | OCH₃ | OCH₃ | N | |
| CH₃ | H | 0 | CH₃ | CH₂Cl | Cl | OCH₃ | CH | |
| CH₃ | H | 0 | CH₃ | CH₂OCH₃ | CH₃ | CH₃ | CH | |
| CH₃ | H | 0 | CH₃ | CH₂OCH₃ | CH₃ | OCH₃ | CH | |
| CH₃ | H | 0 | CH₃ | CH₂OCH₃ | OCH₃ | OCH₃ | CH | |
| CH₃ | H | 0 | CH₃ | CH₂OCH₃ | CH₃ | CH₃ | N | |
| CH₃ | H | 0 | CH₃ | CH₂OCH₃ | CH₃ | OCH₃ | N | |
| CH₃ | H | 0 | CH₃ | CH₂OCH₃ | OCH₃ | OCH₃ | N | |
| CH₃ | H | 0 | CH₃ | CH₂OCH₃ | Cl | OCH₃ | CH | |
| CH₃ | H | 0 | CH₃ | CH₂OCH₂CH₃ | CH₃ | CH₃ | CH | |
| CH₃ | H | 0 | CH₃ | CH₂OCH₂CH₃ | CH₃ | OCH₃ | CH | |
| CH₃ | H | 0 | CH₃ | CH₂OCH₂CH₃ | OCH₃ | OCH₃ | CH | |
| CH₃ | H | 0 | CH₃ | CH₂OCH₂CH₃ | CH₃ | CH₃ | N | |
| CH₃ | H | 0 | CH₃ | CH₂CH₂OCH₃ | CH₃ | OCH₃ | N | |
| CH₃ | H | 0 | CH₃ | CH₂CH₂OCH₃ | OCH₃ | OCH₃ | N | |
| CH₃ | H | 0 | CH₃ | CH₂CH₂OCH₃ | Cl | OCH₃ | CH | |
| CH₃ | H | 0 | CH₃ | CH₂CH₂OCH₃ | CH₃ | CH₃ | CH | |
| CH₃ | H | 0 | CH₃ | CH₂CH₂OCH₃ | CH₃ | OCH₃ | CH | |
| CH₃ | H | 0 | CH₃ | CH₂CH₂OCH₃ | OCH₃ | OCH₃ | CH | |
| CH₃ | H | 0 | CH₃ | CH₂CH₂OCH₃ | CH₃ | CH₃ | N | |
| CH₃ | H | 0 | CH₃ | CH(OCH₃)₂ | CH₃ | OCH₃ | N | |
| CH₃ | H | 0 | CH₃ | CH(OCH₃)₂ | OCH₃ | OCH₃ | N | |
| CH₃ | H | 0 | CH₃ | CH(OCH₃)₂ | Cl | OCH₃ | CH | |
| CH₃ | H | 0 | CH₃ | CH₂SCH₃ | CH₃ | CH₃ | CH | |
| CH₃ | H | 0 | CH₃ | CH₂SCH₃ | CH₃ | OCH₃ | CH | |
| CH₃ | H | 0 | CH₃ | CH₂SCH₃ | OCH₃ | OCH₃ | CH | |
| CH₃ | H | 0 | CH₃ | CH₂SCH₃ | CH₃ | CH₃ | N | |
| CH₃ | H | 0 | CH₃ | CH₂SCH₃ | CH₃ | OCH₃ | N | |
| CH₃ | H | 0 | CH₃ | CH₂SCH₃ | OCH₃ | OCH₃ | N | |
| CH₃ | H | 0 | CH₃ | CH₂SCH₃ | Cl | OCH₃ | CH | |
| CH₃ | H | 0 | Cl | CH₃ | CH₃ | CH₃ | CH | |
| CH₃ | H | 0 | Cl | CH₃ | CH₃ | OCH₃ | CH | |
| CH₃ | H | 0 | Cl | CH₃ | OCH₃ | OCH₃ | CH | |
| CH₃ | H | 0 | Cl | CH₃ | CH₃ | CH₃ | N | |
| CH₃ | H | 0 | Cl | CH₃ | CH₃ | OCH₃ | N | |
| CH₃ | H | 0 | Cl | CH₃ | OCH₃ | OCH₃ | N | |
| CH₃ | H | 0 | Cl | CH₃ | Cl | OCH₃ | CH | |
| CH₃ | H | 0 | Cl | CH₂CH₃ | CH₃ | CH₃ | CH | |
| CH₃ | H | 0 | Cl | CH₂CH₃ | CH₃ | OCH₃ | CH | |
| CH₃ | H | 0 | Cl | CH₂CH₃ | OCH₃ | OCH₃ | CH | |
| CH₃ | H | 0 | Cl | CH₂CH₃ | CH₃ | CH₃ | N | |
| CH₃ | H | 0 | Cl | CH₂CH₃ | CH₃ | OCH₃ | N | |
| CH₃ | H | 0 | Cl | CH₂CH₃ | OCH₃ | OCH₃ | N | |
| CH₃ | H | 0 | Cl | CH₂CH₃ | Cl | OCH₃ | CH | |
| CH₃ | H | 0 | Cl | CH₂CH₂CH₃ | CH₃ | CH₃ | CH | |
| CH₃ | H | 0 | Cl | CH₂CH₂CH₃ | CH₃ | OCH₃ | CH | |
| CH₃ | H | 0 | Cl | CH₂CH₂CH₃ | OCH₃ | OCH₃ | CH | |
| CH₃ | H | 0 | Cl | CH₂CH₂CH₃ | CH₃ | CH₃ | N | |
| CH₃ | H | 0 | Cl | CH₂CH₂CH₃ | CH₃ | OCH₃ | N | |

TABLE 1-continued

| R | R₁ | n | R₂ | R' | X | Y | Z | m.p. (°C.) |
|---|----|---|----|----|----|----|----|----|
| CH₃ | H | 0 | Cl | CH₂CH₂CH₃ | OCH₃ | OCH₃ | N | |
| CH₃ | H | 0 | Cl | CH₂CH₂CH₃ | Cl | OCH₃ | CH | |
| CH₃ | H | 0 | Cl | CH₂CH₂CH₂CH₃ | CH₃ | CH₃ | CH | |
| CH₃ | H | 0 | Cl | CH₂CH₂CH₂CH₃ | CH₃ | OCH₃ | CH | |
| CH₃ | H | 0 | Cl | CH₂CH₂CH₂CH₃ | OCH₃ | OCH₃ | CH | |
| CH₃ | H | 0 | Cl | CH₂CH₂CH₂CH₃ | CH₃ | CH₃ | N | |
| CH₃ | H | 0 | Cl | CH₂CH₂CH₂CH₃ | CH₃ | OCH₃ | N | |
| CH₃ | H | 0 | Cl | CH₂CH₂CH₂CH₃ | OCH₃ | OCH₃ | N | |
| CH₃ | H | 0 | Cl | CH₂CH₂CH₂CH₃ | Cl | OCH₃ | CH | |
| CH₃ | H | 0 | Cl | CH₂OCH₃ | CH₃ | CH₃ | CH | |
| CH₃ | H | 0 | Cl | CH₂OCH₃ | CH₃ | OCH₃ | CH | |
| CH₃ | H | 0 | Cl | CH₂OCH₃ | OCH₃ | OCH₃ | CH | |
| CH₃ | H | 0 | Cl | CH₂OCH₃ | CH₃ | CH₃ | N | |
| CH₃ | H | 0 | Cl | CH₂OCH₃ | CH₃ | OCH₃ | N | |
| CH₃ | H | 0 | Cl | CH₂OCH₃ | OCH₃ | OCH₃ | N | |
| CH₃ | H | 0 | Cl | CH₂OCH₃ | Cl | OCH₃ | CH | |
| CH₃ | H | 0 | Cl | CH₂OCH₂CH₃ | CH₃ | CH₃ | CH | |
| CH₃ | H | 0 | Cl | CH₂OCH₂CH₃ | CH₃ | OCH₃ | CH | |
| CH₃ | H | 0 | Cl | CH₂OCH₂CH₃ | OCH₃ | OCH₃ | CH | |
| CH₃ | H | 0 | Cl | CH₂OCH₂CH₃ | CH₃ | CH₃ | N | |
| CH₃ | H | 0 | Cl | CH₂CH₂OCH₃ | CH₃ | OCH₃ | N | |
| CH₃ | H | 0 | Cl | CH₂CH₂OCH₃ | OCH₃ | OCH₃ | N | |
| CH₃ | H | 0 | Cl | CH₂CH₂OCH₃ | Cl | OCH₃ | CH | |
| CH₃ | H | 0 | Cl | CH₂CH₂OCH₃ | CH₃ | CH₃ | CH | |
| CH₃ | H | 0 | Cl | CH₂CH₂OCH₃ | CH₃ | OCH₃ | CH | |
| CH₃ | H | 0 | Cl | CH₂CH₂OCH₃ | OCH₃ | OCH₃ | CH | |
| CH₃ | H | 0 | Cl | CH₂CH₂OCH₃ | CH₃ | CH₃ | N | |
| CH₃ | H | 0 | Cl | CH(OCH₃)₂ | CH₃ | OCH₃ | N | |
| CH₃ | H | 0 | Cl | CH(OCH₃)₂ | OCH₃ | OCH₃ | N | |
| CH₃ | H | 0 | Cl | CH(OCH₃)₂ | Cl | OCH₃ | CH | |
| CH₃ | H | 0 | Cl | CH₂SCH₃ | CH₃ | CH₃ | CH | |
| CH₃ | H | 0 | Cl | CH₂SCH₃ | CH₃ | OCH₃ | CH | |
| CH₃ | H | 0 | Cl | CH₂SCH₃ | OCH₃ | OCH₃ | CH | |
| CH₃ | H | 0 | Cl | CH₂SCH₃ | CH₃ | CH₃ | N | |
| CH₃ | H | 0 | Cl | CH₂SCH₃ | CH₃ | OCH₃ | N | |
| CH₃ | H | 0 | Cl | CH₂SCH₃ | OCH₃ | OCH₃ | N | |
| CH₃ | H | 0 | Cl | CH₂SCH₃ | Cl | OCH₃ | CH | |
| CH₃ | H | 0 | Cl | CH₂OCH₂F | CH₃ | CH₃ | CH | |
| CH₃ | H | 0 | Cl | CH₂OCH₂F | CH₃ | OCH₃ | CH | |
| CH₃ | H | 0 | Cl | CH₂OCH₂F | OCH₃ | OCH₃ | CH | |
| CH₃ | H | 0 | Cl | CH₂OCH₂F | CH₃ | CH₃ | N | |
| CH₃ | H | 0 | Cl | CH₂OCH₂F | CH₃ | OCH₃ | N | |
| CH₃ | H | 0 | Cl | CH₂OCH₂F | OCH₃ | OCH₃ | N | |
| CH₃ | H | 0 | Cl | CH₂OCH₂F | Cl | OCH₃ | CH | |
| CH₃ | H | 0 | Cl | CH₂SOCH₃ | CH₃ | CH₃ | CH | |
| CH₃ | H | 0 | Cl | CH₂SOCH₃ | CH₃ | OCH₃ | CH | |
| CH₃ | H | 0 | Cl | CH₂SOCH₃ | OCH₃ | OCH₃ | CH | |
| CH₃ | H | 0 | Cl | CH₂SOCH₃ | CH₃ | CH₃ | N | |
| CH₃ | H | 0 | Cl | CH₂SOCH₃ | CH₃ | OCH₃ | N | |
| CH₃ | H | 0 | Cl | CH₂SOCH₃ | OCH₃ | OCH₃ | N | |
| CH₃ | H | 0 | Cl | CH₂SOCH₃ | Cl | OCH₃ | CH | |
| CH₃ | H | 0 | Cl | CH₂SO₂CH₃ | CH₃ | CH₃ | CH | |
| CH₃ | H | 0 | Cl | CH₂SO₂CH₃ | CH₃ | OCH₃ | CH | |
| CH₃ | H | 0 | Cl | CH₂SO₂CH₃ | OCH₃ | OCH₃ | CH | |
| CH₃ | H | 0 | Cl | CH₂SO₂CH₃ | CH₃ | CH₃ | N | |
| CH₃ | H | 0 | Cl | CH₂SO₂CH₃ | CH₃ | OCH₃ | N | |
| CH₃ | H | 0 | Cl | CH₂SO₂CH₃ | OCH₃ | OCH₃ | N | |
| CH₃ | H | 0 | Cl | CH₂SO₂CH₃ | Cl | OCH₃ | CH | |
| CH₃ | H | 0 | Cl | CH₂CN | CH₃ | CH₃ | CH | |
| CH₃ | H | 0 | Cl | CH₂CH₂CN | CH₃ | OCH₃ | CH | |
| CH₃ | H | 0 | Cl | CH(CH₃)CN | OCH₃ | OCH₃ | CH | |
| CH₃ | H | 0 | Cl | CH₂NO₂ | CH₃ | CH₃ | N | |
| CH₃ | H | 0 | Cl | CH₂CH₂NO₂ | CH₃ | OCH₃ | N | |
| CH₃ | H | 0 | Cl | CH₂CN | OCH₃ | OCH₃ | N | |
| CH₃ | H | 0 | Cl | CH₂CN | Cl | OCH₃ | CH | |
| CH₃ | H | 0 | Br | CH₃ | CH₃ | CH₃ | CH | |
| CH₃ | H | 0 | Br | CH₃ | CH₃ | OCH₃ | CH | |
| CH₃ | H | 0 | Br | CH₃ | OCH₃ | OCH₃ | CH | |
| CH₃ | H | 0 | Br | CH₃ | CH₃ | CH₃ | N | |
| CH₃ | H | 0 | Br | CH₃ | CH₃ | OCH₃ | N | |
| CH₃ | H | 0 | Br | CH₃ | OCH₃ | OCH₃ | N | |
| CH₃ | H | 0 | Br | CH₃ | Cl | OCH₃ | CH | |
| CH₃ | H | 0 | Br | CH₂CH₃ | CH₃ | CH₃ | CH | |
| CH₃ | H | 0 | Br | CH₂CH₃ | CH₃ | OCH₃ | CH | |
| CH₃ | H | 0 | Br | CH₂CH₃ | OCH₃ | OCH₃ | CH | |
| CH₃ | H | 0 | Br | CH₂CH₃ | CH₃ | CH₃ | N | |
| CH₃ | H | 0 | Br | CH₂CH₃ | CH₃ | OCH₃ | N | |
| CH₃ | H | 0 | Br | CH₂CH₃ | OCH₃ | OCH₃ | N | |
| CH₃ | H | 0 | Br | CH₂CH₃ | Cl | OCH₃ | CH | |
| CH₃ | H | 0 | Br | CH₂CH₂CH₃ | CH₃ | CH₃ | CH | |
| CH₃ | H | 0 | Br | CH₂CH₂CH₃ | CH₃ | OCH₃ | CH | |

TABLE 1-continued

| R | R₁ | n | R₂ | R' | X | Y | Z |
|---|---|---|---|---|---|---|---|
| CH₃ | H | 0 | Br | CH₂CH₂CH₃ | OCH₃ | OCH₃ | CH |
| CH₃ | H | 0 | Br | CH₂CH₂CH₃ | CH₃ | CH₃ | N |
| CH₃ | H | 0 | Br | CH₂CH₂CH₃ | CH₃ | OCH₃ | N |
| CH₃ | H | 0 | Br | CH₂CH₂CH₃ | OCH₃ | OCH₃ | N |
| CH₃ | H | 0 | Br | CH₂CH₂CH₃ | Cl | OCH₃ | CH |
| CH₃ | H | 0 | Br | CH₂CH₂CH₂CH₃ | CH₃ | CH₃ | CH |
| CH₃ | H | 0 | Br | CH₂CH₂CH₂CH₃ | CH₃ | OCH₃ | CH |
| CH₃ | H | 0 | Br | CH₂CH₂CH₂CH₃ | OCH₃ | OCH₃ | CH |
| CH₃ | H | 0 | Br | CH₂CH₂CH₂CH₃ | CH₃ | CH₃ | N |
| CH₃ | H | 0 | Br | CH₂CH₂CH₂CH₃ | CH₃ | OCH₃ | N |
| CH₃ | H | 0 | Br | CH₂CH₂CH₂CH₃ | OCH₃ | OCH₃ | N |
| CH₃ | H | 0 | Br | CH₂CH₂CH₂CH₃ | Cl | OCH₃ | CH |
| CH₃ | H | 0 | CH₂F | CH₃ | CH₃ | CH₃ | CH |
| CH₃ | H | 0 | CH₂F | CH₃ | CH₃ | OCH₃ | CH |
| CH₃ | H | 0 | CH₂F | CH₃ | OCH₃ | OCH₃ | CH |
| CH₃ | H | 0 | CH₂F | CH₃ | CH₃ | CH₃ | N |
| CH₃ | H | 0 | CH₂F | CH₃ | CH₃ | OCH₃ | N |
| CH₃ | H | 0 | CH₂F | CH₃ | OCH₃ | OCH₃ | N |
| CH₃ | H | 0 | CH₂F | CH₃ | Cl | OCH₃ | CH |
| CH₃ | H | 0 | CH₂F | CH₂CH₃ | CH₃ | CH₃ | CH |
| CH₃ | H | 0 | CH₂F | CH₂CH₃ | CH₃ | OCH₃ | CH |
| CH₃ | H | 0 | CH₂F | CH₂CH₃ | OCH₃ | OCH₃ | CH |
| CH₃ | H | 0 | CH₂F | CH₂CH₃ | CH₃ | CH₃ | N |
| CH₃ | H | 0 | CH₂F | CH₂CH₃ | CH₃ | OCH₃ | N |
| CH₃ | H | 0 | CH₂F | CH₂CH₃ | OCH₃ | OCH₃ | N |
| CH₃ | H | 0 | CH₂F | CH₂CH₃ | Cl | OCH₃ | CH |
| CH₃ | H | 0 | CH₂F | CH₂CH₂CH₃ | CH₃ | CH₃ | CH |
| CH₃ | H | 0 | CH₂F | CH₂CH₂CH₃ | CH₃ | OCH₃ | CH |
| CH₃ | H | 0 | CH₂F | CH₂CH₂CH₃ | OCH₃ | OCH₃ | CH |
| CH₃ | H | 0 | CH₂F | CH₂CH₂CH₃ | CH₃ | CH₃ | N |
| CH₃ | H | 0 | CH₂F | CH₂CH₂CH₃ | CH₃ | OCH₃ | N |
| CH₃ | H | 0 | CH₂F | CH₂CH₂CH₃ | OCH₃ | OCH₃ | N |
| CH₃ | H | 0 | CH₂F | CH₂CH₂CH₃ | Cl | OCH₃ | CH |
| CH₃ | H | 0 | CH₂F | CH₂CH₂CH₂CH₃ | CH₃ | CH₃ | CH |
| CH₃ | H | 0 | CH₂F | CH₂CH₂CH₂CH₃ | CH₃ | OCH₃ | CH |
| CH₃ | H | 0 | CH₂F | CH₂CH₂CH₂CH₃ | OCH₃ | OCH₃ | CH |
| CH₃ | H | 0 | CH₂F | CH₂CH₂CH₂CH₃ | CH₃ | CH₃ | N |
| CH₃ | H | 0 | CH₂F | CH₂CH₂CH₂CH₃ | CH₃ | OCH₃ | N |
| CH₃ | H | 0 | CH₂F | CH₂CH₂CH₂CH₃ | OCH₃ | OCH₃ | N |
| CH₃ | H | 0 | CH₂F | CH₂CH₂CH₂CH₃ | Cl | OCH₃ | CH |
| CH₃ | H | 0 | CF₃ | CH₃ | CH₃ | CH₃ | CH |
| CH₃ | H | 0 | CF₃ | CH₃ | CH₃ | OCH₃ | CH |
| CH₃ | H | 0 | CF₃ | CH₃ | OCH₃ | OCH₃ | CH |
| CH₃ | H | 0 | CF₃ | CH₃ | CH₃ | CH₃ | N |
| CH₃ | H | 0 | CF₃ | CH₃ | CH₃ | OCH₃ | N |
| CH₃ | H | 0 | CF₃ | CH₃ | OCH₃ | OCH₃ | N |
| CH₃ | H | 0 | CF₃ | CH₃ | Cl | OCH₃ | CH |
| CH₃ | H | 0 | CF₃ | CH₂CH₃ | CH₃ | CH₃ | CH |
| CH₃ | H | 0 | CF₃ | CH₂CH₃ | CH₃ | OCH₃ | CH |
| CH₃ | H | 0 | CF₃ | CH₂CH₃ | OCH₃ | OCH₃ | CH |
| CH₃ | H | 0 | CF₃ | CH₂CH₃ | CH₃ | CH₃ | N |
| CH₃ | H | 0 | CF₃ | CH₂CH₃ | CH₃ | OCH₃ | N |
| CH₃ | H | 0 | CF₃ | CH₂CH₃ | OCH₃ | OCH₃ | N |
| CH₃ | H | 0 | CF₃ | CH₂CH₃ | Cl | OCH₃ | CH |
| CH₃ | H | 0 | CF₃ | CH₂CH₂CH₃ | CH₃ | CH₃ | CH |
| CH₃ | H | 0 | CF₃ | CH₂CH₂CH₃ | CH₃ | OCH₃ | CH |
| CH₃ | H | 0 | CF₃ | CH₂CH₂CH₃ | OCH₃ | OCH₃ | CH |
| CH₃ | H | 0 | CF₃ | CH₂CH₂CH₃ | CH₃ | CH₃ | N |
| CH₃ | H | 0 | CF₃ | CH₂CH₂CH₃ | CH₃ | OCH₃ | N |
| CH₃ | H | 0 | CF₃ | CH₂CH₂CH₃ | OCH₃ | OCH₃ | N |
| CH₃ | H | 0 | CF₃ | CH₂CH₂CH₃ | Cl | OCH₃ | CH |
| CH₃ | H | 0 | CF₃ | CH₂CH₂CH₂CH₃ | CH₃ | CH₃ | CH |
| CH₃ | H | 0 | CF₃ | CH₂CH₂CH₂CH₃ | CH₃ | OCH₃ | CH |
| CH₃ | H | 0 | CF₃ | CH₂CH₂CH₂CH₃ | OCH₃ | OCH₃ | CH |
| CH₃ | H | 0 | CF₃ | CH₂CH₂CH₂CH₃ | CH₃ | CH₃ | N |
| CH₃ | H | 0 | CF₃ | CH₂CH₂CH₂CH₃ | CH₃ | OCH₃ | N |
| CH₃ | H | 0 | CF₃ | CH₂CH₂CH₂CH₃ | OCH₃ | OCH₃ | N |
| CH₃ | H | 0 | CF₃ | CH₂CH₂CH₂CH₃ | Cl | OCH₃ | CH |
| CH₃ | H | 0 | OCH₃ | CH₃ | CH₃ | CH₃ | CH |
| CH₃ | H | 0 | OCH₃ | CH₃ | CH₃ | OCH₃ | CH |
| CH₃ | H | 0 | OCH₃ | CH₃ | OCH₃ | OCH₃ | CH |
| CH₃ | H | 0 | OCH₃ | CH₃ | CH₃ | CH₃ | N |
| CH₃ | H | 0 | OCH₃ | CH₃ | CH₃ | OCH₃ | N |
| CH₃ | H | 0 | OCH₃ | CH₃ | OCH₃ | OCH₃ | N |
| CH₃ | H | 0 | OCH₃ | CH₃ | Cl | OCH₃ | CH |
| CH₃ | H | 0 | OCH₃ | CH₂CH₃ | CH₃ | CH₃ | CH |
| CH₃ | H | 0 | OCH₃ | CH₂CH₃ | CH₃ | OCH₃ | CH |
| CH₃ | H | 0 | OCH₃ | CH₂CH₃ | OCH₃ | OCH₃ | CH |
| CH₃ | H | 0 | OCH₃ | CH₂CH₃ | CH₃ | CH₃ | N |
| CH₃ | H | 0 | OCH₃ | CH₂CH₃ | CH₃ | OCH₃ | N |
| CH₃ | H | 0 | OCH₃ | CH₂CH₃ | OCH₃ | OCH₃ | N |

TABLE 1-continued

| R | R₁ | n | R₂ | R' | X | Y | Z | m.p. (°C.) |
|---|---|---|---|---|---|---|---|---|
| CH₃ | H | 0 | OCH₃ | CH₂CH₃ | Cl | OCH₃ | CH | |
| CH₃ | H | 0 | OCH₃ | CH₂CH₂CH₃ | CH₃ | CH₃ | CH | |
| CH₃ | H | 0 | OCH₃ | CH₂CH₂CH₃ | CH₃ | OCH₃ | CH | |
| CH₃ | H | 0 | OCH₃ | CH₂CH₂CH₃ | OCH₃ | OCH₃ | CH | |
| CH₃ | H | 0 | OCH₃ | CH₂CH₂CH₃ | CH₃ | CH₃ | N | |
| CH₃ | H | 0 | OCH₃ | CH₂CH₂CH₃ | CH₃ | OCH₃ | N | |
| CH₃ | H | 0 | OCH₃ | CH₂CH₂CH₃ | OCH₃ | OCH₃ | N | |
| CH₃ | H | 0 | OCH₃ | CH₂CH₂CH₃ | Cl | OCH₃ | CH | |
| CH₃ | H | 0 | OCH₃ | CH₂CH₂CH₂CH₃ | CH₃ | CH₃ | CH | |
| CH₃ | H | 0 | OCH₃ | CH₂CH₂CH₂CH₃ | CH₃ | OCH₃ | CH | |
| CH₃ | H | 0 | OCH₃ | CH₂CH₂CH₂CH₃ | OCH₃ | OCH₃ | CH | |
| CH₃ | H | 0 | OCH₃ | CH₂CH₂CH₂CH₃ | CH₃ | CH₃ | N | |
| CH₃ | H | 0 | OCH₃ | CH₂CH₂CH₂CH₃ | CH₃ | OCH₃ | N | |
| CH₃ | H | 0 | OCH₃ | CH₂CH₂CH₂CH₃ | OCH₃ | OCH₃ | N | |
| CH₃ | H | 0 | OCH₃ | CH₂CH₂CH₂CH₃ | Cl | OCH₃ | CH | |
| CH₃ | H | 0 | SCH₃ | CH₃ | CH₃ | CH₃ | CH | |
| CH₃ | H | 0 | SCH₃ | CH₃ | CH₃ | OCH₃ | CH | |
| CH₃ | H | 0 | SCH₃ | CH₃ | OCH₃ | OCH₃ | CH | |
| CH₃ | H | 0 | SCH₃ | CH₃ | CH₃ | CH₃ | N | |
| CH₃ | H | 0 | SCH₃ | CH₃ | CH₃ | OCH₃ | N | |
| CH₃ | H | 0 | SCH₃ | CH₃ | OCH₃ | OCH₃ | N | |
| CH₃ | H | 0 | SCH₃ | CH₃ | Cl | OCH₃ | CH | |
| CH₃ | H | 0 | SCH₃ | CH₂CH₃ | CH₃ | CH₃ | CH | |
| CH₃ | H | 0 | SCH₃ | CH₂CH₃ | CH₃ | OCH₃ | CH | |
| CH₃ | H | 0 | SCH₃ | CH₂CH₃ | OCH₃ | OCH₃ | CH | |
| CH₃ | H | 0 | SCH₃ | CH₂CH₃ | CH₃ | CH₃ | N | |
| CH₃ | H | 0 | SCH₃ | CH₂CH₃ | CH₃ | OCH₃ | N | |
| CH₃ | H | 0 | SCH₃ | CH₂CH₃ | OCH₃ | OCH₃ | N | |
| CH₃ | H | 0 | SCH₃ | CH₂CH₃ | Cl | OCH₃ | CH | |
| CH₃ | H | 0 | SCH₃ | CH₂CH₂CH₃ | CH₃ | CH₃ | CH | |
| CH₃ | H | 0 | SCH₃ | CH₂CH₂CH₃ | CH₃ | OCH₃ | CH | |
| CH₃ | H | 0 | SCH₃ | CH₂CH₂CH₃ | OCH₃ | OCH₃ | CH | |
| CH₃ | H | 0 | SCH₃ | CH₂CH₂CH₃ | CH₃ | CH₃ | N | |
| CH₃ | H | 0 | SCH₃ | CH₂CH₂CH₃ | CH₃ | OCH₃ | N | |
| CH₃ | H | 0 | SCH₃ | CH₂CH₂CH₃ | OCH₃ | OCH₃ | N | |
| CH₃ | H | 0 | SCH₃ | CH₂CH₂CH₃ | Cl | OCH₃ | CH | |
| CH₃ | H | 0 | SCH₃ | CH₂CH₂CH₂CH₃ | CH₃ | CH₃ | CH | |
| CH₃ | H | 0 | SCH₃ | CH₂CH₂CH₂CH₃ | CH₃ | OCH₃ | CH | |
| CH₃ | H | 0 | SCH₃ | CH₂CH₂CH₂CH₃ | OCH₃ | OCH₃ | CH | |
| CH₃ | H | 0 | SCH₃ | CH₂CH₂CH₂CH₃ | CH₃ | CH₃ | N | |
| CH₃ | H | 0 | SCH₃ | CH₂CH₂CH₂CH₃ | CH₃ | OCH₃ | N | |
| CH₃ | H | 0 | SCH₃ | CH₂CH₂CH₂CH₃ | OCH₃ | OCH₃ | N | |
| CH₃ | H | 0 | SCH₃ | CH₂CH₂CH₂CH₃ | Cl | OCH₃ | CH | |
| CH₃ | H | 0 | CN | CH₃ | CH₃ | CH₃ | CH | |
| CH₃ | H | 0 | CN | CH₃ | CH₃ | OCH₃ | CH | |
| CH₃ | H | 0 | CN | CH₃ | OCH₃ | OCH₃ | CH | |
| CH₃ | H | 0 | CN | CH₃ | CH₃ | CH₃ | N | |
| CH₃ | H | 0 | CN | CH₃ | CH₃ | OCH₃ | N | |
| CH₃ | H | 0 | CN | CH₃ | OCH₃ | OCH₃ | N | |
| CH₃ | H | 0 | CN | CH₃ | Cl | OCH₃ | CH | |
| CH₃ | H | 0 | CN | CH₂CH₃ | CH₃ | CH₃ | CH | |
| CH₃ | H | 0 | CN | CH₂CH₃ | CH₃ | OCH₃ | CH | |
| CH₃ | H | 0 | CN | CH₂CH₃ | OCH₃ | OCH₃ | CH | |
| CH₃ | H | 0 | CN | CH₂CH₃ | CH₃ | CH₃ | N | |
| CH₃ | H | 0 | CN | CH₂CH₃ | CH₃ | OCH₃ | N | |
| CH₃ | H | 0 | CN | CH₂CH₃ | OCH₃ | OCH₃ | N | |
| CH₃ | H | 0 | CN | CH₂CH₃ | Cl | OCH₃ | CH | |
| CH₃ | H | 0 | CN | CH₂CH₂CH₃ | CH₃ | CH₃ | CH | |
| CH₃ | H | 0 | CN | CH₂CH₂CH₃ | CH₃ | OCH₃ | CH | |
| CH₃ | H | 0 | CN | CH₂CH₂CH₃ | OCH₃ | OCH₃ | CH | |
| CH₃ | H | 0 | CN | CH₂CH₂CH₃ | CH₃ | CH₃ | N | |
| CH₃ | H | 0 | CN | CH₂CH₂CH₃ | CH₃ | OCH₃ | N | |
| CH₃ | H | 0 | CN | CH₂CH₂CH₃ | OCH₃ | OCH₃ | N | |
| CH₃ | H | 0 | CN | CH₂CH₂CH₃ | Cl | OCH₃ | CH | |
| CH₃ | H | 0 | CN | CH₂CH₂CH₂CH₃ | CH₃ | CH₃ | CH | |
| CH₃ | H | 0 | CN | CH₂CH₂CH₂CH₃ | CH₃ | OCH₃ | CH | |
| CH₃ | H | 0 | CN | CH₂CH₂CH₂CH₃ | OCH₃ | OCH₃ | CH | |
| CH₃ | H | 0 | CN | CH₂CH₂CH₂CH₃ | CH₃ | CH₃ | N | |
| CH₃ | H | 0 | CN | CH₂CH₂CH₂CH₃ | CH₃ | OCH₃ | N | |
| CH₃ | H | 0 | CN | CH₂CH₂CH₂CH₃ | OCH₃ | OCH₃ | N | |
| CH₃ | H | 0 | CN | CH₂CH₂CH₂CH₃ | Cl | OCH₃ | CH | |
| CH₃ | H | 0 | CO₂CH₃ | CH₃ | CH₃ | CH₃ | CH | |
| CH₃ | H | 0 | CO₂CH₃ | CH₃ | CH₃ | OCH₃ | CH | |
| CH₃ | H | 0 | CO₂CH₃ | CH₃ | OCH₃ | OCH₃ | CH | |
| CH₃ | H | 0 | CO₂CH₃ | CH₃ | CH₃ | CH₃ | N | |
| CH₃ | H | 0 | CO₂CH₃ | CH₃ | CH₃ | OCH₃ | N | |
| CH₃ | H | 0 | CO₂CH₃ | CH₃ | OCH₃ | OCH₃ | N | |
| CH₃ | H | 0 | CO₂CH₃ | CH₃ | Cl | OCH₃ | CH | |
| CH₃ | H | 0 | CO₂CH₃ | CH₂CH₃ | CH₃ | CH₃ | CH | |
| CH₃ | H | 0 | CO₂CH₃ | CH₂CH₃ | CH₃ | OCH₃ | CH | |
| CH₃ | H | 0 | CO₂CH₃ | CH₂CH₃ | OCH₃ | OCH₃ | CH | |

TABLE 1-continued

| R | $R_1$ | n | $R_2$ | R' | X | Y | Z | m.p. (°C.) |
|---|---|---|---|---|---|---|---|---|
| $CH_3$ | H | 0 | $CO_2CH_3$ | $CH_2CH_3$ | $CH_3$ | $CH_3$ | N | |
| $CH_3$ | H | 0 | $CO_2CH_3$ | $CH_2CH_3$ | $CH_3$ | $OCH_3$ | N | |
| $CH_3$ | H | 0 | $CO_2CH_3$ | $CH_2CH_3$ | $OCH_3$ | $OCH_3$ | N | |
| $CH_3$ | H | 0 | $CO_2CH_3$ | $CH_2CH_3$ | Cl | $OCH_3$ | CH | |
| $CH_3$ | H | 0 | $CO_2CH_3$ | $CH_2CH_2CH_3$ | $CH_3$ | $CH_3$ | CH | |
| $CH_3$ | H | 0 | $CO_2CH_3$ | $CH_2CH_2CH_3$ | $CH_3$ | $OCH_3$ | CH | |
| $CH_3$ | H | 0 | $CO_2CH_3$ | $CH_2CH_2CH_3$ | $OCH_3$ | $OCH_3$ | CH | |
| $CH_3$ | H | 0 | $CO_2CH_3$ | $CH_2CH_2CH_3$ | $CH_3$ | $CH_3$ | N | |
| $CH_3$ | H | 0 | $CO_2CH_3$ | $CH_2CH_2CH_3$ | $CH_3$ | $OCH_3$ | N | |
| $CH_3$ | H | 0 | $CO_2CH_3$ | $CH_2CH_2CH_3$ | $OCH_3$ | $OCH_3$ | N | |
| $CH_3$ | H | 0 | $CO_2CH_3$ | $CH_2CH_2CH_3$ | Cl | $OCH_3$ | CH | |
| $CH_3$ | H | 0 | $CO_2CH_3$ | $CH_2CH_2CH_2CH_3$ | $CH_3$ | $CH_3$ | CH | |
| $CH_3$ | H | 0 | $CO_2CH_3$ | $CH_2CH_2CH_2CH_3$ | $CH_3$ | $OCH_3$ | CH | |
| $CH_3$ | H | 0 | $CO_2CH_3$ | $CH_2CH_2CH_2CH_3$ | $OCH_3$ | $OCH_3$ | CH | |
| $CH_3$ | H | 0 | $CO_2CH_3$ | $CH_2CH_2CH_2CH_3$ | $CH_3$ | $CH_3$ | N | |
| $CH_3$ | H | 0 | $CO_2CH_3$ | $CH_2CH_2CH_2CH_3$ | $CH_3$ | $OCH_3$ | N | |
| $CH_3$ | H | 0 | $CO_2CH_3$ | $CH_2CH_2CH_2CH_3$ | $OCH_3$ | $OCH_3$ | N | |
| $CH_3$ | H | 0 | $CO_2CH_3$ | $CH_2CH_2CH_2CH_3$ | Cl | $OCH_3$ | CH | |
| H | H | 0 | H | $CH_3$ | $CH_3$ | $CH_3$ | CH | |
| H | H | 0 | H | $CH_3$ | $CH_3$ | $OCH_3$ | CH | |
| H | H | 0 | H | $CH_3$ | $OCH_3$ | $OCH_3$ | CH | |
| H | H | 0 | H | $CH_3$ | $CH_3$ | $CH_3$ | N | |
| H | H | 0 | H | $CH_3$ | $CH_3$ | $OCH_3$ | N | |
| H | H | 0 | H | $CH_3$ | $OCH_3$ | $OCH_3$ | N | |
| H | H | 0 | H | $CH_3$ | Cl | $OCH_3$ | CH | |
| H | H | 0 | H | $CH_2CH_3$ | $CH_3$ | $CH_3$ | CH | |
| H | H | 0 | H | $CH_2CH_3$ | $CH_3$ | $OCH_3$ | CH | |
| H | H | 0 | H | $CH_2CH_3$ | $OCH_3$ | $OCH_3$ | CH | |
| H | H | 0 | H | $CH_2CH_3$ | $CH_3$ | $CH_3$ | N | |
| H | H | 0 | H | $CH_2CH_3$ | $CH_3$ | $OCH_3$ | N | |
| H | H | 0 | H | $CH_2CH_3$ | $OCH_3$ | $OCH_3$ | N | |
| H | H | 0 | H | $CH_2CH_3$ | Cl | $OCH_3$ | CH | |
| H | H | 0 | H | $CH_2CH_2CH_3$ | $CH_3$ | $CH_3$ | CH | |
| H | H | 0 | H | $CH_2CH_2CH_3$ | $CH_3$ | $OCH_3$ | CH | |
| H | H | 0 | H | $CH_2CH_2CH_3$ | $OCH_3$ | $OCH_3$ | CH | |
| H | H | 0 | H | $CH_2CH_2CH_3$ | $CH_3$ | $CH_3$ | N | |
| H | H | 0 | H | $CH_2CH_2CH_3$ | $CH_3$ | $OCH_3$ | N | |
| H | H | 0 | H | $CH_2CH_2CH_3$ | $OCH_3$ | $OCH_3$ | N | |
| H | H | 0 | H | $CH_2CH_2CH_3$ | Cl | $OCH_3$ | CH | |
| H | H | 0 | H | $CH_2CH_2CH_2CH_3$ | $CH_3$ | $CH_3$ | CH | |
| H | H | 0 | H | $CH_2CH_2CH_2CH_3$ | $CH_3$ | $OCH_3$ | CH | |
| H | H | 0 | H | $CH_2CH_2CH_2CH_3$ | $OCH_3$ | $OCH_3$ | CH | |
| H | H | 0 | H | $CH_2CH_2CH_2CH_3$ | $CH_3$ | $CH_3$ | N | |
| H | H | 0 | H | $CH_2CH_2CH_2CH_3$ | $CH_3$ | $OCH_3$ | N | |
| H | H | 0 | H | $CH_2CH_2CH_2CH_3$ | $OCH_3$ | $OCH_3$ | N | |
| H | H | 0 | H | $CH_2CH_2CH_2CH_3$ | Cl | $OCH_3$ | CH | |
| $CH_2CH_3$ | H | 0 | H | $CH_2CH_2CH_2CH_2CH_3$ | $CH_3$ | $CH_3$ | CH | |
| $CH_2CH_3$ | H | 0 | H | $CH_2CH_2CH_2CH_2CH_3$ | $CH_3$ | $OCH_3$ | CH | |
| $CH_2CH_3$ | H | 0 | H | $CH_2CH_2CH_2CH_2CH_3$ | $OCH_3$ | $OCH_3$ | CH | |
| $CH_2CH_3$ | H | 0 | H | $CH_2CH_2CH_2CH_2CH_3$ | $CH_3$ | $CH_3$ | N | |
| $CH_2CH_3$ | H | 0 | H | $CH_2CH_2CH_2CH_2CH_3$ | $CH_3$ | $OCH_3$ | N | |
| $CH_2CH_3$ | H | 0 | H | $CH_2CH_2CH_2CH_2CH_3$ | $OCH_3$ | $OCH_3$ | N | |
| $CH_2CH_3$ | H | 0 | H | $CH_2CH_2CH_2CH_2CH_3$ | Cl | $OCH_3$ | CH | |
| $CH_2CH_3$ | H | 0 | H | $CH(CH_3)_2$ | $CH_3$ | $CH_3$ | CH | |
| $CH_2CH_3$ | H | 0 | H | $CH(CH_3)_2$ | $CH_3$ | $OCH_3$ | CH | |
| $CH_2CH_3$ | H | 0 | H | $CH(CH_3)_2$ | $OCH_3$ | $OCH_3$ | CH | |
| $CH_2CH_3$ | H | 0 | H | $CH(CH_3)_2$ | $CH_3$ | $CH_3$ | N | |
| $CH_2CH_3$ | H | 0 | H | $CH(CH_3)_2$ | $CH_3$ | $OCH_3$ | N | |
| $CH_2CH_3$ | H | 0 | H | $CH(CH_3)_2$ | $OCH_3$ | $OCH_3$ | N | |
| $CH_2CH_3$ | H | 0 | H | $CH(CH_3)_2$ | Cl | $OCH_3$ | CH | |
| $CH_2CH_3$ | H | 0 | H | $CH_2CH(CH_3)_2$ | $CH_3$ | $CH_3$ | CH | |
| $CH_2CH_3$ | H | 0 | H | $CH_2CH(CH_3)_2$ | $CH_3$ | $OCH_3$ | CH | |
| $CH_2CH_3$ | H | 0 | H | $CH_2CH(CH_3)_2$ | $OCH_3$ | $OCH_3$ | CH | |
| $CH_2CH_3$ | H | 0 | H | $CH_2CH(CH_3)_2$ | $CH_3$ | $CH_3$ | N | |
| $CH_2CH_3$ | H | 0 | H | $CH_2CH(CH_3)_2$ | $CH_3$ | $OCH_3$ | N | |
| $CH_2CH_3$ | H | 0 | H | $CH_2CH(CH_3)_2$ | $OCH_3$ | $OCH_3$ | N | |
| $CH_2CH_3$ | H | 0 | H | $CH_2CH(CH_3)_2$ | Cl | $OCH_3$ | CH | |
| $CH_2CH_3$ | H | 0 | H | $CH(CH_3)CH_2CH_3$ | $CH_3$ | $CH_3$ | CH | |
| $CH_2CH_3$ | H | 0 | H | $CH(CH_3)CH_2CH_3$ | $CH_3$ | $OCH_3$ | CH | |
| $CH_2CH_3$ | H | 0 | H | $CH(CH_3)CH_2CH_3$ | $OCH_3$ | $OCH_3$ | CH | |
| $CH_2CH_3$ | H | 0 | H | $CH_2CH_2CH(CH_3)_2$ | $CH_3$ | $CH_3$ | N | |
| $CH_2CH_3$ | H | 0 | H | $CH_2CH_2CH(CH_3)_2$ | $CH_3$ | $OCH_3$ | N | |
| $CH_2CH_3$ | H | 0 | H | $CH_2CH_2CH(CH_3)_2$ | $OCH_3$ | $OCH_3$ | N | |
| $CH_2CH_3$ | H | 0 | H | $CH_2CH_2CH(CH_3)_2$ | Cl | $OCH_3$ | CH | |
| Ph | H | 0 | H | $CH_3$ | $CH_3$ | $CH_3$ | CH | |
| Ph | H | 0 | H | $CH_3$ | $CH_3$ | $OCH_3$ | CH | |
| Ph | H | 0 | H | $CH_3$ | $OCH_3$ | $OCH_3$ | CH | |
| Ph | H | 0 | H | $CH_3$ | $CH_3$ | $CH_3$ | N | |
| Ph | H | 0 | H | $CH_3$ | $CH_3$ | $OCH_3$ | N | |
| Ph | H | 0 | H | $CH_3$ | $OCH_3$ | $OCH_3$ | N | |
| Ph | H | 0 | H | $CH_3$ | Cl | $OCH_3$ | CH | |

TABLE 1-continued

| R | R₁ | n | R₂ | R' | X | Y | Z | m.p. (°C.) |
|---|---|---|---|---|---|---|---|---|
| Ph | H | 0 | H | CH₂CH₃ | CH₃ | CH₃ | CH | |
| Ph | H | 0 | H | CH₂CH₃ | CH₃ | OCH₃ | CH | |
| Ph | H | 0 | H | CH₂CH₃ | OCH₃ | OCH₃ | CH | |
| Ph | H | 0 | H | CH₂CH₃ | CH₃ | CH₃ | N | |
| Ph | H | 0 | H | CH₂CH₃ | CH₃ | OCH₃ | N | |
| Ph | H | 0 | H | CH₂CH₃ | OCH₃ | OCH₃ | N | |
| Ph | H | 0 | H | CH₂CH₃ | Cl | OCH₃ | CH | |
| Ph | H | 0 | H | CH₂CH₂CH₃ | CH₃ | CH₃ | CH | |
| Ph | H | 0 | H | CH₂CH₂CH₃ | CH₃ | OCH₃ | CH | |
| Ph | H | 0 | H | CH₂CH₂CH₃ | OCH₃ | OCH₃ | CH | |
| Ph | H | 0 | H | CH₂CH₂CH₃ | CH₃ | CH₃ | N | |
| Ph | H | 0 | H | CH₂CH₂CH₃ | CH₃ | OCH₃ | N | |
| Ph | H | 0 | H | CH₂CH₂CH₃ | OCH₃ | OCH₃ | N | |
| Ph | H | 0 | H | CH₂CH₂CH₃ | Cl | OCH₃ | CH | |
| Ph | H | 0 | H | CH₂CH₂CH₂CH₃ | CH₃ | CH₃ | CH | |
| Ph | H | 0 | H | CH₂CH₂CH₂CH₃ | CH₃ | OCH₃ | CH | |
| Ph | H | 0 | H | CH₂CH₂CH₂CH₃ | OCH₃ | OCH₃ | CH | |
| Ph | H | 0 | H | CH₂CH₂CH₂CH₃ | CH₃ | CH₃ | N | |
| Ph | H | 0 | H | CH₂CH₂CH₂CH₃ | CH₃ | OCH₃ | N | |
| Ph | H | 0 | H | CH₂CH₂CH₂CH₃ | OCH₃ | OCH₃ | N | |
| Ph | H | 0 | H | CH₂CH₂CH₂CH₃ | Cl | OCH₃ | CH | |
| CHF₂ | H | 0 | H | CH₂CH₂CH₂CH₂CH₃ | CH₃ | CH₃ | CH | |
| CHF₂ | H | 0 | H | CH₂CH₂CH₂CH₂CH₃ | CH₃ | OCH₃ | CH | |
| CHF₂ | H | 0 | H | CH₂CH₂CH₂CH₂CH₃ | OCH₃ | OCH₃ | CH | |
| CHF₂ | H | 0 | H | CH₂CH₂CH₂CH₂CH₃ | CH₃ | CH₃ | N | |
| CHF₂ | H | 0 | H | CH₂CH₂CH₂CH₂CH₃ | CH₃ | OCH₃ | N | |
| CHF₂ | H | 0 | H | CH₂CH₂CH₂CH₂CH₃ | OCH₃ | OCH₃ | N | |
| CHF₂ | H | 0 | H | CH₂CH₂CH₂CH₂CH₃ | Cl | OCH₃ | CH | |
| CHF₂ | H | 0 | H | CH(CH₃)₂ | CH₃ | CH₃ | CH | |
| CHF₂ | H | 0 | H | CH(CH₃)₂ | CH₃ | OCH₃ | CH | |
| CHF₂ | H | 0 | H | CH(CH₃)₂ | OCH₃ | OCH₃ | CH | |
| CHF₂ | H | 0 | H | CH(CH₃)₂ | CH₃ | CH₃ | N | |
| CHF₂ | H | 0 | H | CH(CH₃)₂ | CH₃ | OCH₃ | N | |
| CHF₂ | H | 0 | H | CH(CH₃)₂ | OCH₃ | OCH₃ | N | |
| CHF₂ | H | 0 | H | CH(CH₃)₂ | Cl | OCH₃ | CH | |
| CHF₂ | H | 0 | H | CH₂CH(CH₃)₂ | CH₃ | CH₃ | CH | |
| CHF₂ | H | 0 | H | CH₂CH(CH₃)₂ | CH₃ | OCH₃ | CH | |
| CHF₂ | H | 0 | H | CH₂CH(CH₃)₂ | OCH₃ | OCH₃ | CH | |
| CHF₂ | H | 0 | H | CH₂CH(CH₃)₂ | CH₃ | CH₃ | N | |
| CHF₂ | H | 0 | H | CH₂CH(CH₃)₂ | CH₃ | OCH₃ | N | |
| CHF₂ | H | 0 | H | CH₂CH(CH₃)₂ | OCH₃ | OCH₃ | N | |
| CHF₂ | H | 0 | H | CH₂CH(CH₃)₂ | Cl | OCH₃ | CH | |
| CHF₂ | H | 0 | H | CH(CH₃)CH₂CH₃ | CH₃ | CH₃ | CH | |
| CHF₂ | H | 0 | H | CH(CH₃)CH₂CH₃ | CH₃ | OCH₃ | CH | |
| CHF₂ | H | 0 | H | CH(CH₃)CH₂CH₃ | OCH₃ | OCH₃ | CH | |
| CHF₂ | H | 0 | H | CH₂CH₂CH(CH₃)₂ | CH₃ | CH₃ | N | |
| CHF₂ | H | 0 | H | CH₂CH₂CH(CH₃)₂ | CH₃ | OCH₃ | N | |
| CHF₂ | H | 0 | H | CH₂CH₂CH(CH₃)₂ | OCH₃ | OCH₃ | N | |
| CHF₂ | H | 0 | H | CH₂CH₂CH(CH₃)₂ | Cl | OCH₃ | CH | |
| CH₂OCH₃ | H | 0 | H | CH₂CH₂CH₂CH₂CH₃ | CH₃ | CH₃ | CH | |
| CH₂OCH₃ | H | 0 | H | CH₂CH₂CH₂CH₂CH₃ | CH₃ | OCH₃ | CH | |
| CH₂OCH₃ | H | 0 | H | CH₂CH₂CH₂CH₂CH₃ | OCH₃ | OCH₃ | CH | |
| CH₂OCH₃ | H | 0 | H | CH₂CH₂CH₂CH₂CH₃ | CH₃ | CH₃ | N | |
| CH₂OCH₃ | H | 0 | H | CH₂CH₂CH₂CH₂CH₃ | CH₃ | OCH₃ | N | |
| CH₂OCH₃ | H | 0 | H | CH₂CH₂CH₂CH₂CH₃ | OCH₃ | OCH₃ | N | |
| CH₂OCH₃ | H | 0 | H | CH₂CH₂CH₂CH₂CH₃ | Cl | OCH₃ | CH | |
| CH₂OCH₃ | H | 0 | H | CH(CH₃)₂ | CH₃ | CH₃ | CH | |
| CH₂OCH₃ | H | 0 | H | CH(CH₃)₂ | CH₃ | OCH₃ | CH | |
| CH₂OCH₃ | H | 0 | H | CH(CH₃)₂ | OCH₃ | OCH₃ | CH | |
| CH₂OCH₃ | H | 0 | H | CH(CH₃)₂ | CH₃ | CH₃ | N | |
| CH₂OCH₃ | H | 0 | H | CH(CH₃)₂ | CH₃ | OCH₃ | N | |
| CH₂OCH₃ | H | 0 | H | CH(CH₃)₂ | OCH₃ | OCH₃ | N | |
| CH₂OCH₃ | H | 0 | H | CH(CH₃)₂ | Cl | OCH₃ | CH | |
| CH₂OCH₃ | H | 0 | H | CH₂CH(CH₃)₂ | CH₃ | CH₃ | CH | |
| CH₂OCH₃ | H | 0 | H | CH₂CH(CH₃)₂ | CH₃ | OCH₃ | CH | |
| CH₂OCH₃ | H | 0 | H | CH₂CH(CH₃)₂ | OCH₃ | OCH₃ | CH | |
| CH₂OCH₃ | H | 0 | H | CH₂CH(CH₃)₂ | CH₃ | CH₃ | N | |
| CH₂OCH₃ | H | 0 | H | CH₂CH(CH₃)₂ | CH₃ | OCH₃ | N | |
| CH₂OCH₃ | H | 0 | H | CH₂CH(CH₃)₂ | OCH₃ | OCH₃ | N | |
| CH₂OCH₃ | H | 0 | H | CH₂CH(CH₃)₂ | Cl | OCH₃ | CH | |
| CH₂OCH₃ | H | 0 | H | CH(CH₃)CH₂CH₃ | CH₃ | CH₃ | CH | |
| CH₂OCH₃ | H | 0 | H | CH(CH₃)CH₂CH₃ | CH₃ | OCH₃ | CH | |
| CH₂OCH₃ | H | 0 | H | CH(CH₃)CH₂CH₃ | OCH₃ | OCH₃ | CH | |
| CH₂OCH₃ | H | 0 | H | CH₂CH₂CH(CH₃)₂ | CH₃ | CH₃ | N | |
| CH₂OCH₃ | H | 0 | H | CH₂CH₂CH(CH₃)₂ | CH₃ | OCH₃ | N | |
| CH₂OCH₃ | H | 0 | H | CH₂CH₂CH(CH₃)₂ | OCH₃ | OCH₃ | N | |
| CH₂OCH₃ | H | 0 | H | CH₂CH₂CH(CH₃)₂ | Cl | OCH₃ | CH | |
| CH₂CN | H | 0 | H | CH₂F | CH₃ | CH₃ | CH | |
| CH₂CN | H | 0 | H | CH₂F | CH₃ | OCH₃ | CH | |
| CH₂CN | H | 0 | H | CH₂F | OCH₃ | OCH₃ | CH | |
| CH₂CN | H | 0 | H | CH₂F | CH₃ | CH₃ | N | |

TABLE 1-continued

| R | R₁ | n | R₂ | R' | X | Y | Z | m.p. (°C.) |
|---|---|---|---|---|---|---|---|---|
| CH₂CN | H | 0 | H | CH₂F | CH₃ | OCH₃ | N | |
| CH₂CN | H | 0 | H | CH₂F | OCH₃ | OCH₃ | N | |
| CH₂CN | H | 0 | H | CH₂F | Cl | OCH₃ | CH | |
| CH₂CN | H | 0 | H | CH₂CH₂F | CH₃ | CH₃ | CH | |
| CH₂CN | H | 0 | H | CH₂CH₂F | CH₃ | OCH₃ | CH | |
| CH₂CN | H | 0 | H | CH₂CH₂F | OCH₃ | OCH₃ | CH | |
| CH₂CN | H | 0 | H | CH₂CH₂F | CH₃ | CH₃ | N | |
| CH₂CN | H | 0 | H | CH₂CH₂F | CH₃ | OCH₃ | N | |
| CH₂CN | H | 0 | H | CH₂CH₂F | OCH₃ | OCH₃ | N | |
| CH₂CN | H | 0 | H | CH₂CH₂F | Cl | OCH₃ | CH | |
| CH₂CN | H | 0 | H | CHF₂ | CH₃ | CH₃ | CH | |
| CH₂CN | H | 0 | H | CHF₂ | CH₃ | OCH₃ | CH | |
| CH₂CN | H | 0 | H | CHF₂ | OCH₃ | OCH₃ | CH | |
| CH₂CN | H | 0 | H | CHF₂ | CH₃ | CH₃ | N | |
| CH₂CN | H | 0 | H | CHF₂ | CH₃ | OCH₃ | N | |
| CH₂CN | H | 0 | H | CHF₂ | OCH₃ | OCH₃ | N | |
| CH₂CN | H | 0 | H | CHF₂ | Cl | OCH₃ | CH | |
| CH₂CN | H | 0 | H | CH₂CF₃ | CH₃ | CH₃ | CH | |
| CH₂CN | H | 0 | H | CH₂CF₃ | CH₃ | OCH₃ | CH | |
| CH₂CN | H | 0 | H | CH₂CF₃ | OCH₃ | OCH₃ | CH | |
| CH₂CN | H | 0 | H | CH₂Cl | CH₃ | CH₃ | N | |
| CH₂CN | H | 0 | H | CH₂Cl | CH₃ | OCH₃ | N | |
| CH₂CN | H | 0 | H | CH₂Cl | OCH₃ | OCH₃ | N | |
| CH₂CN | H | 0 | H | CH₂Cl | Cl | OCH₃ | CH | |
| CH₂SCH₃ | H | 0 | H | CH₂Br | CH₃ | CH₃ | CH | |
| CH₂SCH₃ | H | 0 | H | CH₂Br | CH₃ | OCH₃ | CH | |
| CH₂SCH₃ | H | 0 | H | CH₂Br | OCH₃ | OCH₃ | CH | |
| CH₂SCH₃ | H | 0 | H | CH₂Br | CH₃ | CH₃ | N | |
| CH₂SCH₃ | H | 0 | H | CH₂CH₂Br | CH₃ | OCH₃ | N | |
| CH₂SCH₃ | H | 0 | H | CH₂CH₂Br | OCH₃ | OCH₃ | N | |
| CH₂SCH₃ | H | 0 | H | CH₂CH₂Br | Cl | OCH₃ | CH | |
| CH₂SCH₃ | H | 0 | H | CH(CH₃)CH₂F | CH₃ | CH₃ | CH | |
| CH₂SCH₃ | H | 0 | H | CH(CH₃)CH₂F | CH₃ | OCH₃ | CH | |
| CH₂SCH₃ | H | 0 | H | CH(CH₃)CH₂F | OCH₃ | OCH₃ | CH | |
| CH₂SCH₃ | H | 0 | H | CH(CH₃)CH₂F | CH₃ | CH₃ | N | |
| CH₂SCH₃ | H | 0 | H | CH(CH₃)CH₂F | CH₃ | OCH₃ | N | |
| CH₂SCH₃ | H | 0 | H | CH(CH₃)CH₂F | OCH₃ | OCH₃ | N | |
| CH₂SCH₃ | H | 0 | H | CH(CH₃)CH₂F | Cl | OCH₃ | CH | |
| CH₂SCH₃ | H | 0 | H | CH(CH₂F)₂ | CH₃ | CH₃ | CH | |
| CH₂SCH₃ | H | 0 | H | CH(CH₂F)₂ | CH₃ | OCH₃ | CH | |
| CH₂SCH₃ | H | 0 | H | CH(CH₂F)₂ | OCH₃ | OCH₃ | CH | |
| CH₂SCH₃ | H | 0 | H | CH(CH₂F)₂ | CH₃ | CH₃ | N | |
| CH₂SCH₃ | H | 0 | H | CH(CH₂F)₂ | CH₃ | OCH₃ | N | |
| CH₂SCH₃ | H | 0 | H | CH(CH₂F)₂ | OCH₃ | OCH₃ | N | |
| CH₂SCH₃ | H | 0 | H | CH(CH₂F)₂ | Cl | OCH₃ | CH | |
| CH₂SCH₃ | H | 0 | H | CH₂I | CH₃ | CH₃ | CH | |
| CH₂SCH₃ | H | 0 | H | CH₂I | CH₃ | OCH₃ | CH | |
| CH₂SCH₃ | H | 0 | H | CH₂I | OCH₃ | OCH₃ | CH | |
| CH₂SCH₃ | H | 0 | H | CH₂I | CH₃ | CH₃ | N | |
| CH₂SCH₃ | H | 0 | H | CH₂CH₂CH₂F | CH₃ | OCH₃ | N | |
| CH₂SCH₃ | H | 0 | H | CH₂CH₂CH₂F | OCH₃ | OCH₃ | N | |
| CH₂SCH₃ | H | 0 | H | CH₂CH₂CH₂F | Cl | OCH₃ | CH | |
| CH₃ | H | 0 | H | CH₃ | H | CH₃ | CH | |
| CH₃ | H | 0 | H | CH₃ | H | OCH₃ | CH | |
| CH₃ | H | 0 | H | CH₃ | CH₃ | OCH₂CH₃ | CH | |
| CH₃ | H | 0 | H | CH₃ | CH₃ | OCH(CH₃)₂ | CH | |
| CH₃ | H | 0 | H | CH₃ | H | OCH₃ | N | |
| CH₃ | H | 0 | H | CH₃ | OCH₃ | OCH₂CH₃ | CH | |
| CH₃ | H | 0 | H | CH₃ | CH₂F | CH₃ | CH | |
| CH₃ | H | 0 | H | CH₃ | CH₂F | OCH₃ | CH | |
| CH₃ | H | 0 | H | CH₃ | OCF₂H | CH₃ | CH | |
| CH₃ | H | 0 | H | CH₃ | OCF₂H | OCH₃ | CH | |
| CH₃ | H | 0 | H | CH₃ | OCH₂CF₃ | OCH₃ | N | |
| CH₃ | H | 0 | H | CH₃ | SCH₃ | OCH₃ | CH | |
| CH₃ | H | 0 | H | CH₃ | OCH₃ | NHCH₃ | N | |
| CH₃ | H | 0 | H | CH₃ | OCH₂CH₃ | NHCH₃ | N | 195–197 |
| CH₃ | H | 0 | H | CH₃ | OCH₃ | OCH₂CH₃ | N | |
| CH₃ | H | 0 | H | CH₃ | SCF₂H | OCH₃ | CH | |
| CH₃ | H | 0 | H | CH₃ | Br | OCH₃ | CH | |
| CH₃ | H | 0 | H | CH₃ | CH₂OCH₃ | OCH₃ | CH | |
| CH₃ | H | 0 | H | CH₃ | CH₂OCH₃ | CH₃ | N | |
| CH₃ | H | 0 | H | CH₃ | NH₂ | OCH₃ | N | |
| CH₃ | H | 0 | H | CH₃ | N(CH₃)₂ | OCH₃ | N | |
| CH₃ | H | 0 | H | CH₃ | NHCH₃ | NHCH₃ | N | |
| CH₃ | H | 0 | H | CH₃ | cyclopropyl | OCH₃ | CH | |
| CH₃ | H | 0 | H | CH₃ | cyclopropyl | CH₃ | N | |
| CH₃ | H | 0 | H | CH₃ | cyclopropyl | CH₃ | CH | |
| CH₃ | H | 0 | H | CH₃ | cyclopropyl | OCH₃ | N | |
| CH₃ | H | 0 | H | CH₃ | CH₃ | CH(OCH₃)₂ | CH | |
| CH₃ | H | 0 | H | CH₃ | CF₃ | OCH₃ | CH | |
| CH₃ | H | 0 | H | CH₃ | OCH₃ | C≡CH | CH | |

TABLE 1-continued

| R | R₁ | n | R₂ | R' | X | Y | Z | m.p. (°C.) |
|---|---|---|---|---|---|---|---|---|
| CH₃ | H | 0 | H | CH₂CH₃ | H | CH₃ | CH | |
| CH₃ | H | 0 | H | CH₂CH₃ | H | OCH₃ | CH | |
| CH₃ | H | 0 | H | CH₂CH₃ | CH₃ | OCH₂CH₃ | CH | |
| CH₃ | H | 0 | H | CH₂CH₃ | CH₃ | OCH(CH₃)₂ | CH | |
| CH₃ | H | 0 | H | CH₂CH₃ | H | OCH₃ | N | |
| CH₃ | H | 0 | H | CH₂CH₃ | OCH₃ | OCH₂CH₃ | CH | |
| CH₃ | H | 0 | H | CH₂CH₃ | CH₂F | CH₃ | CH | |
| CH₃ | H | 0 | H | CH₂CH₃ | CH₂F | OCH₃ | CH | |
| CH₃ | H | 0 | H | CH₂CH₃ | OCF₂H | CH₃ | CH | |
| CH₃ | H | 0 | H | CH₂CH₃ | OCF₂H | OCH₃ | CH | |
| CH₃ | H | 0 | H | CH₂CH₃ | OCH₂CF₃ | OCH₃ | N | |
| CH₃ | H | 0 | H | CH₂CH₃ | SCH₃ | OCH₃ | CH | |
| CH₃ | H | 0 | H | CH₂CH₃ | OCH₃ | NHCH₃ | N | |
| CH₃ | H | 0 | H | CH₂CH₃ | OCH₂CH₃ | NHCH₃ | N | |
| CH₃ | H | 0 | H | CH₂CH₃ | OCH₃ | OCH₂CH₃ | N | |
| CH₃ | H | 0 | H | CH₂CH₃ | SCF₂H | OCH₃ | CH | |
| CH₃ | H | 0 | H | CH₂CH₃ | Br | OCH₃ | CH | |
| CH₃ | H | 0 | H | CH₂CH₃ | CH₂OCH₃ | OCH₃ | CH | |
| CH₃ | H | 0 | H | CH₂CH₃ | CH₂OCH₃ | CH₃ | N | |
| CH₃ | H | 0 | H | CH₂CH₃ | NH₂ | OCH₃ | N | |
| CH₃ | H | 0 | H | CH₂CH₃ | N(CH₃)₂ | OCH₃ | N | |
| CH₃ | H | 0 | H | CH₂CH₃ | NHCH₃ | NHCH₃ | N | |
| CH₃ | H | 0 | H | CH₂CH₃ | cyclopropyl | OCH₃ | CH | |
| CH₃ | H | 0 | H | CH₂CH₃ | cyclopropyl | CH₃ | N | |
| CH₃ | H | 0 | H | CH₂CH₃ | cyclopropyl | CH₃ | CH | |
| CH₃ | H | 0 | H | CH₂CH₃ | cyclopropyl | OCH₃ | N | |
| CH₃ | H | 0 | H | CH₂CH₃ | CH₃ | CH(OCH₃)₂ | CH | |
| CH₃ | H | 0 | H | CH₂CH₃ | CF₃ | OCH₃ | CH | |
| CH₃ | H | 0 | H | CH₂CH₃ | OCH₃ | C≡CH | CH | |
| E is CH₂ |||||||||
| CH₃ | H | 0 | H | CH₃ | CH₃ | CH₃ | CH | |
| CH₃ | H | 0 | H | CH₃ | CH₃ | OCH₃ | CH | |
| CH₃ | H | 0 | H | CH₃ | OCH₃ | OCH₃ | CH | |
| CH₃ | H | 0 | H | CH₃ | CH₃ | CH₃ | N | |
| CH₃ | H | 0 | H | CH₃ | CH₃ | OCH₃ | N | |
| CH₃ | H | 0 | H | CH₃ | OCH₃ | OCH₃ | N | |
| CH₃ | H | 0 | H | CH₃ | Cl | OCH₃ | CH | |
| CH₃ | H | 0 | H | CH₂CH₃ | CH₃ | CH₃ | CH | |
| CH₃ | H | 0 | H | CH₂CH₃ | CH₃ | OCH₃ | CH | |
| CH₃ | H | 0 | H | CH₂CH₃ | OCH₃ | OCH₃ | CH | |
| CH₃ | H | 0 | H | CH₂CH₃ | CH₃ | CH₃ | N | |
| CH₃ | H | 0 | H | CH₂CH₃ | CH₃ | OCH₃ | N | |
| CH₃ | H | 0 | H | CH₂CH₃ | OCH₃ | OCH₃ | N | |
| CH₃ | H | 0 | H | CH₂CH₃ | Cl | OCH₃ | CH | |
| CH₃ | H | 0 | H | CH₂CH₂CH₃ | CH₃ | CH₃ | CH | |
| CH₃ | H | 0 | H | CH₂CH₂CH₃ | CH₃ | OCH₃ | CH | |
| CH₃ | H | 0 | H | CH₂CH₂CH₃ | OCH₃ | OCH₃ | CH | |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | |
| CH₃ | H | 0 | H | CH₂CH₂CH₃ | OCH₃ | OCH₃ | N | |
| CH₃ | H | 0 | H | CH₂CH₂CH₃ | Cl | OCH₃ | CH | |
| CH₃ | H | 0 | H | CH₂CH₂CH₂CH₃ | CH₃ | CH₃ | CH | |
| CH₃ | H | 0 | H | CH₂CH₂CH₂CH₃ | CH₃ | OCH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |
| W = S |||||||||
| CH₃ | H | 0 | H | CH₃ | CH₃ | CH₃ | CH | |
| CH₃ | H | 0 | H | CH₃ | CH₃ | OCH₃ | CH | |
| CH₃ | H | 0 | H | CH₃ | OCH₃ | OCH₃ | CH | |
| CH₃ | H | 0 | H | CH₃ | CH₃ | CH₃ | N | |
| CH₃ | H | 0 | H | CH₃ | CH₃ | OCH₃ | N | |
| CH₃ | H | 0 | H | CH₃ | OCH₃ | OCH₃ | N | |
| CH₃ | H | 0 | H | CH₃ | Cl | OCH₃ | CH | |
| CH₃ | H | 0 | H | CH₂CH₃ | CH₃ | CH₃ | CH | |
| CH₃ | H | 0 | H | CH₂CH₃ | CH₃ | OCH₃ | CH | |
| CH₃ | H | 0 | H | CH₂CH₃ | OCH₃ | OCH₃ | CH | |
| CH₃ | H | 0 | H | CH₂CH₃ | CH₃ | CH₃ | N | |
| CH₃ | H | 0 | H | CH₂CH₃ | CH₃ | OCH₃ | N | |
| CH₃ | H | 0 | H | CH₂CH₃ | OCH₃ | OCH₃ | N | |
| CH₃ | H | 0 | H | CH₂CH₃ | Cl | OCH₃ | CH | |
| CH₃ | H | 0 | H | CH₂CH₂CH₃ | CH₃ | CH₃ | CH | |
| CH₃ | H | 0 | H | CH₂CH₂CH₃ | CH₃ | OCH₃ | CH | |
| CH₃ | H | 0 | H | CH₂CH₂CH₃ | OCH₃ | OCH₃ | CH | |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | |
| CH₃ | H | 0 | H | CH₂CH₂CH₃ | OCH₃ | OCH₃ | N | |
| CH₃ | H | 0 | H | CH₂CH₂CH₃ | Cl | OCH₃ | CH | |

TABLE 1-continued

| R | R₁ | n | R₂ | R' | X | Y | Z | m.p. (°C.) |
|---|---|---|---|---|---|---|---|---|
| CH₃ | H | 0 | H | CH₂CH₂CH₂CH₃ | CH₃ | CH₃ | CH | |
| CH₃ | H | 0 | H | CH₂CH₂CH₂CH₃ | CH₃ | OCH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |

TABLE II

| R | R₁ | n | R₂ | R' | X | Y | Z | m.p. (°C.) |
|---|---|---|---|---|---|---|---|---|
| CH₃ | H | 0 | H | CH₃ | CH₃ | CH₃ | CH | |
| CH₃ | H | 0 | H | CH₃ | CH₃ | OCH₃ | CH | |
| CH₃ | H | 0 | H | CH₃ | OCH₃ | OCH₃ | CH | |
| CH₃ | H | 0 | H | CH₃ | CH₃ | CH₃ | N | |
| CH₃ | H | 0 | H | CH₃ | CH₃ | OCH₃ | N | |
| CH₃ | H | 0 | H | CH₃ | OCH₃ | OCH₃ | N | |
| CH₃ | H | 0 | H | CH₃ | Cl | OCH₃ | CH | |
| CH₃ | H | 0 | H | CH₂CH₃ | CH₃ | CH₃ | CH | |
| CH₃ | H | 0 | H | CH₂CH₃ | CH₃ | OCH₃ | CH | |
| CH₃ | H | 0 | H | CH₂CH₃ | OCH₃ | OCH₃ | CH | |
| CH₃ | H | 0 | H | CH₂CH₃ | CH₃ | CH₃ | N | |
| CH₃ | H | 0 | H | CH₂CH₃ | CH₃ | OCH₃ | N | |
| CH₃ | H | 0 | H | CH₂CH₃ | OCH₃ | OCH₃ | N | |
| CH₃ | H | 0 | H | CH₂CH₃ | Cl | OCH₃ | CH | |
| CH₃ | H | 0 | H | CH₂CH₂CH₃ | CH₃ | CH₃ | CH | |
| CH₃ | H | 0 | H | CH₂CH₂CH₃ | CH₃ | OCH₃ | CH | |
| CH₃ | H | 0 | H | CH₂CH₂CH₃ | OCH₃ | OCH₃ | CH | |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | |
| CH₃ | H | 0 | H | CH₂CH₂CH₃ | OCH₃ | OCH₃ | N | |
| CH₃ | H | 0 | H | CH₂CH₂CH₃ | Cl | OCH₃ | CH | |
| CH₃ | H | 0 | H | CH₂CH₂CH₂CH₃ | CH₃ | CH₃ | CH | |
| CH₃ | H | 0 | H | CH₂CH₂CH₂CH₃ | CH₃ | OCH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |
| CH₃ | H | 0 | H | CH₂F | CH₃ | CH₃ | CH | |
| CH₃ | H | 0 | H | CH₂F | CH₃ | OCH₃ | CH | |
| CH₃ | H | 0 | H | CH₂F | OCH₃ | OCH₃ | CH | |
| CH₃ | H | 0 | H | CH₂F | CH₃ | CH₃ | N | |
| CH₃ | H | 0 | H | CH₂F | CH₃ | OCH₃ | N | |
| CH₃ | H | 0 | H | CH₂F | OCH₃ | OCH₃ | N | |
| CH₃ | H | 0 | H | CH₂F | Cl | OCH₃ | CH | |
| CH₃ | H | 0 | H | CH₂CH₂F | CH₃ | CH₃ | CH | |
| CH₃ | H | 0 | H | CH₂CH₂F | CH₃ | OCH₃ | CH | |
| CH₃ | H | 0 | H | CH₂CH₂F | OCH₃ | OCH₃ | CH | |
| CH₃ | H | 0 | H | CH₂CH₂F | CH₃ | CH₃ | N | |
| CH₃ | H | 0 | H | CH₂CH₂F | CH₃ | OCH₃ | N | |
| CH₃ | H | 0 | H | CH₂CH₂F | OCH₃ | OCH₃ | N | |
| CH₃ | H | 0 | H | CH₂CH₂F | Cl | OCH₃ | CH | |
| CH₃ | H | 0 | H | CHF₂ | CH₃ | CH₃ | CH | |
| CH₃ | H | 0 | H | CHF₂ | CH₃ | OCH₃ | CH | |
| CH₃ | H | 0 | H | CHF₂ | OCH₃ | OCH₃ | CH | |
| CH₃ | H | 0 | H | CHF₂ | CH₃ | CH₃ | N | |
| CH₃ | H | 0 | H | CHF₂ | CH₃ | OCH₃ | N | |
| CH₃ | H | 0 | H | CHF₂ | OCH₃ | OCH₃ | N | |
| CH₃ | H | 0 | H | CHF₂ | Cl | OCH₃ | CH | |
| CH₃ | H | 0 | H | CH₂CF₃ | CH₃ | CH₃ | CH | |
| CH₃ | H | 0 | H | CH₂CF₃ | CH₃ | OCH₃ | CH | |
| CH₃ | H | 0 | H | CH₂CF₃ | OCH₃ | OCH₃ | CH | |
| CH₃ | H | 0 | H | CH₂Cl | CH₃ | CH₃ | N | |
| CH₃ | H | 0 | H | CH₂Cl | CH₃ | OCH₃ | N | |
| CH₃ | H | 0 | H | CH₂Cl | OCH₃ | OCH₃ | N | |
| CH₃ | H | 0 | H | CH₂Cl | Cl | OCH₃ | CH | |
| CH₃ | H | 0 | H | CH₂OCH₃ | CH₃ | CH₃ | CH | |
| CH₃ | H | 0 | H | CH₂OCH₃ | CH₃ | OCH₃ | CH | |
| CH₃ | H | 0 | H | CH₂OCH₃ | OCH₃ | OCH₃ | CH | |
| CH₃ | H | 0 | H | CH₂OCH₃ | CH₃ | CH₃ | N | |
| CH₃ | H | 0 | H | CH₂OCH₃ | CH₃ | OCH₃ | N | |
| CH₃ | H | 0 | H | CH₂OCH₃ | OCH₃ | OCH₃ | N | |
| CH₃ | H | 0 | H | CH₂OCH₃ | Cl | OCH₃ | CH | |
| CH₃ | H | 0 | H | CH₂OCH₂CH₃ | CH₃ | CH₃ | CH | |
| CH₃ | H | 0 | H | CH₂OCH₂CH₃ | CH₃ | OCH₃ | CH | |
| CH₃ | H | 0 | H | CH₂OCH₂CH₃ | OCH₃ | OCH₃ | CH | |
| CH₃ | H | 0 | H | CH₂OCH₂CH₃ | CH₃ | CH₃ | N | |
| CH₃ | H | 0 | H | CH₂CH₂OCH₃ | CH₃ | OCH₃ | N | |

TABLE II-continued

| R | R₁ | n | R₂ | R' | X | Y | Z | m.p. (°C.) |
|---|---|---|---|---|---|---|---|---|
| CH₃ | H | 0 | H | CH₂CH₂OCH₃ | OCH₃ | OCH₃ | N | |
| CH₃ | H | 0 | H | CH₂CH₂OCH₃ | Cl | OCH₃ | CH | |
| CH₃ | H | 0 | H | CH₂CH₂OCH₃ | CH₃ | CH₃ | CH | |
| CH₃ | H | 0 | H | CH₂CH₂OCH₃ | CH₃ | OCH₃ | CH | |
| CH₃ | H | 0 | H | CH₂CH₂OCH₃ | OCH₃ | OCH₃ | CH | |
| CH₃ | H | 0 | H | CH₂CH₂OCH₃ | CH₃ | CH₃ | N | |
| CH₃ | H | 0 | H | CH(OCH₃)₂ | CH₃ | OCH₃ | N | |
| CH₃ | H | 0 | H | CH(OCH₃)₂ | OCH₃ | OCH₃ | N | |
| CH₃ | H | 0 | H | CH(OCH₃)₂ | Cl | OCH₃ | CH | |
| CH₃ | H | 0 | H | CH₂SCH₃ | CH₃ | CH₃ | CH | |
| CH₃ | H | 0 | H | CH₂SCH₃ | CH₃ | OCH₃ | CH | |
| CH₃ | H | 0 | H | CH₂SCH₃ | OCH₃ | OCH₃ | CH | |
| CH₃ | H | 0 | H | CH₂SCH₃ | CH₃ | CH₃ | N | |
| CH₃ | H | 0 | H | CH₂SCH₃ | CH₃ | OCH₃ | N | |
| CH₃ | H | 0 | H | CH₂SCH₃ | OCH₃ | OCH₃ | N | |
| CH₃ | H | 0 | H | CH₂SCH₃ | Cl | OCH₃ | CH | |
| CH₃ | H | 0 | H | CH₂OH | CH₃ | CH₃ | CH | |
| CH₃ | H | 0 | H | CH₂OH | CH₃ | OCH₃ | CH | |
| CH₃ | H | 0 | H | CH₂OH | OCH₃ | OCH₃ | CH | |
| CH₃ | H | 0 | H | CH₂OH | CH₃ | CH₃ | N | |
| CH₃ | H | 0 | H | CH₂OH | CH₃ | OCH₃ | N | |
| CH₃ | H | 0 | H | CH₂OH | OCH₃ | OCH₃ | N | |
| CH₃ | H | 0 | H | CH₂OH | Cl | OCH₃ | CH | |
| CH₃ | H | 0 | H | CH(CH₃)OH | CH₃ | CH₃ | CH | |
| CH₃ | H | 0 | H | CH(CH₃)OH | CH₃ | OCH₃ | CH | |
| CH₃ | H | 0 | H | CH(CH₃)OH | OCH₃ | OCH₃ | CH | |
| CH₃ | H | 0 | H | CH(CH₃)OH | CH₃ | CH₃ | N | |
| CH₃ | H | 0 | H | CH(CH₃)OH | CH₃ | OCH₃ | N | |
| CH₃ | H | 0 | H | CH(CH₃)OH | OCH₃ | OCH₃ | N | |
| CH₃ | H | 0 | H | CH(CH₃)OH | Cl | OCH₃ | CH | |
| CH₃ | H | 0 | H | CH₂OSi(CH₃)₃ | CH₃ | CH₃ | CH | |
| CH₃ | H | 0 | H | CH₂OSi(CH₃)₃ | CH₃ | OCH₃ | CH | |
| CH₃ | H | 0 | H | CH₂OSi(CH₃)₃ | OCH₃ | OCH₃ | CH | |
| CH₃ | H | 0 | H | CH₂OSi(CH₃)₃ | CH₃ | CH₃ | N | |
| CH₃ | H | 0 | H | CH₂OSi(CH₃)₃ | CH₃ | OCH₃ | N | |
| CH₃ | H | 0 | H | CH₂OSi(CH₃)₃ | OCH₃ | OCH₃ | N | |
| CH₃ | H | 0 | H | CH₂OSi(CH₃)₃ | Cl | OCH₃ | CH | |
| CH₃ | H | 0 | H | CH₂COCH₃ | CH₃ | CH₃ | CH | |
| CH₃ | H | 0 | H | CH₂COCH₃ | CH₃ | OCH₃ | CH | |
| CH₃ | H | 0 | H | CH₂COCH₃ | OCH₃ | OCH₃ | CH | |
| CH₃ | H | 0 | H | CH₂COCH₃ | CH₃ | CH₃ | N | |
| CH₃ | H | 0 | H | CH₂COCH₃ | CH₃ | OCH₃ | N | |
| CH₃ | H | 0 | H | CH₂CO₂CH₃ | OCH₃ | OCH₃ | N | |
| CH₃ | H | 0 | H | CH₂CO₂CH₃ | Cl | OCH₃ | CH | |
| CH₃ | H | 0 | CH₃ | CH₂N(CH₃)₂ | CH₃ | CH₃ | CH | |
| CH₃ | H | 0 | CH₃ | CH₂N(CH₃)₂ | CH₃ | OCH₃ | CH | |
| CH₃ | H | 0 | CH₃ | CH₂N(CH₃)₂ | OCH₃ | OCH₃ | CH | |
| CH₃ | H | 0 | CH₃ | CH₂N(CH₃)₂ | CH₃ | CH₃ | N | |
| CH₃ | H | 0 | CH₃ | CH₂N(CH₃)₂ | CH₃ | OCH₃ | N | |
| CH₃ | H | 0 | CH₃ | CH₂N(CH₃)₂ | OCH₃ | OCH₃ | N | |
| CH₃ | H | 0 | CH₃ | CH₂N(CH₃)₂ | Cl | OCH₃ | CH | |
| CH₃ | H | 0 | CH₃ | CH₂CH₂N(CH₃)₂ | CH₃ | CH₃ | CH | |
| CH₃ | H | 0 | CH₃ | CH₂CH₂N(CH₃)₂ | CH₃ | OCH₃ | CH | |
| CH₃ | H | 0 | CH₃ | CH₂CH₂N(CH₃)₂ | OCH₃ | OCH₃ | CH | |
| CH₃ | H | 0 | CH₃ | CH₂CH₂N(CH₃)₂ | CH₃ | CH₃ | N | |
| CH₃ | H | 0 | CH₃ | CH₂CH₂N(CH₃)₂ | CH₃ | OCH₃ | N | |
| CH₃ | H | 0 | CH₃ | CH₂CH₂N(CH₃)₂ | OCH₃ | OCH₃ | N | |
| CH₃ | H | 0 | CH₃ | CH₂CH₂N(CH₃)₂ | Cl | OCH₃ | CH | |
| CH₃ | H | 0 | CH₃ | CH₂CH=CH₂ | CH₃ | CH₃ | CH | |
| CH₃ | H | 0 | CH₃ | CH₂CH=CH₂ | CH₃ | OCH₃ | CH | |
| CH₃ | H | 0 | CH₃ | CH₂CH=CH₂ | OCH₃ | OCH₃ | CH | |
| CH₃ | H | 0 | CH₃ | CH₂CH=CH₂ | CH₃ | CH₃ | N | |
| CH₃ | H | 0 | CH₃ | CH₂CH=CH₂ | CH₃ | OCH₃ | N | |
| CH₃ | H | 0 | CH₃ | CH₂CH=CH₂ | OCH₃ | OCH₃ | N | |
| CH₃ | H | 0 | CH₃ | CH₂CH=CH₂ | Cl | OCH₃ | CH | |
| CH₃ | H | 0 | CH₃ | CH=CH₂ | CH₃ | CH₃ | CH | |
| CH₃ | H | 0 | CH₃ | CH=CH₂ | CH₃ | OCH₃ | CH | |
| CH₃ | H | 0 | CH₃ | CH=CH₂ | OCH₃ | OCH₃ | CH | |
| CH₃ | H | 0 | CH₃ | CH=CH₂ | CH₃ | CH₃ | N | |
| CH₃ | H | 0 | CH₃ | CH=CH₂ | CH₃ | OCH₃ | N | |
| CH₃ | H | 0 | CH₃ | CH=CH₂ | OCH₃ | OCH₃ | N | |
| CH₃ | H | 0 | CH₃ | CH=CH₂ | Cl | OCH₃ | CH | |
| CH₃ | H | 0 | Cl | CH=CHOCH₃ | CH₃ | CH₃ | CH | |
| CH₃ | H | 0 | Cl | CH=CHOCH₃ | CH₃ | OCH₃ | CH | |
| CH₃ | H | 0 | Cl | CH=CHOCH₃ | OCH₃ | OCH₃ | CH | |
| CH₃ | H | 0 | Cl | CH=CHCN | CH₃ | CH₃ | N | |
| CH₃ | H | 0 | Cl | CH=CHCN | CH₃ | OCH₃ | N | |
| CH₃ | H | 0 | Cl | CH(CH₃)CH=CH₂ | OCH₃ | OCH₃ | N | |
| CH₃ | H | 0 | Cl | CH(CH₃)CH=CH₂ | Cl | OCH₃ | CH | |
| CH₃ | H | 0 | Cl | C≡CH | CH₃ | CH₃ | CH | |
| CH₃ | H | 0 | Cl | C≡CH | CH₃ | OCH₃ | CH | |

TABLE II-continued

| R | R₁ | n | R₂ | R' | X | Y | Z | m.p. (°C.) |
|---|---|---|---|---|---|---|---|---|
| CH₃ | H | 0 | Cl | C≡CH | OCH₃ | OCH₃ | CH | |
| CH₃ | H | 0 | Cl | C≡CH | CH₃ | CH₃ | N | |
| CH₃ | H | 0 | Cl | C≡CH | CH₃ | OCH₃ | N | |
| CH₃ | H | 0 | Cl | C≡CH | OCH₃ | OCH₃ | N | |
| CH₃ | H | 0 | Cl | C≡CH | Cl | OCH₃ | CH | |
| CH₃ | H | 0 | Cl | CH₂C≡CH | CH₃ | CH₃ | CH | |
| CH₃ | H | 0 | Cl | CH₂C≡CH | CH₃ | OCH₃ | CH | |
| CH₃ | H | 0 | Cl | CH₂C≡CH | OCH₃ | OCH₃ | CH | |
| CH₃ | H | 0 | Cl | CH₂C≡CH | CH₃ | CH₃ | N | |
| CH₃ | H | 0 | Cl | CH₂C≡CH | CH₃ | OCH₃ | N | |
| CH₃ | H | 0 | Cl | CH₂C≡CH | OCH₃ | OCH₃ | N | |
| CH₃ | H | 0 | Cl | CH₂C≡CH | Cl | OCH₃ | CH | |
| CH₃ | H | 0 | Cl | CH₂CH₂C≡CH | CH₃ | CH₃ | CH | |
| CH₃ | H | 0 | Cl | CH₂CH₂C≡CH | CH₃ | OCH₃ | CH | |
| CH₃ | H | 0 | Cl | CH₂CH₂C≡CH | OCH₃ | OCH₃ | CH | |
| CH₃ | H | 0 | Cl | CH₂CH₂C≡CH | CH₃ | CH₃ | N | |
| CH₃ | H | 0 | Cl | CH(CH₃)C≡CH | CH₃ | OCH₃ | N | |
| CH₃ | H | 0 | Cl | CH(CH₃)C≡CH | OCH₃ | OCH₃ | N | |
| CH₃ | H | 0 | Cl | CH(CH₃)C≡CH | Cl | OCH₃ | CH | |
| CH₃ | H | 0 | CH₂F | CH₃ | CH₃ | CH₃ | CH | |
| CH₃ | H | 0 | CH₂F | CH₃ | CH₃ | OCH₃ | CH | |
| CH₃ | H | 0 | CH₂F | CH₃ | OCH₃ | OCH₃ | CH | |
| CH₃ | H | 0 | CH₂F | CH₃ | CH₃ | CH₃ | N | |
| CH₃ | H | 0 | CH₂F | CH₃ | CH₃ | OCH₃ | N | |
| CH₃ | H | 0 | CH₂F | CH₃ | OCH₃ | OCH₃ | N | |
| CH₃ | H | 0 | CH₂F | CH₃ | Cl | OCH₃ | CH | |
| CH₃ | H | 0 | CH₂F | CH₂CH₃ | CH₃ | CH₃ | CH | |
| CH₃ | H | 0 | CH₂F | CH₂CH₃ | CH₃ | OCH₃ | CH | |
| CH₃ | H | 0 | CH₂F | CH₂CH₃ | OCH₃ | OCH₃ | CH | |
| CH₃ | H | 0 | CH₂F | CH₂CH₃ | CH₃ | CH₃ | N | |
| CH₃ | H | 0 | CH₂F | CH₂CH₃ | CH₃ | OCH₃ | N | |
| CH₃ | H | 0 | CH₂F | CH₂CH₃ | OCH₃ | OCH₃ | N | |
| CH₃ | H | 0 | CH₂F | CH₂CH₃ | Cl | OCH₃ | CH | |
| CH₃ | H | 0 | CH₂F | CH₂CH₂CH₃ | CH₃ | CH₃ | CH | |
| CH₃ | H | 0 | CH₂F | CH₂CH₂CH₃ | CH₃ | OCH₃ | CH | |
| CH₃ | H | 0 | CH₂F | CH₂CH₂CH₃ | OCH₃ | OCH₃ | CH | |
| CH₃ | H | 0 | CH₂F | CH₂CH₂CH₃ | CH₃ | CH₃ | N | |
| CH₃ | H | 0 | CH₂F | CH₂CH₂CH₃ | CH₃ | OCH₃ | N | |
| CH₃ | H | 0 | CH₂F | CH₂CH₂CH₃ | OCH₃ | OCH₃ | N | |
| CH₃ | H | 0 | CH₂F | CH₂CH₂CH₃ | Cl | OCH₃ | CH | |
| CH₃ | H | 0 | CH₂F | CH₂CH₂CH₂CH₃ | CH₃ | CH₃ | CH | |
| CH₃ | H | 0 | CH₂F | CH₂CH₂CH₂CH₃ | CH₃ | OCH₃ | CH | |
| CH₃ | H | 0 | CH₂F | CH₂CH₂CH₂CH₃ | OCH₃ | OCH₃ | CH | |
| CH₃ | H | 0 | CH₂F | CH₂CH₂CH₂CH₃ | CH₃ | CH₃ | N | |
| CH₃ | H | 0 | CH₂F | CH₂CH₂CH₂CH₃ | CH₃ | OCH₃ | N | |
| CH₃ | H | 0 | CH₂F | CH₂CH₂CH₂CH₃ | OCH₃ | OCH₃ | N | |
| CH₃ | H | 0 | CH₂F | CH₂CH₂CH₂CH₃ | Cl | OCH₃ | CH | |
| CH₃ | H | 0 | OCHF₂ | CH₃ | CH₃ | CH₃ | CH | |
| CH₃ | H | 0 | OCHF₂ | CH₃ | CH₃ | OCH₃ | CH | |
| CH₃ | H | 0 | OCHF₂ | CH₃ | OCH₃ | OCH₃ | CH | |
| CH₃ | H | 0 | OCHF₂ | CH₃ | CH₃ | CH₃ | N | |
| CH₃ | H | 0 | OCHF₂ | CH₃ | CH₃ | OCH₃ | N | |
| CH₃ | H | 0 | OCHF₂ | CH₃ | OCH₃ | OCH₃ | N | |
| CH₃ | H | 0 | OCHF₂ | CH₃ | Cl | OCH₃ | CH | |
| CH₃ | H | 0 | OCHF₂ | CH₂CH₃ | CH₃ | CH₃ | CH | |
| CH₃ | H | 0 | OCHF₂ | CH₂CH₃ | CH₃ | OCH₃ | CH | |
| CH₃ | H | 0 | OCHF₂ | CH₂CH₃ | OCH₃ | OCH₃ | CH | |
| CH₃ | H | 0 | OCHF₂ | CH₂CH₃ | CH₃ | CH₃ | N | |
| CH₃ | H | 0 | OCHF₂ | CH₂CH₃ | CH₃ | OCH₃ | N | |
| CH₃ | H | 0 | OCHF₂ | CH₂CH₃ | OCH₃ | OCH₃ | N | |
| CH₃ | H | 0 | OCHF₂ | CH₂CH₃ | Cl | OCH₃ | CH | |
| CH₃ | H | 0 | OCHF₂ | CH₂CH₂CH₃ | CH₃ | CH₃ | CH | |
| CH₃ | H | 0 | OCHF₂ | CH₂CH₂CH₃ | CH₃ | OCH₃ | CH | |
| CH₃ | H | 0 | OCHF₂ | CH₂CH₂CH₃ | OCH₃ | OCH₃ | CH | |
| CH₃ | H | 0 | OCHF₂ | CH₂CH₂CH₃ | CH₃ | CH₃ | N | |
| CH₃ | H | 0 | OCHF₂ | CH₂CH₂CH₃ | CH₃ | OCH₃ | N | |
| CH₃ | H | 0 | OCHF₂ | CH₂CH₂CH₃ | OCH₃ | OCH₃ | N | |
| CH₃ | H | 0 | OCHF₂ | CH₂CH₂CH₃ | Cl | OCH₃ | CH | |
| CH₃ | H | 0 | OCHF₂ | CH₂CH₂CH₂CH₃ | CH₃ | CH₃ | CH | |
| CH₃ | H | 0 | OCHF₂ | CH₂CH₂CH₂CH₃ | CH₃ | OCH₃ | CH | |
| CH₃ | H | 0 | OCHF₂ | CH₂CH₂CH₂CH₃ | OCH₃ | OCH₃ | CH | |
| CH₃ | H | 0 | OCHF₂ | CH₂CH₂CH₂CH₃ | CH₃ | CH₃ | N | |
| CH₃ | H | 0 | OCHF₂ | CH₂CH₂CH₂CH₃ | CH₃ | OCH₃ | N | |
| CH₃ | H | 0 | OCHF₂ | CH₂CH₂CH₂CH₃ | OCH₃ | OCH₃ | N | |
| CH₃ | H | 0 | OCHF₂ | CH₂CH₂CH₂CH₃ | Cl | OCH₃ | CH | |
| CH₂CH=CH₂ | H | 0 | H | CH₂F | CH₃ | CH₃ | CH | |
| CH₂CH=CH₂ | H | 0 | H | CH₂F | CH₃ | OCH₃ | CH | |
| CH₂CH=CH₂ | H | 0 | H | CH₂F | OCH₃ | OCH₃ | CH | |
| CH₂CH=CH₂ | H | 0 | H | CH₂F | CH₃ | CH₃ | N | |
| CH₂CH=CH₂ | H | 0 | H | CH₂F | CH₃ | OCH₃ | N | |
| CH₂CH=CH₂ | H | 0 | H | CH₂F | OCH₃ | OCH₃ | N | |

TABLE II-continued

| R | R₁ | n | R₂ | R' | X | Y | Z | m.p. (°C.) |
|---|---|---|---|---|---|---|---|---|
| CH₂CH=CH₂ | H | 0 | H | CH₂F | Cl | OCH₃ | CH | |
| CH₂CH=CH₂ | H | 0 | H | CH₂CH₂F | CH₃ | CH₃ | CH | |
| CH₂CH=CH₂ | H | 0 | H | CH₂CH₂F | CH₃ | OCH₃ | CH | |
| CH₂CH=CH₂ | H | 0 | H | CH₂CH₂F | OCH₃ | OCH₃ | CH | |
| CH₂CH=CH₂ | H | 0 | H | CH₂CH₂F | CH₃ | CH₃ | N | |
| CH₂CH=CH₂ | H | 0 | H | CH₂CH₂F | CH₃ | OCH₃ | N | |
| CH₂CH=CH₂ | H | 0 | H | CH₂CH₂F | OCH₃ | OCH₃ | N | |
| CH₂CH=CH₂ | H | 0 | H | CH₂CH₂F | Cl | OCH₃ | CH | |
| CH₂CH=CH₂ | H | 0 | H | CHF₂ | CH₃ | CH₃ | CH | |
| CH₂CH=CH₂ | H | 0 | H | CHF₂ | CH₃ | OCH₃ | CH | |
| CH₂CH=CH₂ | H | 0 | H | CHF₂ | OCH₃ | OCH₃ | CH | |
| CH₂CH=CH₂ | H | 0 | H | CHF₂ | CH₃ | CH₃ | N | |
| CH₂CH=CH₂ | H | 0 | H | CHF₂ | CH₃ | OCH₃ | N | |
| CH₂CH=CH₂ | H | 0 | H | CHF₂ | OCH₃ | OCH₃ | N | |
| CH₂CH=CH₂ | H | 0 | H | CHF₂ | Cl | OCH₃ | CH | |
| CH₂CH=CH₂ | H | 0 | H | CH₂CF₃ | CH₃ | CH₃ | CH | |
| CH₂CH=CH₂ | H | 0 | H | CH₂CF₃ | CH₃ | OCH₃ | CH | |
| CH₂CH=CH₂ | H | 0 | H | CH₂CF₃ | OCH₃ | OCH₃ | CH | |
| CH₂CH=CH₂ | H | 0 | H | CH₂Cl | CH₃ | CH₃ | N | |
| CH₂CH=CH₂ | H | 0 | H | CH₂Cl | CH₃ | OCH₃ | N | |
| CH₂CH=CH₂ | H | 0 | H | CH₂Cl | OCH₃ | OCH₃ | N | |
| CH₂CH=CH₂ | H | 0 | H | CH₂Cl | Cl | OCH₃ | CH | |
| CH₂OCH₃ | H | 0 | H | CH₂CH₂CH₂CH₂CH₃ | CH₃ | CH₃ | CH | |
| CH₂OCH₃ | H | 0 | H | CH₂CH₂CH₂CH₂CH₃ | CH₃ | OCH₃ | CH | |
| CH₂OCH₃ | H | 0 | H | CH₂CH₂CH₂CH₂CH₃ | OCH₃ | OCH₃ | CH | |
| CH₂OCH₃ | H | 0 | H | CH₂CH₂CH₂CH₂CH₃ | CH₃ | CH₃ | N | |
| CH₂OCH₃ | H | 0 | H | CH₂CH₂CH₂CH₂CH₃ | CH₃ | OCH₃ | N | |
| CH₂OCH₃ | H | 0 | H | CH₂CH₂CH₂CH₂CH₃ | OCH₃ | OCH₃ | N | |
| CH₂OCH₃ | H | 0 | H | CH₂CH₂CH₂CH₂CH₃ | Cl | OCH₃ | CH | |
| CH₂OCH₃ | H | 0 | H | CH(CH₃)₂ | CH₃ | CH₃ | CH | |
| CH₂OCH₃ | H | 0 | H | CH(CH₃)₂ | CH₃ | OCH₃ | CH | |
| CH₂OCH₃ | H | 0 | H | CH(CH₃)₂ | OCH₃ | OCH₃ | CH | |
| CH₂OCH₃ | H | 0 | H | CH(CH₃)₂ | CH₃ | CH₃ | N | |
| CH₂OCH₃ | H | 0 | H | CH(CH₃)₂ | CH₃ | OCH₃ | N | |
| CH₂OCH₃ | H | 0 | H | CH(CH₃)₂ | OCH₃ | OCH₃ | N | |
| CH₂OCH₃ | H | 0 | H | CH(CH₃)₂ | Cl | OCH₃ | CH | |
| CH₂OCH₃ | H | 0 | H | CH₂CH(CH₃)₂ | CH₃ | CH₃ | CH | |
| CH₂OCH₃ | H | 0 | H | CH₂CH(CH₃)₂ | CH₃ | OCH₃ | CH | |
| CH₂OCH₃ | H | 0 | H | CH₂CH(CH₃)₂ | OCH₃ | OCH₃ | CH | |
| CH₂OCH₃ | H | 0 | H | CH₂CH(CH₃)₂ | CH₃ | CH₃ | N | |
| CH₂OCH₃ | H | 0 | H | CH₂CH(CH₃)₂ | CH₃ | OCH₃ | N | |
| CH₂OCH₃ | H | 0 | H | CH₂CH(CH₃)₂ | OCH₃ | OCH₃ | N | |
| CH₂OCH₃ | H | 0 | H | CH₂CH(CH₃)₂ | Cl | OCH₃ | CH | |
| CH₂OCH₃ | H | 0 | H | CH(CH₃)CH₂CH₃ | CH₃ | CH₃ | CH | |
| CH₂OCH₃ | H | 0 | H | CH(CH₃)CH₂CH₃ | CH₃ | OCH₃ | CH | |
| CH₂OCH₃ | H | 0 | H | CH(CH₃)CH₂CH₃ | OCH₃ | OCH₃ | CH | |
| CH₂OCH₃ | H | 0 | H | CH₂CH₂CH(CH₃)₂ | CH₃ | CH₃ | N | |
| CH₂OCH₃ | H | 0 | H | CH₂CH₂CH(CH₃)₂ | CH₃ | OCH₃ | N | |
| CH₂OCH₃ | H | 0 | H | CH₂CH₂CH(CH₃)₂ | OCH₃ | OCH₃ | N | |
| CH₂OCH₃ | H | 0 | H | CH₂CH₂CH(CH₃)₂ | Cl | OCH₃ | CH | |
| CH₂SCH₃ | H | 0 | H | CH₂Br | CH₃ | CH₃ | CH | |
| CH₂SCH₃ | H | 0 | H | CH₂Br | CH₃ | OCH₃ | CH | |
| CH₂SCH₃ | H | 0 | H | CH₂Br | OCH₃ | OCH₃ | CH | |
| CH₂SCH₃ | H | 0 | H | CH₂Br | CH₃ | CH₃ | N | |
| CH₂SCH₃ | H | 0 | H | CH₂CH₂Br | CH₃ | OCH₃ | N | |
| CH₂SCH₃ | H | 0 | H | CH₂CH₂Br | OCH₃ | OCH₃ | N | |
| CH₂SCH₃ | H | 0 | H | CH₂CH₂Br | Cl | OCH₃ | CH | |
| CH₂SCH₃ | H | 0 | H | CH(CH₃)CH₂F | CH₃ | CH₃ | CH | |
| CH₂SCH₃ | H | 0 | H | CH(CH₃)CH₂F | CH₃ | OCH₃ | CH | |
| CH₂SCH₃ | H | 0 | H | CH(CH₃)CH₂F | OCH₃ | OCH₃ | CH | |
| CH₂SCH₃ | H | 0 | H | CH(CH₃)CH₂F | CH₃ | CH₃ | N | |
| CH₂SCH₃ | H | 0 | H | CH(CH₃)CH₂F | CH₃ | OCH₃ | N | |
| CH₂SCH₃ | H | 0 | H | CH(CH₃)CH₂F | OCH₃ | OCH₃ | N | |
| CH₂SCH₃ | H | 0 | H | CH(CH₃)CH₂F | Cl | OCH₃ | CH | |
| CH₂SCH₃ | H | 0 | H | CH(CH₂F)₂ | CH₃ | CH₃ | CH | |
| CH₂SCH₃ | H | 0 | H | CH(CH₂F)₂ | CH₃ | OCH₃ | CH | |
| CH₂SCH₃ | H | 0 | H | CH(CH₂F)₂ | OCH₃ | OCH₃ | CH | |
| CH₂SCH₃ | H | 0 | H | CH(CH₂F)₂ | CH₃ | CH₃ | N | |
| CH₂SCH₃ | H | 0 | H | CH(CH₂F)₂ | CH₃ | OCH₃ | N | |
| CH₂SCH₃ | H | 0 | H | CH(CH₂F)₂ | OCH₃ | OCH₃ | N | |
| CH₂SCH₃ | H | 0 | H | CH(CH₂F)₂ | Cl | OCH₃ | CH | |
| CH₂SCH₃ | H | 0 | H | CH₂I | CH₃ | CH₃ | CH | |
| CH₂SCH₃ | H | 0 | H | CH₂I | CH₃ | OCH₃ | CH | |
| CH₂SCH₃ | H | 0 | H | CH₂I | OCH₃ | OCH₃ | CH | |
| CH₂SCH₃ | H | 0 | H | CH₂I | CH₃ | CH₃ | N | |
| CH₂SCH₃ | H | 0 | H | CH₂CH₂CH₂F | CH₃ | OCH₃ | N | |
| CH₂SCH₃ | H | 0 | H | CH₂CH₂CH₂F | OCH₃ | OCH₃ | N | |
| CH₂SCH₃ | H | 0 | H | CH₂CH₂CH₂F | Cl | OCH₃ | CH | |
| Ph | H | 0 | H | CH₃ | CH₃ | CH₃ | CH | |
| Ph | H | 0 | H | CH₃ | CH₃ | OCH₃ | CH | |
| Ph | H | 0 | H | CH₃ | OCH₃ | OCH₃ | CH | |

TABLE II-continued

| R | R₁ | n | R₂ | R' | X | Y | Z | m.p. (°C.) |
|---|----|---|----|----|----|----|----|----|
| Ph | H | 0 | H | CH₃ | CH₃ | CH₃ | N | |
| Ph | H | 0 | H | CH₃ | CH₃ | OCH₃ | N | |
| Ph | H | 0 | H | CH₃ | OCH₃ | OCH₃ | N | |
| Ph | H | 0 | H | CH₃ | Cl | OCH₃ | CH | |
| Ph | H | 0 | H | CH₂CH₃ | CH₃ | CH₃ | CH | |
| Ph | H | 0 | H | CH₂CH₃ | CH₃ | OCH₃ | CH | |
| Ph | H | 0 | H | CH₂CH₃ | OCH₃ | OCH₃ | CH | |
| Ph | H | 0 | H | CH₂CH₃ | CH₃ | CH₃ | N | |
| Ph | H | 0 | H | CH₂CH₃ | CH₃ | OCH₃ | N | |
| Ph | H | 0 | H | CH₂CH₃ | OCH₃ | OCH₃ | N | |
| Ph | H | 0 | H | CH₂CH₃ | Cl | OCH₃ | CH | |
| Ph | H | 0 | H | CH₂CH₂CH₃ | CH₃ | CH₃ | CH | |
| Ph | H | 0 | H | CH₂CH₂CH₃ | CH₃ | OCH₃ | CH | |
| Ph | H | 0 | H | CH₂CH₂CH₃ | OCH₃ | OCH₃ | CH | |
| Ph | H | 0 | H | CH₂CH₂CH₃ | CH₃ | CH₃ | N | |
| Ph | H | 0 | H | CH₂CH₂CH₃ | CH₃ | OCH₃ | N | |
| Ph | H | 0 | H | CH₂CH₂CH₃ | OCH₃ | OCH₃ | N | |
| Ph | H | 0 | H | CH₂CH₂CH₃ | Cl | OCH₃ | CH | |
| Ph | H | 0 | H | CH₂CH₂CH₂CH₃ | CH₃ | CH₃ | CH | |
| Ph | H | 0 | H | CH₂CH₂CH₂CH₃ | CH₃ | OCH₃ | CH | |
| Ph | H | 0 | H | CH₂CH₂CH₂CH₃ | OCH₃ | OCH₃ | CH | |
| Ph | H | 0 | H | CH₂CH₂CH₂CH₃ | CH₃ | CH₃ | N | |
| Ph | H | 0 | H | CH₂CH₂CH₂CH₃ | CH₃ | OCH₃ | N | |
| Ph | H | 0 | H | CH₂CH₂CH₂CH₃ | OCH₃ | OCH₃ | N | |
| Ph | H | 0 | H | CH₂CH₂CH₂CH₃ | Cl | OCH₃ | CH | |

TABLE III

| R | R₁ | n | R₂ | R' | X | Y | Z | m.p. (°C.) |
|---|----|---|----|----|----|----|----|----|
| CH₃ | H | 0 | H | CH₃ | CH₃ | CH₃ | CH | |
| CH₃ | H | 0 | H | CH₃ | CH₃ | OCH₃ | CH | |
| CH₃ | H | 0 | H | CH₃ | OCH₃ | OCH₃ | CH | |
| CH₃ | H | 0 | H | CH₃ | CH₃ | CH₃ | N | |
| CH₃ | H | 0 | H | CH₃ | CH₃ | OCH₃ | N | |
| CH₃ | H | 0 | H | CH₃ | OCH₃ | OCH₃ | N | |
| CH₃ | H | 0 | H | CH₃ | Cl | OCH₃ | CH | |
| CH₃ | H | 0 | H | CH₂CH₃ | CH₃ | CH₃ | CH | |
| CH₃ | H | 0 | H | CH₂CH₃ | CH₃ | OCH₃ | CH | |
| CH₃ | H | 0 | H | CH₂CH₃ | OCH₃ | OCH₃ | CH | |
| CH₃ | H | 0 | H | CH₂CH₃ | CH₃ | CH₃ | N | |
| CH₃ | H | 0 | H | CH₂CH₃ | CH₃ | OCH₃ | N | |
| CH₃ | H | 0 | H | CH₂CH₃ | OCH₃ | OCH₃ | N | |
| CH₃ | H | 0 | H | CH₂CH₃ | Cl | OCH₃ | CH | |
| CH₃ | H | 0 | H | CH₂CH₂CH₃ | CH₃ | CH₃ | CH | |
| CH₃ | H | 0 | H | CH₂CH₂CH₃ | CH₃ | OCH₃ | CH | |
| CH₃ | H | 0 | H | CH₂CH₂CH₃ | OCH₃ | OCH₃ | CH | |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | |
| CH₃ | H | 0 | H | CH₂CH₂CH₃ | OCH₃ | OCH₃ | N | |
| CH₃ | H | 0 | H | CH₂CH₂CH₃ | Cl | OCH₃ | CH | |
| CH₃ | H | 0 | H | CH₂CH₂CH₂CH₃ | CH₃ | CH₃ | CH | |
| CH₃ | H | 0 | H | CH₂CH₂CH₂CH₃ | CH₃ | OCH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |
| CH₃ | H | 0 | H | CH₂Br | CH₃ | CH₃ | CH | |
| CH₃ | H | 0 | H | CH₂Br | CH₃ | OCH₃ | CH | |
| CH₃ | H | 0 | H | CH₂Br | OCH₃ | OCH₃ | CH | |
| CH₃ | H | 0 | H | CH₂Br | CH₃ | CH₃ | N | |
| CH₃ | H | 0 | H | CH₂CH₂Br | CH₃ | OCH₃ | N | |
| CH₃ | H | 0 | H | CH₂CH₂Br | OCH₃ | OCH₃ | N | |
| CH₃ | H | 0 | H | CH₂CH₂Br | Cl | OCH₃ | CH | |
| CH₃ | H | 0 | H | CH(CH₃)CH₂F | CH₃ | CH₃ | CH | |
| CH₃ | H | 0 | H | CH(CH₃)CH₂F | CH₃ | OCH₃ | CH | |
| CH₃ | H | 0 | H | CH(CH₃)CH₂F | OCH₃ | OCH₃ | CH | |
| CH₃ | H | 0 | H | CH(CH₃)CH₂F | CH₃ | CH₃ | N | |
| CH₃ | H | 0 | H | CH(CH₃)CH₂F | CH₃ | OCH₃ | N | |
| CH₃ | H | 0 | H | CH(CH₃)CH₂F | OCH₃ | OCH₃ | N | |
| CH₃ | H | 0 | H | CH(CH₃)CH₂F | Cl | OCH₃ | CH | |
| CH₃ | H | 0 | H | CH(CH₂F)₂ | CH₃ | CH₃ | CH | |
| CH₃ | H | 0 | H | CH(CH₂F)₂ | CH₃ | OCH₃ | CH | |
| CH₃ | H | 0 | H | CH(CH₂F)₂ | OCH₃ | OCH₃ | CH | |
| CH₃ | H | 0 | H | CH(CH₂F)₂ | CH₃ | CH₃ | N | |
| CH₃ | H | 0 | H | CH(CH₂F)₂ | CH₃ | OCH₃ | N | |
| CH₃ | H | 0 | H | CH(CH₂F)₂ | OCH₃ | OCH₃ | N | |
| CH₃ | H | 0 | H | CH(CH₂F)₂ | Cl | OCH₃ | CH | |
| CH₃ | H | 0 | H | CH₂I | CH₃ | CH₃ | CH | |

TABLE III-continued

| R | R₁ | n | R₂ | R' | X | Y | Z | m.p. (°C.) |
|---|---|---|---|---|---|---|---|---|
| CH₃ | H | 0 | H | CH₂I | CH₃ | OCH₃ | CH | |
| CH₃ | H | 0 | H | CH₂I | OCH₃ | OCH₃ | CH | |
| CH₃ | H | 0 | H | CH₂I | CH₃ | CH₃ | N | |
| CH₃ | H | 0 | H | CH₂CH₂CH₂F | CH₃ | OCH₃ | N | |
| CH₃ | H | 0 | H | CH₂CH₂CH₂F | OCH₃ | OCH₃ | N | |
| CH₃ | H | 0 | H | CH₂CH₂CH₂F | Cl | OCH₃ | CH | |
| CH₃ | H | 0 | H | CH₂OH | CH₃ | CH₃ | CH | |
| CH₃ | H | 0 | H | CH₂OH | CH₃ | OCH₃ | CH | |
| CH₃ | H | 0 | H | CH₂OH | OCH₃ | OCH₃ | CH | |
| CH₃ | H | 0 | H | CH₂OH | CH₃ | CH₃ | N | |
| CH₃ | H | 0 | H | CH₂OH | CH₃ | OCH₃ | N | |
| CH₃ | H | 0 | H | CH₂OH | OCH₃ | OCH₃ | N | |
| CH₃ | H | 0 | H | CH₂OH | Cl | OCH₃ | CH | |
| CH₃ | H | 0 | H | CH(CH₃)OH | CH₃ | CH₃ | CH | |
| CH₃ | H | 0 | H | CH(CH₃)OH | CH₃ | OCH₃ | CH | |
| CH₃ | H | 0 | H | CH(CH₃)OH | OCH₃ | OCH₃ | CH | |
| CH₃ | H | 0 | H | CH(CH₃)OH | CH₃ | CH₃ | N | |
| CH₃ | H | 0 | H | CH(CH₃)OH | CH₃ | OCH₃ | N | |
| CH₃ | H | 0 | H | CH(CH₃)OH | OCH₃ | OCH₃ | N | |
| CH₃ | H | 0 | H | CH(CH₃)OH | Cl | OCH₃ | CH | |
| CH₃ | H | 0 | H | CH₂OSi(CH₃)₃ | CH₃ | CH₃ | CH | |
| CH₃ | H | 0 | H | CH₂OSi(CH₃)₃ | CH₃ | OCH₃ | CH | |
| CH₃ | H | 0 | H | CH₂OSi(CH₃)₃ | OCH₃ | OCH₃ | CH | |
| CH₃ | H | 0 | H | CH₂OSi(CH₃)₃ | CH₃ | CH₃ | N | |
| CH₃ | H | 0 | H | CH₂OSi(CH₃)₃ | CH₃ | OCH₃ | N | |
| CH₃ | H | 0 | H | CH₂OSi(CH₃)₃ | OCH₃ | OCH₃ | N | |
| CH₃ | H | 0 | H | CH₂OSi(CH₃)₃ | Cl | OCH₃ | CH | |
| CH₃ | H | 0 | H | CH₂COCH₃ | CH₃ | CH₃ | CH | |
| CH₃ | H | 0 | H | CH₂COCH₃ | CH₃ | OCH₃ | CH | |
| CH₃ | H | 0 | H | CH₂COCH₃ | OCH₃ | OCH₃ | CH | |
| CH₃ | H | 0 | H | CH₂COCH₃ | CH₃ | CH₃ | N | |
| CH₃ | H | 0 | H | CH₂COCH₃ | CH₃ | OCH₃ | N | |
| CH₃ | H | 0 | H | CH₂CO₂CH₃ | OCH₃ | OCH₃ | N | |
| CH₃ | H | 0 | H | CH₂CO₂CH₃ | Cl | OCH₃ | CH | |
| CH₃ | H | 0 | CH₃ | CH₂OCH₂F | CH₃ | CH₃ | CH | |
| CH₃ | H | 0 | CH₃ | CH₂OCH₂F | CH₃ | OCH₃ | CH | |
| CH₃ | H | 0 | CH₃ | CH₂OCH₂F | OCH₃ | OCH₃ | CH | |
| CH₃ | H | 0 | CH₃ | CH₂OCH₂F | CH₃ | CH₃ | N | |
| CH₃ | H | 0 | CH₃ | CH₂OCH₂F | CH₃ | OCH₃ | N | |
| CH₃ | H | 0 | CH₃ | CH₂OCH₂F | OCH₃ | OCH₃ | N | |
| CH₃ | H | 0 | CH₃ | CH₂OCH₂F | Cl | OCH₃ | CH | |
| CH₃ | H | 0 | CH₃ | CH₂SOCH₃ | CH₃ | CH₃ | CH | |
| CH₃ | H | 0 | CH₃ | CH₂SOCH₃ | CH₃ | OCH₃ | CH | |
| CH₃ | H | 0 | CH₃ | CH₂SOCH₃ | OCH₃ | OCH₃ | CH | |
| CH₃ | H | 0 | CH₃ | CH₂SOCH₃ | CH₃ | CH₃ | N | |
| CH₃ | H | 0 | CH₃ | CH₂SOCH₃ | CH₃ | OCH₃ | N | |
| CH₃ | H | 0 | CH₃ | CH₂SOCH₃ | OCH₃ | OCH₃ | N | |
| CH₃ | H | 0 | CH₃ | CH₂SOCH₃ | Cl | OCH₃ | CH | |
| CH₃ | H | 0 | CH₃ | CH₂SO₂CH₃ | CH₃ | CH₃ | CH | |
| CH₃ | H | 0 | CH₃ | CH₂SO₂CH₃ | CH₃ | OCH₃ | CH | |
| CH₃ | H | 0 | CH₃ | CH₂SO₂CH₃ | OCH₃ | OCH₃ | CH | |
| CH₃ | H | 0 | CH₃ | CH₂SO₂CH₃ | CH₃ | CH₃ | N | |
| CH₃ | H | 0 | CH₃ | CH₂SO₂CH₃ | CH₃ | OCH₃ | N | |
| CH₃ | H | 0 | CH₃ | CH₂SO₂CH₃ | OCH₃ | OCH₃ | N | |
| CH₃ | H | 0 | CH₃ | CH₂SO₂CH₃ | Cl | OCH₃ | CH | |
| CH₃ | H | 0 | CH₃ | CH₂CN | CH₃ | CH₃ | CH | |
| CH₃ | H | 0 | CH₃ | CH₂CH₂CN | CH₃ | OCH₃ | CH | |
| CH₃ | H | 0 | CH₃ | CH₂(CH₃)CN | OCH₃ | OCH₃ | CH | |
| CH₃ | H | 0 | CH₃ | CH₂NO₂ | CH₃ | CH₃ | N | |
| CH₃ | H | 0 | CH₃ | CH₂CH₂NO₂ | CH₃ | OCH₃ | N | |
| CH₃ | H | 0 | CH₃ | CH₂CN | OCH₃ | OCH₃ | N | |
| CH₃ | H | 0 | CH₃ | CH₂CN | Cl | OCH₃ | CH | |
| CH₃ | H | 0 | Cl | CH₂CH₂CH₂CH₂CH₃ | CH₃ | CH₃ | CH | |
| CH₃ | H | 0 | Cl | CH₂CH₂CH₂CH₂CH₃ | CH₃ | OCH₃ | CH | |
| CH₃ | H | 0 | Cl | CH₂CH₂CH₂CH₂CH₃ | OCH₃ | OCH₃ | CH | |
| CH₃ | H | 0 | Cl | CH₂CH₂CH₂CH₂CH₃ | CH₃ | CH₃ | N | |
| CH₃ | H | 0 | Cl | CH₂CH₂CH₂CH₂CH₃ | CH₃ | OCH₃ | N | |
| CH₃ | H | 0 | Cl | CH₂CH₂CH₂CH₂CH₃ | OCH₃ | OCH₃ | N | |
| CH₃ | H | 0 | Cl | CH₂CH₂CH₂CH₂CH₃ | Cl | OCH₃ | CH | |
| CH₃ | H | 0 | Cl | CH(CH₃)₂ | CH₃ | CH₃ | CH | |
| CH₃ | H | 0 | Cl | CH(CH₃)₂ | CH₃ | OCH₃ | CH | |
| CH₃ | H | 0 | Cl | CH(CH₃)₂ | OCH₃ | OCH₃ | CH | |
| CH₃ | H | 0 | Cl | CH(CH₃)₂ | CH₃ | CH₃ | N | |
| CH₃ | H | 0 | Cl | CH(CH₃)₂ | CH₃ | OCH₃ | N | |
| CH₃ | H | 0 | Cl | CH(CH₃)₂ | OCH₃ | OCH₃ | N | |
| CH₃ | H | 0 | Cl | CH(CH₃)₂ | Cl | OCH₃ | CH | |
| CH₃ | H | 0 | Cl | CH₂CH(CH₃)₂ | CH₃ | CH₃ | CH | |
| CH₃ | H | 0 | Cl | CH₂CH(CH₃)₂ | CH₃ | OCH₃ | CH | |
| CH₃ | H | 0 | Cl | CH₂CH(CH₃)₂ | OCH₃ | OCH₃ | CH | |
| CH₃ | H | 0 | Cl | CH₂CH(CH₃)₂ | CH₃ | CH₃ | N | |
| CH₃ | H | 0 | Cl | CH₂CH(CH₃)₂ | CH₃ | OCH₃ | N | |

TABLE III-continued

| R | R₁ | n | R₂ | R' | X | Y | Z | m.p. (°C.) |
|---|----|---|----|----|----|----|----|------------|
| CH₃ | H | 0 | Cl | CH₂CH(CH₃)₂ | OCH₃ | OCH₃ | N | |
| CH₃ | H | 0 | Cl | CH₂CH(CH₃)₂ | Cl | OCH₃ | CH | |
| CH₃ | H | 0 | Cl | CH(CH₃)CH₂CH₃ | CH₃ | CH₃ | CH | |
| CH₃ | H | 0 | Cl | CH(CH₃)CH₂CH₃ | CH₃ | OCH₃ | CH | |
| CH₃ | H | 0 | Cl | CH(CH₃)CH₂CH₃ | OCH₃ | OCH₃ | CH | |
| CH₃ | H | 0 | Cl | CH₂CH₂CH(CH₃)₂ | CH₃ | CH₃ | N | |
| CH₃ | H | 0 | Cl | CH₂CH₂CH(CH₃)₂ | CH₃ | OCH₃ | N | |
| CH₃ | H | 0 | Cl | CH₂CH₂CH(CH₃)₂ | OCH₃ | OCH₃ | N | |
| CH₃ | H | 0 | Cl | CH₂CH₂CH(CH₃)₂ | Cl | OCH₃ | CH | |
| CH₃ | H | 0 | Cl | CH₂N(CH₃)₂ | CH₃ | CH₃ | CH | |
| CH₃ | H | 0 | Cl | CH₂N(CH₃)₂ | CH₃ | OCH₃ | CH | |
| CH₃ | H | 0 | Cl | CH₂N(CH₃)₂ | OCH₃ | OCH₃ | CH | |
| CH₃ | H | 0 | Cl | CH₂N(CH₃)₂ | CH₃ | CH₃ | N | |
| CH₃ | H | 0 | Cl | CH₂N(CH₃)₂ | CH₃ | OCH₃ | N | |
| CH₃ | H | 0 | Cl | CH₂N(CH₃)₂ | OCH₃ | OCH₃ | N | |
| CH₃ | H | 0 | Cl | CH₂N(CH₃)₂ | Cl | OCH₃ | CH | |
| CH₃ | H | 0 | Cl | CH₂CH₂N(CH₃)₂ | CH₃ | CH₃ | CH | |
| CH₃ | H | 0 | Cl | CH₂CH₂N(CH₃)₂ | CH₃ | OCH₃ | CH | |
| CH₃ | H | 0 | Cl | CH₂CH₂N(CH₃)₂ | OCH₃ | OCH₃ | CH | |
| CH₃ | H | 0 | Cl | CH₂CH₂N(CH₃)₂ | CH₃ | CH₃ | N | |
| CH₃ | H | 0 | Cl | CH₂CH₂N(CH₃)₂ | CH₃ | OCH₃ | N | |
| CH₃ | H | 0 | Cl | CH₂CH₂N(CH₃)₂ | OCH₃ | OCH₃ | N | |
| CH₃ | H | 0 | Cl | CH₂CH₂N(CH₃)₂ | Cl | OCH₃ | CH | |
| CH₃ | H | 0 | Cl | CH₂CH=CH₂ | CH₃ | CH₃ | CH | |
| CH₃ | H | 0 | Cl | CH₂CH=CH₂ | CH₃ | OCH₃ | CH | |
| CH₃ | H | 0 | Cl | CH₂CH=CH₂ | OCH₃ | OCH₃ | CH | |
| CH₃ | H | 0 | Cl | CH₂CH=CH₂ | CH₃ | CH₃ | N | |
| CH₃ | H | 0 | Cl | CH₂CH=CH₂ | CH₃ | OCH₃ | N | |
| CH₃ | H | 0 | Cl | CH₂CH=CH₂ | OCH₃ | OCH₃ | N | |
| CH₃ | H | 0 | Cl | CH₂CH=CH₂ | Cl | OCH₃ | CH | |
| CH₃ | H | 0 | Cl | CH=CH₂ | CH₃ | CH₃ | CH | |
| CH₃ | H | 0 | Cl | CH=CH₂ | CH₃ | OCH₃ | CH | |
| CH₃ | H | 0 | Cl | CH=CH₂ | OCH₃ | OCH₃ | CH | |
| CH₃ | H | 0 | Cl | CH=CH₂ | CH₃ | CH₃ | N | |
| CH₃ | H | 0 | Cl | CH=CH₂ | CH₃ | OCH₃ | N | |
| CH₃ | H | 0 | Cl | CH=CH₂ | OCH₃ | OCH₃ | N | |
| CH₃ | H | 0 | Cl | CH=CH₂ | Cl | OCH₃ | CH | |
| CH₃ | H | 0 | Br | CH₃ | CH₃ | CH₃ | CH | |
| CH₃ | H | 0 | Br | CH₃ | CH₃ | OCH₃ | CH | |
| CH₃ | H | 0 | Br | CH₃ | OCH₃ | OCH₃ | CH | |
| CH₃ | H | 0 | Br | CH₃ | CH₃ | CH₃ | N | |
| CH₃ | H | 0 | Br | CH₃ | CH₃ | OCH₃ | N | |
| CH₃ | H | 0 | Br | CH₃ | OCH₃ | OCH₃ | N | |
| CH₃ | H | 0 | Br | CH₃ | Cl | OCH₃ | CH | |
| CH₃ | H | 0 | Br | CH₂CH₃ | CH₃ | CH₃ | CH | |
| CH₃ | H | 0 | Br | CH₂CH₃ | CH₃ | OCH₃ | CH | |
| CH₃ | H | 0 | Br | CH₂CH₃ | OCH₃ | OCH₃ | CH | |
| CH₃ | H | 0 | Br | CH₂CH₃ | CH₃ | CH₃ | N | |
| CH₃ | H | 0 | Br | CH₂CH₃ | CH₃ | OCH₃ | N | |
| CH₃ | H | 0 | Br | CH₂CH₃ | OCH₃ | OCH₃ | N | |
| CH₃ | H | 0 | Br | CH₂CH₃ | Cl | OCH₃ | CH | |
| CH₃ | H | 0 | Br | CH₂CH₂CH₃ | CH₃ | CH₃ | CH | |
| CH₃ | H | 0 | Br | CH₂CH₂CH₃ | CH₃ | OCH₃ | CH | |
| CH₃ | H | 0 | Br | CH₂CH₂CH₃ | OCH₃ | OCH₃ | CH | |
| CH₃ | H | 0 | Br | CH₂CH₂CH₃ | CH₃ | CH₃ | N | |
| CH₃ | H | 0 | Br | CH₂CH₂CH₃ | CH₃ | OCH₃ | N | |
| CH₃ | H | 0 | Br | CH₂CH₂CH₃ | OCH₃ | OCH₃ | N | |
| CH₃ | H | 0 | Br | CH₂CH₂CH₃ | Cl | OCH₃ | CH | |
| CH₃ | H | 0 | Br | CH₂CH₂CH₂CH₃ | CH₃ | CH₃ | CH | |
| CH₃ | H | 0 | Br | CH₂CH₂CH₂CH₃ | CH₃ | OCH₃ | CH | |
| CH₃ | H | 0 | Br | CH₂CH₂CH₂CH₃ | OCH₃ | OCH₃ | CH | |
| CH₃ | H | 0 | Br | CH₂CH₂CH₂CH₃ | CH₃ | CH₃ | N | |
| CH₃ | H | 0 | Br | CH₂CH₂CH₂CH₃ | CH₃ | OCH₃ | N | |
| CH₃ | H | 0 | Br | CH₂CH₂CH₂CH₃ | OCH₃ | OCH₃ | N | |
| CH₃ | H | 0 | Br | CH₂CH₂CH₂CH₃ | Cl | OCH₃ | CH | |
| CH₃ | H | 0 | N(CH₃)₂ | CH₃ | CH₃ | CH₃ | CH | |
| CH₃ | H | 0 | N(CH₃)₂ | CH₃ | CH₃ | OCH₃ | CH | |
| CH₃ | H | 0 | N(CH₃)₂ | CH₃ | OCH₃ | OCH₃ | CH | |
| CH₃ | H | 0 | N(CH₃)₂ | CH₃ | CH₃ | CH₃ | N | |
| CH₃ | H | 0 | N(CH₃)₂ | CH₃ | CH₃ | OCH₃ | N | |
| CH₃ | H | 0 | N(CH₃)₂ | CH₃ | OCH₃ | OCH₃ | N | |
| CH₃ | H | 0 | N(CH₃)₂ | CH₃ | Cl | OCH₃ | CH | |
| CH₃ | H | 0 | N(CH₃)₂ | CH₂CH₃ | CH₃ | CH₃ | CH | |
| CH₃ | H | 0 | N(CH₃)₂ | CH₂CH₃ | CH₃ | OCH₃ | CH | |
| CH₃ | H | 0 | N(CH₃)₂ | CH₂CH₃ | OCH₃ | OCH₃ | CH | |
| CH₃ | H | 0 | N(CH₃)₂ | CH₂CH₃ | CH₃ | CH₃ | N | |
| CH₃ | H | 0 | N(CH₃)₂ | CH₂CH₃ | CH₃ | OCH₃ | N | |
| CH₃ | H | 0 | N(CH₃)₂ | CH₂CH₃ | OCH₃ | OCH₃ | N | |
| CH₃ | H | 0 | N(CH₃)₂ | CH₂CH₃ | Cl | OCH₃ | CH | |
| CH₃ | H | 0 | N(CH₃)₂ | CH₂CH₂CH₃ | CH₃ | CH₃ | CH | |
| CH₃ | H | 0 | N(CH₃)₂ | CH₂CH₂CH₃ | CH₃ | OCH₃ | CH | |

TABLE III-continued

| R | R₁ | n | R₂ | R' | X | Y | Z | m.p. (°C.) |
|---|---|---|---|---|---|---|---|---|
| CH₃ | H | 0 | N(CH₃)₂ | CH₂CH₂CH₃ | OCH₃ | OCH₃ | CH | |
| CH₃ | H | 0 | N(CH₃)₂ | CH₂CH₂CH₃ | CH₃ | CH₃ | N | |
| CH₃ | H | 0 | N(CH₃)₂ | CH₂CH₂CH₃ | CH₃ | OCH₃ | N | |
| CH₃ | H | 0 | N(CH₃)₂ | CH₂CH₂CH₃ | OCH₃ | OCH₃ | N | |
| CH₃ | H | 0 | N(CH₃)₂ | CH₂CH₂CH₃ | Cl | OCH₃ | CH | |
| CH₃ | H | 0 | N(CH₃)₂ | CH₂CH₂CH₂CH₃ | CH₃ | CH₃ | CH | |
| CH₃ | H | 0 | N(CH₃)₂ | CH₂CH₂CH₂CH₃ | CH₃ | OCH₃ | CH | |
| CH₃ | H | 0 | N(CH₃)₂ | CH₂CH₂CH₂CH₃ | OCH₃ | OCH₃ | CH | |
| CH₃ | H | 0 | N(CH₃)₂ | CH₂CH₂CH₂CH₃ | CH₃ | CH₃ | N | |
| CH₃ | H | 0 | N(CH₃)₂ | CH₂CH₂CH₂CH₃ | CH₃ | OCH₃ | N | |
| CH₃ | H | 0 | N(CH₃)₂ | CH₂CH₂CH₂CH₃ | OCH₃ | OCH₃ | N | |
| CH₃ | H | 0 | N(CH₃)₂ | CH₂CH₂CH₂CH₃ | Cl | OCH₃ | CH | |
| CO₂CH₃ | H | 0 | H | CH₂CH₂CH₂CH₂CH₃ | CH₃ | CH₃ | CH | |
| CO₂CH₃ | H | 0 | H | CH₂CH₂CH₂CH₂CH₃ | CH₃ | OCH₃ | CH | |
| CO₂CH₃ | H | 0 | H | CH₂CH₂CH₂CH₂CH₃ | OCH₃ | OCH₃ | CH | |
| CO₂CH₃ | H | 0 | H | CH₂CH₂CH₂CH₂CH₃ | CH₃ | CH₃ | N | |
| CO₂CH₃ | H | 0 | H | CH₂CH₂CH₂CH₂CH₃ | CH₃ | OCH₃ | N | |
| CO₂CH₃ | H | 0 | H | CH₂CH₂CH₂CH₂CH₃ | OCH₃ | OCH₃ | N | |
| CO₂CH₃ | H | 0 | H | CH₂CH₂CH₂CH₂CH₃ | Cl | OCH₃ | CH | |
| CO₂CH₃ | H | 0 | H | CH(CH₃)₂ | CH₃ | CH₃ | CH | |
| CO₂CH₃ | H | 0 | H | CH(CH₃)₂ | CH₃ | OCH₃ | CH | |
| CO₂CH₃ | H | 0 | H | CH(CH₃)₂ | OCH₃ | OCH₃ | CH | |
| CO₂CH₃ | H | 0 | H | CH(CH₃)₂ | CH₃ | CH₃ | N | |
| CO₂CH₃ | H | 0 | H | CH(CH₃)₂ | CH₃ | OCH₃ | N | |
| CO₂CH₃ | H | 0 | H | CH(CH₃)₂ | OCH₃ | OCH₃ | N | |
| CO₂CH₃ | H | 0 | H | CH(CH₃)₂ | Cl | OCH₃ | CH | |
| CO₂CH₃ | H | 0 | H | CH₂CH(CH₃)₂ | CH₃ | CH₃ | CH | |
| CO₂CH₃ | H | 0 | H | CH₂CH(CH₃)₂ | CH₃ | OCH₃ | CH | |
| CO₂CH₃ | H | 0 | H | CH₂CH(CH₃)₂ | OCH₃ | OCH₃ | CH | |
| CO₂CH₃ | H | 0 | H | CH₂CH(CH₃)₂ | CH₃ | CH₃ | N | |
| CO₂CH₃ | H | 0 | H | CH₂CH(CH₃)₂ | CH₃ | OCH₃ | N | |
| CO₂CH₃ | H | 0 | H | CH₂CH(CH₃)₂ | OCH₃ | OCH₃ | N | |
| CO₂CH₃ | H | 0 | H | CH₂CH(CH₃)₂ | Cl | OCH₃ | CH | |
| CO₂CH₃ | H | 0 | H | CH(CH₃)CH₂CH₃ | CH₃ | CH₃ | CH | |
| CO₂CH₃ | H | 0 | H | CH(CH₃)CH₂CH₃ | CH₃ | OCH₃ | CH | |
| CO₂CH₃ | H | 0 | H | CH(CH₃)CH₂CH₃ | OCH₃ | OCH₃ | CH | |
| CO₂CH₃ | H | 0 | H | CH₂CH₂CH(CH₃)₂ | CH₃ | CH₃ | N | |
| CO₂CH₃ | H | 0 | H | CH₂CH₂CH(CH₃)₂ | CH₃ | OCH₃ | N | |
| CO₂CH₃ | H | 0 | H | CH₂CH₂CH(CH₃)₂ | OCH₃ | OCH₃ | N | |
| CO₂CH₃ | H | 0 | H | CH₂CH₂CH(CH₃)₂ | Cl | OCH₃ | CH | |

TABLE IV

| R | R₁ | n | R₂ | R' | X | Y | Z | m.p. (°C.) |
|---|---|---|---|---|---|---|---|---|
| CH₃ | H | 0 | H | CH₃ | CH₃ | CH₃ | CH | |
| CH₃ | H | 0 | H | CH₃ | CH₃ | OCH₃ | CH | |
| CH₃ | H | 0 | H | CH₃ | OCH₃ | OCH₃ | CH | |
| CH₃ | H | 0 | H | CH₃ | CH₃ | CH₃ | N | |
| CH₃ | H | 0 | H | CH₃ | CH₃ | OCH₃ | N | |
| CH₃ | H | 0 | H | CH₃ | OCH₃ | OCH₃ | N | |
| CH₃ | H | 0 | H | CH₃ | Cl | OCH₃ | CH | |
| CH₃ | H | 0 | H | CH₂CH₃ | CH₃ | CH₃ | CH | |
| CH₃ | H | 0 | H | CH₂CH₃ | CH₃ | OCH₃ | CH | |
| CH₃ | H | 0 | H | CH₂CH₃ | OCH₃ | OCH₃ | CH | |
| CH₃ | H | 0 | H | CH₂CH₃ | CH₃ | CH₃ | N | |
| CH₃ | H | 0 | H | CH₂CH₃ | CH₃ | OCH₃ | N | |
| CH₃ | H | 0 | H | CH₂CH₃ | OCH₃ | OCH₃ | N | |
| CH₃ | H | 0 | H | CH₂CH₃ | Cl | OCH₃ | CH | |
| CH₃ | H | 0 | H | CH₂CH₂CH₃ | CH₃ | CH₃ | CH | |
| CH₃ | H | 0 | H | CH₂CH₂CH₃ | CH₃ | OCH₃ | CH | |
| CH₃ | H | 0 | H | CH₂CH₂CH₃ | OCH₃ | OCH₃ | CH | |
| CH₃ | H | 0 | H | CH₂CH₂CH₃ | CH₃ | CH₃ | N | |
| CH₃ | H | 0 | H | CH₂CH₂CH₃ | CH₃ | OCH₃ | N | |
| CH₃ | H | 0 | H | CH₂CH₂CH₃ | OCH₃ | OCH₃ | N | |
| CH₃ | H | 0 | H | CH₂CH₂CH₃ | Cl | OCH₃ | CH | |
| CH₃ | H | 0 | H | CH₂CH₂CH₂CH₃ | CH₃ | CH₃ | CH | |
| CH₃ | H | 0 | H | CH₂CH₂CH₂CH₃ | OCH₃ | OCH₃ | CH | |
| CH₃ | H | 0 | H | CH₂CH₂CH₂CH₃ | CH₃ | CH₃ | N | |
| CH₃ | H | 0 | H | CH₂CH₂CH₂CH₃ | CH₃ | OCH₃ | N | |
| CH₃ | H | 0 | H | CH₂CH₂CH₂CH₃ | OCH₃ | OCH₃ | N | |
| CH₃ | H | 0 | H | CH₂CH₂CH₂CH₃ | Cl | OCH₃ | CH | |
| CH₃ | H | 0 | CH₃ | CH₂F | CH₃ | CH₃ | CH | |
| CH₃ | H | 0 | CH₃ | CH₂F | CH₃ | OCH₃ | CH | |
| CH₃ | H | 0 | CH₃ | CH₂F | OCH₃ | OCH₃ | CH | |
| CH₃ | H | 0 | CH₃ | CH₂F | CH₃ | CH₃ | N | |
| CH₃ | H | 0 | CH₃ | CH₂F | CH₃ | OCH₃ | N | |
| CH₃ | H | 0 | CH₃ | CH₂F | OCH₃ | OCH₃ | N | |
| CH₃ | H | 0 | CH₃ | CH₂F | Cl | OCH₃ | CH | |

TABLE IV-continued

| R | R₁ | n | R₂ | R' | X | Y | Z | m.p. (°C.) |
|---|---|---|---|---|---|---|---|---|
| CH₃ | H | 0 | CH₃ | CH₂CH₂F | CH₃ | CH₃ | CH | |
| CH₃ | H | 0 | CH₃ | CH₂CH₂F | CH₃ | OCH₃ | CH | |
| CH₃ | H | 0 | CH₃ | CH₂CH₂F | OCH₃ | OCH₃ | CH | |
| CH₃ | H | 0 | CH₃ | CH₂CH₂F | CH₃ | CH₃ | N | |
| CH₃ | H | 0 | CH₃ | CH₂CH₂F | CH₃ | OCH₃ | N | |
| CH₃ | H | 0 | CH₃ | CH₂CH₂F | OCH₃ | OCH₃ | N | |
| CH₃ | H | 0 | CH₃ | CH₂CH₂F | Cl | OCH₃ | CH | |
| CH₃ | H | 0 | CH₃ | CHF₂ | CH₃ | CH₃ | CH | |
| CH₃ | H | 0 | CH₃ | CHF₂ | CH₃ | OCH₃ | CH | |
| CH₃ | H | 0 | CH₃ | CHF₂ | OCH₃ | OCH₃ | CH | |
| CH₃ | H | 0 | CH₃ | CHF₂ | CH₃ | CH₃ | N | |
| CH₃ | H | 0 | CH₃ | CHF₂ | CH₃ | OCH₃ | N | |
| CH₃ | H | 0 | CH₃ | CHF₂ | OCH₃ | OCH₃ | N | |
| CH₃ | H | 0 | CH₃ | CHF₂ | Cl | OCH₃ | CH | |
| CH₃ | H | 0 | CH₃ | CH₂CF₃ | CH₃ | CH₃ | CH | |
| CH₃ | H | 0 | CH₃ | CH₂CF₃ | CH₃ | OCH₃ | CH | |
| CH₃ | H | 0 | CH₃ | CH₂CF₃ | OCH₃ | OCH₃ | CH | |
| CH₃ | H | 0 | CH₃ | CH₂Cl | CH₃ | CH₃ | N | |
| CH₃ | H | 0 | CH₃ | CH₂Cl | CH₃ | OCH₃ | N | |
| CH₃ | H | 0 | CH₃ | CH₂Cl | OCH₃ | OCH₃ | N | |
| CH₃ | H | 0 | CH₃ | CH₂Cl | Cl | OCH₃ | CH | |
| CH₃ | H | 0 | Cl | CH₃ | CH₃ | CH₃ | CH | |
| CH₃ | H | 0 | Cl | CH₃ | CH₃ | OCH₃ | CH | |
| CH₃ | H | 0 | Cl | CH₃ | OCH₃ | OCH₃ | CH | |
| CH₃ | H | 0 | Cl | CH₃ | CH₃ | CH₃ | N | |
| CH₃ | H | 0 | Cl | CH₃ | CH₃ | OCH₃ | N | |
| CH₃ | H | 0 | Cl | CH₃ | OCH₃ | OCH₃ | N | |
| CH₃ | H | 0 | Cl | CH₃ | Cl | OCH₃ | CH | |
| CH₃ | H | 0 | Cl | CH₂CH₃ | CH₃ | CH₃ | CH | |
| CH₃ | H | 0 | Cl | CH₂CH₃ | CH₃ | OCH₃ | CH | |
| CH₃ | H | 0 | Cl | CH₂CH₃ | OCH₃ | OCH₃ | CH | |
| CH₃ | H | 0 | Cl | CH₂CH₃ | CH₃ | CH₃ | N | |
| CH₃ | H | 0 | Cl | CH₂CH₃ | CH₃ | OCH₃ | N | |
| CH₃ | H | 0 | Cl | CH₂CH₃ | OCH₃ | OCH₃ | N | |
| CH₃ | H | 0 | Cl | CH₂CH₃ | Cl | OCH₃ | CH | |
| CH₃ | H | 0 | Cl | CH₂CH₂CH₃ | CH₃ | CH₃ | CH | |
| CH₃ | H | 0 | Cl | CH₂CH₂CH₃ | CH₃ | OCH₃ | CH | |
| CH₃ | H | 0 | Cl | CH₂CH₂CH₃ | OCH₃ | OCH₃ | CH | |
| CH₃ | H | 0 | Cl | CH₂CH₂CH₃ | CH₃ | CH₃ | N | |
| CH₃ | H | 0 | Cl | CH₂CH₂CH₃ | CH₃ | OCH₃ | N | |
| CH₃ | H | 0 | Cl | CH₂CH₂CH₃ | OCH₃ | OCH₃ | N | |
| CH₃ | H | 0 | Cl | CH₂CH₂CH₃ | Cl | OCH₃ | CH | |
| CH₃ | H | 0 | Cl | CH₂CH₂CH₂CH₃ | CH₃ | CH₃ | CH | |
| CH₃ | H | 0 | Cl | CH₂CH₂CH₂CH₃ | CH₃ | OCH₃ | CH | |
| CH₃ | H | 0 | Cl | CH₂CH₂CH₂CH₃ | OCH₃ | OCH₃ | CH | |
| CH₃ | H | 0 | Cl | CH₂CH₂CH₂CH₃ | CH₃ | CH₃ | N | |
| CH₃ | H | 0 | Cl | CH₂CH₂CH₂CH₃ | CH₃ | OCH₃ | N | |
| CH₃ | H | 0 | Cl | CH₂CH₂CH₂CH₃ | OCH₃ | OCH₃ | N | |
| CH₃ | H | 0 | Cl | CH₂CH₂CH₂CH₃ | Cl | OCH₃ | CH | |
| CH₃ | H | 0 | Cl | C(CH₃)=CH₂ | CH₃ | CH₃ | CH | |
| CH₃ | H | 0 | Cl | C(CH₃)=CH₂ | CH₃ | OCH₃ | CH | |
| CH₃ | H | 0 | Cl | C(CH₃)=CH₂ | OCH₃ | OCH₃ | CH | |
| CH₃ | H | 0 | Cl | C(CH₃)=CH₂ | CH₃ | CH₃ | N | |
| CH₃ | H | 0 | Cl | C(CH₃)=CH₂ | CH₃ | OCH₃ | N | |
| CH₃ | H | 0 | Cl | C(CH₃)=CH₂ | OCH₃ | OCH₃ | N | |
| CH₃ | H | 0 | Cl | C(CH₃)=CH₂ | Cl | OCH₃ | CH | |
| CH₃ | H | 0 | Cl | CH₂CH=CHCH₃ | CH₃ | CH₃ | CH | |
| CH₃ | H | 0 | Cl | CH=CH—CH₂CH₃ | CH₃ | OCH₃ | CH | |
| CH₃ | H | 0 | Cl | CH=CH—CH₂CH₃ | OCH₃ | OCH₃ | CH | |
| CH₃ | H | 0 | Cl | CH=CH—CH₂CH₃ | CH₃ | CH₃ | N | |
| CH₃ | H | 0 | Cl | CH=CH—CH₂CH₃ | CH₃ | OCH₃ | N | |
| CH₃ | H | 0 | Cl | CH=CH—CH₂CH₃ | OCH₃ | OCH₃ | N | |
| CH₃ | H | 0 | Cl | CH=CH—CH₂CH₃ | Cl | OCH₃ | CH | |
| CH₃ | H | 0 | Cl | CH=CHCH₂F | CH₃ | CH₃ | CH | |
| CH₃ | H | 0 | Cl | CH=CHCH₂F | CH₃ | OCH₃ | CH | |
| CH₃ | H | 0 | Cl | CH=CHCH₂F | OCH₃ | OCH₃ | CH | |
| CH₃ | H | 0 | Cl | CH=CHCH₂F | CH₃ | CH₃ | N | |
| CH₃ | H | 0 | Cl | CH=CHCH₂F | CH₃ | OCH₃ | N | |
| CH₃ | H | 0 | Cl | CH=CHCH₂F | OCH₃ | OCH₃ | N | |
| CH₃ | H | 0 | Cl | CH=CHCH₂F | Cl | OCH₃ | CH | |
| CH₃ | H | 0 | Cl | CH=CHF | CH₃ | CH₃ | CH | |
| CH₃ | H | 0 | Cl | CH=CHF | CH₃ | OCH₃ | CH | |
| CH₃ | H | 0 | Cl | CH=CHF | OCH₃ | OCH₃ | CH | |
| CH₃ | H | 0 | Cl | CH=CHF | CH₃ | CH₃ | N | |
| CH₃ | H | 0 | Cl | CH=CHF | CH₃ | OCH₃ | N | |
| CH₃ | H | 0 | Cl | CH=CHF | OCH₃ | OCH₃ | N | |
| CH₃ | H | 0 | Cl | CH=CHF | Cl | OCH₃ | CH | |
| CH₃ | H | 0 | CF₃ | CH₃ | CH₃ | CH₃ | CH | |
| CH₃ | H | 0 | CF₃ | CH₃ | CH₃ | OCH₃ | CH | |
| CH₃ | H | 0 | CF₃ | CH₃ | OCH₃ | OCH₃ | CH | |
| CH₃ | H | 0 | CF₃ | CH₃ | CH₃ | CH₃ | N | |

TABLE IV-continued

| R | R₁ | n | R₂ | R' | X | Y | Z | m.p. (°C.) |
|---|---|---|---|---|---|---|---|---|
| CH₃ | H | 0 | CF₃ | CH₃ | CH₃ | OCH₃ | N | |
| CH₃ | H | 0 | CF₃ | CH₃ | OCH₃ | OCH₃ | N | |
| CH₃ | H | 0 | CF₃ | CH₃ | Cl | OCH₃ | CH | |
| CH₃ | H | 0 | CF₃ | CH₂CH₃ | CH₃ | CH₃ | CH | |
| CH₃ | H | 0 | CF₃ | CH₂CH₃ | CH₃ | OCH₃ | CH | |
| CH₃ | H | 0 | CF₃ | CH₂CH₃ | OCH₃ | OCH₃ | CH | |
| CH₃ | H | 0 | CF₃ | CH₂CH₃ | CH₃ | CH₃ | N | |
| CH₃ | H | 0 | CF₃ | CH₂CH₃ | CH₃ | OCH₃ | N | |
| CH₃ | H | 0 | CF₃ | CH₂CH₃ | OCH₃ | OCH₃ | N | |
| CH₃ | H | 0 | CF₃ | CH₂CH₃ | Cl | OCH₃ | CH | |
| CH₃ | H | 0 | CF₃ | CH₂CH₂CH₃ | CH₃ | CH₃ | CH | |
| CH₃ | H | 0 | CF₃ | CH₂CH₂CH₃ | CH₃ | OCH₃ | CH | |
| CH₃ | H | 0 | CF₃ | CH₂CH₂CH₃ | OCH₃ | OCH₃ | CH | |
| CH₃ | H | 0 | CF₃ | CH₂CH₂CH₃ | CH₃ | CH₃ | N | |
| CH₃ | H | 0 | CF₃ | CH₂CH₂CH₃ | CH₃ | OCH₃ | N | |
| CH₃ | H | 0 | CF₃ | CH₂CH₂CH₃ | OCH₃ | OCH₃ | N | |
| CH₃ | H | 0 | CF₃ | CH₂CH₂CH₃ | Cl | OCH₃ | CH | |
| CH₃ | H | 0 | CF₃ | CH₂CH₂CH₂CH₃ | CH₃ | CH₃ | CH | |
| CH₃ | H | 0 | CF₃ | CH₂CH₂CH₂CH₃ | CH₃ | OCH₃ | CH | |
| CH₃ | H | 0 | CF₃ | CH₂CH₂CH₂CH₃ | OCH₃ | OCH₃ | CH | |
| CH₃ | H | 0 | CF₃ | CH₂CH₂CH₂CH₃ | CH₃ | CH₃ | N | |
| CH₃ | H | 0 | CF₃ | CH₂CH₂CH₂CH₃ | CH₃ | OCH₃ | N | |
| CH₃ | H | 0 | CF₃ | CH₂CH₂CH₂CH₃ | OCH₃ | OCH₃ | N | |
| CH₃ | H | 0 | CF₃ | CH₂CH₂CH₂CH₃ | Cl | OCH₃ | CH | |
| CH₃ | H | 0 | CO₂CH₃ | CH₃ | CH₃ | CH₃ | CH | |
| CH₃ | H | 0 | CO₂CH₃ | CH₃ | CH₃ | OCH₃ | CH | |
| CH₃ | H | 0 | CO₂CH₃ | CH₃ | OCH₃ | OCH₃ | CH | |
| CH₃ | H | 0 | CO₂CH₃ | CH₃ | CH₃ | CH₃ | N | |
| CH₃ | H | 0 | CO₂CH₃ | CH₃ | CH₃ | OCH₃ | N | |
| CH₃ | H | 0 | CO₂CH₃ | CH₃ | OCH₃ | OCH₃ | N | |
| CH₃ | H | 0 | CO₂CH₃ | CH₃ | Cl | OCH₃ | CH | |
| CH₃ | H | 0 | CO₂CH₃ | CH₂CH₃ | CH₃ | CH₃ | CH | |
| CH₃ | H | 0 | CO₂CH₃ | CH₂CH₃ | CH₃ | OCH₃ | CH | |
| CH₃ | H | 0 | CO₂CH₃ | CH₂CH₃ | OCH₃ | OCH₃ | CH | |
| CH₃ | H | 0 | CO₂CH₃ | CH₂CH₃ | CH₃ | CH₃ | N | |
| CH₃ | H | 0 | CO₂CH₃ | CH₂CH₃ | CH₃ | OCH₃ | N | |
| CH₃ | H | 0 | CO₂CH₃ | CH₂CH₃ | OCH₃ | OCH₃ | N | |
| CH₃ | H | 0 | CO₂CH₃ | CH₂CH₃ | Cl | OCH₃ | CH | |
| CH₃ | H | 0 | CO₂CH₃ | CH₂CH₂CH₃ | CH₃ | CH₃ | CH | |
| CH₃ | H | 0 | CO₂CH₃ | CH₂CH₂CH₃ | CH₃ | OCH₃ | CH | |
| CH₃ | H | 0 | CO₂CH₃ | CH₂CH₂CH₃ | OCH₃ | OCH₃ | CH | |
| CH₃ | H | 0 | CO₂CH₃ | CH₂CH₂CH₃ | CH₃ | CH₃ | N | |
| CH₃ | H | 0 | CO₂CH₃ | CH₂CH₂CH₃ | CH₃ | OCH₃ | N | |
| CH₃ | H | 0 | CO₂CH₃ | CH₂CH₂CH₃ | OCH₃ | OCH₃ | N | |
| CH₃ | H | 0 | CO₂CH₃ | CH₂CH₂CH₃ | Cl | OCH₃ | CH | |
| CH₃ | H | 0 | CO₂CH₃ | CH₂CH₂CH₂CH₃ | CH₃ | CH₃ | CH | |
| CH₃ | H | 0 | CO₂CH₃ | CH₂CH₂CH₂CH₃ | CH₃ | OCH₃ | CH | |
| CH₃ | H | 0 | CO₂CH₃ | CH₂CH₂CH₂CH₃ | OCH₃ | OCH₃ | CH | |
| CH₃ | H | 0 | CO₂CH₃ | CH₂CH₂CH₂CH₃ | CH₃ | CH₃ | N | |
| CH₃ | H | 0 | CO₂CH₃ | CH₂CH₂CH₂CH₃ | CH₃ | OCH₃ | N | |
| CH₃ | H | 0 | CO₂CH₃ | CH₂CH₂CH₂CH₃ | OCH₃ | OCH₃ | N | |
| CH₃ | H | 0 | CO₂CH₃ | CH₂CH₂CH₂CH₃ | Cl | OCH₃ | CH | |
| CH₂CN | H | 0 | H | CH₂F | CH₃ | CH₃ | CH | |
| CH₂CN | H | 0 | H | CH₂F | CH₃ | OCH₃ | CH | |
| CH₂CN | H | 0 | H | CH₂F | OCH₃ | OCH₃ | CH | |
| CH₂CN | H | 0 | H | CH₂F | CH₃ | CH₃ | N | |
| CH₂CN | H | 0 | H | CH₂F | CH₃ | OCH₃ | N | |
| CH₂CN | H | 0 | H | CH₂F | OCH₃ | OCH₃ | N | |
| CH₂CN | H | 0 | H | CH₂F | Cl | OCH₃ | CH | |
| CH₂CN | H | 0 | H | CH₂CH₂F | CH₃ | CH₃ | CH | |
| CH₂CN | H | 0 | H | CH₂CH₂F | CH₃ | OCH₃ | CH | |
| CH₂CN | H | 0 | H | CH₂CH₂F | OCH₃ | OCH₃ | CH | |
| CH₂CN | H | 0 | H | CH₂CH₂F | CH₃ | CH₃ | N | |
| CH₂CN | H | 0 | H | CH₂CH₂F | CH₃ | OCH₃ | N | |
| CH₂CN | H | 0 | H | CH₂CH₂F | OCH₃ | OCH₃ | N | |
| CH₂CN | H | 0 | H | CH₂CH₂F | Cl | OCH₃ | CH | |
| CH₂CN | H | 0 | H | CHF₂ | CH₃ | CH₃ | CH | |
| CH₂CN | H | 0 | H | CHF₂ | CH₃ | OCH₃ | CH | |
| CH₂CN | H | 0 | H | CHF₂ | OCH₃ | OCH₃ | CH | |
| CH₂CN | H | 0 | H | CHF₂ | CH₃ | CH₃ | N | |
| CH₂CN | H | 0 | H | CHF₂ | CH₃ | OCH₃ | N | |
| CH₂CN | H | 0 | H | CHF₂ | OCH₃ | OCH₃ | N | |
| CH₂CN | H | 0 | H | CHF₂ | Cl | OCH₃ | CH | |
| CH₂CN | H | 0 | H | CH₂CF₃ | CH₃ | CH₃ | CH | |
| CH₂CN | H | 0 | H | CH₂CF₃ | CH₃ | OCH₃ | CH | |
| CH₂CN | H | 0 | H | CH₂CF₃ | OCH₃ | OCH₃ | CH | |
| CH₂CN | H | 0 | H | CH₂Cl | CH₃ | CH₃ | N | |
| CH₂CN | H | 0 | H | CH₂Cl | CH₃ | OCH₃ | N | |
| CH₂CN | H | 0 | H | CH₂Cl | OCH₃ | OCH₃ | N | |

TABLE IV-continued

| R | R₁ | n | R₂ | R' | X | Y | Z | m.p. (°C.) |
|---|----|----|----|----|----|----|----|----|
| CH₂CN | H | 0 | H | CH₂Cl | Cl | OCH₃ | CH | |

TABLE V

| R₁ | R₂ | R' | X | Y | Z | m.p. (°C.) |
|----|----|----|----|----|----|----|
| H | H | cyclopropyl | CH₃ | CH₃ | CH | 154–157 |
| H | H | cyclopropyl | CH₃ | OCH₃ | CH | 167–171 |
| H | H | cyclopropyl | OCH₃ | OCH₃ | CH | 165–168 |
| H | H | cyclopropyl | CH₃ | CH₃ | N | |
| H | H | cyclopropyl | CH₃ | OCH₃ | N | 146–148 |
| H | H | cyclopropyl | OCH₃ | OCH₃ | N | 146–149 |
| H | H | cyclopropyl | Cl | OCH₃ | CH | 122–125 |
| H | H | cyclobutyl | CH₃ | CH₃ | CH | |
| H | H | cyclobutyl | CH₃ | OCH₃ | CH | |
| H | H | cyclobutyl | OCH₃ | OCH₃ | CH | |
| H | H | cyclobutyl | CH₃ | CH₃ | N | |
| H | H | cyclobutyl | CH₃ | OCH₃ | N | |
| H | H | cyclobutyl | OCH₃ | OCH₃ | N | |
| H | H | cyclobutyl | Cl | OCH₃ | CH | |
| H | H | 2-fluorocyclopropyl | CH₃ | CH₃ | CH | |
| H | H | 2-fluorocyclopropyl | CH₃ | OCH₃ | CH | |
| H | H | 2-fluorocyclopropyl | OCH₃ | OCH₃ | CH | |
| H | H | 2-fluorocyclopropyl | CH₃ | CH₃ | N | |
| H | H | 2-fluorocyclopropyl | CH₃ | OCH₃ | N | |
| H | H | 2-fluorocyclopropyl | OCH₃ | OCH₃ | N | |
| H | H | 2-fluorocyclopropyl | Cl | OCH₃ | CH | |
| H | H | 2,2-difluorocyclopropl | CH₃ | CH₃ | CH | |
| H | H | 2,2-difluorocyclopropl | CH₃ | OCH₃ | CH | |
| H | H | 2,2-difluorocyclopropl | OCH₃ | OCH₃ | CH | |
| H | H | 2,2-difluorocyclopropyl | CH₃ | CH₃ | N | |
| H | H | 2,2-difluorocyclopropyl | CH₃ | OCH₃ | N | |
| H | H | 2,2-difluorocyclopropyl | OCH₃ | OCH₃ | N | |
| H | H | 2,2-difluorocyclopropyl | Cl | OCH₃ | CH | |
| H | CH₃ | cyclopropyl | CH₃ | CH₃ | CH | |
| H | CH₃ | cyclopropyl | CH₃ | OCH₃ | CH | |
| H | CH₃ | cyclopropyl | OCH₃ | OCH₃ | CH | |
| H | CH₃ | cyclopropyl | CH₃ | CH₃ | N | |
| H | CH₃ | cyclopropyl | CH₃ | OCH₃ | N | |
| H | CH₃ | cyclopropyl | OCH₃ | OCH₃ | N | |
| H | CH₃ | cyclopropyl | Cl | OCH₃ | CH | |
| H | CH₃ | cyclobutyl | CH₃ | CH₃ | CH | |
| H | CH₃ | cyclobutyl | CH₃ | OCH₃ | CH | |
| H | CH₃ | cyclobutyl | OCH₃ | OCH₃ | CH | |
| H | CH₃ | cyclobutyl | CH₃ | CH₃ | N | |
| H | CH₃ | cyclobutyl | CH₃ | OCH₃ | N | |
| H | CH₃ | cyclobutyl | OCH₃ | OCH₃ | N | |
| H | CH₃ | cyclobutyl | Cl | OCH₃ | CH | |
| H | CH₃ | 2-fluorocyclopropyl | CH₃ | CH₃ | CH | |
| H | CH₃ | 2-fluorocyclopropyl | CH₃ | OCH₃ | CH | |
| H | CH₃ | 2-fluorocyclopropyl | OCH₃ | OCH₃ | CH | |
| H | CH₃ | 2-fluorocyclopropyl | CH₃ | CH₃ | N | |
| H | CH₃ | 2-fluorocyclopropyl | CH₃ | OCH₃ | N | |
| H | CH₃ | 2-fluorocyclopropyl | OCH₃ | OCH₃ | N | |
| H | CH₃ | 2-fluorocyclopropyl | Cl | OCH₃ | CH | |
| H | CH₃ | 2,2-difluorocyclopropyl | CH₃ | CH₃ | CH | |
| H | CH₃ | 2,2-difluorocyclopropyl | CH₃ | OCH₃ | CH | |
| H | CH₃ | 2,2-difluorocyclopropyl | OCH₃ | OCH₃ | CH | |
| H | CH₃ | 2,2-difluorocyclopropyl | CH₃ | CH₃ | N | |
| H | CH₃ | 2,2-difluorocyclopropyl | CH₃ | OCH₃ | N | |
| H | CH₃ | 2,2-difluorocyclopropyl | OCH₃ | OCH₃ | N | |
| H | CH₃ | 2,2-difluorocyclopropyl | Cl | OCH₃ | CH | |
| H | Cl | cyclopropyl | CH₃ | CH₃ | CH | |
| H | Cl | cyclopropyl | CH₃ | OCH₃ | CH | |
| H | Cl | cyclopropyl | OCH₃ | OCH₃ | CH | |
| H | Cl | cyclopropyl | CH₃ | CH₃ | N | |
| H | Cl | cyclopropyl | CH₃ | OCH₃ | N | |
| H | Cl | cyclopropyl | OCH₃ | OCH₃ | N | |
| H | Cl | cyclopropyl | Cl | OCH₃ | CH | |
| H | Cl | cyclobutyl | CH₃ | CH₃ | CH | |
| H | Cl | cyclobutyl | CH₃ | OCH₃ | CH | |
| H | Cl | cyclobutyl | OCH₃ | OCH₃ | CH | |
| H | Cl | cyclobutyl | CH₃ | CH₃ | N | |
| H | Cl | cyclobutyl | CH₃ | OCH₃ | N | |
| H | Cl | cyclobutyl | OCH₃ | OCH₃ | N | |
| H | Cl | cyclobutyl | Cl | OCH₃ | CH | |
| H | Cl | 2-fluorocyclopropyl | CH₃ | CH₃ | CH | |
| H | Cl | 2-fluorocyclopropyl | CH₃ | OCH₃ | CH | |
| H | Cl | 2-fluorocyclopropyl | OCH₃ | OCH₃ | CH | |
| H | Cl | 2-fluorocyclopropyl | CH₃ | CH₃ | N | |

TABLE V-continued

| R₁ | R₂ | R' | X | Y | Z | m.p. (°C.) |
|---|---|---|---|---|---|---|
| H | Cl | 2-fluorocyclopropyl | CH₃ | OCH₃ | N | |
| H | Cl | 2-fluorocyclopropyl | OCH₃ | OCH₃ | N | |
| H | Cl | 2-fluorocyclopropyl | Cl | OCH₃ | CH | |
| H | Cl | 2,2-difluorocyclopropyl | CH₃ | CH₃ | CH | |
| H | Cl | 2,2-difluorocyclopropyl | CH₃ | OCH₃ | CH | |
| H | Cl | 2,2-difluorocyclopropyl | OCH₃ | OCH₃ | CH | |
| H | Cl | 2,2-difluorocyclopropyl | CH₃ | CH₃ | N | |
| H | Cl | 2,2-difluorocyclopropyl | CH₃ | OCH₃ | N | |
| H | Cl | 2,2-difluorocyclopropyl | OCH₃ | OCH₃ | N | |
| H | Cl | 2,2-difluorocyclopropyl | Cl | OCH₃ | CH | |
| H | F | cyclopropyl | CH₃ | CH₃ | CH | |
| H | F | cyclopropyl | CH₃ | OCH₃ | CH | |
| H | F | cyclopropyl | OCH₃ | OCH₃ | CH | |
| H | F | cyclopropyl | CH₃ | CH₃ | N | |
| H | F | cyclopropyl | CH₃ | OCH₃ | N | |
| H | F | cyclopropyl | OCH₃ | OCH₃ | N | |
| H | F | cyclopropyl | Cl | OCH₃ | CH | |
| H | F | cyclobutyl | CH₃ | CH₃ | CH | |
| H | F | cyclobutyl | CH₃ | OCH₃ | CH | |
| H | F | cyclobutyl | OCH₃ | OCH₃ | CH | |
| H | F | cyclobutyl | CH₃ | CH₃ | N | |
| H | F | cyclobutyl | CH₃ | OCH₃ | N | |
| H | F | cyclobutyl | OCH₃ | OCH₃ | N | |
| H | F | cyclobutyl | Cl | OCH₃ | CH | |
| H | F | 2-fluorocyclopropyl | CH₃ | CH₃ | CH | |
| H | F | 2-fluorocyclopropyl | CH₃ | OCH₃ | CH | |
| H | F | 2-fluorocyclopropyl | OCH₃ | OCH₃ | CH | |
| H | F | 2-fluorocyclopropyl | CH₃ | CH₃ | N | |
| H | F | 2-fluorocyclopropyl | CH₃ | OCH₃ | N | |
| H | F | 2-fluorocyclopropyl | OCH₃ | OCH₃ | N | |
| H | F | 2-fluorocyclopropyl | Cl | OCH₃ | CH | |
| H | F | 2,2-difluorocyclopropyl | CH₃ | CH₃ | CH | |
| H | F | 2,2-difluorocyclopropyl | CH₃ | OCH₃ | CH | |
| H | F | 2,2-difluorocyclopropyl | OCH₃ | OCH₃ | CH | |
| H | F | 2,2-difluorocyclopropyl | CH₃ | CH₃ | N | |
| H | F | 2,2-difluorocyclopropyl | CH₃ | OCH₃ | N | |
| H | F | 2,2-difluorocyclopropyl | OCH₃ | OCH₃ | N | |
| H | F | 2,2-difluorocyclopropyl | Cl | OCH₃ | CH | |
| H | OCH₃ | cyclopropyl | CH₃ | CH₃ | CH | |
| H | OCH₃ | cyclopropyl | CH₃ | OCH₃ | CH | |
| H | OCH₃ | cyclopropyl | OCH₃ | OCH₃ | CH | |
| H | OCH₃ | cyclopropyl | CH₃ | CH₃ | N | |
| H | OCH₃ | cyclopropyl | CH₃ | OCH₃ | N | |
| H | OCH₃ | cyclopropyl | OCH₃ | OCH₃ | N | |
| H | OCH₃ | cyclopropyl | Cl | OCH₃ | CH | |
| H | OCH₃ | cyclobutyl | CH₃ | CH₃ | CH | |
| H | OCH₃ | cyclobutyl | CH₃ | OCH₃ | CH | |
| H | OCH₃ | cyclobutyl | OCH₃ | OCH₃ | CH | |
| H | OCH₃ | cyclobutyl | CH₃ | CH₃ | N | |
| H | OCH₃ | cyclobutyl | CH₃ | OCH₃ | N | |
| H | OCH₃ | cyclobutyl | OCH₃ | OCH₃ | N | |
| H | OCH₃ | cyclobutyl | Cl | OCH₃ | CH | |
| H | OCH₃ | 2-fluorocyclopropyl | CH₃ | CH₃ | CH | |
| H | OCH₃ | 2-fluorocyclopropyl | CH₃ | OCH₃ | CH | |
| H | OCH₃ | 2-fluorocyclopropyl | OCH₃ | OCH₃ | CH | |
| H | OCH₃ | 2-fluorocyclopropyl | CH₃ | CH₃ | N | |
| H | OCH₃ | 2-fluorocyclopropyl | CH₃ | OCH₃ | N | |
| H | OCH₃ | 2-fluorocyclopropyl | OCH₃ | OCH₃ | N | |
| H | OCH₃ | 2-fluorocyclopropyl | Cl | OCH₃ | CH | |
| H | OCH₃ | 2,2-difluorocyclopropyl | CH₃ | CH₃ | CH | |
| H | OCH₃ | 2,2-difluorocyclopropyl | CH₃ | OCH₃ | CH | |
| H | OCH₃ | 2,2-difluorocyclopropyl | OCH₃ | OCH₃ | CH | |
| H | OCH₃ | 2,2-difluorocyclopropyl | CH₃ | CH₃ | N | |
| H | OCH₃ | 2,2-difluorocyclopropyl | CH₃ | OCH₃ | N | |
| H | OCH₃ | 2,2-difluorocyclopropyl | OCH₃ | OCH₃ | N | |
| H | OCH₃ | 2,2-difluorocyclopropyl | Cl | OCH₃ | CH | |
| H | SCH₃ | cyclopropyl | CH₃ | CH₃ | CH | |
| H | SCH₃ | cyclopropyl | CH₃ | OCH₃ | CH | |
| H | SCH₃ | cyclopropyl | OCH₃ | OCH₃ | CH | |
| H | SCH₃ | cyclopropyl | CH₃ | CH₃ | N | |
| H | SCH₃ | cyclopropyl | CH₃ | OCH₃ | N | |
| H | SCH₃ | cyclopropyl | OCH₃ | OCH₃ | N | |
| H | SCH₃ | cyclopropyl | Cl | OCH₃ | CH | |
| H | SCH₃ | cyclobutyl | CH₃ | CH₃ | CH | |
| H | SCH₃ | cyclobutyl | CH₃ | OCH₃ | CH | |
| H | SCH₃ | cyclobutyl | OCH₃ | OCH₃ | CH | |
| H | SCH₃ | cyclobutyl | CH₃ | CH₃ | N | |
| H | SCH₃ | cyclobutyl | CH₃ | OCH₃ | N | |
| H | SCH₃ | cyclobutyl | OCH₃ | OCH₃ | N | |
| H | SCH₃ | cyclobutyl | Cl | OCH₃ | CH | |
| H | SCH₃ | 2-fluorocyclopropyl | CH₃ | CH₃ | CH | |

TABLE V-continued

| R₁ | R₂ | R' | X | Y | Z | m.p. (°C.) |
|---|---|---|---|---|---|---|
| H | SCH₃ | 2-fluorocyclopropyl | CH₃ | CH₃ | CH | |
| H | SCH₃ | 2-fluorocyclopropyl | CH₃ | OCH₃ | CH | |
| H | SCH₃ | 2-fluorocyclopropyl | OCH₃ | OCH₃ | CH | |
| H | SCH₃ | 2-fluorocyclopropyl | CH₃ | CH₃ | N | |
| H | SCH₃ | 2-fluorocyclopropyl | CH₃ | OCH₃ | N | |
| H | SCH₃ | 2-fluorocyclopropyl | OCH₃ | OCH₃ | N | |
| H | SCH₃ | 2-fluorocyclopropyl | Cl | OCH₃ | CH | |
| H | SCH₃ | 2,2-difluorocyclopropyl | CH₃ | CH₃ | CH | |
| H | SCH₃ | 2,2-difluorocyclopropyl | CH₃ | OCH₃ | CH | |
| H | SCH₃ | 2,2-difluorocyclopropyl | OCH₃ | OCH₃ | CH | |
| H | SCH₃ | 2,2-difluorocyclopropyl | CH₃ | CH₃ | N | |
| H | SCH₃ | 2,2-difluorocyclopropyl | CH₃ | OCH₃ | N | |
| H | SCH₃ | 2,2-difluorocyclopropyl | OCH₃ | OCH₃ | N | |
| H | SCH₃ | 2,2-difluorocyclopropyl | Cl | OCH₃ | CH | |
| H | CO₂CH₃ | cyclopropyl | CH₃ | CH₃ | CH | |
| H | CO₂CH₃ | cyclopropyl | CH₃ | OCH₃ | CH | |
| H | CO₂CH₃ | cyclopropyl | OCH₃ | OCH₃ | CH | |
| H | CO₂CH₃ | cyclopropyl | CH₃ | CH₃ | N | |
| H | CO₂CH₃ | cyclopropyl | CH₃ | OCH₃ | N | |
| H | CO₂CH₃ | cyclopropyl | OCH₃ | OCH₃ | N | |
| H | CO₂CH₃ | cyclopropyl | Cl | OCH₃ | CH | |
| H | CO₂CH₃ | cyclobutyl | CH₃ | CH₃ | CH | |
| H | CO₂CH₃ | cyclobutyl | CH₃ | OCH₃ | CH | |
| H | CO₂CH₃ | cyclobutyl | OCH₃ | OCH₃ | CH | |
| H | CO₂CH₃ | cyclobutyl | CH₃ | CH₃ | N | |
| H | CO₂CH₃ | cyclobutyl | CH₃ | OCH₃ | N | |
| H | CO₂CH₃ | cyclobutyl | OCH₃ | OCH₃ | N | |
| H | CO₂CH₃ | cyclobutyl | Cl | OCH₃ | CH | |
| H | CO₂CH₃ | 2-fluorocyclopropyl | CH₃ | CH₃ | CH | |
| H | CO₂CH₃ | 2-fluorocyclopropyl | CH₃ | OCH₃ | CH | |
| H | CO₂CH₃ | 2-fluorocyclopropyl | OCH₃ | OCH₃ | CH | |
| H | CO₂CH₃ | 2-fluorocyclopropyl | CH₃ | CH₃ | N | |
| H | CO₂CH₃ | 2-fluorocyclopropyl | CH₃ | OCH₃ | N | |
| H | CO₂CH₃ | 2-fluorocyclopropyl | OCH₃ | OCH₃ | N | |
| H | CO₂CH₃ | 2-fluorocyclopropyl | Cl | OCH₃ | CH | |
| H | CO₂CH₃ | 2,2-difluorocyclopropyl | CH₃ | CH₃ | CH | |
| H | CO₂CH₃ | 2,2-difluorocyclopropyl | CH₃ | OCH₃ | CH | |
| H | CO₂CH₃ | 2,2-difluorocyclopropyl | OCH₃ | OCH₃ | CH | |
| H | CO₂CH₃ | 2,2-difluorocyclopropyl | CH₃ | CH₃ | N | |
| H | CO₂CH₃ | 2,2-difluorocyclopropyl | CH₃ | OCH₃ | N | |
| H | CO₂CH₃ | 2,2-difluorocyclopropyl | OCH₃ | OCH₃ | N | |
| H | CO₂CH₃ | 2,2-difluorocyclopropyl | Cl | OCH₃ | CH | |
| H | N(CH₃)₂ | cyclopropyl | CH₃ | CH₃ | CH | |
| H | N(CH₃)₂ | cyclopropyl | CH₃ | OCH₃ | CH | |
| H | N(CH₃)₂ | cyclopropyl | OCH₃ | OCH₃ | CH | |
| H | N(CH₃)₂ | cyclopropyl | CH₃ | CH₃ | N | |
| H | N(CH₃)₂ | cyclopropyl | CH₃ | OCH₃ | N | |
| H | N(CH₃)₂ | cyclopropyl | OCH₃ | OCH₃ | N | |
| H | N(CH₃)₂ | cyclopropyl | Cl | OCH₃ | CH | |
| H | N(CH₃)₂ | cyclobutyl | CH₃ | CH₃ | CH | |
| H | N(CH₃)₂ | cyclobutyl | CH₃ | OCH₃ | CH | |
| H | N(CH₃)₂ | cyclobutyl | OCH₃ | OCH₃ | CH | |
| H | N(CH₃)₂ | cyclobutyl | CH₃ | CH₃ | N | |
| H | N(CH₃)₂ | cyclobutyl | CH₃ | OCH₃ | N | |
| H | N(CH₃)₂ | cyclobutyl | OCH₃ | OCH₃ | N | |
| H | N(CH₃)₂ | cyclobutyl | Cl | OCH₃ | CH | |
| H | N(CH₃)₂ | 2-fluorocyclopropyl | CH₃ | CH₃ | CH | |
| H | N(CH₃)₂ | 2-fluorocyclopropyl | CH₃ | OCH₃ | CH | |
| H | N(CH₃)₂ | 2-fluorocyclopropyl | OCH₃ | OCH₃ | CH | |
| H | N(CH₃)₂ | 2-fluorocyclopropyl | CH₃ | CH₃ | N | |
| H | N(CH₃)₂ | 2-fluorocyclopropyl | CH₃ | OCH₃ | N | |
| H | N(CH₃)₂ | 2-fluorocyclopropyl | OCH₃ | OCH₃ | N | |
| H | N(CH₃)₂ | 2-fluorocyclopropyl | Cl | OCH₃ | CH | |
| H | N(CH₃)₂ | 2,2-difluorocyclopropyl | CH₃ | CH₃ | CH | |
| H | N(CH₃)₂ | 2,2-difluorocyclopropyl | CH₃ | OCH₃ | CH | |
| H | N(CH₃)₂ | 2,2-difluorocyclopropyl | OCH₃ | OCH₃ | CH | |
| H | N(CH₃)₂ | 2,2-difluorocyclopropyl | CH₃ | CH₃ | N | |
| H | N(CH₃)₂ | 2,2-difluorocyclopropyl | CH₃ | OCH₃ | N | |
| H | N(CH₃)₂ | 2,2-difluorocyclopropyl | OCH₃ | OCH₃ | N | |
| H | N(CH₃)₂ | 2,2-difluorocyclopropyl | Cl | OCH₃ | CH | |
| H | CH₂CN | cyclopropyl | CH₃ | CH₃ | CH | |
| H | CH₂CN | cyclopropyl | CH₃ | OCH₃ | CH | |
| H | CH₂CN | cyclopropyl | OCH₃ | OCH₃ | CH | |
| H | CH₂CN | cyclopropyl | CH₃ | CH₃ | N | |
| H | CH₂CN | cyclopropyl | CH₃ | OCH₃ | N | |
| H | CH₂CN | cyclopropyl | OCH₃ | OCH₃ | N | |
| H | CH₂CN | cyclopropyl | Cl | OCH₃ | CH | |
| H | CH₂CN | cyclobutyl | CH₃ | CH₃ | CH | |
| H | CH₂CN | cyclobutyl | CH₃ | OCH₃ | CH | |
| H | CH₂CN | cyclobutyl | OCH₃ | OCH₃ | CH | |
| H | CH₂CN | cyclobutyl | CH₃ | CH₃ | N | |
| H | CH₂CN | cyclobutyl | CH₃ | OCH₃ | N | |

TABLE V-continued

| R₁ | R₂ | R' | X | Y | Z | m.p. (°C.) |
|---|---|---|---|---|---|---|
| H | CH₂CN | cyclobutyl | OCH₃ | OCH₃ | N | |
| H | CH₂CN | cyclobutyl | Cl | OCH₃ | CH | |
| H | CH₂CN | 2-fluorocyclopropyl | CH₃ | CH₃ | CH | |
| H | CH₂CN | 2-fluorocyclopropyl | CH₃ | OCH₃ | CH | |
| H | CH₂CN | 2-fluorocyclopropyl | OCH₃ | OCH₃ | CH | |
| H | CH₂CN | 2-fluorocyclopropyl | CH₃ | CH₃ | N | |
| H | CH₂CN | 2-fluorocyclopropyl | CH₃ | OCH₃ | N | |
| H | CH₂CN | 2-fluorocyclopropyl | OCH₃ | OCH₃ | N | |
| H | CH₂CN | 2-fluorocyclopropyl | Cl | OCH₃ | CH | |
| H | CH₂CN | 2,2-difluorocyclopropyl | CH₃ | CH₃ | CH | |
| H | CH₂CN | 2,2-difluorocyclopropyl | CH₃ | OCH₃ | CH | |
| H | CH₂CN | 2,2-difluorocyclopropyl | OCH₃ | OCH₃ | CH | |
| H | CH₂CN | 2,2-difluorocyclopropyl | CH₃ | CH₃ | N | |
| H | CH₂CN | 2,2-difluorocyclopropyl | CH₃ | OCH₃ | N | |
| H | CH₂CN | 2,2-difluorocyclopropyl | OCH₃ | OCH₃ | N | |
| H | CH₂CN | 2,2-difluorocyclopropyl | Cl | OCH₃ | CH | |
| H | H | cyclopropyl | H | CH₃ | CH | |
| H | H | cyclopropyl | H | OCH₃ | CH | |
| H | H | cyclopropyl | CH₃ | OCH₂CH₃ | CH | |
| H | H | cyclopropyl | CH₃ | OCH(CH₃)₂ | CH | |
| H | H | cyclopropyl | H | OCH₃ | N | |
| H | H | cyclopropyl | OCH₃ | OCH₂CH₃ | CH | |
| H | H | cyclopropyl | CH₂F | CH₃ | CH | |
| H | H | cyclopropyl | CH₂F | OCH₃ | CH | |
| H | H | cyclopropyl | OCF₂H | CH₃ | CH | |
| H | H | cyclopropyl | OCF₂H | OCH₃ | CH | |
| H | H | cyclopropyl | OCH₂CF₃ | OCH₃ | N | |
| H | H | cyclopropyl | SCH₃ | OCH₃ | CH | |
| H | H | cyclopropyl | OCH₃ | NHCH₃ | N | |
| H | H | cyclopropyl | OCH₂CH₃ | NHCH₃ | N | |
| H | H | cyclopropyl | OCH₃ | OCH₂CH₃ | N | |
| H | H | cyclopropyl | SCF₂H | OCH₃ | CH | |
| H | H | cyclopropyl | Br | OCH₃ | CH | |
| H | H | cyclopropyl | CH₂OCH₃ | OCH₃ | CH | |
| H | H | cyclopropyl | CH₂OCH₃ | CH₃ | N | |
| H | H | cyclopropyl | NH₂ | OCH₃ | N | |
| H | H | cyclopropyl | N(CH₃)₂ | OCH₃ | N | |
| H | H | cyclopropyl | NHCH₃ | NHCH₃ | N | |
| H | H | cyclopropyl | cyclopropyl | OCH₃ | CH | |
| H | H | cyclopropyl | cyclopropyl | CH₃ | N | |
| H | H | cyclopropyl | cyclopropyl | CH₃ | CH | |
| H | H | cyclopropyl | cyclopropyl | OCH₃ | N | |
| H | H | cyclopropyl | CH₃ | CH(OCH₃)₂ | CH | |
| H | H | cyclopropyl | CF₃ | OCH₃ | CH | |
| H | H | cyclopropyl | OCH₃ | C≡CH | CH | |

TABLE VI

| R₁ | R₂ | R' | X | Y | Z | m.p. (°C.) |
|---|---|---|---|---|---|---|
| H | H | cyclopropyl | CH₃ | CH₃ | CH | |
| H | H | cyclopropyl | CH₃ | OCH₃ | CH | |
| H | H | cyclopropyl | OCH₃ | OCH₃ | CH | |
| H | H | cyclopropyl | CH₃ | CH₃ | N | |
| H | H | cyclopropyl | CH₃ | OCH₃ | N | |
| H | H | cyclopropyl | OCH₃ | OCH₃ | N | |
| H | H | cyclopropyl | Cl | OCH₃ | CH | |
| H | H | cyclobutyl | CH₃ | CH₃ | CH | |
| H | H | cyclobutyl | CH₃ | OCH₃ | CH | |
| H | H | cyclobutyl | OCH₃ | OCH₃ | CH | |
| H | H | cyclobutyl | CH₃ | CH₃ | N | |
| H | H | cyclobutyl | CH₃ | OCH₃ | N | |
| H | H | cyclobutyl | OCH₃ | OCH₃ | N | |
| H | H | cyclobutyl | Cl | OCH₃ | CH | |
| H | H | 2-fluorocyclopropyl | CH₃ | CH₃ | CH | |
| H | H | 2-fluorocyclopropyl | CH₃ | OCH₃ | CH | |
| H | H | 2-fluorocyclopropyl | OCH₃ | OCH₃ | CH | |
| H | H | 2-fluorocyclopropyl | CH₃ | CH₃ | N | |
| H | H | 2-fluorocyclopropyl | CH₃ | OCH₃ | N | |
| H | H | 2-fluorocyclopropyl | OCH₃ | OCH₃ | N | |
| H | H | 2-fluorocyclopropyl | Cl | OCH₃ | CH | |
| H | H | 2,2-difluorocyclopropyl | CH₃ | CH₃ | CH | |
| H | H | 2,2-difluorocyclopropyl | CH₃ | OCH₃ | CH | |
| H | H | 2,2-difluorocyclopropyl | OCH₃ | OCH₃ | CH | |
| H | H | 2,2-difluorocyclopropyl | CH₃ | CH₃ | N | |
| H | H | 2,2-difluorocyclopropyl | CH₃ | OCH₃ | N | |
| H | H | 2,2-difluorocyclopropyl | OCH₃ | OCH₃ | N | |
| H | H | 2,2-difluorocyclopropyl | Cl | OCH₃ | CH | |
| H | CH₃ | cyclopropyl | CH₃ | CH₃ | CH | |
| H | CH₃ | cyclopropyl | CH₃ | OCH₃ | CH | |
| H | CH₃ | cyclopropyl | OCH₃ | OCH₃ | CH | |
| H | CH₃ | cyclopropyl | CH₃ | CH₃ | N | |
| H | CH₃ | cyclopropyl | CH₃ | OCH₃ | N | |
| H | CH₃ | cyclopropyl | OCH₃ | OCH₃ | N | |
| H | CH₃ | cyclopropyl | Cl | OCH₃ | CH | |
| H | CH₃ | cyclobutyl | CH₃ | CH₃ | CH | |
| H | CH₃ | cyclobutyl | CH₃ | OCH₃ | CH | |
| H | CH₃ | cyclobutyl | OCH₃ | OCH₃ | CH | |
| H | CH₃ | cyclobutyl | CH₃ | CH₃ | N | |
| H | CH₃ | cyclobutyl | CH₃ | OCH₃ | N | |
| H | CH₃ | cyclobutyl | OCH₃ | OCH₃ | N | |
| H | CH₃ | cyclobutyl | Cl | OCH₃ | CH | |
| H | CH₃ | 2-fluorocyclopropyl | CH₃ | CH₃ | CH | |
| H | CH₃ | 2-fluorocyclopropyl | CH₃ | OCH₃ | CH | |
| H | CH₃ | 2-fluorocyclopropyl | OCH₃ | OCH₃ | CH | |
| H | CH₃ | 2-fluorocyclopropyl | CH₃ | CH₃ | N | |
| H | CH₃ | 2-fluorocyclopropyl | CH₃ | OCH₃ | N | |
| H | CH₃ | 2-fluorocyclopropyl | OCH₃ | OCH₃ | N | |
| H | CH₃ | 2-fluorocyclopropyl | Cl | OCH₃ | CH | |
| H | CH₃ | 2,2-difluorocyclopropyl | CH₃ | CH₃ | CH | |
| H | CH₃ | 2,2-difluorocyclopropyl | CH₃ | OCH₃ | CH | |
| H | CH₃ | 2,2-difluorocyclopropyl | OCH₃ | OCH₃ | CH | |
| H | CH₃ | 2,2-difluorocyclopropyl | CH₃ | CH₃ | N | |
| H | CH₃ | 2,2-difluorocyclopropyl | CH₃ | OCH₃ | N | |
| H | CH₃ | 2,2-difluorocyclopropyl | OCH₃ | OCH₃ | N | |
| H | CH₃ | 2,2-difluorocyclopropyl | Cl | OCH₃ | CH | |
| H | CH₂F | cyclopropyl | CH₃ | CH₃ | CH | |
| H | CH₂F | cyclopropyl | CH₃ | OCH₃ | CH | |

TABLE VI-continued

| $R_1$ | $R_2$ | R' | X | Y | Z | m.p. (°C.) |
|---|---|---|---|---|---|---|
| H | $CH_2F$ | cyclopropyl | $OCH_3$ | $OCH_3$ | CH | |
| H | $CH_2F$ | cyclopropyl | $CH_3$ | $CH_3$ | N | |
| H | $CH_2F$ | cyclopropyl | $CH_3$ | $OCH_3$ | N | |
| H | $CH_2F$ | cyclopropyl | $OCH_3$ | $OCH_3$ | N | |
| H | $CH_2F$ | cyclopropyl | Cl | $OCH_3$ | CH | |
| H | $CH_2F$ | cyclobutyl | $CH_3$ | $CH_3$ | CH | |
| H | $CH_2F$ | cyclobutyl | $CH_3$ | $OCH_3$ | CH | |
| H | $CH_2F$ | cyclobutyl | $OCH_3$ | $OCH_3$ | CH | |
| H | $CH_2F$ | cyclobutyl | $CH_3$ | $CH_3$ | N | |
| H | $CH_2F$ | cyclobutyl | $CH_3$ | $OCH_3$ | N | |
| H | $CH_2F$ | cyclobutyl | $OCH_3$ | $OCH_3$ | N | |
| H | $CH_2F$ | cyclobutyl | Cl | $OCH_3$ | CH | |
| H | $CH_2F$ | 2-fluorocyclopropyl | $CH_3$ | $CH_3$ | CH | |
| H | $CH_2F$ | 2-fluorocyclopropyl | $CH_3$ | $OCH_3$ | CH | |
| H | $CH_2F$ | 2-fluorocyclopropyl | $OCH_3$ | $OCH_3$ | CH | |
| H | $CH_2F$ | 2-fluorocyclopropyl | $CH_3$ | $CH_3$ | N | |
| H | $CH_2F$ | 2-fluorocyclopropyl | $CH_3$ | $OCH_3$ | N | |
| H | $CH_2F$ | 2-fluorocyclopropyl | $OCH_3$ | $OCH_3$ | N | |
| H | $CH_2F$ | 2-fluorocyclopropyl | Cl | $OCH_3$ | CH | |
| H | $CH_2F$ | 2,2-difluorocyclopropyl | $CH_3$ | $CH_3$ | CH | |
| H | $CH_2F$ | 2,2-difluorocyclopropyl | $CH_3$ | $OCH_3$ | CH | |
| H | $CH_2F$ | 2,2-difluorocyclopropyl | $OCH_3$ | $OCH_3$ | CH | |
| H | $CH_2F$ | 2,2-difluorocyclopropyl | $CH_3$ | $CH_3$ | N | |
| H | $CH_2F$ | 2,2-difluorocyclopropyl | $CH_3$ | $OCH_3$ | N | |
| H | $CH_2F$ | 2,2-difluorocyclopropyl | $OCH_3$ | $OCH_3$ | N | |
| H | $CH_2F$ | 2,2-difluorocyclopropyl | Cl | $OCH_3$ | CH | |
| H | $OCH_3$ | cyclopropyl | $CH_3$ | $CH_3$ | CH | |
| H | $OCH_3$ | cyclopropyl | $CH_3$ | $OCH_3$ | CH | |
| H | $OCH_3$ | cyclopropyl | $OCH_3$ | $OCH_3$ | CH | |
| H | $OCH_3$ | cyclopropyl | $CH_3$ | $CH_3$ | N | |
| H | $OCH_3$ | cyclopropyl | $CH_3$ | $OCH_3$ | N | |
| H | $OCH_3$ | cyclopropyl | $OCH_3$ | $OCH_3$ | N | |
| H | $OCH_3$ | cyclopropyl | Cl | $OCH_3$ | CH | |
| H | $OCH_3$ | cyclobutyl | $CH_3$ | $CH_3$ | CH | |
| H | $OCH_3$ | cyclobutyl | $CH_3$ | $OCH_3$ | CH | |
| H | $OCH_3$ | cyclobutyl | $OCH_3$ | $OCH_3$ | CH | |
| H | $OCH_3$ | cyclobutyl | $CH_3$ | $CH_3$ | N | |
| H | $OCH_3$ | cyclobutyl | $CH_3$ | $OCH_3$ | N | |
| H | $OCH_3$ | cyclobutyl | $OCH_3$ | $OCH_3$ | N | |
| H | $OCH_3$ | cyclobutyl | Cl | $OCH_3$ | CH | |
| H | $OCH_3$ | 2-fluorocyclopropyl | $CH_3$ | $CH_3$ | CH | |
| H | $OCH_3$ | 2-fluorocyclopropyl | $CH_3$ | $OCH_3$ | CH | |
| H | $OCH_3$ | 2-fluorocyclopropyl | $OCH_3$ | $OCH_3$ | CH | |
| H | $OCH_3$ | 2-fluorocyclopropyl | $CH_3$ | $CH_3$ | N | |
| H | $OCH_3$ | 2-fluorocyclopropyl | $CH_3$ | $OCH_3$ | N | |
| H | $OCH_3$ | 2-fluorocyclopropyl | $OCH_3$ | $OCH_3$ | N | |
| H | $OCH_3$ | 2-fluorocyclopropyl | Cl | $OCH_3$ | CH | |
| H | $OCH_3$ | 2,2-difluorocyclopropyl | $CH_3$ | $CH_3$ | CH | |
| H | $OCH_3$ | 2,2-difluorocyclopropyl | $CH_3$ | $OCH_3$ | CH | |
| H | $OCH_3$ | 2,2-difluorocyclopropyl | $OCH_3$ | $OCH_3$ | CH | |
| H | $OCH_3$ | 2,2-difluorocyclopropyl | $CH_3$ | $CH_3$ | N | |
| H | $OCH_3$ | 2,2-difluorocyclopropyl | $CH_3$ | $OCH_3$ | N | |
| H | $OCH_3$ | 2,2-difluorocyclopropyl | $OCH_3$ | $OCH_3$ | N | |
| H | $OCH_3$ | 2,2-difluorocyclopropyl | Cl | $OCH_3$ | CH | |
| H | $CO_2CH_3$ | cyclopropyl | $CH_3$ | $CH_3$ | CH | |
| H | $CO_2CH_3$ | cyclopropyl | $CH_3$ | $OCH_3$ | CH | |
| H | $CO_2CH_3$ | cyclopropyl | $OCH_3$ | $OCH_3$ | CH | |
| H | $CO_2CH_3$ | cyclopropyl | $CH_3$ | $CH_3$ | N | |
| H | $CO_2CH_3$ | cyclopropyl | $CH_3$ | $OCH_3$ | N | |
| H | $CO_2CH_3$ | cyclopropyl | $OCH_3$ | $OCH_3$ | N | |
| H | $CO_2CH_3$ | cyclopropyl | Cl | $OCH_3$ | CH | |
| H | $CO_2CH_3$ | cyclobutyl | $CH_3$ | $CH_3$ | CH | |
| H | $CO_2CH_3$ | cyclobutyl | $CH_3$ | $OCH_3$ | CH | |
| H | $CO_2CH_3$ | cyclobutyl | $OCH_3$ | $OCH_3$ | CH | |
| H | $CO_2CH_3$ | cyclobutyl | $CH_3$ | $CH_3$ | N | |
| H | $CO_2CH_3$ | cyclobutyl | $CH_3$ | $OCH_3$ | N | |
| H | $CO_2CH_3$ | cyclobutyl | $OCH_3$ | $OCH_3$ | N | |
| H | $CO_2CH_3$ | cyclobutyl | Cl | $OCH_3$ | CH | |
| H | $CO_2CH_3$ | 2-fluorocyclopropyl | $CH_3$ | $CH_3$ | CH | |
| H | $CO_2CH_3$ | 2-fluorocyclopropyl | $CH_3$ | $OCH_3$ | CH | |
| H | $CO_2CH_3$ | 2-fluorocyclopropyl | $OCH_3$ | $OCH_3$ | CH | |
| H | $CO_2CH_3$ | 2-fluorocyclopropyl | $CH_3$ | $CH_3$ | N | |
| H | $CO_2CH_3$ | 2-fluorocyclopropyl | $CH_3$ | $OCH_3$ | N | |
| H | $CO_2CH_3$ | 2-fluorocyclopropyl | $OCH_3$ | $OCH_3$ | N | |
| H | $CO_2CH_3$ | 2-fluorocyclopropyl | Cl | $OCH_3$ | CH | |
| H | $CO_2CH_3$ | 2,2-difluorocyclopropyl | $CH_3$ | $CH_3$ | CH | |
| H | $CO_2CH_3$ | 2,2-difluorocyclopropyl | $CH_3$ | $OCH_3$ | CH | |
| H | $CO_2CH_3$ | 2,2-difluorocyclopropyl | $OCH_3$ | $OCH_3$ | CH | |
| H | $CO_2CH_3$ | 2,2-difluorocyclopropyl | $CH_3$ | $CH_3$ | N | |
| H | $CO_2CH_3$ | 2,2-difluorocyclopropyl | $CH_3$ | $OCH_3$ | N | |
| H | $CO_2CH_3$ | 2,2-difluorocyclopropyl | $OCH_3$ | $OCH_3$ | N | |
| H | $CO_2CH_3$ | 2,2-difluorocyclopropyl | Cl | $OCH_3$ | CH | |
| H | $SCHF_2$ | cyclopropyl | $CH_3$ | $CH_3$ | CH | |
| H | $SCHF_2$ | cyclopropyl | $CH_3$ | $OCH_3$ | CH | |
| H | $SCHF_2$ | cyclopropyl | $OCH_3$ | $OCH_3$ | CH | |
| H | $SCHF_2$ | cyclopropyl | $CH_3$ | $CH_3$ | N | |
| H | $SCHF_2$ | cyclopropyl | $CH_3$ | $OCH_3$ | N | |
| H | $SCHF_2$ | cyclopropyl | $OCH_3$ | $OCH_3$ | N | |
| H | $SCHF_2$ | cyclopropyl | Cl | $OCH_3$ | CH | |
| H | $SCHF_2$ | cyclobutyl | $CH_3$ | $CH_3$ | CH | |
| H | $SCHF_2$ | cyclobutyl | $CH_3$ | $OCH_3$ | CH | |
| H | $SCHF_2$ | cyclobutyl | $OCH_3$ | $OCH_3$ | CH | |
| H | $SCHF_2$ | cyclobutyl | $CH_3$ | $CH_3$ | N | |
| H | $SCHF_2$ | cyclobutyl | $CH_3$ | $OCH_3$ | N | |
| H | $SCHF_2$ | cyclobutyl | $OCH_3$ | $OCH_3$ | N | |
| H | $SCHF_2$ | cyclobutyl | Cl | $OCH_3$ | CH | |
| H | $SCHF_2$ | 2-fluorocyclopropyl | $CH_3$ | $CH_3$ | CH | |
| H | $SCHF_2$ | 2-fluorocyclopropyl | $CH_3$ | $OCH_3$ | CH | |
| H | $SCHF_2$ | 2-fluorocyclopropyl | $OCH_3$ | $OCH_3$ | CH | |
| H | $SCHF_2$ | 2-fluorocyclopropyl | $CH_3$ | $CH_3$ | N | |
| H | $SCHF_2$ | 2-fluorocyclopropyl | $CH_3$ | $OCH_3$ | N | |
| H | $SCHF_2$ | 2-fluorocyclopropyl | $OCH_3$ | $OCH_3$ | N | |
| H | $SCHF_2$ | 2-fluorocyclopropyl | Cl | $OCH_3$ | CH | |
| H | $SCHF_2$ | 2,2-difluorocyclopropyl | $CH_3$ | $CH_3$ | CH | |
| H | $SCHF_2$ | 2,2-difluorocyclopropyl | $CH_3$ | $OCH_3$ | CH | |
| H | $SCHF_2$ | 2,2-difluorocyclopropyl | $OCH_3$ | $OCH_3$ | CH | |
| H | $SCHF_2$ | 2,2-difluorocyclopropyl | $CH_3$ | $CH_3$ | N | |
| H | $SCHF_2$ | 2,2-difluorocyclopropyl | $CH_3$ | $OCH_3$ | N | |
| H | $SCHF_2$ | 2,2-difluorocyclopropyl | $OCH_3$ | $OCH_3$ | N | |
| H | $SCHF_2$ | 2,2-difluorocyclopropyl | Cl | $OCH_3$ | CH | |

TABLE VII

| $R_1$ | $R_2$ | R' | X | Y | Z | m.p. (°C.) |
|---|---|---|---|---|---|---|
| H | H | cyclopropyl | $CH_3$ | $CH_3$ | CH | |
| H | H | cyclopropyl | $CH_3$ | $OCH_3$ | CH | |
| H | H | cyclopropyl | $OCH_3$ | $OCH_3$ | CH | |
| H | H | cyclopropyl | $CH_3$ | $CH_3$ | N | |
| H | H | cyclopropyl | $CH_3$ | $OCH_3$ | N | |
| H | H | cyclopropyl | $OCH_3$ | $OCH_3$ | N | |
| H | H | cyclopropyl | Cl | $OCH_3$ | CH | |
| H | H | cyclobutyl | $CH_3$ | $CH_3$ | CH | |
| H | H | cyclobutyl | $CH_3$ | $OCH_3$ | CH | |
| H | H | cyclobutyl | $OCH_3$ | $OCH_3$ | CH | |
| H | H | cyclobutyl | $CH_3$ | $CH_3$ | N | |
| H | H | cyclobutyl | $CH_3$ | $OCH_3$ | N | |
| H | H | cyclobutyl | $OCH_3$ | $OCH_3$ | N | |
| H | H | cyclobutyl | Cl | $OCH_3$ | CH | |
| H | H | 2-fluorocyclopropyl | $CH_3$ | $CH_3$ | CH | |
| H | H | 2-fluorocyclopropyl | $CH_3$ | $OCH_3$ | CH | |
| H | H | 2-fluorocyclopropyl | $OCH_3$ | $OCH_3$ | CH | |
| H | H | 2-fluorocyclopropyl | $CH_3$ | $CH_3$ | N | |

TABLE VII-continued

| R₁ | R₂ | R' | X | Y | Z | m.p. (°C.) |
|---|---|---|---|---|---|---|
| H | H | 2-fluorocyclopropyl | CH₃ | OCH₃ | N | |
| H | H | 2-fluorocyclopropyl | OCH₃ | OCH₃ | N | |
| H | H | 2-fluorocyclopropyl | Cl | OCH₃ | CH | |
| H | H | 2,2-difluorocyclopropyl | CH₃ | CH₃ | CH | |
| H | H | 2,2-difluorocyclopropyl | CH₃ | OCH₃ | CH | |
| H | H | 2,2-difluorocyclopropyl | OCH₃ | OCH₃ | CH | |
| H | H | 2,2-difluorocyclopropyl | CH₃ | CH₃ | N | |
| H | H | 2,2-difluorocyclopropyl | CH₃ | OCH₃ | N | |
| H | H | 2,2-difluorocyclopropyl | OCH₃ | OCH₃ | N | |
| H | H | 2,2-difluorocyclopropyl | Cl | OCH₃ | CH | |
| H | Cl | cyclopropyl | CH₃ | CH₃ | CH | |
| H | Cl | cyclopropyl | CH₃ | OCH₃ | CH | |
| H | Cl | cyclopropyl | OCH₃ | OCH₃ | CH | |
| H | Cl | cyclopropyl | CH₃ | CH₃ | N | |
| H | Cl | cyclopropyl | CH₃ | OCH₃ | N | |
| H | Cl | cyclopropyl | OCH₃ | OCH₃ | N | |
| H | Cl | cyclopropyl | Cl | OCH₃ | CH | |
| H | Cl | cyclobutyl | CH₃ | CH₃ | CH | |
| H | Cl | cyclobutyl | CH₃ | OCH₃ | CH | |
| H | Cl | cyclobutyl | OCH₃ | OCH₃ | CH | |
| H | Cl | cyclobutyl | CH₃ | CH₃ | N | |
| H | Cl | cyclobutyl | CH₃ | OCH₃ | N | |
| H | Cl | cyclobutyl | OCH₃ | OCH₃ | N | |
| H | Cl | cyclobutyl | Cl | OCH₃ | CH | |
| H | Cl | 2-fluorocyclopropyl | CH₃ | CH₃ | CH | |
| H | Cl | 2-fluorocyclopropyl | CH₃ | OCH₃ | CH | |
| H | Cl | 2-fluorocyclopropyl | OCH₃ | OCH₃ | CH | |
| H | Cl | 2-fluorocyclopropyl | CH₃ | CH₃ | N | |
| H | Cl | 2-fluorocyclopropyl | CH₃ | OCH₃ | N | |
| H | Cl | 2-fluorocyclopropyl | OCH₃ | OCH₃ | N | |
| H | Cl | 2-fluorocyclopropyl | Cl | OCH₃ | CH | |
| H | Cl | 2,2-difluorocyclopropyl | CH₃ | CH₃ | CH | |
| H | Cl | 2,2-difluorocyclopropyl | CH₃ | OCH₃ | CH | |
| H | Cl | 2,2-difluorocyclopropyl | OCH₃ | OCH₃ | CH | |
| H | Cl | 2,2-difluorocyclopropyl | CH₃ | CH₃ | N | |
| H | Cl | 2,2-difluorocyclopropyl | CH₃ | OCH₃ | N | |
| H | Cl | 2,2-difluorocyclopropyl | OCH₃ | OCH₃ | N | |
| H | Cl | 2,2-difluorocyclopropyl | Cl | OCH₃ | CH | |
| H | F | cyclopropyl | CH₃ | CH₃ | CH | |
| H | F | cyclopropyl | CH₃ | OCH₃ | CH | |
| H | F | cyclopropyl | OCH₃ | OCH₃ | CH | |
| H | F | cyclopropyl | CH₃ | CH₃ | N | |
| H | F | cyclopropyl | CH₃ | OCH₃ | N | |
| H | F | cyclopropyl | OCH₃ | OCH₃ | N | |
| H | F | cyclopropyl | Cl | OCH₃ | CH | |
| H | F | cyclobutyl | CH₃ | CH₃ | CH | |
| H | F | cyclobutyl | CH₃ | OCH₃ | CH | |
| H | F | cyclobutyl | OCH₃ | OCH₃ | CH | |
| H | F | cyclobutyl | CH₃ | CH₃ | N | |
| H | F | cyclobutyl | CH₃ | OCH₃ | N | |
| H | F | cyclobutyl | OCH₃ | OCH₃ | N | |
| H | F | cyclobutyl | Cl | OCH₃ | CH | |
| H | F | 2-fluorocyclopropyl | CH₃ | CH₃ | CH | |
| H | F | 2-fluorocyclopropyl | CH₃ | OCH₃ | CH | |
| H | F | 2-fluorocyclopropyl | OCH₃ | OCH₃ | CH | |
| H | F | 2-fluorocyclopropyl | CH₃ | CH₃ | N | |
| H | F | 2-fluorocyclopropyl | CH₃ | OCH₃ | N | |
| H | F | 2-fluorocyclopropyl | OCH₃ | OCH₃ | N | |
| H | F | 2-fluorocyclopropyl | Cl | OCH₃ | CH | |
| H | F | 2,2-difluorocyclopropyl | CH₃ | CH₃ | CH | |
| H | F | 2,2-difluorocyclopropyl | CH₃ | OCH₃ | CH | |
| H | F | 2,2-difluorocyclopropyl | OCH₃ | OCH₃ | CH | |
| H | F | 2,2-difluorocyclopropyl | CH₃ | CH₃ | N | |
| H | F | 2,2-difluorocyclopropyl | CH₃ | OCH₃ | N | |
| H | F | 2,2-difluorocyclopropyl | OCH₃ | OCH₃ | N | |
| H | F | 2,2-difluorocyclopropyl | Cl | OCH₃ | CH | |
| H | SO₂N(CH₃)₂ | cyclopropyl | CH₃ | CH₃ | CH | |
| H | SO₂N(CH₃)₂ | cyclopropyl | CH₃ | OCH₃ | CH | |
| H | SO₂N(CH₃)₂ | cyclopropyl | OCH₃ | OCH₃ | CH | |
| H | SO₂N(CH₃)₂ | cyclopropyl | CH₃ | CH₃ | N | |
| H | SO₂N(CH₃)₂ | cyclopropyl | CH₃ | OCH₃ | N | |
| H | SO₂N(CH₃)₂ | cyclopropyl | OCH₃ | OCH₃ | N | |
| H | SO₂N(CH₃)₂ | cyclopropyl | Cl | OCH₃ | CH | |
| H | SO₂N(CH₃)₂ | cyclobutyl | CH₃ | CH₃ | CH | |
| H | SO₂N(CH₃)₂ | cyclobutyl | CH₃ | OCH₃ | CH | |
| H | SO₂N(CH₃)₂ | cyclobutyl | OCH₃ | OCH₃ | CH | |
| H | SO₂N(CH₃)₂ | cyclobutyl | CH₃ | CH₃ | N | |
| H | SO₂N(CH₃)₂ | cyclobutyl | CH₃ | OCH₃ | N | |
| H | SO₂N(CH₃)₂ | cyclobutyl | OCH₃ | OCH₃ | N | |
| H | SO₂N(CH₃)₂ | cyclobutyl | Cl | OCH₃ | CH | |

TABLE VII-continued

| R₁ | R₂ | R' | X | Y | Z | m.p. (°C.) |
|---|---|---|---|---|---|---|
| H | SO₂N(CH₃)₂ | 2-fluorocyclopropyl | CH₃ | CH₃ | CH | |
| H | SO₂N(CH₃)₂ | 2-fluorocyclopropyl | CH₃ | OCH₃ | CH | |
| H | SO₂N(CH₃)₂ | 2-fluorocyclopropyl | OCH₃ | OCH₃ | CH | |
| H | SO₂N(CH₃)₂ | 2-fluorocyclopropyl | CH₃ | CH₃ | N | |
| H | SO₂N(CH₃)₂ | 2-fluorocyclopropyl | CH₃ | OCH₃ | N | |
| H | SO₂N(CH₃)₂ | 2-fluorocyclopropyl | OCH₃ | OCH₃ | N | |
| H | SO₂N(CH₃)₂ | 2-fluorocyclopropyl | Cl | OCH₃ | CH | |
| H | SO₂N(CH₃)₂ | 2,2-difluorocyclopropyl | CH₃ | CH₃ | CH | |
| H | SO₂N(CH₃)₂ | 2,2-difluorocyclopropyl | CH₃ | OCH₃ | CH | |
| H | SO₂N(CH₃)₂ | 2,2-difluorocyclopropyl | OCH₃ | OCH₃ | CH | |
| H | SO₂N(CH₃)₂ | 2,2-difluorocyclopropyl | CH₃ | CH₃ | N | |
| H | SO₂N(CH₃)₂ | 2,2-difluorocyclopropyl | CH₃ | OCH₃ | N | |
| H | SO₂N(CH₃)₂ | 2,2-difluorocyclopropyl | OCH₃ | OCH₃ | N | |
| H | SO₂N(CH₃)₂ | 2,2-difluorocyclopropyl | Cl | OCH₃ | CH | |
| H | OCHF₂ | cyclopropyl | CH₃ | CH₃ | CH | |
| H | OCHF₂ | cyclopropyl | CH₃ | OCH₃ | CH | |
| H | OCHF₂ | cyclopropyl | OCH₃ | OCH₃ | CH | |
| H | OCHF₂ | cyclopropyl | CH₃ | CH₃ | N | |
| H | OCHF₂ | cyclopropyl | CH₃ | OCH₃ | N | |
| H | OCHF₂ | cyclopropyl | OCH₃ | OCH₃ | N | |
| H | OCHF₂ | cyclopropyl | Cl | OCH₃ | CH | |
| H | OCHF₂ | cyclobutyl | CH₃ | CH₃ | CH | |
| H | OCHF₂ | cyclobutyl | CH₃ | OCH₃ | CH | |
| H | OCHF₂ | cyclobutyl | OCH₃ | OCH₃ | CH | |
| H | OCHF₂ | cyclobutyl | CH₃ | CH₃ | N | |
| H | OCHF₂ | cyclobutyl | CH₃ | OCH₃ | N | |
| H | OCHF₂ | cyclobutyl | OCH₃ | OCH₃ | N | |
| H | OCHF₂ | cyclobutyl | Cl | OCH₃ | CH | |
| H | OCHF₂ | 2-fluorocyclopropyl | CH₃ | CH₃ | CH | |
| H | OCHF₂ | 2-fluorocyclopropyl | CH₃ | OCH₃ | CH | |
| H | OCHF₂ | 2-fluorocyclopropyl | OCH₃ | OCH₃ | CH | |
| H | OCHF₂ | 2-fluorocyclopropyl | CH₃ | CH₃ | N | |
| H | OCHF₂ | 2-fluorocyclopropyl | CH₃ | OCH₃ | N | |
| H | OCHF₂ | 2-fluorocyclopropyl | OCH₃ | OCH₃ | N | |
| H | OCHF₂ | 2-fluorocyclopropyl | Cl | OCH₃ | CH | |
| H | OCHF₂ | 2,2-difluorocyclopropyl | CH₃ | CH₃ | CH | |
| H | OCHF₂ | 2,2-difluorocyclopropyl | CH₃ | OCH₃ | CH | |
| H | OCHF₂ | 2,2-difluorocyclopropyl | OCH₃ | OCH₃ | CH | |
| H | OCHF₂ | 2,2-difluorocyclopropyl | CH₃ | CH₃ | N | |
| H | OCHF₂ | 2,2-difluorocyclopropyl | CH₃ | OCH₃ | N | |
| H | OCHF₂ | 2,2-difluorocyclopropyl | OCH₃ | OCH₃ | N | |
| H | OCHF₂ | 2,2-difluorocyclopropyl | Cl | OCH₃ | CH | |
| H | CH₂CN | cyclopropyl | CH₃ | CH₃ | CH | |
| H | CH₂CN | cyclopropyl | CH₃ | OCH₃ | CH | |
| H | CH₂CN | cyclopropyl | OCH₃ | OCH₃ | CH | |
| H | CH₂CN | cyclopropyl | CH₃ | CH₃ | N | |
| H | CH₂CN | cyclopropyl | CH₃ | OCH₃ | N | |
| H | CH₂CN | cyclopropyl | OCH₃ | OCH₃ | N | |
| H | CH₂CN | cyclopropyl | Cl | OCH₃ | CH | |
| H | CH₂CN | cyclobutyl | CH₃ | CH₃ | CH | |
| H | CH₂CN | cyclobutyl | CH₃ | OCH₃ | CH | |
| H | CH₂CN | cyclobutyl | OCH₃ | OCH₃ | CH | |
| H | CH₂CN | cyclobutyl | CH₃ | CH₃ | N | |
| H | CH₂CN | cyclobutyl | CH₃ | OCH₃ | N | |
| H | CH₂CN | cyclobutyl | OCH₃ | OCH₃ | N | |
| H | CH₂CN | cyclobutyl | Cl | OCH₃ | CH | |
| H | CH₂CN | 2-fluorocyclopropyl | CH₃ | CH₃ | CH | |
| H | CH₂CN | 2-fluorocyclopropyl | CH₃ | OCH₃ | CH | |
| H | CH₂CN | 2-fluorocyclopropyl | OCH₃ | OCH₃ | CH | |
| H | CH₂CN | 2-fluorocyclopropyl | CH₃ | CH₃ | N | |
| H | CH₂CN | 2-fluorocyclopropyl | CH₃ | OCH₃ | N | |
| H | CH₂CN | 2-fluorocyclopropyl | OCH₃ | OCH₃ | N | |
| H | CH₂CN | 2-fluorocyclopropyl | Cl | OCH₃ | CH | |
| H | CH₂CN | 2,2-difluorocyclopropyl | CH₃ | CH₃ | CH | |
| H | CH₂CN | 2,2-difluorocyclopropyl | CH₃ | OCH₃ | CH | |
| H | CH₂CN | 2,2-difluorocyclopropyl | OCH₃ | OCH₃ | CH | |
| H | CH₂CN | 2,2-difluorocyclopropyl | CH₃ | CH₃ | N | |
| H | CH₂CN | 2,2-difluorocyclopropyl | CH₃ | OCH₃ | N | |
| H | CH₂CN | 2,2-difluorocyclopropyl | OCH₃ | OCH₃ | N | |
| H | CH₂CN | 2,2-difluorocyclopropyl | Cl | OCH₃ | CH | |

TABLE VIII

| R₁ | n | R₂ | R' | X | Y | Z | m.p. (°C.) |
|---|---|---|---|---|---|---|---|
| H | 0 | H | cyclopropyl | CH₃ | CH₃ | CH | |
| H | 0 | H | cyclopropyl | CH₃ | OCH₃ | CH | |
| H | 0 | H | cyclopropyl | OCH₃ | OCH₃ | CH | |

TABLE VIII-continued

| R₁ | n | R₂ | R' | X | Y | Z | m.p. (°C.) |
|---|---|---|---|---|---|---|---|
| H | 0 | H | cyclopropyl | CH₃ | CH₃ | N | |
| H | 0 | H | cyclopropyl | CH₃ | OCH₃ | N | |
| H | 0 | H | cyclopropyl | OCH₃ | OCH₃ | N | |
| H | 0 | H | cyclopropyl | Cl | OCH₃ | CH | |
| H | 0 | H | cyclobutyl | CH₃ | CH₃ | CH | |
| H | 0 | H | cyclobutyl | CH₃ | OCH₃ | CH | |
| H | 0 | H | cyclobutyl | OCH₃ | OCH₃ | CH | |
| H | 0 | H | cyclobutyl | CH₃ | CH₃ | N | |
| H | 0 | H | cyclobutyl | CH₃ | OCH₃ | N | |
| H | 0 | H | cyclobutyl | OCH₃ | OCH₃ | N | |
| H | 0 | H | cyclobutyl | Cl | OCH₃ | CH | |
| H | 0 | H | cyclopentyl | CH₃ | CH₃ | CH | |
| H | 0 | H | cyclopentyl | CH₃ | OCH₃ | CH | |
| H | 0 | H | cyclopentyl | OCH₃ | OCH₃ | CH | |
| H | 0 | H | cyclopentyl | CH₃ | CH₃ | N | |
| H | 0 | H | cyclopentyl | CH₃ | OCH₃ | N | |
| H | 0 | H | cyclopentyl | OCH₃ | OCH₃ | N | |
| H | 0 | H | cyclopentyl | Cl | OCH₃ | CH | |
| H | 0 | H | 2-fluorocyclopropyl | CH₃ | CH₃ | CH | |
| H | 0 | H | 2-fluorocyclopropyl | CH₃ | OCH₃ | CH | |
| H | 0 | H | 2-fluorocyclopropyl | OCH₃ | OCH₃ | CH | |
| H | 0 | H | 2-fluorocyclopropyl | CH₃ | CH₃ | N | |
| H | 0 | H | 2-fluorocyclopropyl | CH₃ | OCH₃ | N | |
| H | 0 | H | 2-fluorocyclopropyl | OCH₃ | OCH₃ | N | |
| H | 0 | H | 2-fluorocyclopropyl | Cl | OCH₃ | CH | |
| H | 0 | Cl | cyclopropyl | CH₃ | CH₃ | CH | |
| H | 0 | Cl | cyclopropyl | CH₃ | OCH₃ | CH | |
| H | 0 | Cl | cyclopropyl | OCH₃ | OCH₃ | CH | |
| H | 0 | Cl | cyclopropyl | CH₃ | CH₃ | N | |
| H | 0 | Cl | cyclopropyl | CH₃ | OCH₃ | N | |
| H | 0 | Cl | cyclopropyl | OCH₃ | OCH₃ | N | |
| H | 0 | Cl | cyclopropyl | Cl | OCH₃ | CH | |
| H | 0 | Cl | cyclobutyl | CH₃ | CH₃ | CH | |
| H | 0 | Cl | cyclobutyl | CH₃ | OCH₃ | CH | |
| H | 0 | Cl | cyclobutyl | OCH₃ | OCH₃ | CH | |
| H | 0 | Cl | cyclobutyl | CH₃ | CH₃ | N | |
| H | 0 | Cl | cyclobutyl | CH₃ | OCH₃ | N | |
| H | 0 | Cl | cyclobutyl | OCH₃ | OCH₃ | N | |
| H | 0 | Cl | cyclobutyl | Cl | OCH₃ | CH | |
| H | 0 | Cl | cyclopentyl | CH₃ | CH₃ | CH | |
| H | 0 | Cl | cyclopentyl | CH₃ | OCH₃ | CH | |
| H | 0 | Cl | cyclopentyl | OCH₃ | OCH₃ | CH | |
| H | 0 | Cl | cyclopentyl | CH₃ | CH₃ | N | |
| H | 0 | Cl | cyclopentyl | CH₃ | OCH₃ | N | |
| H | 0 | Cl | cyclopentyl | OCH₃ | OCH₃ | N | |
| H | 0 | Cl | cyclopentyl | Cl | OCH₃ | CH | |
| H | 0 | Cl | 2-fluorocyclopropyl | CH₃ | CH₃ | CH | |
| H | 0 | Cl | 2-fluorocyclopropyl | CH₃ | OCH₃ | CH | |
| H | 0 | Cl | 2-fluorocyclopropyl | OCH₃ | OCH₃ | CH | |
| H | 0 | Cl | 2-fluorocyclopropyl | CH₃ | CH₃ | N | |
| H | 0 | Cl | 2-fluorocyclopropyl | CH₃ | OCH₃ | N | |
| H | 0 | Cl | 2-fluorocyclopropyl | OCH₃ | OCH₃ | N | |
| H | 0 | Cl | 2-fluorocyclopropyl | Cl | OCH₃ | CH | |
| H | 0 | CH₂CH₃ | cyclopropyl | CH₃ | CH₃ | CH | |
| H | 0 | CH₂CH₃ | cyclopropyl | CH₃ | OCH₃ | CH | |
| H | 0 | CH₂CH₃ | cyclopropyl | OCH₃ | OCH₃ | CH | |
| H | 0 | CH₂CH₃ | cyclopropyl | CH₃ | CH₃ | N | |
| H | 0 | CH₂CH₃ | cyclopropyl | CH₃ | OCH₃ | N | |
| H | 0 | CH₂CH₃ | cyclopropyl | OCH₃ | OCH₃ | N | |
| H | 0 | CH₂CH₃ | cyclopropyl | Cl | OCH₃ | CH | |
| H | 0 | CH₂CH₃ | cyclobutyl | CH₃ | CH₃ | CH | |
| H | 0 | CH₂CH₃ | cyclobutyl | CH₃ | OCH₃ | CH | |
| H | 0 | CH₂CH₃ | cyclobutyl | OCH₃ | OCH₃ | CH | |
| H | 0 | CH₂CH₃ | cyclobutyl | CH₃ | CH₃ | N | |
| H | 0 | CH₂CH₃ | cyclobutyl | CH₃ | OCH₃ | N | |
| H | 0 | CH₂CH₃ | cyclobutyl | OCH₃ | OCH₃ | N | |
| H | 0 | CH₂CH₃ | cyclobutyl | Cl | OCH₃ | CH | |
| H | 0 | CH₂CH₃ | cyclopentyl | CH₃ | CH₃ | CH | |
| H | 0 | CH₂CH₃ | cyclopentyl | CH₃ | OCH₃ | CH | |
| H | 0 | CH₂CH₃ | cyclopentyl | OCH₃ | OCH₃ | CH | |
| H | 0 | CH₂CH₃ | cyclopentyl | CH₃ | CH₃ | N | |
| H | 0 | CH₂CH₃ | cyclopentyl | CH₃ | OCH₃ | N | |
| H | 0 | CH₂CH₃ | cyclopentyl | OCH₃ | OCH₃ | N | |
| H | 0 | CH₂CH₃ | cyclopentyl | Cl | OCH₃ | CH | |
| H | 0 | CH₂CH₃ | 2-fluorocyclopropyl | CH₃ | CH₃ | CH | |
| H | 0 | CH₂CH₃ | 2-fluorocyclopropyl | CH₃ | OCH₃ | CH | |
| H | 0 | CH₂CH₃ | 2-fluorocyclopropyl | OCH₃ | OCH₃ | CH | |
| H | 0 | CH₂CH₃ | 2-fluorocyclopropyl | CH₃ | CH₃ | N | |
| H | 0 | CH₂CH₃ | 2-fluorocyclopropyl | CH₃ | OCH₃ | N | |
| H | 0 | CH₂CH₃ | 2-fluorocyclopropyl | OCH₃ | OCH₃ | N | |

TABLE VIII-continued

| R₁ | n | R₂ | R' | X | Y | Z | m.p. (°C.) |
|---|---|---|---|---|---|---|---|
| H | 0 | CH₂CH₃ | 2-fluorocyclopropyl | Cl | OCH₃ | CH | |
| H | 0 | OCHF₂ | cyclopropyl | CH₃ | CH₃ | CH | |
| H | 0 | OCHF₂ | cyclopropyl | CH₃ | OCH₃ | CH | |
| H | 0 | OCHF₂ | cyclopropyl | OCH₃ | OCH₃ | CH | |
| H | 0 | OCHF₂ | cyclopropyl | CH₃ | CH₃ | N | |
| H | 0 | OCHF₂ | cyclopropyl | CH₃ | OCH₃ | N | |
| H | 0 | OCHF₂ | cyclopropyl | OCH₃ | OCH₃ | N | |
| H | 0 | OCHF₂ | cyclopropyl | Cl | OCH₃ | CH | |
| H | 0 | OCHF₂ | cyclobutyl | CH₃ | CH₃ | CH | |
| H | 0 | OCHF₂ | cyclobutyl | CH₃ | OCH₃ | CH | |
| H | 0 | OCHF₂ | cyclobutyl | OCH₃ | OCH₃ | CH | |
| H | 0 | OCHF₂ | cyclobutyl | CH₃ | CH₃ | N | |
| H | 0 | OCHF₂ | cyclobutyl | CH₃ | OCH₃ | N | |
| H | 0 | OCHF₂ | cyclobutyl | OCH₃ | OCH₃ | N | |
| H | 0 | OCHF₂ | cyclobutyl | Cl | OCH₃ | CH | |
| H | 0 | OCHF₂ | cyclopentyl | CH₃ | CH₃ | CH | |
| H | 0 | OCHF₂ | cyclopentyl | CH₃ | OCH₃ | CH | |
| H | 0 | OCHF₂ | cyclopentyl | OCH₃ | OCH₃ | CH | |
| H | 0 | OCHF₂ | cyclopentyl | CH₃ | CH₃ | N | |
| H | 0 | OCHF₂ | cyclopentyl | CH₃ | OCH₃ | N | |
| H | 0 | OCHF₂ | cyclopentyl | OCH₃ | OCH₃ | N | |
| H | 0 | OCHF₂ | cyclopentyl | Cl | OCH₃ | CH | |
| H | 0 | OCHF₂ | 2-fluorocyclopropyl | CH₃ | CH₃ | CH | |
| H | 0 | OCHF₂ | 2-fluorocyclopropyl | CH₃ | OCH₃ | CH | |
| H | 0 | OCHF₂ | 2-fluorocyclopropyl | OCH₃ | OCH₃ | CH | |
| H | 0 | OCHF₂ | 2-fluorocyclopropyl | CH₃ | CH₃ | N | |
| H | 0 | OCHF₂ | 2-fluorocyclopropyl | CH₃ | OCH₃ | N | |
| H | 0 | OCHF₂ | 2-fluorocyclopropyl | OCH₃ | OCH₃ | N | |
| H | 0 | OCHF₂ | 2-fluorocyclopropyl | Cl | OCH₃ | CH | |
| H | 0 | CN | cyclopropyl | CH₃ | CH₃ | CH | |
| H | 0 | CN | cyclopropyl | CH₃ | OCH₃ | CH | |
| H | 0 | CN | cyclopropyl | OCH₃ | OCH₃ | CH | |
| H | 0 | CN | cyclopropyl | CH₃ | CH₃ | N | |
| H | 0 | CN | cyclopropyl | CH₃ | OCH₃ | N | |
| H | 0 | CN | cyclopropyl | OCH₃ | OCH₃ | N | |
| H | 0 | CN | cyclopropyl | Cl | OCH₃ | CH | |
| H | 0 | CN | cyclobutyl | CH₃ | CH₃ | CH | |
| H | 0 | CN | cyclobutyl | CH₃ | OCH₃ | CH | |
| H | 0 | CN | cyclobutyl | OCH₃ | OCH₃ | CH | |
| H | 0 | CN | cyclobutyl | CH₃ | CH₃ | N | |
| H | 0 | CN | cyclobutyl | CH₃ | OCH₃ | N | |
| H | 0 | CN | cyclobutyl | OCH₃ | OCH₃ | N | |
| H | 0 | CN | cyclobutyl | Cl | OCH₃ | CH | |
| H | 0 | CN | cyclopentyl | CH₃ | CH₃ | CH | |
| H | 0 | CN | cyclopentyl | CH₃ | OCH₃ | CH | |
| H | 0 | CN | cyclopentyl | OCH₃ | OCH₃ | CH | |
| H | 0 | CN | cyclopentyl | CH₃ | CH₃ | N | |
| H | 0 | CN | cyclopentyl | CH₃ | OCH₃ | N | |
| H | 0 | CN | cyclopentyl | OCH₃ | OCH₃ | N | |
| H | 0 | CN | cyclopentyl | Cl | OCH₃ | CH | |
| H | 0 | CN | 2-fluorocyclopropyl | CH₃ | CH₃ | CH | |
| H | 0 | CN | 2-fluorocyclopropyl | CH₃ | OCH₃ | CH | |
| H | 0 | CN | 2-fluorocyclopropyl | OCH₃ | OCH₃ | CH | |
| H | 0 | CN | 2-fluorocyclopropyl | CH₃ | CH₃ | N | |
| H | 0 | CN | 2-fluorocyclopropyl | CH₃ | OCH₃ | N | |
| H | 0 | CN | 2-fluorocyclopropyl | OCH₃ | OCH₃ | N | |
| H | 0 | CN | 2-fluorocyclopropyl | Cl | OCH₃ | CH | |
| H | 0 | CH₃ | CH₃ | CH₃ | CH₃ | CH | |
| H | 0 | CH₃ | CH₃ | CH₃ | OCH₃ | CH | |
| H | 0 | CH₃ | CH₃ | OCH₃ | OCH₃ | CH | |
| H | 0 | CH₃ | CH₃ | CH₃ | CH₃ | N | |
| H | 0 | CH₃ | CH₃ | CH₃ | OCH₃ | N | |
| H | 0 | CH₃ | CH₃ | OCH₃ | OCH₃ | N | |
| H | 0 | CH₃ | CH₃ | Cl | OCH₃ | CH | |
| H | 0 | CH₃ | CH₂CH₃ | CH₃ | CH₃ | CH | |
| H | 0 | CH₃ | CH₂CH₃ | CH₃ | OCH₃ | CH | |
| H | 0 | CH₃ | CH₂CH₃ | OCH₃ | OCH₃ | CH | |
| H | 0 | CH₃ | CH₂CH₃ | CH₃ | CH₃ | N | |
| H | 0 | CH₃ | CH₂CH₃ | CH₃ | OCH₃ | N | |
| H | 0 | CH₃ | CH₂CH₃ | OCH₃ | OCH₃ | N | |
| H | 0 | CH₃ | CH₂CH₃ | Cl | OCH₃ | CH | |
| H | 0 | CH₃ | CH₂CH₂CH₃ | CH₃ | CH₃ | CH | |
| H | 0 | CH₃ | CH₂CH₂CH₃ | CH₃ | OCH₃ | CH | |
| H | 0 | CH₃ | CH₂CH₂CH₃ | OCH₃ | OCH₃ | CH | |
| H | 0 | CH₃ | CH₂CH₂CH₃ | CH₃ | CH₃ | N | |
| H | 0 | CH₃ | CH₂CH₂CH₃ | CH₃ | OCH₃ | N | |
| H | 0 | CH₃ | CH₂CH₂CH₃ | OCH₃ | OCH₃ | N | |
| H | 0 | CH₃ | CH₂CH₂CH₃ | Cl | OCH₃ | CH | |
| H | 0 | CH₃ | CH₂CH₂CH₂CH₃ | CH₃ | CH₃ | CH | |
| H | 0 | CH₃ | CH₂CH₂CH₂CH₃ | CH₃ | OCH₃ | CH | |

TABLE VIII-continued

| R₁ | n | R₂ | R' | X | Y | Z | m.p. (°C.) |
|---|---|---|---|---|---|---|---|
| H | 0 | CH₃ | CH₂CH₂CH₂CH₃ | OCH₃ | OCH₃ | CH | |
| H | 0 | CH₃ | CH₂CH₂CH₂CH₃ | CH₃ | CH₃ | N | |
| H | 0 | CH₃ | CH₂CH₂CH₂CH₃ | CH₃ | OCH₃ | N | |
| H | 0 | CH₃ | CH₂CH₂CH₂CH₃ | OCH₃ | OCH₃ | N | |
| H | 0 | CH₃ | CH₂CH₂CH₂CH₃ | Cl | OCH₃ | CH | |
| H | 0 | OCH₃ | CH₃ | CH₃ | CH₃ | CH | |
| H | 0 | OCH₃ | CH₃ | CH₃ | OCH₃ | CH | |
| H | 0 | OCH₃ | CH₃ | OCH₃ | OCH₃ | CH | |
| H | 0 | OCH₃ | CH₃ | CH₃ | CH₃ | N | |
| H | 0 | OCH₃ | CH₃ | CH₃ | OCH₃ | N | |
| H | 0 | OCH₃ | CH₃ | OCH₃ | OCH₃ | N | |
| H | 0 | OCH₃ | CH₃ | Cl | OCH₃ | CH | |
| H | 0 | OCH₃ | CH₂CH₃ | CH₃ | CH₃ | CH | |
| H | 0 | OCH₃ | CH₂CH₃ | CH₃ | OCH₃ | CH | |
| H | 0 | OCH₃ | CH₂CH₃ | OCH₃ | OCH₃ | CH | |
| H | 0 | OCH₃ | CH₂CH₃ | CH₃ | CH₃ | N | |
| H | 0 | OCH₃ | CH₂CH₃ | CH₃ | OCH₃ | N | |
| H | 0 | OCH₃ | CH₂CH₃ | OCH₃ | OCH₃ | N | |
| H | 0 | OCH₃ | CH₂CH₃ | Cl | OCH₃ | CH | |
| H | 0 | OCH₃ | CH₂CH₂CH₃ | CH₃ | CH₃ | CH | |
| H | 0 | OCH₃ | CH₂CH₂CH₃ | CH₃ | OCH₃ | CH | |
| H | 0 | OCH₃ | CH₂CH₂CH₃ | OCH₃ | OCH₃ | CH | |
| H | 0 | OCH₃ | CH₂CH₂CH₃ | CH₃ | CH₃ | N | |
| H | 0 | OCH₃ | CH₂CH₂CH₃ | CH₃ | OCH₃ | N | |
| H | 0 | OCH₃ | CH₂CH₂CH₃ | OCH₃ | OCH₃ | N | |
| H | 0 | OCH₃ | CH₂CH₂CH₃ | Cl | OCH₃ | CH | |
| H | 0 | OCH₃ | CH₂CH₂CH₂CH₃ | CH₃ | CH₃ | CH | |
| H | 0 | OCH₃ | CH₂CH₂CH₂CH₃ | CH₃ | OCH₃ | CH | |
| H | 0 | OCH₃ | CH₂CH₂CH₂CH₃ | OCH₃ | OCH₃ | CH | |
| H | 0 | OCH₃ | CH₂CH₂CH₂CH₃ | CH₃ | CH₃ | N | |
| H | 0 | OCH₃ | CH₂CH₂CH₂CH₃ | CH₃ | OCH₃ | N | |
| H | 0 | OCH₃ | CH₂CH₂CH₂CH₃ | OCH₃ | OCH₃ | N | |
| H | 0 | OCH₃ | CH₂CH₂CH₂CH₃ | Cl | OCH₃ | CH | |
| H | 0 | SCH₃ | CH₃ | CH₃ | CH₃ | CH | |
| H | 0 | SCH₃ | CH₃ | CH₃ | OCH₃ | CH | |
| H | 0 | SCH₃ | CH₃ | OCH₃ | OCH₃ | CH | |
| H | 0 | SCH₃ | CH₃ | CH₃ | CH₃ | N | |
| H | 0 | SCH₃ | CH₃ | CH₃ | OCH₃ | N | |
| H | 0 | SCH₃ | CH₃ | OCH₃ | OCH₃ | N | |
| H | 0 | SCH₃ | CH₃ | Cl | OCH₃ | CH | |
| H | 0 | SCH₃ | CH₂CH₃ | CH₃ | CH₃ | CH | |
| H | 0 | SCH₃ | CH₂CH₃ | CH₃ | OCH₃ | CH | |
| H | 0 | SCH₃ | CH₂CH₃ | OCH₃ | OCH₃ | CH | |
| H | 0 | SCH₃ | CH₂CH₃ | CH₃ | CH₃ | N | |
| H | 0 | SCH₃ | CH₂CH₃ | CH₃ | OCH₃ | N | |
| H | 0 | SCH₃ | CH₂CH₃ | OCH₃ | OCH₃ | N | |
| H | 0 | SCH₃ | CH₂CH₃ | Cl | OCH₃ | CH | |
| H | 0 | SCH₃ | CH₂CH₂CH₃ | CH₃ | CH₃ | CH | |
| H | 0 | SCH₃ | CH₂CH₂CH₃ | CH₃ | OCH₃ | CH | |
| H | 0 | SCH₃ | CH₂CH₂CH₃ | OCH₃ | OCH₃ | CH | |
| H | 0 | SCH₃ | CH₂CH₂CH₃ | CH₃ | CH₃ | N | |
| H | 0 | SCH₃ | CH₂CH₂CH₃ | CH₃ | OCH₃ | N | |
| H | 0 | SCH₃ | CH₂CH₂CH₃ | OCH₃ | OCH₃ | N | |
| H | 0 | SCH₃ | CH₂CH₂CH₃ | Cl | OCH₃ | CH | |
| H | 0 | SCH₃ | CH₂CH₂CH₂CH₃ | CH₃ | CH₃ | CH | |
| H | 0 | SCH₃ | CH₂CH₂CH₂CH₃ | CH₃ | OCH₃ | CH | |
| H | 0 | SCH₃ | CH₂CH₂CH₂CH₃ | OCH₃ | OCH₃ | CH | |
| H | 0 | SCH₃ | CH₂CH₂CH₂CH₃ | CH₃ | CH₃ | N | |
| H | 0 | SCH₃ | CH₂CH₂CH₂CH₃ | CH₃ | OCH₃ | N | |
| H | 0 | SCH₃ | CH₂CH₂CH₂CH₃ | OCH₃ | OCH₃ | N | |
| H | 0 | SCH₃ | CH₂CH₂CH₂CH₃ | Cl | OCH₃ | CH | |
| H | 0 | N(CH₃)₂ | CH₃ | CH₃ | CH₃ | CH | |
| H | 0 | N(CH₃)₂ | CH₃ | CH₃ | OCH₃ | CH | |
| H | 0 | N(CH₃)₂ | CH₃ | OCH₃ | OCH₃ | CH | |
| H | 0 | N(CH₃)₂ | CH₃ | CH₃ | CH₃ | N | |
| H | 0 | N(CH₃)₂ | CH₃ | CH₃ | OCH₃ | N | |
| H | 0 | N(CH₃)₂ | CH₃ | OCH₃ | OCH₃ | N | |
| H | 0 | N(CH₃)₂ | CH₃ | Cl | OCH₃ | CH | |
| H | 0 | N(CH₃)₂ | CH₂CH₃ | CH₃ | CH₃ | CH | |
| H | 0 | N(CH₃)₂ | CH₂CH₃ | CH₃ | OCH₃ | CH | |
| H | 0 | N(CH₃)₂ | CH₂CH₃ | OCH₃ | OCH₃ | CH | |
| H | 0 | N(CH₃)₂ | CH₂CH₃ | CH₃ | CH₃ | N | |
| H | 0 | N(CH₃)₂ | CH₂CH₃ | CH₃ | OCH₃ | N | |
| H | 0 | N(CH₃)₂ | CH₂CH₃ | OCH₃ | OCH₃ | N | |
| H | 0 | N(CH₃)₂ | CH₂CH₃ | Cl | OCH₃ | CH | |
| H | 0 | N(CH₃)₂ | CH₂CH₂CH₃ | CH₃ | CH₃ | CH | |
| H | 0 | N(CH₃)₂ | CH₂CH₂CH₃ | CH₃ | OCH₃ | CH | |
| H | 0 | N(CH₃)₂ | CH₂CH₂CH₃ | OCH₃ | OCH₃ | CH | |
| H | 0 | N(CH₃)₂ | CH₂CH₂CH₃ | CH₃ | CH₃ | N | |
| H | 0 | N(CH₃)₂ | CH₂CH₂CH₃ | CH₃ | OCH₃ | N | |

TABLE VIII-continued

| R₁ | n | R₂ | R' | X | Y | Z | m.p. (°C.) |
|---|---|---|---|---|---|---|---|
| H | 0 | N(CH₃)₂ | CH₂CH₂CH₃ | OCH₃ | OCH₃ | N | |
| H | 0 | N(CH₃)₂ | CH₂CH₂CH₃ | Cl | OCH₃ | CH | |
| H | 0 | N(CH₃)₂ | CH₂CH₂CH₂CH₃ | CH₃ | CH₃ | CH | |
| H | 0 | N(CH₃)₂ | CH₂CH₂CH₂CH₃ | CH₃ | OCH₃ | CH | |
| H | 0 | N(CH₃)₂ | CH₂CH₂CH₂CH₃ | OCH₃ | OCH₃ | CH | |
| H | 0 | N(CH₃)₂ | CH₂CH₂CH₂CH₃ | CH₃ | CH₃ | N | |
| H | 0 | N(CH₃)₂ | CH₂CH₂CH₂CH₃ | CH₃ | OCH₃ | N | |
| H | 0 | N(CH₃)₂ | CH₂CH₂CH₂CH₃ | OCH₃ | OCH₃ | N | |
| H | 0 | N(CH₃)₂ | CH₂CH₂CH₂CH₃ | Cl | OCH₃ | CH | |
| H | 0 | H | CH₂CH₂CH₂CH₂CH₃ | CH₃ | CH₃ | CH | |
| H | 0 | H | CH₂CH₂CH₂CH₂CH₃ | CH₃ | OCH₃ | CH | |
| H | 0 | H | CH₂CH₂CH₂CH₂CH₃ | OCH₃ | OCH₃ | CH | |
| H | 0 | H | CH₂CH₂CH₂CH₂CH₃ | CH₃ | CH₃ | N | |
| H | 0 | H | CH₂CH₂CH₂CH₂CH₃ | CH₃ | OCH₃ | N | |
| H | 0 | H | CH₂CH₂CH₂CH₂CH₃ | OCH₃ | OCH₃ | N | |
| H | 0 | H | CH₂CH₂CH₂CH₂CH₃ | Cl | OCH₃ | CH | |
| H | 0 | H | CH(CH₃)₂ | CH₃ | CH₃ | CH | |
| H | 0 | H | CH(CH₃)₂ | CH₃ | OCH₃ | CH | |
| H | 0 | H | CH(CH₃)₂ | OCH₃ | OCH₃ | CH | |
| H | 0 | H | CH(CH₃)₂ | CH₃ | CH₃ | N | |
| H | 0 | H | CH(CH₃)₂ | CH₃ | OCH₃ | N | |
| H | 0 | H | CH(CH₃)₂ | OCH₃ | OCH₃ | N | |
| H | 0 | H | CH(CH₃)₂ | Cl | OCH₃ | CH | |
| H | 0 | H | CH₂CH(CH₃)₂ | CH₃ | CH₃ | CH | |
| H | 0 | H | CH₂CH(CH₃)₂ | CH₃ | OCH₃ | CH | |
| H | 0 | H | CH₂CH(CH₃)₂ | OCH₃ | OCH₃ | CH | |
| H | 0 | H | CH₂CH(CH₃)₂ | CH₃ | CH₃ | N | |
| H | 0 | H | CH₂CH(CH₃)₂ | CH₃ | OCH₃ | N | |
| H | 0 | H | CH₂CH(CH₃)₂ | OCH₃ | OCH₃ | N | |
| H | 0 | H | CH₂CH(CH₃)₂ | Cl | OCH₃ | CH | |
| H | 0 | H | CH(CH₃)CH₂CH₃ | CH₃ | CH₃ | CH | |
| H | 0 | H | CH(CH₃)CH₂CH₃ | CH₃ | OCH₃ | CH | |
| H | 0 | H | CH(CH₃)CH₂CH₃ | OCH₃ | OCH₃ | CH | |
| H | 0 | H | CH₂CH₂CH(CH₃)₂ | CH₃ | CH₃ | N | |
| H | 0 | H | CH₂CH₂CH(CH₃)₂ | CH₃ | OCH₃ | N | |
| H | 0 | H | CH₂CH₂CH(CH₃)₂ | OCH₃ | OCH₃ | N | |
| H | 0 | H | CH₂CH₂CH(CH₃)₂ | Cl | OCH₃ | CH | |
| H | 0 | H | CH₂Br | CH₃ | CH₃ | CH | |
| H | 0 | H | CH₂Br | CH₃ | OCH₃ | CH | |
| H | 0 | H | CH₂Br | OCH₃ | OCH₃ | CH | |
| H | 0 | H | CH₂CH₂Br | CH₃ | CH₃ | N | |
| H | 0 | H | CH₂CH₂Br | CH₃ | OCH₃ | N | |
| H | 0 | H | CH₂CH₂Br | OCH₃ | OCH₃ | N | |
| H | 0 | H | CH₂CH₂Br | Cl | OCH₃ | CH | |
| H | 0 | H | CH(CH₃)CH₂F | CH₃ | CH₃ | CH | |
| H | 0 | H | CH(CH₃)CH₂F | CH₃ | OCH₃ | CH | |
| H | 0 | H | CH(CH₃)CH₂F | OCH₃ | OCH₃ | CH | |
| H | 0 | H | CH(CH₃)CH₂F | CH₃ | CH₃ | N | |
| H | 0 | H | CH(CH₃)CH₂F | CH₃ | OCH₃ | N | |
| H | 0 | H | CH(CH₃)CH₂F | OCH₃ | OCH₃ | N | |
| H | 0 | H | CH(CH₃)CH₂F | Cl | OCH₃ | CH | |
| H | 0 | H | CH(CH₂F)₂ | CH₃ | CH₃ | CH | |
| H | 0 | H | CH(CH₂F)₂ | CH₃ | OCH₃ | CH | |
| H | 0 | H | CH(CH₂F)₂ | OCH₃ | OCH₃ | CH | |
| H | 0 | H | CH(CH₂F)₂ | CH₃ | CH₃ | N | |
| H | 0 | H | CH(CH₂F)₂ | CH₃ | OCH₃ | N | |
| H | 0 | H | CH(CH₂F)₂ | OCH₃ | OCH₃ | N | |
| H | 0 | H | CH(CH₂F)₂ | Cl | OCH₃ | CH | |
| H | 0 | H | CH₂I | CH₃ | CH₃ | CH | |
| H | 0 | H | CH₂I | CH₃ | OCH₃ | CH | |
| H | 0 | H | CH₂I | OCH₃ | OCH₃ | CH | |
| H | 0 | H | CH₂I | CH₃ | CH₃ | N | |
| H | 0 | H | CH₂CH₂CH₂F | CH₃ | OCH₃ | N | |
| H | 0 | H | CH₂CH₂CH₂F | OCH₃ | OCH₃ | N | |
| H | 0 | H | CH₂CH₂CH₂F | Cl | OCH₃ | CH | |
| H | 0 | H | CH₂OCH₂F | CH₃ | CH₃ | CH | |
| H | 0 | H | CH₂OCH₂F | CH₃ | OCH₃ | CH | |
| H | 0 | H | CH₂OCH₂F | OCH₃ | OCH₃ | CH | |
| H | 0 | H | CH₂OCH₂F | CH₃ | CH₃ | N | |
| H | 0 | H | CH₂OCH₂F | CH₃ | OCH₃ | N | |
| H | 0 | H | CH₂OCH₂F | OCH₃ | OCH₃ | N | |
| H | 0 | H | CH₂OCH₂F | Cl | OCH₃ | CH | |
| H | 0 | H | CH₂SOCH₃ | CH₃ | CH₃ | CH | |
| H | 0 | H | CH₂SOCH₃ | CH₃ | OCH₃ | CH | |
| H | 0 | H | CH₂SOCH₃ | OCH₃ | OCH₃ | CH | |
| H | 0 | H | CH₂SOCH₃ | CH₃ | CH₃ | N | |
| H | 0 | H | CH₂SOCH₃ | CH₃ | OCH₃ | N | |
| H | 0 | H | CH₂SOCH₃ | OCH₃ | OCH₃ | N | |
| H | 0 | H | CH₂SOCH₃ | Cl | OCH₃ | CH | |
| H | 0 | H | CH₂SO₂CH₃ | CH₃ | CH₃ | CH | |

TABLE VIII-continued

| R₁ | n | R₂ | R' | X | Y | Z | m.p. (°C.) |
|---|---|---|---|---|---|---|---|
| H | 0 | H | CH₂SO₂CH₃ | CH₃ | OCH₃ | CH | |
| H | 0 | H | CH₂SO₂CH₃ | OCH₃ | OCH₃ | CH | |
| H | 0 | H | CH₂SO₂CH₃ | CH₃ | CH₃ | N | |
| H | 0 | H | CH₂SO₂CH₃ | CH₃ | OCH₃ | N | |
| H | 0 | H | CH₂SO₂CH₃ | OCH₃ | OCH₃ | N | |
| H | 0 | H | CH₂SO₂CH₃ | Cl | OCH₃ | CH | |
| H | 0 | H | CH₂CN | CH₃ | CH₃ | CH | |
| H | 0 | H | CH₂CH₂CN | CH₃ | OCH₃ | CH | |
| H | 0 | H | CH₂(CH₃)CN | OCH₃ | OCH₃ | CH | |
| H | 0 | H | CH₂NO₂ | CH₃ | CH₃ | N | |
| H | 0 | H | CH₂CH₂NO₂ | CH₃ | OCH₃ | N | |
| H | 0 | H | CH₂CN | OCH₃ | OCH₃ | N | |
| H | 0 | H | CH₂CN | Cl | OCH₃ | CH | |
| H | 0 | H | CH₂N(CH₃)₂ | CH₃ | CH₃ | CH | |
| H | 0 | H | CH₂N(CH₃)₂ | CH₃ | OCH₃ | CH | |
| H | 0 | H | CH₂N(CH₃)₂ | OCH₃ | OCH₃ | CH | |
| H | 0 | H | CH₂N(CH₃)₂ | CH₃ | CH₃ | N | |
| H | 0 | H | CH₂N(CH₃)₂ | CH₃ | OCH₃ | N | |
| H | 0 | H | CH₂N(CH₃)₂ | OCH₃ | OCH₃ | N | |
| H | 0 | H | CH₂N(CH₃)₂ | Cl | OCH₃ | CH | |
| H | 0 | H | CH₂CH₂N(CH₃)₂ | CH₃ | CH₃ | CH | |
| H | 0 | H | CH₂CH₂N(CH₃)₂ | CH₃ | OCH₃ | CH | |
| H | 0 | H | CH₂CH₂N(CH₃)₂ | OCH₃ | OCH₃ | CH | |
| H | 0 | H | CH₂CH₂N(CH₃)₂ | CH₃ | CH₃ | N | |
| H | 0 | H | CH₂CH₂N(CH₃)₂ | CH₃ | OCH₃ | N | |
| H | 0 | H | CH₂CH₂N(CH₃)₂ | OCH₃ | OCH₃ | N | |
| H | 0 | H | CH₂CH₂N(CH₃)₂ | Cl | OCH₃ | CH | |
| H | 0 | H | CH₂CH=CH₂ | CH₃ | CH₃ | CH | |
| H | 0 | H | CH₂CH=CH₂ | CH₃ | OCH₃ | CH | |
| H | 0 | H | CH₂CH=CH₂ | OCH₃ | OCH₃ | CH | |
| H | 0 | H | CH₂CH=CH₂ | CH₃ | CH₃ | N | |
| H | 0 | H | CH₂CH=CH₂ | CH₃ | OCH₃ | N | |
| H | 0 | H | CH₂CH=CH₂ | OCH₃ | OCH₃ | N | |
| H | 0 | H | CH₂CH=CH₂ | Cl | OCH₃ | CH | |
| H | 0 | H | CH=CH₂ | CH₃ | CH₃ | CH | |
| H | 0 | H | CH=CH₂ | CH₃ | OCH₃ | CH | |
| H | 0 | H | CH=CH₂ | OCH₃ | OCH₃ | CH | |
| H | 0 | H | CH=CH₂ | CH₃ | CH₃ | N | |
| H | 0 | H | CH=CH₂ | CH₃ | OCH₃ | N | |
| H | 0 | H | CH=CH₂ | OCH₃ | OCH₃ | N | |
| H | 0 | H | CH=CH₂ | Cl | OCH₃ | CH | |
| H | 1 | H | CH₃ | CH₃ | CH₃ | CH | |
| H | 1 | H | CH₃ | CH₃ | OCH₃ | CH | |
| H | 1 | H | CH₃ | OCH₃ | OCH₃ | CH | |
| H | 1 | H | CH₃ | CH₃ | CH₃ | N | |
| H | 1 | H | CH₃ | CH₃ | OCH₃ | N | |
| H | 1 | H | CH₃ | OCH₃ | OCH₃ | N | |
| H | 1 | H | CH₃ | Cl | OCH₃ | CH | |
| H | 1 | H | CH₂CH₃ | CH₃ | CH₃ | CH | |
| H | 1 | H | CH₂CH₃ | CH₃ | OCH₃ | CH | |
| H | 1 | H | CH₂CH₃ | OCH₃ | OCH₃ | CH | |
| H | 1 | H | CH₂CH₃ | CH₃ | CH₃ | N | |
| H | 1 | H | CH₂CH₃ | CH₃ | OCH₃ | N | |
| H | 1 | H | CH₂CH₃ | OCH₃ | OCH₃ | N | |
| H | 1 | H | CH₂CH₃ | Cl | OCH₃ | CH | |
| H | 1 | H | CH₂CH₂CH₃ | CH₃ | CH₃ | CH | |
| H | 1 | H | CH₂CH₂CH₃ | CH₃ | OCH₃ | CH | |
| H | 1 | H | CH₂CH₂CH₃ | OCH₃ | OCH₃ | CH | |
| H | 1 | H | CH₂CH₂CH₃ | CH₃ | CH₃ | N | |
| H | 1 | H | CH₂CH₂CH₃ | CH₃ | OCH₃ | N | |
| H | 1 | H | CH₂CH₂CH₃ | OCH₃ | OCH₃ | N | |
| H | 1 | H | CH₂CH₂CH₃ | Cl | OCH₃ | CH | |
| H | 1 | H | CH₂CH₂CH₂CH₃ | CH₃ | CH₃ | CH | |
| H | 1 | H | CH₂CH₂CH₂CH₃ | CH₃ | OCH₃ | CH | |
| H | 1 | H | CH₂CH₂CH₂CH₃ | OCH₃ | OCH₃ | CH | |
| H | 1 | H | CH₂CH₂CH₂CH₃ | CH₃ | CH₃ | N | |
| H | 1 | H | CH₂CH₂CH₂CH₃ | CH₃ | OCH₃ | N | |
| H | 1 | H | CH₂CH₂CH₂CH₃ | OCH₃ | OCH₃ | N | |
| H | 1 | H | CH₂CH₂CH₂CH₃ | Cl | OCH₃ | CH | |

TABLE IX

| R₁ | n | R₂ | R' | X | Y | Z | m.p. (°C.) |
|---|---|---|---|---|---|---|---|
| H | 0 | H | cyclopropyl | CH₃ | CH₃ | CH | |
| H | 0 | H | cyclopropyl | CH₃ | OCH₃ | CH | |
| H | 0 | H | cyclopropyl | OCH₃ | OCH₃ | CH | |
| H | 0 | H | cyclopropyl | CH₃ | CH₃ | N | |
| H | 0 | H | cyclopropyl | CH₃ | OCH₃ | N | |

TABLE IX-continued

| R$_1$ | n | R$_2$ | R' | X | Y | Z | m.p. (°C.) |
|---|---|---|---|---|---|---|---|
| H | 0 | H | cyclopropyl | OCH$_3$ | OCH$_3$ | N | |
| H | 0 | H | cyclopropyl | Cl | OCH$_3$ | CH | |
| H | 0 | H | cyclobutyl | CH$_3$ | CH$_3$ | CH | |
| H | 0 | H | cyclobutyl | CH$_3$ | OCH$_3$ | CH | |
| H | 0 | H | cyclobutyl | OCH$_3$ | OCH$_3$ | CH | |
| H | 0 | H | cyclobutyl | CH$_3$ | CH$_3$ | N | |
| H | 0 | H | cyclobutyl | CH$_3$ | OCH$_3$ | N | |
| H | 0 | H | cyclobutyl | OCH$_3$ | OCH$_3$ | N | |
| H | 0 | H | cyclobutyl | Cl | OCH$_3$ | CH | |
| H | 0 | H | cyclopentyl | CH$_3$ | CH$_3$ | CH | |
| H | 0 | H | cyclopentyl | CH$_3$ | OCH$_3$ | CH | |
| H | 0 | H | cyclopentyl | OCH$_3$ | OCH$_3$ | CH | |
| H | 0 | H | cyclopentyl | CH$_3$ | CH$_3$ | N | |
| H | 0 | H | cyclopentyl | CH$_3$ | OCH$_3$ | N | |
| H | 0 | H | cyclopentyl | OCH$_3$ | OCH$_3$ | N | |
| H | 0 | H | cyclopentyl | Cl | OCH$_3$ | CH | |
| H | 0 | H | 2-fluorocyclopropyl | CH$_3$ | CH$_3$ | CH | |
| H | 0 | H | 2-fluorocyclopropyl | CH$_3$ | OCH$_3$ | CH | |
| H | 0 | H | 2-fluorocyclopropyl | OCH$_3$ | OCH$_3$ | CH | |
| H | 0 | H | 2-fluorocyclopropyl | CH$_3$ | CH$_3$ | N | |
| H | 0 | H | 2-fluorocyclopropyl | CH$_3$ | OCH$_3$ | N | |
| H | 0 | H | 2-fluorocyclopropyl | OCH$_3$ | OCH$_3$ | N | |
| H | 0 | H | 2-fluorocyclopropyl | Cl | OCH$_3$ | CH | |
| H | 0 | CH$_3$ | cyclopropyl | CH$_3$ | CH$_3$ | CH | |
| H | 0 | CH$_3$ | cyclopropyl | CH$_3$ | OCH$_3$ | CH | |
| H | 0 | CH$_3$ | cyclopropyl | OCH$_3$ | OCH$_3$ | CH | |
| H | 0 | CH$_3$ | cyclopropyl | CH$_3$ | CH$_3$ | N | |
| H | 0 | CH$_3$ | cyclopropyl | CH$_3$ | OCH$_3$ | N | |
| H | 0 | CH$_3$ | cyclopropyl | OCH$_3$ | OCH$_3$ | N | |
| H | 0 | CH$_3$ | cyclopropyl | Cl | OCH$_3$ | CH | |
| H | 0 | CH$_3$ | cyclobutyl | CH$_3$ | CH$_3$ | CH | |
| H | 0 | CH$_3$ | cyclobutyl | CH$_3$ | OCH$_3$ | CH | |
| H | 0 | CH$_3$ | cyclobutyl | OCH$_3$ | OCH$_3$ | CH | |
| H | 0 | CH$_3$ | cyclobutyl | CH$_3$ | CH$_3$ | N | |
| H | 0 | CH$_3$ | cyclobutyl | CH$_3$ | OCH$_3$ | N | |
| H | 0 | CH$_3$ | cyclobutyl | OCH$_3$ | OCH$_3$ | N | |
| H | 0 | CH$_3$ | cyclobutyl | Cl | OCH$_3$ | CH | |
| H | 0 | CH$_3$ | cyclopentyl | CH$_3$ | CH$_3$ | CH | |
| H | 0 | CH$_3$ | cyclopentyl | CH$_3$ | OCH$_3$ | CH | |
| H | 0 | CH$_3$ | cyclopentyl | OCH$_3$ | OCH$_3$ | CH | |
| H | 0 | CH$_3$ | cyclopentyl | CH$_3$ | CH$_3$ | N | |
| H | 0 | CH$_3$ | cyclopentyl | CH$_3$ | OCH$_3$ | N | |
| H | 0 | CH$_3$ | cyclopentyl | OCH$_3$ | OCH$_3$ | N | |
| H | 0 | CH$_3$ | cyclopentyl | Cl | OCH$_3$ | CH | |
| H | 0 | CH$_3$ | 2-fluorocyclopropyl | CH$_3$ | CH$_3$ | CH | |
| H | 0 | CH$_3$ | 2-fluorocyclopropyl | CH$_3$ | OCH$_3$ | CH | |
| H | 0 | CH$_3$ | 2-fluorocyclopropyl | OCH$_3$ | OCH$_3$ | CH | |
| H | 0 | CH$_3$ | 2-fluorocyclopropyl | CH$_3$ | CH$_3$ | N | |
| H | 0 | CH$_3$ | 2-fluorocyclopropyl | CH$_3$ | OCH$_3$ | N | |
| H | 0 | CH$_3$ | 2-fluorocyclopropyl | OCH$_3$ | OCH$_3$ | N | |
| H | 0 | CH$_3$ | 2-fluorocyclopropyl | Cl | OCH$_3$ | CH | |
| H | 0 | CO$_2$CH$_3$ | cyclopropyl | CH$_3$ | CH$_3$ | CH | |
| H | 0 | CO$_2$CH$_3$ | cyclopropyl | CH$_3$ | OCH$_3$ | CH | |
| H | 0 | CO$_2$CH$_3$ | cyclopropyl | OCH$_3$ | OCH$_3$ | CH | |
| H | 0 | CO$_2$CH$_3$ | cyclopropyl | CH$_3$ | CH$_3$ | N | |
| H | 0 | CO$_2$CH$_3$ | cyclopropyl | CH$_3$ | OCH$_3$ | N | |
| H | 0 | CO$_2$CH$_3$ | cyclopropyl | OCH$_3$ | OCH$_3$ | N | |
| H | 0 | CO$_2$CH$_3$ | cyclopropyl | Cl | OCH$_3$ | CH | |
| H | 0 | CO$_2$CH$_3$ | cyclobutyl | CH$_3$ | CH$_3$ | CH | |
| H | 0 | CO$_2$CH$_3$ | cyclobutyl | CH$_3$ | OCH$_3$ | CH | |
| H | 0 | CO$_2$CH$_3$ | cyclobutyl | OCH$_3$ | OCH$_3$ | CH | |
| H | 0 | CO$_2$CH$_3$ | cyclobutyl | CH$_3$ | CH$_3$ | N | |
| H | 0 | CO$_2$CH$_3$ | cyclobutyl | CH$_3$ | OCH$_3$ | N | |
| H | 0 | CO$_2$CH$_3$ | cyclobutyl | OCH$_3$ | OCH$_3$ | N | |
| H | 0 | CO$_2$CH$_3$ | cyclobutyl | Cl | OCH$_3$ | CH | |
| H | 0 | CO$_2$CH$_3$ | cyclopentyl | CH$_3$ | CH$_3$ | CH | |
| H | 0 | CO$_2$CH$_3$ | cyclopentyl | CH$_3$ | OCH$_3$ | CH | |
| H | 0 | CO$_2$CH$_3$ | cyclopentyl | OCH$_3$ | OCH$_3$ | CH | |
| H | 0 | CO$_2$CH$_3$ | cyclopentyl | CH$_3$ | CH$_3$ | N | |
| H | 0 | CO$_2$CH$_3$ | cyclopentyl | CH$_3$ | OCH$_3$ | N | |
| H | 0 | CO$_2$CH$_3$ | cyclopentyl | OCH$_3$ | OCH$_3$ | N | |
| H | 0 | CO$_2$CH$_3$ | cyclopentyl | Cl | OCH$_3$ | CH | |
| H | 0 | CO$_2$CH$_3$ | 2-fluorocyclopropyl | CH$_3$ | CH$_3$ | CH | |
| H | 0 | CO$_2$CH$_3$ | 2-fluorocyclopropyl | CH$_3$ | OCH$_3$ | CH | |
| H | 0 | CO$_2$CH$_3$ | 2-fluorocyclopropyl | OCH$_3$ | OCH$_3$ | CH | |
| H | 0 | CO$_2$CH$_3$ | 2-fluorocyclopropyl | CH$_3$ | CH$_3$ | N | |
| H | 0 | CO$_2$CH$_3$ | 2-fluorocyclopropyl | CH$_3$ | OCH$_3$ | N | |
| H | 0 | CO$_2$CH$_3$ | 2-fluorocyclopropyl | OCH$_3$ | OCH$_3$ | N | |
| H | 0 | CO$_2$CH$_3$ | 2-fluorocyclopropyl | Cl | OCH$_3$ | CH | |
| H | 0 | OCHF$_2$ | cyclopropyl | CH$_3$ | CH$_3$ | CH | |
| H | 0 | OCHF$_2$ | cyclopropyl | CH$_3$ | OCH$_3$ | CH | |

TABLE IX-continued

| R₁ | n | R₂ | R' | X | Y | Z | m.p. (°C.) |
|---|---|---|---|---|---|---|---|
| H | 0 | OCHF₂ | cyclopropyl | OCH₃ | OCH₃ | CH | |
| H | 0 | OCHF₂ | cyclopropyl | CH₃ | CH₃ | N | |
| H | 0 | OCHF₂ | cyclopropyl | CH₃ | OCH₃ | N | |
| H | 0 | OCHF₂ | cyclopropyl | OCH₃ | OCH₃ | N | |
| H | 0 | OCHF₂ | cyclopropyl | Cl | OCH₃ | CH | |
| H | 0 | OCHF₂ | cyclobutyl | CH₃ | CH₃ | CH | |
| H | 0 | OCHF₂ | cyclobutyl | CH₃ | OCH₃ | CH | |
| H | 0 | OCHF₂ | cyclobutyl | OCH₃ | OCH₃ | CH | |
| H | 0 | OCHF₂ | cyclobutyl | CH₃ | CH₃ | N | |
| H | 0 | OCHF₂ | cyclobutyl | CH₃ | OCH₃ | N | |
| H | 0 | OCHF₂ | cyclobutyl | OCH₃ | OCH₃ | N | |
| H | 0 | OCHF₂ | cyclobutyl | Cl | OCH₃ | CH | |
| H | 0 | OCHF₂ | cyclopentyl | CH₃ | CH₃ | CH | |
| H | 0 | OCHF₂ | cyclopentyl | CH₃ | OCH₃ | CH | |
| H | 0 | OCHF₂ | cyclopentyl | OCH₃ | OCH₃ | CH | |
| H | 0 | OCHF₂ | cyclopentyl | CH₃ | CH₃ | N | |
| H | 0 | OCHF₂ | cyclopentyl | CH₃ | OCH₃ | N | |
| H | 0 | OCHF₂ | cyclopentyl | OCH₃ | OCH₃ | N | |
| H | 0 | OCHF₂ | cyclopentyl | Cl | OCH₃ | CH | |
| H | 0 | OCHF₂ | 2-fluorocyclopropyl | CH₃ | CH₃ | CH | |
| H | 0 | OCHF₂ | 2-fluorocyclopropyl | CH₃ | OCH₃ | CH | |
| H | 0 | OCHF₂ | 2-fluorocyclopropyl | OCH₃ | OCH₃ | CH | |
| H | 0 | OCHF₂ | 2-fluorocyclopropyl | CH₃ | CH₃ | N | |
| H | 0 | OCHF₂ | 2-fluorocyclopropyl | CH₃ | OCH₃ | N | |
| H | 0 | OCHF₂ | 2-fluorocyclopropyl | OCH₃ | OCH₃ | N | |
| H | 0 | OCHF₂ | 2-fluorocyclopropyl | Cl | OCH₃ | CH | |
| H | 0 | OCH₃ | CH₃ | CH₃ | CH₃ | CH | |
| H | 0 | OCH₃ | CH₃ | CH₃ | OCH₃ | CH | |
| H | 0 | OCH₃ | CH₃ | OCH₃ | OCH₃ | CH | |
| H | 0 | OCH₃ | CH₃ | CH₃ | CH₃ | N | |
| H | 0 | OCH₃ | CH₃ | CH₃ | OCH₃ | N | |
| H | 0 | OCH₃ | CH₃ | OCH₃ | OCH₃ | N | |
| H | 0 | OCH₃ | CH₃ | Cl | OCH₃ | CH | |
| H | 0 | OCH₃ | CH₂CH₃ | CH₃ | CH₃ | CH | |
| H | 0 | OCH₃ | CH₂CH₃ | CH₃ | OCH₃ | CH | |
| H | 0 | OCH₃ | CH₂CH₃ | OCH₃ | OCH₃ | CH | |
| H | 0 | OCH₃ | CH₂CH₃ | CH₃ | CH₃ | N | |
| H | 0 | OCH₃ | CH₂CH₃ | CH₃ | OCH₃ | N | |
| H | 0 | OCH₃ | CH₂CH₃ | OCH₃ | OCH₃ | N | |
| H | 0 | OCH₃ | CH₂CH₃ | Cl | OCH₃ | CH | |
| H | 0 | OCH₃ | CH₂CH₂CH₃ | CH₃ | CH₃ | CH | |
| H | 0 | OCH₃ | CH₂CH₂CH₃ | CH₃ | OCH₃ | CH | |
| H | 0 | OCH₃ | CH₂CH₂CH₃ | OCH₃ | OCH₃ | CH | |
| H | 0 | OCH₃ | CH₂CH₂CH₃ | CH₃ | CH₃ | N | |
| H | 0 | OCH₃ | CH₂CH₂CH₃ | CH₃ | OCH₃ | N | |
| H | 0 | OCH₃ | CH₂CH₂CH₃ | OCH₃ | OCH₃ | N | |
| H | 0 | OCH₃ | CH₂CH₂CH₃ | Cl | OCH₃ | CH | |
| H | 0 | OCH₃ | CH₂CH₂CH₂CH₃ | CH₃ | CH₃ | CH | |
| H | 0 | OCH₃ | CH₂CH₂CH₂CH₃ | CH₃ | OCH₃ | CH | |
| H | 0 | OCH₃ | CH₂CH₂CH₂CH₃ | OCH₃ | OCH₃ | CH | |
| H | 0 | OCH₃ | CH₂CH₂CH₂CH₃ | CH₃ | CH₃ | N | |
| H | 0 | OCH₃ | CH₂CH₂CH₂CH₃ | CH₃ | OCH₃ | N | |
| H | 0 | OCH₃ | CH₂CH₂CH₂CH₃ | OCH₃ | OCH₃ | N | |
| H | 0 | OCH₃ | CH₂CH₂CH₂CH₃ | Cl | OCH₃ | CH | |
| H | 0 | SCH₃ | CH₃ | CH₃ | CH₃ | CH | |
| H | 0 | SCH₃ | CH₃ | CH₃ | OCH₃ | CH | |
| H | 0 | SCH₃ | CH₃ | OCH₃ | OCH₃ | CH | |
| H | 0 | SCH₃ | CH₃ | CH₃ | CH₃ | N | |
| H | 0 | SCH₃ | CH₃ | CH₃ | OCH₃ | N | |
| H | 0 | SCH₃ | CH₃ | OCH₃ | OCH₃ | N | |
| H | 0 | SCH₃ | CH₃ | Cl | OCH₃ | CH | |
| H | 0 | SCH₃ | CH₂CH₃ | CH₃ | CH₃ | CH | |
| H | 0 | SCH₃ | CH₂CH₃ | CH₃ | OCH₃ | CH | |
| H | 0 | SCH₃ | CH₂CH₃ | OCH₃ | OCH₃ | CH | |
| H | 0 | SCH₃ | CH₂CH₃ | CH₃ | CH₃ | N | |
| H | 0 | SCH₃ | CH₂CH₃ | CH₃ | OCH₃ | N | |
| H | 0 | SCH₃ | CH₂CH₃ | OCH₃ | OCH₃ | N | |
| H | 0 | SCH₃ | CH₂CH₃ | Cl | OCH₃ | CH | |
| H | 0 | SCH₃ | CH₂CH₂CH₃ | CH₃ | CH₃ | CH | |
| H | 0 | SCH₃ | CH₂CH₂CH₃ | CH₃ | OCH₃ | CH | |
| H | 0 | SCH₃ | CH₂CH₂CH₃ | OCH₃ | OCH₃ | CH | |
| H | 0 | SCH₃ | CH₂CH₂CH₃ | CH₃ | CH₃ | N | |
| H | 0 | SCH₃ | CH₂CH₂CH₃ | CH₃ | OCH₃ | N | |
| H | 0 | SCH₃ | CH₂CH₂CH₃ | OCH₃ | OCH₃ | N | |
| H | 0 | SCH₃ | CH₂CH₂CH₃ | Cl | OCH₃ | CH | |
| H | 0 | SCH₃ | CH₂CH₂CH₂CH₃ | CH₃ | CH₃ | CH | |
| H | 0 | SCH₃ | CH₂CH₂CH₂CH₃ | CH₃ | OCH₃ | CH | |
| H | 0 | SCH₃ | CH₂CH₂CH₂CH₃ | OCH₃ | OCH₃ | CH | |
| H | 0 | SCH₃ | CH₂CH₂CH₂CH₃ | CH₃ | CH₃ | N | |
| H | 0 | SCH₃ | CH₂CH₂CH₂CH₃ | CH₃ | OCH₃ | N | |
| H | 0 | SCH₃ | CH₂CH₂CH₂CH₃ | OCH₃ | OCH₃ | N | |

TABLE IX-continued

| R₁ | n | R₂ | R' | X | Y | Z | m.p. (°C.) |
|---|---|---|---|---|---|---|---|
| H | 0 | SCH₃ | CH₂CH₂CH₂CH₃ | Cl | OCH₃ | CH | |
| H | 0 | H | CH₂F | CH₃ | CH₃ | CH | |
| H | 0 | H | CH₂F | CH₃ | OCH₃ | CH | |
| H | 0 | H | CH₂F | OCH₃ | OCH₃ | CH | |
| H | 0 | H | CH₂F | CH₃ | CH₃ | N | |
| H | 0 | H | CH₂F | CH₃ | OCH₃ | N | |
| H | 0 | H | CH₂F | OCH₃ | OCH₃ | N | |
| H | 0 | H | CH₂F | Cl | OCH₃ | CH | |
| H | 0 | H | CH₂CH₂F | CH₃ | CH₃ | CH | |
| H | 0 | H | CH₂CH₂F | CH₃ | OCH₃ | CH | |
| H | 0 | H | CH₂CH₂F | OCH₃ | OCH₃ | CH | |
| H | 0 | H | CH₂CH₂F | CH₃ | CH₃ | N | |
| H | 0 | H | CH₂CH₂F | CH₃ | OCH₃ | N | |
| H | 0 | H | CH₂CH₂F | OCH₃ | OCH₃ | N | |
| H | 0 | H | CH₂CH₂F | Cl | OCH₃ | CH | |
| H | 0 | H | CHF₂ | CH₃ | CH₃ | CH | |
| H | 0 | H | CHF₂ | CH₃ | OCH₃ | CH | |
| H | 0 | H | CHF₂ | OCH₃ | OCH₃ | CH | |
| H | 0 | H | CHF₂ | CH₃ | CH₃ | N | |
| H | 0 | H | CHF₂ | CH₃ | OCH₃ | N | |
| H | 0 | H | CHF₂ | OCH₃ | OCH₃ | N | |
| H | 0 | H | CHF₂ | Cl | OCH₃ | CH | |
| H | 0 | H | CH₂CF₃ | CH₃ | CH₃ | CH | |
| H | 0 | H | CH₂CF₃ | CH₃ | OCH₃ | CH | |
| H | 0 | H | CH₂CF₃ | OCH₃ | OCH₃ | CH | |
| H | 0 | H | CH₂Cl | CH₃ | CH₃ | N | |
| H | 0 | H | CH₂Cl | CH₃ | OCH₃ | N | |
| H | 0 | H | CH₂Cl | OCH₃ | OCH₃ | N | |
| H | 0 | H | CH₂Cl | Cl | OCH₃ | CH | |
| H | 0 | H | CH₂OCH₃ | CH₃ | CH₃ | CH | |
| H | 0 | H | CH₂OCH₃ | OCH₃ | OCH₃ | CH | |
| H | 0 | H | CH₂OCH₃ | CH₃ | CH₃ | N | |
| H | 0 | H | CH₂OCH₃ | CH₃ | OCH₃ | N | |
| H | 0 | H | CH₂OCH₃ | OCH₃ | OCH₃ | N | |
| H | 0 | H | CH₂OCH₃ | Cl | OCH₃ | CH | |
| H | 0 | H | CH₂OCH₂CH₃ | CH₃ | CH₃ | CH | |
| H | 0 | H | CH₂OCH₂CH₃ | CH₃ | OCH₃ | CH | |
| H | 0 | H | CH₂OCH₃CH₃ | OCH₃ | OCH₃ | CH | |
| H | 0 | H | CH₂OCH₃CH₃ | CH₃ | CH₃ | N | |
| H | 0 | H | CH₂CH₂OCH₃ | CH₃ | OCH₃ | N | |
| H | 0 | H | CH₂CH₂OCH₃ | OCH₃ | OCH₃ | N | |
| H | 0 | H | CH₂CH₂OCH₃ | Cl | OCH₃ | CH | |
| H | 0 | H | CH₂CH₂OCH₃ | CH₃ | CH₃ | CH | |
| H | 0 | H | CH₂CH₂OCH₃ | CH₃ | OCH₃ | CH | |
| H | 0 | H | CH₂CH₂OCH₃ | OCH₃ | OCH₃ | CH | |
| H | 0 | H | CH₂CH₂OCH₃ | CH₃ | CH₃ | N | |
| H | 0 | H | CH(OCH₃)₂ | CH₃ | OCH₃ | N | |
| H | 0 | H | CH(OCH₃)₂ | OCH₃ | OCH₃ | N | |
| H | 0 | H | CH(OCH₃)₂ | Cl | OCH₃ | CH | |
| H | 0 | H | CH₂SCH₃ | CH₃ | CH₃ | CH | |
| H | 0 | H | CH₂SCH₃ | CH₃ | OCH₃ | CH | |
| H | 0 | H | CH₂SCH₃ | OCH₃ | OCH₃ | CH | |
| H | 0 | H | CH₂SCH₃ | CH₃ | CH₃ | N | |
| H | 0 | H | CH₂SCH₃ | CH₃ | OCH₃ | N | |
| H | 0 | H | CH₂SCH₃ | OCH₃ | OCH₃ | N | |
| H | 0 | H | CH₂SCH₃ | Cl | OCH₃ | CH | |
| H | 1 | H | CH₃ | CH₃ | CH₃ | CH | |
| H | 1 | H | CH₃ | CH₃ | OCH₃ | CH | |
| H | 1 | H | CH₃ | OCH₃ | OCH₃ | CH | |
| H | 1 | H | CH₃ | CH₃ | CH₃ | N | |
| H | 1 | H | CH₃ | CH₃ | OCH₃ | N | |
| H | 1 | H | CH₃ | OCH₃ | OCH₃ | N | |
| H | 1 | H | CH₃ | Cl | OCH₃ | CH | |
| H | 1 | H | CH₂CH₃ | CH₃ | CH₃ | CH | |
| H | 1 | H | CH₂CH₃ | CH₃ | OCH₃ | CH | |
| H | 1 | H | CH₂CH₃ | OCH₃ | OCH₃ | CH | |
| H | 1 | H | CH₂CH₃ | CH₃ | CH₃ | N | |
| H | 1 | H | CH₂CH₃ | CH₃ | OCH₃ | N | |
| H | 1 | H | CH₂CH₃ | OCH₃ | OCH₃ | N | |
| H | 1 | H | CH₂CH₃ | Cl | OCH₃ | CH | |
| H | 1 | H | CH₂CH₂CH₃ | CH₃ | CH₃ | CH | |
| H | 1 | H | CH₂CH₂CH₃ | CH₃ | OCH₃ | CH | |
| H | 1 | H | CH₂CH₂CH₃ | OCH₃ | OCH₃ | CH | |
| H | 1 | H | CH₂CH₂CH₃ | CH₃ | CH₃ | N | |
| H | 1 | H | CH₂CH₂CH₃ | CH₃ | OCH₃ | N | |
| H | 1 | H | CH₂CH₂CH₃ | OCH₃ | OCH₃ | N | |
| H | 1 | H | CH₂CH₂CH₃ | Cl | OCH₃ | CH | |
| H | 1 | H | CH₂CH₂CH₂CH₃ | CH₃ | CH₃ | CH | |
| H | 1 | H | CH₂CH₂CH₂CH₃ | CH₃ | OCH₃ | CH | |
| H | 1 | H | CH₂CH₂CH₂CH₃ | OCH₃ | OCH₃ | CH | |

TABLE IX-continued

| R₁ | n | R₂ | R' | X | Y | Z | m.p. (°C.) |
|---|---|---|---|---|---|---|---|
| H | 1 | H | CH₂CH₂CH₂CH₃ | CH₃ | CH₃ | N | |
| H | 1 | H | CH₂CH₂CH₂CH₃ | CH₃ | OCH₃ | N | |
| H | 1 | H | CH₂CH₂CH₂CH₃ | OCH₃ | OCH₃ | N | |
| H | 1 | H | CH₂CH₂CH₂CH₃ | Cl | OCH₃ | CH | |

TABLE X

| R₁ | n | R₂ | R' | X | Y | Z | m.p. (°C.) |
|---|---|---|---|---|---|---|---|
| H | 0 | H | cyclopropyl | CH₃ | CH₃ | CH | |
| H | 0 | H | cyclopropyl | CH₃ | OCH₃ | CH | |
| H | 0 | H | cyclopropyl | OCH₃ | OCH₃ | CH | |
| H | 0 | H | cyclopropyl | CH₃ | CH₃ | N | |
| H | 0 | H | cyclopropyl | CH₃ | OCH₃ | N | |
| H | 0 | H | cyclopropyl | OCH₃ | OCH₃ | N | |
| H | 0 | H | cyclopropyl | Cl | OCH₃ | CH | |
| H | 0 | H | cyclobutyl | CH₃ | CH₃ | CH | |
| H | 0 | H | cyclobutyl | CH₃ | OCH₃ | CH | |
| H | 0 | H | cyclobutyl | OCH₃ | OCH₃ | CH | |
| H | 0 | H | cyclobutyl | CH₃ | CH₃ | N | |
| H | 0 | H | cyclobutyl | CH₃ | OCH₃ | N | |
| H | 0 | H | cyclobutyl | OCH₃ | OCH₃ | N | |
| H | 0 | H | cyclobutyl | Cl | OCH₃ | CH | |
| H | 0 | H | cyclopentyl | CH₃ | CH₃ | CH | |
| H | 0 | H | cyclopentyl | CH₃ | OCH₃ | CH | |
| H | 0 | H | cyclopentyl | OCH₃ | OCH₃ | CH | |
| H | 0 | H | cyclopentyl | CH₃ | CH₃ | N | |
| H | 0 | H | cyclopentyl | CH₃ | OCH₃ | N | |
| H | 0 | H | cyclopentyl | OCH₃ | OCH₃ | N | |
| H | 0 | H | cyclopentyl | Cl | OCH₃ | CH | |
| H | 0 | H | 2-fluorocyclopropyl | CH₃ | CH₃ | CH | |
| H | 0 | H | 2-fluorocyclopropyl | CH₃ | OCH₃ | CH | |
| H | 0 | H | 2-fluorocyclopropyl | OCH₃ | OCH₃ | CH | |
| H | 0 | H | 2-fluorocyclopropyl | CH₃ | CH₃ | N | |
| H | 0 | H | 2-fluorocyclopropyl | CH₃ | OCH₃ | N | |
| H | 0 | H | 2-fluorocyclopropyl | OCH₃ | OCH₃ | N | |
| H | 0 | H | 2-fluorocyclopropyl | Cl | OCH₃ | CH | |
| H | 0 | CH₃ | cyclopropyl | CH₃ | CH₃ | CH | |
| H | 0 | CH₃ | cyclopropyl | CH₃ | OCH₃ | CH | |
| H | 0 | CH₃ | cyclopropyl | OCH₃ | OCH₃ | CH | |
| H | 0 | CH₃ | cyclopropyl | CH₃ | CH₃ | N | |
| H | 0 | CH₃ | cyclopropyl | CH₃ | OCH₃ | N | |
| H | 0 | CH₃ | cyclopropyl | OCH₃ | OCH₃ | N | |
| H | 0 | CH₃ | cyclopropyl | Cl | OCH₃ | CH | |
| H | 0 | CH₃ | cyclobutyl | CH₃ | CH₃ | CH | |
| H | 0 | CH₃ | cyclobutyl | CH₃ | OCH₃ | CH | |
| H | 0 | CH₃ | cyclobutyl | OCH₃ | OCH₃ | CH | |
| H | 0 | CH₃ | cyclobutyl | CH₃ | CH₃ | N | |
| H | 0 | CH₃ | cyclobutyl | CH₃ | OCH₃ | N | |
| H | 0 | CH₃ | cyclobutyl | OCH₃ | OCH₃ | N | |
| H | 0 | CH₃ | cyclobutyl | Cl | OCH₃ | CH | |
| H | 0 | CH₃ | cyclopentyl | CH₃ | CH₃ | CH | |
| H | 0 | CH₃ | cyclopentyl | CH₃ | OCH₃ | CH | |
| H | 0 | CH₃ | cyclopentyl | OCH₃ | OCH₃ | CH | |
| H | 0 | CH₃ | cyclopentyl | CH₃ | CH₃ | N | |
| H | 0 | CH₃ | cyclopentyl | CH₃ | OCH₃ | N | |
| H | 0 | CH₃ | cyclopentyl | OCH₃ | OCH₃ | N | |
| H | 0 | CH₃ | cyclopentyl | Cl | OCH₃ | CH | |
| H | 0 | CH₃ | 2-fluorocyclopropyl | CH₃ | CH₃ | CH | |
| H | 0 | CH₃ | 2-fluorocyclopropyl | CH₃ | OCH₃ | CH | |
| H | 0 | CH₃ | 2-fluorocyclopropyl | OCH₃ | OCH₃ | CH | |
| H | 0 | CH₃ | 2-fluorocyclopropyl | CH₃ | CH₃ | N | |
| H | 0 | CH₃ | 2-fluorocyclopropyl | CH₃ | OCH₃ | N | |
| H | 0 | CH₃ | 2-fluorocyclopropyl | OCH₃ | OCH₃ | N | |
| H | 0 | CH₃ | 2-fluorocyclopropyl | Cl | OCH₃ | CH | |
| H | 0 | CO₂CH₃ | cyclopropyl | CH₃ | CH₃ | CH | |
| H | 0 | CO₂CH₃ | cyclopropyl | CH₃ | OCH₃ | CH | |
| H | 0 | CO₂CH₃ | cyclopropyl | OCH₃ | OCH₃ | CH | |
| H | 0 | CO₂CH₃ | cyclopropyl | CH₃ | CH₃ | N | |
| H | 0 | CO₂CH₃ | cyclopropyl | CH₃ | OCH₃ | N | |
| H | 0 | CO₂CH₃ | cyclopropyl | OCH₃ | OCH₃ | N | |
| H | 0 | CO₂CH₃ | cyclopropyl | Cl | OCH₃ | CH | |
| H | 0 | CO₂CH₃ | cyclobutyl | CH₃ | CH₃ | CH | |
| H | 0 | CO₂CH₃ | cyclobutyl | CH₃ | OCH₃ | CH | |
| H | 0 | CO₂CH₃ | cyclobutyl | OCH₃ | OCH₃ | CH | |
| H | 0 | CO₂CH₃ | cyclobutyl | CH₃ | CH₃ | N | |
| H | 0 | CO₂CH₃ | cyclobutyl | CH₃ | OCH₃ | N | |
| H | 0 | CO₂CH₃ | cyclobutyl | OCH₃ | OCH₃ | N | |
| H | 0 | CO₂CH₃ | cyclobutyl | Cl | OCH₃ | CH | |
| H | 0 | CO₂CH₃ | cyclopentyl | CH₃ | CH₃ | CH | |

TABLE X-continued

| $R_1$ | n | $R_2$ | R' | X | Y | Z | m.p. (°C.) |
|---|---|---|---|---|---|---|---|
| H | 0 | $CO_2CH_3$ | cyclopentyl | $CH_3$ | $OCH_3$ | CH | |
| H | 0 | $CO_2CH_3$ | cyclopentyl | $OCH_3$ | $OCH_3$ | CH | |
| H | 0 | $CO_2CH_3$ | cyclopentyl | $CH_3$ | $CH_3$ | N | |
| H | 0 | $CO_2CH_3$ | cyclopentyl | $CH_3$ | $OCH_3$ | N | |
| H | 0 | $CO_2CH_3$ | cyclopentyl | $OCH_3$ | $OCH_3$ | N | |
| H | 0 | $CO_2CH_3$ | cyclopentyl | Cl | $OCH_3$ | CH | |
| H | 0 | $CO_2CH_3$ | 2-fluorocyclopropyl | $CH_3$ | $CH_3$ | CH | |
| H | 0 | $CO_2CH_3$ | 2-fluorocyclopropyl | $CH_3$ | $OCH_3$ | CH | |
| H | 0 | $CO_2CH_3$ | 2-fluorocyclopropyl | $OCH_3$ | $OCH_3$ | CH | |
| H | 0 | $CO_2CH_3$ | 2-fluorocyclopropyl | $CH_3$ | $CH_3$ | N | |
| H | 0 | $CO_2CH_3$ | 2-fluorocyclopropyl | $CH_3$ | $OCH_3$ | N | |
| H | 0 | $CO_2CH_3$ | 2-fluorocyclopropyl | $OCH_3$ | $OCH_3$ | N | |
| H | 0 | $CO_2CH_3$ | 2-fluorocyclopropyl | Cl | $OCH_3$ | CH | |
| H | 0 | $CH_3$ | $CH_3$ | $CH_3$ | $CH_3$ | CH | |
| H | 0 | $CH_3$ | $CH_3$ | $CH_3$ | $OCH_3$ | CH | |
| H | 0 | $CH_3$ | $CH_3$ | $OCH_3$ | $OCH_3$ | CH | |
| H | 0 | $CH_3$ | $CH_3$ | $CH_3$ | $CH_3$ | N | |
| H | 0 | $CH_3$ | $CH_3$ | $CH_3$ | $OCH_3$ | N | |
| H | 0 | $CH_3$ | $CH_3$ | $OCH_3$ | $OCH_3$ | N | |
| H | 0 | $CH_3$ | $CH_3$ | Cl | $OCH_3$ | CH | |
| H | 0 | $CH_3$ | $CH_2CH_3$ | $CH_3$ | $CH_3$ | CH | |
| H | 0 | $CH_3$ | $CH_2CH_3$ | $CH_3$ | $OCH_3$ | CH | |
| H | 0 | $CH_3$ | $CH_2CH_3$ | $OCH_3$ | $OCH_3$ | CH | |
| H | 0 | $CH_3$ | $CH_2CH_3$ | $CH_3$ | $CH_3$ | N | |
| H | 0 | $CH_3$ | $CH_2CH_3$ | $CH_3$ | $OCH_3$ | N | |
| H | 0 | $CH_3$ | $CH_2CH_3$ | $OCH_3$ | $OCH_3$ | N | |
| H | 0 | $CH_3$ | $CH_2CH_3$ | Cl | $OCH_3$ | CH | |
| H | 0 | $CH_3$ | $CH_2CH_2CH_3$ | $CH_3$ | $CH_3$ | CH | |
| H | 0 | $CH_3$ | $CH_2CH_2CH_3$ | $CH_3$ | $OCH_3$ | CH | |
| H | 0 | $CH_3$ | $CH_2CH_2CH_3$ | $OCH_3$ | $OCH_3$ | CH | |
| H | 0 | $CH_3$ | $CH_2CH_2CH_3$ | $CH_3$ | $CH_3$ | N | |
| H | 0 | $CH_3$ | $CH_2CH_2CH_3$ | $CH_3$ | $OCH_3$ | N | |
| H | 0 | $CH_3$ | $CH_2CH_2CH_3$ | $OCH_3$ | $OCH_3$ | N | |
| H | 0 | $CH_3$ | $CH_2CH_2CH_3$ | Cl | $OCH_3$ | CH | |
| H | 0 | $CH_3$ | $CH_2CH_2CH_2CH_3$ | $CH_3$ | $CH_3$ | CH | |
| H | 0 | $CH_3$ | $CH_2CH_2CH_2CH_3$ | $CH_3$ | $OCH_3$ | CH | |
| H | 0 | $CH_3$ | $CH_2CH_2CH_2CH_3$ | $OCH_3$ | $OCH_3$ | CH | |
| H | 0 | $CH_3$ | $CH_2CH_2CH_2CH_3$ | $CH_3$ | $CH_3$ | N | |
| H | 0 | $CH_3$ | $CH_2CH_2CH_2CH_3$ | $CH_3$ | $OCH_3$ | N | |
| H | 0 | $CH_3$ | $CH_2CH_2CH_2CH_3$ | $OCH_3$ | $OCH_3$ | N | |
| H | 0 | $CH_3$ | $CH_2CH_2CH_2CH_3$ | Cl | $OCH_3$ | CH | |
| H | 0 | H | $CH_2F$ | $CH_3$ | $CH_3$ | CH | |
| H | 0 | H | $CH_2F$ | $CH_3$ | $OCH_3$ | CH | |
| H | 0 | H | $CH_2F$ | $OCH_3$ | $OCH_3$ | CH | |
| H | 0 | H | $CH_2F$ | $CH_3$ | $CH_3$ | N | |
| H | 0 | H | $CH_2F$ | $CH_3$ | $OCH_3$ | N | |
| H | 0 | H | $CH_2F$ | $OCH_3$ | $OCH_3$ | N | |
| H | 0 | H | $CH_2F$ | Cl | $OCH_3$ | CH | |
| H | 0 | H | $CH_2CH_2F$ | $CH_3$ | $CH_3$ | CH | |
| H | 0 | H | $CH_2CH_2F$ | $CH_3$ | $OCH_3$ | CH | |
| H | 0 | H | $CH_2CH_2F$ | $OCH_3$ | $OCH_3$ | CH | |
| H | 0 | H | $CH_2CH_2F$ | $CH_3$ | $CH_3$ | N | |
| H | 0 | H | $CH_2CH_2F$ | $CH_3$ | $OCH_3$ | N | |
| H | 0 | H | $CH_2CH_2F$ | $OCH_3$ | $OCH_3$ | N | |
| H | 0 | H | $CH_2CH_2F$ | Cl | $OCH_3$ | CH | |
| H | 0 | H | $CHF_2$ | $CH_3$ | $CH_3$ | CH | |
| H | 0 | H | $CHF_2$ | $CH_3$ | $OCH_3$ | CH | |
| H | 0 | H | $CHF_2$ | $OCH_3$ | $OCH_3$ | CH | |
| H | 0 | H | $CHF_2$ | $CH_3$ | $CH_3$ | N | |
| H | 0 | H | $CHF_2$ | $CH_3$ | $OCH_3$ | N | |
| H | 0 | H | $CHF_2$ | $OCH_3$ | $OCH_3$ | N | |
| H | 0 | H | $CHF_2$ | Cl | $OCH_3$ | CH | |
| H | 0 | H | $CH_2CF_3$ | $CH_3$ | $CH_3$ | CH | |
| H | 0 | H | $CH_2CF_3$ | $CH_3$ | $OCH_3$ | CH | |
| H | 0 | H | $CH_2CF_3$ | $OCH_3$ | $OCH_3$ | CH | |
| H | 0 | H | $CH_2Cl$ | $CH_3$ | $CH_3$ | N | |
| H | 0 | H | $CH_2Cl$ | $CH_3$ | $OCH_3$ | N | |
| H | 0 | H | $CH_2Cl$ | $OCH_3$ | $OCH_3$ | N | |
| H | 0 | H | $CH_2Cl$ | Cl | $OCH_3$ | CH | |

TABLE XI

| $R_1$ | n | $R_2$ | R' | X | Y | Z | m.p. (°C.) |
|---|---|---|---|---|---|---|---|
| H | 0 | H | cyclopropyl | $CH_3$ | $CH_3$ | CH | |
| H | 0 | H | cyclopropyl | $CH_3$ | $OCH_3$ | CH | |
| H | 0 | H | cyclopropyl | $OCH_3$ | $OCH_3$ | CH | |
| H | 0 | H | cyclopropyl | $CH_3$ | $CH_3$ | N | |
| H | 0 | H | cyclopropyl | $CH_3$ | $OCH_3$ | N | |
| H | 0 | H | cyclopropyl | $OCH_3$ | $OCH_3$ | N | |

TABLE XI-continued

| R₁ | n | R₂ | R' | X | Y | Z | m.p. (°C.) |
|---|---|---|---|---|---|---|---|
| H | 0 | H | cyclopropyl | Cl | OCH₃ | CH | |
| H | 0 | H | cyclobutyl | CH₃ | CH₃ | CH | |
| H | 0 | H | cyclobutyl | CH₃ | OCH₃ | CH | |
| H | 0 | H | cyclobutyl | OCH₃ | OCH₃ | CH | |
| H | 0 | H | cyclobutyl | CH₃ | CH₃ | N | |
| H | 0 | H | cyclobutyl | CH₃ | OCH₃ | N | |
| H | 0 | H | cyclobutyl | OCH₃ | OCH₃ | N | |
| H | 0 | H | cyclobutyl | Cl | OCH₃ | CH | |
| H | 0 | H | cyclopentyl | CH₃ | CH₃ | CH | |
| H | 0 | H | cyclopentyl | CH₃ | OCH₃ | CH | |
| H | 0 | H | cyclopentyl | OCH₃ | OCH₃ | CH | |
| H | 0 | H | cyclopentyl | CH₃ | CH₃ | N | |
| H | 0 | H | cyclopentyl | CH₃ | OCH₃ | N | |
| H | 0 | H | cyclopentyl | OCH₃ | OCH₃ | N | |
| H | 0 | H | cyclopentyl | Cl | OCH₃ | CH | |
| H | 0 | H | 2-fluorocyclopropyl | CH₃ | CH₃ | CH | |
| H | 0 | H | 2-fluorocyclopropyl | CH₃ | OCH₃ | CH | |
| H | 0 | H | 2-fluorocyclopropyl | OCH₃ | OCH₃ | CH | |
| H | 0 | H | 2-fluorocyclopropyl | CH₃ | CH₃ | N | |
| H | 0 | H | 2-fluorocyclopropyl | CH₃ | OCH₃ | N | |
| H | 0 | H | 2-fluorocyclopropyl | OCH₃ | OCH₃ | N | |
| H | 0 | H | 2-fluorocyclopropyl | Cl | OCH₃ | CH | |
| H | 0 | CH₃ | cyclopropyl | CH₃ | CH₃ | CH | |
| H | 0 | CH₃ | cyclopropyl | CH₃ | OCH₃ | CH | |
| H | 0 | CH₃ | cyclopropyl | OCH₃ | OCH₃ | CH | |
| H | 0 | CH₃ | cyclopropyl | CH₃ | CH₃ | N | |
| H | 0 | CH₃ | cyclopropyl | CH₃ | OCH₃ | N | |
| H | 0 | CH₃ | cyclopropyl | OCH₃ | OCH₃ | N | |
| H | 0 | CH₃ | cyclopropyl | Cl | OCH₃ | CH | |
| H | 0 | CH₃ | cyclobutyl | CH₃ | CH₃ | CH | |
| H | 0 | CH₃ | cyclobutyl | CH₃ | OCH₃ | CH | |
| H | 0 | CH₃ | cyclobutyl | OCH₃ | OCH₃ | CH | |
| H | 0 | CH₃ | cyclobutyl | CH₃ | CH₃ | N | |
| H | 0 | CH₃ | cyclobutyl | CH₃ | OCH₃ | N | |
| H | 0 | CH₃ | cyclobutyl | OCH₃ | OCH₃ | N | |
| H | 0 | CH₃ | cyclobutyl | Cl | OCH₃ | CH | |
| H | 0 | CH₃ | cyclopentyl | CH₃ | CH₃ | CH | |
| H | 0 | CH₃ | cyclopentyl | CH₃ | OCH₃ | CH | |
| H | 0 | CH₃ | cyclopentyl | OCH₃ | OCH₃ | CH | |
| H | 0 | CH₃ | cyclopentyl | CH₃ | CH₃ | N | |
| H | 0 | CH₃ | cyclopentyl | CH₃ | OCH₃ | N | |
| H | 0 | CH₃ | cyclopentyl | OCH₃ | OCH₃ | N | |
| H | 0 | CH₃ | cyclopentyl | Cl | OCH₃ | CH | |
| H | 0 | CH₃ | 2-fluorocyclopropyl | CH₃ | CH₃ | CH | |
| H | 0 | CH₃ | 2-fluorocyclopropyl | CH₃ | OCH₃ | CH | |
| H | 0 | CH₃ | 2-fluorocyclopropyl | OCH₃ | OCH₃ | CH | |
| H | 0 | CH₃ | 2-fluorocyclopropyl | CH₃ | CH₃ | N | |
| H | 0 | CH₃ | 2-fluorocyclopropyl | CH₃ | OCH₃ | N | |
| H | 0 | CH₃ | 2-fluorocyclopropyl | OCH₃ | OCH₃ | N | |
| H | 0 | CH₃ | 2-fluorocyclopropyl | Cl | OCH₃ | CH | |
| H | 0 | OCH₂CF₃ | cyclopropyl | CH₃ | CH₃ | CH | |
| H | 0 | OCH₂CF₃ | cyclopropyl | CH₃ | OCH₃ | CH | |
| H | 0 | OCH₂CF₃ | cyclopropyl | OCH₃ | OCH₃ | CH | |
| H | 0 | OCH₂CF₃ | cyclopropyl | CH₃ | CH₃ | N | |
| H | 0 | OCH₂CF₃ | cyclopropyl | CH₃ | OCH₃ | N | |
| H | 0 | OCH₂CF₃ | cyclopropyl | OCH₃ | OCH₃ | N | |
| H | 0 | OCH₂CF₃ | cyclopropyl | Cl | OCH₃ | CH | |
| H | 0 | OCH₂CF₃ | cyclobutyl | CH₃ | CH₃ | CH | |
| H | 0 | OCH₂CF₃ | cyclobutyl | CH₃ | OCH₃ | CH | |
| H | 0 | OCH₂CF₃ | cyclobutyl | OCH₃ | OCH₃ | CH | |
| H | 0 | OCH₂CF₃ | cyclobutyl | CH₃ | CH₃ | N | |
| H | 0 | OCH₂CF₃ | cyclobutyl | CH₃ | OCH₃ | N | |
| H | 0 | OCH₂CF₃ | cyclobutyl | OCH₃ | OCH₃ | N | |
| H | 0 | OCH₂CF₃ | cyclobutyl | Cl | OCH₃ | CH | |
| H | 0 | OCH₂CF₃ | cyclopentyl | CH₃ | CH₃ | CH | |
| H | 0 | OCH₂CF₃ | cyclopentyl | CH₃ | OCH₃ | CH | |
| H | 0 | OCH₂CF₃ | cyclopentyl | OCH₃ | OCH₃ | CH | |
| H | 0 | OCH₂CF₃ | cyclopentyl | CH₃ | CH₃ | N | |
| H | 0 | OCH₂CF₃ | cyclopentyl | CH₃ | OCH₃ | N | |
| H | 0 | OCH₂CF₃ | cyclopentyl | OCH₃ | OCH₃ | N | |
| H | 0 | OCH₂CF₃ | cyclopentyl | Cl | OCH₃ | CH | |
| H | 0 | OCH₂CF₃ | 2-fluorocyclopropyl | CH₃ | CH₃ | CH | |
| H | 0 | OCH₂CF₃ | 2-fluorocyclopropyl | CH₃ | OCH₃ | CH | |
| H | 0 | OCH₂CF₃ | 2-fluorocyclopropyl | OCH₃ | OCH₃ | CH | |
| H | 0 | OCH₂CF₃ | 2-fluorocyclopropyl | CH₃ | CH₃ | N | |
| H | 0 | OCH₂CF₃ | 2-fluorocyclopropyl | CH₃ | OCH₃ | N | |
| H | 0 | OCH₂CF₃ | 2-fluorocyclopropyl | OCH₃ | OCH₃ | N | |
| H | 0 | OCH₂CF₃ | 2-fluorocyclopropyl | Cl | OCH₃ | CH | |
| H | 1 | H | cyclopropyl | CH₃ | CH₃ | CH | |
| H | 1 | H | cyclopropyl | CH₃ | OCH₃ | CH | |
| H | 1 | H | cyclopropyl | OCH₃ | OCH₃ | CH | |

TABLE XI-continued

| R₁ | n | R₂ | R' | X | Y | Z | m.p. (°C.) |
|---|---|---|---|---|---|---|---|
| H | 1 | H | cyclopropyl | CH₃ | CH₃ | N | |
| H | 1 | H | cyclopropyl | CH₃ | OCH₃ | N | |
| H | 1 | H | cyclopropyl | OCH₃ | OCH₃ | N | |
| H | 1 | H | cyclopropyl | Cl | OCH₃ | CH | |
| H | 1 | H | cyclobutyl | CH₃ | CH₃ | CH | |
| H | 1 | H | cyclobutyl | CH₃ | OCH₃ | CH | |
| H | 1 | H | cyclobutyl | OCH₃ | OCH₃ | CH | |
| H | 1 | H | cyclobutyl | CH₃ | CH₃ | N | |
| H | 1 | H | cyclobutyl | CH₃ | OCH₃ | N | |
| H | 1 | H | cyclobutyl | OCH₃ | OCH₃ | N | |
| H | 1 | H | cyclobutyl | Cl | OCH₃ | CH | |
| H | 1 | H | cyclopentyl | CH₃ | CH₃ | CH | |
| H | 1 | H | cyclopentyl | CH₃ | OCH₃ | CH | |
| H | 1 | H | cyclopentyl | OCH₃ | OCH₃ | CH | |
| H | 1 | H | cyclopentyl | CH₃ | CH₃ | N | |
| H | 1 | H | cyclopentyl | CH₃ | OCH₃ | N | |
| H | 1 | H | cyclopentyl | OCH₃ | OCH₃ | N | |
| H | 1 | H | cyclopentyl | Cl | OCH₃ | CH | |
| H | 1 | H | 2-fluorocyclopropyl | CH₃ | CH₃ | CH | |
| H | 1 | H | 2-fluorocyclopropyl | CH₃ | OCH₃ | CH | |
| H | 1 | H | 2-fluorocyclopropyl | OCH₃ | OCH₃ | CH | |
| H | 1 | H | 2-fluorocyclopropyl | CH₃ | CH₃ | N | |
| H | 1 | H | 2-fluorocyclopropyl | CH₃ | OCH₃ | N | |
| H | 1 | H | 2-fluorocyclopropyl | OCH₃ | OCH₃ | N | |
| H | 1 | H | 2-fluorocyclopropyl | Cl | OCH₃ | CH | |
| H | 0 | SO₂N(CH₃)₂ | CH₃ | CH₃ | CH₃ | CH | |
| H | 0 | SO₂N(CH₃)₂ | CH₃ | CH₃ | OCH₃ | CH | |
| H | 0 | SO₂N(CH₃)₂ | CH₃ | OCH₃ | OCH₃ | CH | |
| H | 0 | SO₂N(CH₃)₂ | CH₃ | CH₃ | CH₃ | N | |
| H | 0 | SO₂N(CH₃)₂ | CH₃ | CH₃ | OCH₃ | N | |
| H | 0 | SO₂N(CH₃)₂ | CH₃ | OCH₃ | OCH₃ | N | |
| H | 0 | SO₂N(CH₃)₂ | CH₃ | Cl | OCH₃ | CH | |
| H | 0 | SO₂N(CH₃)₂ | CH₂CH₃ | CH₃ | CH₃ | CH | |
| H | 0 | SO₂N(CH₃)₂ | CH₂CH₃ | CH₃ | OCH₃ | CH | |
| H | 0 | SO₂N(CH₃)₂ | CH₂CH₃ | OCH₃ | OCH₃ | CH | |
| H | 0 | SO₂N(CH₃)₂ | CH₂CH₃ | CH₃ | CH₃ | N | |
| H | 0 | SO₂N(CH₃)₂ | CH₂CH₃ | CH₃ | OCH₃ | N | |
| H | 0 | SO₂N(CH₃)₂ | CH₂CH₃ | OCH₃ | OCH₃ | N | |
| H | 0 | SO₂N(CH₃)₂ | CH₂CH₃ | Cl | OCH₃ | CH | |
| H | 0 | SO₂N(CH₃)₂ | CH₂CH₂CH₃ | CH₃ | CH₃ | CH | |
| H | 0 | SO₂N(CH₃)₂ | CH₂CH₂CH₃ | CH₃ | OCH₃ | CH | |
| H | 0 | SO₂N(CH₃)₂ | CH₂CH₂CH₃ | OCH₃ | OCH₃ | CH | |
| H | 0 | SO₂N(CH₃)₂ | CH₂CH₂CH₃ | CH₃ | CH₃ | N | |
| H | 0 | SO₂N(CH₃)₂ | CH₂CH₂CH₃ | CH₃ | OCH₃ | N | |
| H | 0 | SO₂N(CH₃)₂ | CH₂CH₂CH₃ | OCH₃ | OCH₃ | N | |
| H | 0 | SO₂N(CH₃)₂ | CH₂CH₂CH₃ | Cl | OCH₃ | CH | |
| H | 0 | SO₂N(CH₃)₂ | CH₂CH₂CH₂CH₃ | CH₃ | CH₃ | CH | |
| H | 0 | SO₂N(CH₃)₂ | CH₂CH₂CH₂CH₃ | CH₃ | OCH₃ | CH | |
| H | 0 | SO₂N(CH₃)₂ | CH₂CH₂CH₂CH₃ | OCH₃ | OCH₃ | CH | |
| H | 0 | SO₂N(CH₃)₂ | CH₂CH₂CH₂CH₃ | CH₃ | CH₃ | N | |
| H | 0 | SO₂N(CH₃)₂ | CH₂CH₂CH₂CH₃ | CH₃ | OCH₃ | N | |
| H | 0 | SO₂N(CH₃)₂ | CH₂CH₂CH₂CH₃ | OCH₃ | OCH₃ | N | |
| H | 0 | SO₂N(CH₃)₂ | CH₂CH₂CH₂CH₃ | Cl | OCH₃ | CH | |
| H | 0 | H | CH₃ | CH₃ | CH₃ | CH | |
| H | 0 | H | CH₃ | CH₃ | OCH₃ | CH | |
| H | 0 | H | CH₃ | OCH₃ | OCH₃ | CH | |
| H | 0 | H | CH₃ | CH₃ | CH₃ | N | |
| H | 0 | H | CH₃ | CH₃ | OCH₃ | N | |
| H | 0 | H | CH₃ | OCH₃ | OCH₃ | N | |
| H | 0 | H | CH₃ | Cl | OCH₃ | CH | |
| H | 0 | H | CH₂CH₃ | CH₃ | CH₃ | CH | |
| H | 0 | H | CH₂CH₃ | CH₃ | OCH₃ | CH | |
| H | 0 | H | CH₂CH₃ | OCH₃ | OCH₃ | CH | |
| H | 0 | H | CH₂CH₃ | CH₃ | CH₃ | N | |
| H | 0 | H | CH₂CH₃ | CH₃ | OCH₃ | N | |
| H | 0 | H | CH₂CH₃ | OCH₃ | OCH₃ | N | |
| H | 0 | H | CH₂CH₃ | Cl | OCH₃ | CH | |
| H | 0 | H | CH₂CH₂CH₃ | CH₃ | CH₃ | CH | |
| H | 0 | H | CH₂CH₂CH₃ | CH₃ | OCH₃ | CH | |
| H | 0 | H | CH₂CH₂CH₃ | OCH₃ | OCH₃ | CH | |
| H | 0 | H | CH₂CH₂CH₃ | CH₃ | CH₃ | N | |
| H | 0 | H | CH₂CH₂CH₃ | CH₃ | OCH₃ | N | |
| H | 0 | H | CH₂CH₂CH₃ | OCH₃ | OCH₃ | N | |
| H | 0 | H | CH₂CH₂CH₃ | Cl | OCH₃ | CH | |
| H | 0 | H | CH₂CH₂CH₂CH₃ | CH₃ | CH₃ | CH | |
| H | 0 | H | CH₂CH₂CH₂CH₃ | CH₃ | OCH₃ | CH | |
| H | 0 | H | CH₂CH₂CH₂CH₃ | OCH₃ | OCH₃ | CH | |
| H | 0 | H | CH₂CH₂CH₂CH₃ | CH₃ | CH₃ | N | |
| H | 0 | H | CH₂CH₂CH₂CH₃ | CH₃ | OCH₃ | N | |
| H | 0 | H | CH₂CH₂CH₂CH₃ | OCH₃ | OCH₃ | N | |
| H | 0 | H | CH₂CH₂CH₂CH₃ | Cl | OCH₃ | CH | |

TABLE XI-continued

| R₁ | n | R₂ | R' | X | Y | Z | m.p. (°C.) |
|---|---|---|---|---|---|---|---|
| H | 0 | H | CH₂OCH₃ | CH₃ | CH₃ | CH | |
| H | 0 | H | CH₂OCH₃ | CH₃ | OCH₃ | CH | |
| H | 0 | H | CH₂OCH₃ | OCH₃ | OCH₃ | CH | |
| H | 0 | H | CH₂OCH₃ | CH₃ | CH₃ | N | |
| H | 0 | H | CH₂OCH₃ | CH₃ | OCH₃ | N | |
| H | 0 | H | CH₂OCH₃ | OCH₃ | OCH₃ | N | |
| H | 0 | H | CH₂OCH₃ | Cl | OCH₃ | CH | |
| H | 0 | H | CH₂OCH₂CH₃ | CH₃ | CH₃ | CH | |
| H | 0 | H | CH₂OCH₂CH₃ | CH₃ | OCH₃ | CH | |
| H | 0 | H | CH₂OCH₂CH₃ | OCH₃ | OCH₃ | CH | |
| H | 0 | H | CH₂OCH₂CH₃ | CH₃ | CH₃ | N | |
| H | 0 | H | CH₂CH₂OCH₃ | CH₃ | CH₃ | N | |
| H | 0 | H | CH₂CH₂OCH₃ | OCH₃ | OCH₃ | N | |
| H | 0 | H | CH₂CH₂OCH₃ | Cl | OCH₃ | CH | |
| H | 0 | H | CH₂CH₂OCH₃ | CH₃ | CH₃ | CH | |
| H | 0 | H | CH₂CH₂OCH₃ | CH₃ | OCH₃ | CH | |
| H | 0 | H | CH₂CH₂OCH₃ | OCH₃ | OCH₃ | CH | |
| H | 0 | H | CH₂CH₂OCH₃ | CH₃ | CH₃ | N | |
| H | 0 | H | CH(OCH₃)₂ | CH₃ | OCH₃ | N | |
| H | 0 | H | CH(OCH₃)₂ | OCH₃ | OCH₃ | N | |
| H | 0 | H | CH(OCH₃)₂ | Cl | OCH₃ | CH | |
| H | 0 | H | CH₂SCH₃ | CH₃ | CH₃ | CH | |
| H | 0 | H | CH₂SCH₃ | CH₃ | OCH₃ | CH | |
| H | 0 | H | CH₂SCH₃ | OCH₃ | OCH₃ | CH | |
| H | 0 | H | CH₂SCH₃ | CH₃ | CH₃ | N | |
| H | 0 | H | CH₂SCH₃ | CH₃ | OCH₃ | N | |
| H | 0 | H | CH₂SCH₃ | OCH₃ | OCH₃ | N | |
| H | 0 | H | CH₂SCH₃ | Cl | OCH₃ | CH | |
| H | 1 | H | CH₃ | CH₃ | CH₃ | CH | |
| H | 1 | H | CH₃ | CH₃ | OCH₃ | CH | |
| H | 1 | H | CH₃ | OCH₃ | OCH₃ | CH | |
| H | 1 | H | CH₃ | CH₃ | CH₃ | N | |
| H | 1 | H | CH₃ | OCH₃ | OCH₃ | N | |
| H | 1 | H | CH₃ | Cl | OCH₃ | CH | |
| H | 1 | H | CH₂CH₃ | CH₃ | CH₃ | CH | |
| H | 1 | H | CH₂CH₃ | OCH₃ | OCH₃ | CH | |
| H | 1 | H | CH₂CH₃ | CH₃ | CH₃ | N | |
| H | 1 | H | CH₂CH₃ | CH₃ | OCH₃ | N | |
| H | 1 | H | CH₂CH₃ | OCH₃ | OCH₃ | N | |
| H | 1 | H | CH₂CH₃ | Cl | OCH₃ | CH | |
| H | 1 | H | CH₂CH₂CH₃ | CH₃ | CH₃ | CH | |
| H | 1 | H | CH₂CH₂CH₃ | CH₃ | OCH₃ | CH | |
| H | 1 | H | CH₂CH₂CH₃ | OCH₃ | OCH₃ | CH | |
| H | 1 | H | CH₂CH₂CH₃ | CH₃ | CH₃ | N | |
| H | 1 | H | CH₂CH₂CH₃ | CH₃ | OCH₃ | N | |
| H | 1 | H | CH₂CH₂CH₃ | OCH₃ | OCH₃ | N | |
| H | 1 | H | CH₂CH₂CH₃ | Cl | OCH₃ | CH | |
| H | 1 | H | CH₂CH₂CH₂CH₃ | CH₃ | CH₃ | CH | |
| H | 1 | H | CH₂CH₂CH₂CH₃ | CH₃ | OCH₃ | CH | |
| H | 1 | H | CH₂CH₂CH₂CH₃ | OCH₃ | OCH₃ | CH | |
| H | 1 | H | CH₂CH₂CH₂CH₃ | CH₃ | CH₃ | N | |
| H | 1 | H | CH₂CH₂CH₂CH₃ | CH₃ | OCH₃ | N | |
| H | 1 | H | CH₂CH₂CH₂CH₃ | OCH₃ | OCH₃ | N | |
| H | 1 | H | CH₂CH₂CH₂CH₃ | Cl | OCH₃ | CH | |

TABLE XII

| J | R | R' | A | X₁ | Y₁ | m.p. (°C.) |
|---|---|---|---|---|---|---|
| J-1 | CH₃ | CH₃ | A-2 | CH₃ | O | |
| J-1 | CH₃ | CH₃ | A-2 | OCH₃ | O | |
| J-1 | CH₃ | CH₃ | A-2 | OCH₂CH₃ | O | |
| J-1 | CH₃ | CH₃ | A-2 | OCF₂H | O | |
| J-1 | CH₃ | CH₃ | A-2 | CH₃ | CH₂ | |
| J-1 | CH₃ | CH₃ | A-2 | OCH₃ | CH₂ | |
| J-2 | — | cyclopropyl | A-2 | CH₃ | O | |
| J-2 | — | cyclopropyl | A-2 | OCH₃ | O | |
| J-2 | — | cyclopropyl | A-2 | OCH₂CH₃ | O | |
| J-2 | — | cyclopropyl | A-2 | OCF₂H | O | |
| J-2 | — | cyclopropyl | A-2 | CH₃ | CH₂ | |
| J-2 | — | cyclopropyl | A-2 | OCH₃ | CH₂ | |
| J-3 | — | cyclopropyl | A-2 | CH₃ | O | |
| J-3 | — | cyclopropyl | A-2 | OCH₃ | O | |
| J-3 | — | cyclopropyl | A-2 | OCH₂CH₃ | O | |
| J-3 | — | cyclopropyl | A-2 | OCF₂H | O | |
| J-3 | — | cyclopropyl | A-2 | CH₃ | CH₂ | |
| J-3 | — | cyclopropyl | A-2 | OCH₃ | CH₂ | |

| J | R | R' | A | X₁ | m.p. (°C.) |
|---|---|---|---|---|---|
| J-1 | CH₃ | CH₃ | A-3 | CH₃ | |
| J-1 | CH₃ | CH₃ | A-3 | OCH₃ | |
| J-1 | CH₃ | CH₃ | A-3 | OCH₂CH₃ | |
| J-1 | CH₃ | CH₃ | A-3 | OCF₂H | |
| J-2 | — | cyclopropyl | A-3 | CH₃ | |
| J-2 | — | cyclopropyl | A-3 | OCH₃ | |
| J-2 | — | cyclopropyl | A-3 | OCH₂CH₃ | |
| J-2 | — | cyclopropyl | A-3 | OCF₂H | |
| J-3 | — | cyclopropyl | A-3 | CH₃ | |
| J-3 | — | cyclopropyl | A-3 | OCH₃ | |
| J-3 | — | cyclopropyl | A-3 | OCH₂CH₃ | |
| J-3 | — | cyclopropyl | A-3 | OCF₂H | |

| J | R | R' | A | X₁ | Y₃ | m.p. (°C.) |
|---|---|---|---|---|---|---|
| J-1 | CH₃ | CH₃ | A-4 | CH₃ | H | |
| J-1 | CH₃ | CH₃ | A-4 | OCH₃ | H | |
| J-1 | CH₃ | CH₃ | A-4 | OCH₂CH₃ | H | |

TABLE XII-continued

| J | R | R' | A | X | Y |
|---|---|---|---|---|---|
| J-1 | CH$_3$ | CH$_3$ | A-4 | OCF$_2$H | H |
| J-1 | CH$_3$ | CH$_3$ | A-4 | CH$_3$ | CH$_3$ |
| J-1 | CH$_3$ | CH$_3$ | A-4 | OCH$_3$ | CH$_3$ |
| J-2 | — | cyclopropyl | A-4 | CH$_3$ | H |
| J-2 | — | cyclopropyl | A-4 | OCH$_3$ | H |
| J-2 | — | cyclopropyl | A-4 | OCH$_2$CH$_3$ | H |
| J-2 | — | cyclopropyl | A-4 | OCF$_2$H | H |
| J-2 | — | cyclopropyl | A-4 | CH$_3$ | CH$_3$ |
| J-2 | — | cyclopropyl | A-4 | OCH$_3$ | CH$_3$ |
| J-3 | — | cyclopropyl | A-4 | CH$_3$ | H |
| J-3 | — | cyclopropyl | A-4 | OCH$_3$ | H |
| J-3 | — | cyclopropyl | A-4 | OCH$_2$CH$_3$ | H |
| J-3 | — | cyclopropyl | A-4 | OCF$_2$H | H |
| J-3 | — | cyclopropyl | A-4 | CH$_3$ | CH$_3$ |
| J-3 | — | cyclopropyl | A-4 | OCH$_3$ | CH$_3$ |

| J | R | R' | A | X$_2$ | Y$_2$ | m.p. (°C.) |
|---|---|---|---|---|---|---|
| J-1 | CH$_3$ | CH$_3$ | A-5 | CH$_3$ | OCH$_3$ | |
| J-1 | CH$_3$ | CH$_3$ | A-5 | CH$_3$ | OCH$_2$CH$_3$ | |
| J-1 | CH$_3$ | CH$_3$ | A-5 | CH$_3$ | SCH$_3$ | |
| J-1 | CH$_3$ | CH$_3$ | A-5 | CH$_3$ | CH$_3$ | |
| J-1 | CH$_3$ | CH$_3$ | A-5 | CH$_3$ | CH$_2$CH$_3$ | |
| J-1 | CH$_3$ | CH$_3$ | A-5 | CH$_2$CH$_3$ | OCH$_3$ | |
| J-1 | CH$_3$ | CH$_3$ | A-5 | CH$_2$CF$_3$ | CH$_3$ | |
| J-2 | — | cyclopropyl | A-5 | CH$_3$ | OCH$_3$ | |
| J-2 | — | cyclopropyl | A-5 | CH$_3$ | OCH$_2$CH$_3$ | |
| J-2 | — | cyclopropyl | A-5 | CH$_3$ | SCH$_3$ | |
| J-2 | — | cyclopropyl | A-5 | CH$_3$ | CH$_3$ | |
| J-2 | — | cyclopropyl | A-5 | CH$_3$ | CH$_2$CH$_3$ | |
| J-2 | — | cyclopropyl | A-5 | CH$_2$CH$_3$ | OCH$_3$ | |
| J-2 | — | cyclopropyl | A-5 | CH$_2$CF$_3$ | CH$_3$ | |
| J-3 | — | cyclopropyl | A-5 | CH$_3$ | OCH$_3$ | |
| J-3 | — | cyclopropyl | A-5 | CH$_3$ | OCH$_2$CH$_3$ | |
| J-3 | — | cyclopropyl | A-5 | CH$_3$ | SCH$_3$ | |
| J-3 | — | cyclopropyl | A-5 | CH$_3$ | CH$_3$ | |
| J-3 | — | cyclopropyl | A-5 | CH$_3$ | CH$_2$CH$_3$ | |
| J-3 | — | cyclopropyl | A-5 | CH$_2$CH$_3$ | OCH$_3$ | |
| J-3 | — | cyclopropyl | A-5 | CH$_2$CF$_3$ | CH$_3$ | |

| J | R | R' | A | X$_3$ | m.p. (°C.) |
|---|---|---|---|---|---|
| J-1 | CH$_3$ | CH$_3$ | A-6 | CH$_3$ | |
| J-1 | CH$_3$ | CH$_3$ | A-6 | OCH$_3$ | |
| J-2 | — | cyclopropyl | A-6 | CH$_3$ | |
| J-2 | — | cyclopropyl | A-6 | OCH$_3$ | |
| J-3 | — | cyclopropyl | A-6 | CH$_3$ | |
| J-3 | — | cyclopropyl | A-6 | OCH$_3$ | |

| J | R | R' | A | X$_4$ | Y$_4$ | m.p. (°C.) |
|---|---|---|---|---|---|---|
| J-1 | CH$_3$ | CH$_3$ | A-7 | CH$_3$ | OCH$_3$ | |
| J-1 | CH$_3$ | CH$_3$ | A-7 | OCH$_3$ | OCH$_3$ | |
| J-2 | — | cyclopropyl | A-7 | CH$_3$ | OCH$_3$ | |
| J-2 | — | cyclopropyl | A-7 | OCH$_3$ | OCH$_3$ | |
| J-3 | — | cyclopropyl | A-7 | CH$_3$ | OCH$_3$ | |
| J-3 | — | cyclopropyl | A-7 | OCH$_3$ | OCH$_3$ | |

TABLE XIII

Compounds of Formula I where W=O, A is A-1, E is CH$_2$, R is CH$_3$ and n' is 0

| J | R$_1$ | R$_2$ | n | R' | X | Y | Z | m.p. (°C.) |
|---|---|---|---|---|---|---|---|---|
| J-8 | H | H | 1 | CH$_3$ | CH$_3$ | CH$_3$ | CH | |
| J-8 | H | H | 1 | CH$_3$ | CH$_3$ | OCH$_3$ | CH | |
| J-8 | H | H | 1 | CH$_3$ | OCH$_3$ | OCH$_3$ | CH | |
| J-8 | CH$_3$ | H | 1 | CH$_3$ | OCH$_3$ | OCH$_3$ | CH | |
| J-8 | H | H | 1 | CH$_3$ | OCH$_3$ | OCH$_3$ | N | |
| J-8 | H | H | 1 | CH$_3$ | OCH$_3$ | CH$_3$ | N | |
| J-8 | H | H | 1 | CH$_2$CH$_3$ | CH$_3$ | CH$_3$ | CH | |
| J-8 | H | H | 1 | CH$_2$CH$_3$ | OCH$_3$ | CH$_3$ | CH | |
| J-8 | H | H | 1 | CH$_2$CH$_3$ | OCH$_3$ | OCH$_3$ | CH | |
| J-8 | H | H | 1 | CH$_2$CH$_3$ | OCH$_3$ | OCH$_3$ | N | |
| J-8 | H | H | 1 | CH$_2$CH$_3$ | OCH$_3$ | CH$_3$ | N | |
| J-9 | H | H | 1 | CH$_2$CH$_2$CH$_3$ | OCH$_3$ | OCH$_3$ | CH | |
| J-1 | H | H | — | CH$_3$ | OCH$_3$ | OCH$_3$ | CH | |
| J-6 | H | H | — | CH$_3$ | OCH$_3$ | OCH$_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser one for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 8

Wettable Powder

| | |
|---|---|
| 4-Acetyl-N—[(4,6-dimethoxypyrimidin-2-yl)aminocarbonyl]-1-methyl-1-H—pyrazole-5-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

Wettable Powder

| | |
|---|---|
| 4-Acetyl-N—[(4,6-dimethoxypyrimidin-2-yl)aminocarbonyl]-1-methyl-1-H—pyrazole-5-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to product particles essentially all below 10 microns in diameter. The product is reblended before packaging.

EXAMPLE 10

Granule

| | |
|---|---|
| Wettable Powder of Example 9 | 5% |
| attapulgite granules | 95% |
| (U.S.S. 20 to 40 mesh; 0.84–0.42 mm) | |

A slurry of wettable powder containing 25% solids is sprayed on the surface of attapulgite granules in a double-cone blender. The granules are dried and packaged.

EXAMPLE 11

Extruded Pellet

| | |
|---|---|
| 4-Acetyl-N—[(4,6-dimethoxypyrimidin-2-yl)aminocarbonyl]-1-methyl-1-H—pyrazole-5-sulfonamide | 25% |
| anhydrous sodium sulfite | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

Low Strength Granule

| | |
|---|---|
| 4-Acetyl-N—[(4,6-dimethoxypyrimidin-2-yl)aminocarbonyl]-1-methyl-1-H—pyrazole-5-sulfonamide | 0.1% |
| attapulgite granules | 99.9% |
| (U.S.S. 20 to 40 mesh) | |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

| | |
|---|---|
| 4-Acetyl-N—[(4,6-dimethoxypyrimidin-2-yl)aminocarbonyl]-1-methyl-1-H—pyrazole-5-sulfonamide | 80% |
| wetting agent | 1% |
| crude ligninsulfonate salt (containing 5 to 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 14

Low Strength Granule

| | |
|---|---|
| 4-Acetyl-N—[(4,6-dimethoxypyrimidin-2-yl)aminocarbonyl]-1-methyl-1-H—pyrazole-5-sulfonamide | 1% |
| N,N—dimethylformamide | 9% |
| attapulgite granules | 90% |
| (U.S.S. 20 to 40 sieve) | |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

Aqueous Suspension

| | |
|---|---|
| 4-Acetyl-N—[(4,6-dimethoxypyrimidin-2-yl)aminocarbonyl]-1-methyl-1-H—pyrazole-5-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

Solution

| | |
|---|---|
| 4-Acetyl-N—[(4,6-dimethoxypyrimidin-2-yl)aminocarbonyl]-1-methyl-1-H—pyrazole-5-sulfonamide, ammonium salt | 5 |
| water | 95% |

The salt is added directly to the water with stirring to produce the solution, which may then be packaged for use.

EXAMPLE 17

High Strength Concentrate

| | |
|---|---|
| 4-Acetyl-N—[(4,6-dimethoxypyrimidin-2-yl)aminocarbonyl]-1-methyl-1-H—pyrazole-5-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 18

Wettable Powder

| | |
|---|---|
| 4-Acetyl-N—[(4,6-dimethoxypyrimidin-2-yl)aminocarbonyl]-1-methyl-1-H—pyrazole-5-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 19

Wettable Powder

| | |
|---|---|
| 4-Acetyl-N—[(4,6-dimethoxypyrimidin-2-yl)aminocarbonyl]-1-methyl-1-H—pyrazole-5-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

Oil Suspension

| | |
|---|---|
| 4-Acetyl-N—[(4,6-dimethoxypyrimidin-2-yl)aminocarbonyl]-1-methyl-1-H—pyrazole-5-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 21

Dust

| | |
|---|---|
| 4-Acetyl-N—[(4,6-dimethoxypyrimidin-2-yl)aminocarbonyl]-1-methyl-1-H—pyrazole-5-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 22

Oil Suspension

| | |
|---|---|
| 4-Acetyl-N—[(4,6-dimethoxypyrimidin-2-yl)aminocarbonyl]-1-methyl-1-H—pyrazole-5-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 23

Wettable Powder

| | |
|---|---|
| 4-Acetyl-N—[(4,6-dimethoxypyrimidin-2-yl)-[aminocarbonyl]-1-methyl-1-H—pyrazole-5-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are highly active preemergent or postemergent herbicides or plant growth regulants. Many of them have utility for broad-spectrum pre- and/or postemergence weed control in areas where complete control of all vegetation is desired, such as around fuel shortage tanks, industrial storage areas, parking lots, drive-in theaters, around billboards, highway and railroad structures. Some of the compounds have utility for selective weed control in crops such as wheat, barley, rice, soybeans and corn. Alternatively, the subject compounds are useful to modify plant growth.

The rates of application for the compounds of the invention are determined by a number of factors, including their use as plant growth modifiers or as herbicies, the crop species involved, the types of weeds to be controlled, weather and climate, formulations selected, mode of application, amount of foilage present, etc. In general terms, the subject compounds should be applied at levels of around 0.001 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, imidazolinone, uracil, urea, amide, diphenylether, carbamate and bipyridylium types as well as other sulfonylureas. They are particularly useful with the following herbicides.

| Chemical Name | |
|---|---|
| Common Name | |
| alachlor | 2-chloro-2',6'-diethyl-N—(methoxymethyl)-acetanilide |
| atrazine | 2-chloro-4-(ethylamino)-6-(isopropylamino)-s-triazine |
| butylate | S—ethyl-diisobutylthiocarbamate |
| cyanazine | 2-[[4-chloro-6-(ethylamino)-s-triazin-2-yl]-amino]-2-methylpropionitrile |
| dicamba | 3,6-dichloro-o-anisic acid |
| EPTC | S—ethyl dipropylthiocarbamate |
| linuron | 3-(3,4-dichlorophenyl)-1-methoxy-1-methylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)-one |
| tridiphane | 2-(3,5-dichlorophenyl)-2-(2,2,2-trichloroethyl)oxirane |
| 2,4-D | (2,4-dichlorophenoxy)acetic acid |
| thiobencarb | S—4-chlorobenzyldiethylthiocarbamate |
| molinate | S—ethyl N,N—hexamethylenethiocarbamate |
| butachlor | N—(butoxymethyl)-2-chloro-2',6'-diethylacetanilide |
| naproanilide | N—phenyl-2-(1-naphthyloxy)propionamide |
| pyrazolate | 4-(2,4-dichlorobenzoyl)-1,3-dimethyl-pyrazol-5-yl-4-toluenesulfonate |
| pretilachlor | 2-chloro-2',6'-diethyl-N—(n-propoxyethyl)acetanilide |
| oxidiazon | 3-[2,4-dichloro-5-(1-methylethoxy)-phenyl]-5-(1,1-dimethylethyl)-1,3,4-oxadiazol-2(3H)—one |
| Trade Name or Code Number | |
| Harmony ® | 3-[[(4-methoxy-6-methyl-1,3,5-triazin-2-yl)aminocarbonyl]aminosulfonyl]-2-thiophenecarboxylic acid, methyl ester |
| Cinch ® | exo-1-methyl-4-(1-methylethyl)-2-[(2-methylphenyl)methoxy]-7-oxabicyclo-[2,2,1]heptane |
| MY-93 | S—(1-methyl-1-phenethyl)piperidine-1-carbothioate |
| CH-83 | S—(2-methylpropyl)-hexahydro-1H—azepine-1-carbothioic acid, ester |
| X-52 | 2,4-dichlorophenyl-3-methoxy-4-nitrophenyl ether |
| SC-2957 | S—benzyl-N—ethyl-N—propylthiocarbamate |
| HW-52 | N—(2,3-dichlorophenyl)-4-(ethoxymethoxy)benzamide |
| NTN-801 | 2-(benzothiazol-2-yl)-N—methyl-N—phenylacetamide |
| SL-49 | 2-[4-[(2,4-dichlorophenyl)carbonyl]-1,3-dimethyl-1H—pyrazol-5-yloxy]-1-phenylethanone |
| 20 | |
| BAS-514 | 3,7-dichloro-8-quinoline carboxylic acid |

The herbicidal properties of the subject compounds were discovered in a number of greenhouse tests. The test procedures and results follow.

Compounds

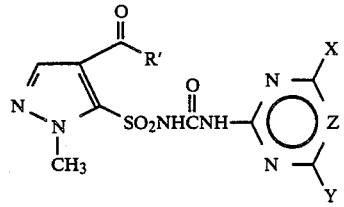

| Compound | R' | X | Y | Z |
|---|---|---|---|---|
| 1 | CH₃ | OCH₃ | OCH₃ | CH |
| 2 | CH₂CH₂CH₃ | CH₃ | CH₃ | CH |
| 3 | CH₂CH₂CH₃ | OCH₃ | CH₃ | CH |
| 4 | CH₂CH₂CH₃ | OCH₃ | OCH₃ | CH |
| 5 | CH₂CH₂CH₃ | OCH₃ | CH₃ | N |
| 6 | CH₂CH₂CH₃ | OCH₃ | OCH₃ | N |
| 7 | CH₂CH₂CH₃ | Cl | OCH₃ | CH |
| 8 | CH₂CH₃ | OCH₃ | OCH₃ | CH |
| 9 | CH₂CH₃ | CH₃ | CH₃ | CH |
| 10 | CH₂CH₃ | CH₃ | OCH₃ | CH |
| 11 | CH₂CH₃ | CH₃ | OCH₃ | N |
| 12 | CH₂CH₃ | OCH₃ | OCH₃ | N |
| 13 | CH₂CH₃ | Cl | OCH₃ | CH |
| 14 | CH(CH₃)₂ | CH₃ | CH₃ | CH |
| 15 | CH(CH₃)₂ | CH₃ | OCH₃ | CH |
| 16 | CH(CH₃)₂ | OCH₃ | OCH₃ | CH |
| 17 | CH(CH₃)₂ | CH₃ | OCH₃ | N |
| 18 | CH(CH₃)₂ | OCH₃ | OCH₃ | N |
| 19 | CH(CH₃)₂ | Cl | OCH₃ | CH |

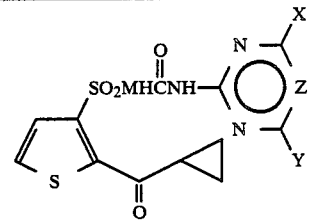

| Compound | X | Y | Z |
|---|---|---|---|
| 20 | CH₃ | CH₃ | CH |
| 21 | CH₃ | OCH₃ | CH |
| 22 | OCH₃ | OCH₃ | CH |
| 23 | CH₃ | OCH₃ | N |
| 24 | OCH₃ | OCH₃ | N |
| 25 | Cl | OCH₃ | CH |

TEST A

Seeds of crabgrass (Digitaria spp.), barnyardgrass (Echinochloa crusgalli), giant foxtail (Setaria faberi), wild oats (Avena fatua), cheatgrass (Bromus secalinus), velvetleaf (Abutilon theophrasti), morningglory (Ipomoea spp.), cocklebur (Xanthium pennsylvanicum), sorghum, corn soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a solid/foilage application. At the time of treatment, the plants range in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axillary stimulation
S=albinism
6Y=abscised buds or flowers.

TABLE A

| | Compound 1 | | Compound 2 | | Compound 3 | | Compound 4 | | Compound 5 | | Compound 6 | | Compound 7 | | Compound 8 | | Compound 9 | | CMPD 10 | |
|---|---|---|---|---|---|---|---|---|---|---|---|---|---|---|---|---|---|---|---|---|
| Rate g/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| Corn | 9H | 3C,5H | 0 | 0 | 3C,9H | 1C,4H | 3C,9H | 3C,9H | 3C,9H | 0 | 6H | 2C,6H | 0 | 0 | 9C | 4C,9G | 2C,9H | 4G | 9C | 9H |
| Wheat | 2G | 0 | 0 | 0 | 0 | 0 | 0 | 0 | 0 | 0 | 0 | 0 | 0 | 0 | 0 | 0 | 7G | 0 | 7G | 0 |
| Barley | 5G | 0 | 0 | 0 | 2C | 0 | 0 | 0 | 0 | 0 | 0 | 0 | 0 | 0 | 5G | 3C,5H | 3C,8G | 6G | 3C,7G | 3C,7G |
| Rice | 5C,9G | 8G | 0 | 0 | 7G | 3G | 2G | 0 | 5G | 3G | 4C,9G | 3G | 2G | 0 | 3C,8H | 10C | 9C | 8G | 2C,7G | 2C,7G |
| Soybean | 4C,9G | 6H | 4G | 0 | 2C,4H | 1H | 3H | 0 | 0 | 0 | 0 | 0 | 1C | 0 | 10C | 10C | 6H | 3H | 3C,7G | 3C,7G |
| Cotton | 9G | 9H | 3C,8H | 3C,8H | 10C | 4C,8H | 4C,9G | 4C,9G | 8G | 0 | 4C,9G | 3G | 7G | 0 | 10C | 10C | 9C | 10C | 10C | 10C |
| Sugar beet | 9C | 9C | 3C,6G | 2C,3G | 4C,9H | 3C,6G | 4C,8G | 4C,8G | 1C | 2G | 3C,5G | 2H | 3C,6G | 0 | 10C | 2G | 9C | 10C | 9C | 9C |
| Crabgrass | 3C,8G | 2C,6G | 0 | 0 | 2G | 0 | 4G | 0 | 0 | 0 | 0 | 0 | 0 | 0 | 3C,7G | 0 | 3G | 3G | 9C | 9C |
| Barnyardgrass | 9C | 5C,9H | 0 | 0 | 4C,9H | 2C,5G | 3C,5H | 3C,5H | 2C,5H | 2H | 9H | 2C,5H | 0 | 0 | 9C | 5C,9G | 9C | 4C,9H | 9C | 4C,9H |
| Nutsedge | 3C,9G | 9G | 0 | 0 | 4C,9G | 2C,5G | 4C,9G | 4C,9G | 5C,9G | 4C,9H | 4G | 0 | 0 | 0 | 9C | 9C | 5C,9G | 4C,9G | 9C | 5C,9G |
| Giant Foxtail | 5C,9G | 3C,8G | 7G | 2H | 3C,7G | 5G | 4C,8G | 4C,8G | 3C,7G | 0 | 2C,5G | 0 | 3C,6G | 0 | 9C | 2C,5G | 9C | 3C,8G | 9C | 3C,8G |
| Cheatgrass | 4C,9G | 8G | 2G | 0 | 8G | 5G | 8G | 8G | 2G | 0 | 5G | 0 | 7G | 0 | 9C | 2C,8G | 5C,9G | 7G | 9C | 7G |
| Wild Oats | 2C,5G | 0 | 6G | 0 | 1C | 0 | 2G | 0 | 0 | 0 | 0 | 0 | 0 | 0 | 10C | 9C | 3C,6G | 0 | 2C,6G | 0 |
| Cocklebur | 9C | 3C,9H | 4C,9G | 3C,9H | 4C,9G | 4C,9G | 6C,9H | 6C,9H | 4C,9H | 4C,9H | 4C,9G | 3C,9H | 3C,9G | 2C,8H | 10C | 10C | 10C | 10C | 10C | 10C |
| Morningglory | 9C | 3C,9H | 3C,8G | 2H | 3C,8G | 3C,8G | 9C | 9C | 3C,7G | 3C,7G | 5C,9G | 3C,8H | 3G | 3G | 10C | 3C,8G | 10C | 3C,8G | 10C | 9C |
| Velvetleaf | 4C,9G | 8G | 4C,9G | 3G | 9C | 4C,9G | 4C,9G | 4C,9G | 2C,5G | 2C,5G | 3C,8H | 0 | 0 | 0 | 9C | 3G | 10C | 4C,9H | 10C | 9C |
| Sorghum | 9C | 9C | | | 9C | 4C,9G | 10C | 4C,9G | 10C | 10C | 6G | 0 | — | — | 3C,8H | | 9C | 7G | 9C | 4C,9H |
| PREEMERGENCE | | | | | | | | | | | | | | | | | | | | |
| Corn | 3C,9H | 3C,7H | 0 | 3C,9G | 3C,8G | 2C,7G | 2C,6G | 2C,6G | 3C,6G | 2C,4G | 2C,5G | 2C,5G | 2C,3G | 2C,3G | 2C,9G | 0 | 2C,9G | 0 | 3C,9H | 3C,9H |
| Wheat | 3G | 0 | 0 | 0 | 0 | 0 | 0 | 0 | 0 | 0 | 0 | 0 | 0 | 0 | 2G | 0 | 4G | 0 | 3G | 0 |
| Barley | 2C,5G | 2C,4G | 2C | 0 | 2G | 0 | 2C,6G | 2C,6G | 4G | 3G | 2G | 0 | 2C,3G | 0 | 2G | 7G | 2C,8G | 2G | 3C,8H | 7G |
| Rice | 9H | 8H | 7G | 0 | 2C,2G | 0 | 0 | 0 | 3G | 0 | 2C,2G | 0 | 5G | 0 | 8H | 8H | 9H | 5G | 3C,8H | 3G |
| Soybean | 3C,6H | 3C,4H | 1H | 0 | 1H | 0 | 8G | 0 | 4G | 5G | 5G | 2G | 8G | 0 | 6H | 6G | 5G | 8H | 2C,7H | 8G |
| Cotton | 9G | 6H | 7G | 5G | 9G | 8G | 6G | 8G | 2C,2G | 5G | 8G | 2C,2G | 8G | 0 | 9G | 9G | 9G | 9G | 9G | 4C,9G |
| Sugar beet | 9G | 4C,8G | 0 | 0 | 9G | 8G | 3G | 3G | 4H | 5G | 9G | 5G | 2G | 9H | 2G | 8H | 2G | 0 | 4G | 0 |
| Crabgrass | 5G | 2C,5G | 0 | 0 | 8G | 5G | 9G | 9G | 5G | 0 | 6G | 0 | 3C,5G | 0 | 9H | 4G | 9H | 7G | 9H | 6H |
| Barnyardgrass | 9H | 9H | 2G | 0 | 3C,7G | 2G | 3C,8G | 3C,8G | 3G | 4C,9H | 6G | 2C,2G | 0 | 0 | 9G | 10E | 9G | 0 | 10E | 8G |
| Nutsedge | 10E | 10E | 3C,7G | 8H | 7G | 8G | 3C,7G | 3C,7G | 0 | 3C,7G | 0 | 5G | 5G | 3G | 9H | 5G | 9G | 5G | 9G | 2C,4G |
| Giant Foxtail | 7G | 3C,7H | 2C,4G | 0 | 2C,4G | 0 | 3C,7G | 3C,7G | 4G | 5G | 5G | 0 | 4G | 0 | 9G | 0 | 2G | 2G | 9G | 8G |
| Cheatgrass | 9H | 9H | 4G | 0 | 9H | 5G | 0 | 0 | 0 | 0 | 5G | 0 | 5G | 0 | 1C | 5G | 2G | 5G | 2G | 2C |
| Wild Oats | 3G | 2G | 9H | 0 | 9H | 4C,9G | 9H | 9H | 7H | 7H | 3H | 3H | 9H | 0 | 8H | 8H | 9H | 9H | 9H | 9H |
| Cocklebur | 2C,7H | 5H | 8H | 8H | 9G | 8G | 8G | 8G | 5G | 5G | 5H | 8H | 8H | — | 8H | 7H | 9H | 7H | 9H | 9H |
| Morningglory | 8H | 8G | 2G | 0 | 9G | 8G | 8G | 8G | 6G | 6G | 3G | 3G | 7G | 0 | 8H | 5H | 5H | 9H | 8H | 9H |
| Velvetleaf | 7H | | 5G | 0 | 9C | 3C,7G | 4C,9G | 4C,9G | 8C | 8C | 8G | 8G | 7G | — | 9H | 9H | 9H | 9H | 9C | 10H |
| Sorghum | | | | | | | | | | | | | — | — | | | | | | |

| RATE = | CMPD 11 | | CMPD 12 | | CMPD 13 | | CMPD 14 | | CMPD 15 | | CMPD 16 | | CMPD 17 | | CMPD 18 | | CMPD 19 | | CMPD 20 | | CMPD 21 | |
|---|---|---|---|---|---|---|---|---|---|---|---|---|---|---|---|---|---|---|---|---|---|---|
| KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | | | | |
| CORN | 9H | 3C,9H | 3H | 7H | 3C,9G | 0 | 0 | 7H | 9G | 3C,6G | 8H | 9G | 3C,8H | 3C,8H | 0 | 3C,8H | 2G | 7H | 3C,9H | 8H |
| WHEAT | 0 | 0 | 0 | 0 | 3G | 0 | 0 | 0 | 0 | 0 | 0 | 0 | 0 | 0 | 0 | 0 | 3G | 2C,7G | 7G | 3G |
| BARLEY | 0 | 0 | 5G | 3G | 3G | 3G | 0 | 4G | 5G | 2C,6G | 3G | 0 | 0 | 0 | 0 | 0 | 3G | 9G | 8G | 5G |
| RICE | 2G | 3C,9G | 0 | 7G | 7G | 2G | 3G | 2G | 1C | 2C,6G | 1H | 7G | 7G | 3C,8H | 2G | 7G | 8G | 5C,9G | 3C,9G | 7G |
| SOYBEAN | 0 | 2H | 6G | 0 | 3G | 10C | 2H | 3C,5H | 3H | 8G | 3H | 1H | 3C,6H | 3C,6H | 5H | 6H | 4C,9G | 5C,8G | 4C,9G | 5C,9G |
| COTTON | 7G | 10C | 6G | 10C | 10C | 9C | 3C,8G | 9H | 3C,5H | 9G | 3C,6G | 3C,6G | 3C,6H | 3C,6H | | 7G | 4C,9G | 5C,9G | 5C,9G | 5C,9G |
| SUGAR BEETS | 5G | 4C,8G | 2H | 5G | 10C | 9C | 3C,8G | 5C,9G | 5C,9G | 4C,8G | 4C,9G | 4C,9G | 2C,3G | | 2G | 4C,9G | 4C,8G | 4C,8G | 10C | 9C |

TABLE A-continued

| | | | | | | | | | | | | | | | | | | |
|---|---|---|---|---|---|---|---|---|---|---|---|---|---|---|---|---|---|---|
| CRABGRASS | 0 | 4G | 0 | 0 | 4G | 0 | | 0 | 2G | | 0 | | 0 | 0 | 0 | 0 | 0 | 4G |
| BARNYARD | 6H | 4C,9H | 3H | 4C,9H | 5C,9H | 7H | | 3C,5H | 3C,5H | | 0 | | 3C,7H | 4C,9H | 3C,8G | 3C,9H | 4C,9H | 9C |
| GRASS | | | | | | | | | | | | | | | | | | |
| NUTSEDGE | 2G | 3C,8G | 0 | 0 | 10C | 4C,9G | | 3C,8G | 5C,9G | | 3C,8G | | 3C,8G | 3C,3G | 4C,8G | 4C,8G | 4C,9G | 9C |
| GIANT FOXTAIL | 0 | 3C,7H | 0 | 4G | 5C,9H | 5G | | 2C | 4G | | 2G | | 2G | 3C,5G | 3G | 3G | 3C,3G | 3C,8G |
| CHEATGRASS | 5G | 5C,9G | 0 | 4C,9G | 5C,9G | 5G | | 2G | 3G | | 3C,8G | | 3C,7G | 3C,9G | 5C,9G | 5C,9G | 3C,9G | 5C,9G |
| WILD OATS | 0 | 0 | 0 | 1C | 0 | 9C | | 0 | 0 | | 3G | | 3G | 3C,9G | 5G | 5G | 5G | 7G |
| COCKLEBUR | 5C,9G | 10C | 3C,7H | 9C | 10C | 9C | | 4C,8H | 5C,9G | | 10C | | 5C,9G | 9C | 5C,9G | 9C | 9C | 10C |
| MORNING GLORY | 4C,8H | 10C | 3C,8H | 10C | 10C | 4C,9G | | 3C,7G | 3C,7H | | 9C | | 3H | 10C | 10C | 10C | 10C | 10C |
| VELVETLEAF | 2G | 3C,8H | 0 | 3C,7G | 3C,7G | 5G | | 3C,6G | 2C,5G | | 3C,6G | | 10C | 9C | 9C | 10C | 10C | 10C |
| SORGHUM | 2C,9H | 2C,9G | 3C,8H | 4C,9G | 3C,9H | 5G | | 3C,8G | 3C,8G | | 3C,5G | | 4C,9G | 9C | 9C | 10C | 10C | 10C |

PREEMERGENCE

| | | | | | | | | | | | | | | | | | | |
|---|---|---|---|---|---|---|---|---|---|---|---|---|---|---|---|---|---|---|
| CORN | 2C,9H | 2C,9G | 4H | 2C,9H | 9G | 0 | | 2C | 3C,4G | | 2C,5G | | 3C,6G | 0 | 0 | 7H | 2C,8H | 9G |
| WHEAT | 0 | 6G | 2G | 2G | 0 | 0 | | 0 | 0 | | 0 | | 0 | 0 | 0 | 7G | 2G | 7G |
| BARLEY | 0 | 9H | 8G | 5G | 2C,3G | 0 | | 0 | 0 | | 0 | | 0 | 0 | 0 | 7G | 2G | 2C,8G |
| RICE | 7H | 3C,4G | 0 | 9H | 8G | 0 | | 0 | 2G | | 3G | | 8G | 0 | 8G | 9H | 8G | 3C,9H |
| SOYBEAN | 0 | 8H | 0 | 1C,1H | 0 | 3G | | 1H | 3G | | 0 | | 2G | 8G | 3C,3H | 3C,5G | 3C,5G | 3C,9H |
| COTTON | 0 | 3C,8G | 4H | 5G | 8G | 8G | | 2G | 7G | | 2C,5G | | 2G | 0 | 8G | 8G | 7G | 8H |
| SUGAR BEETS | 7H | | | 5G | 2G | 9G | | 3G | 8G | | | | 5H | 4G | 7G | 3C,8G | 3C,8G | 5C,9G |

POSTEMERGENCE

| | | | | | | | | | | | | | | | | | | |
|---|---|---|---|---|---|---|---|---|---|---|---|---|---|---|---|---|---|---|
| CRABGRASS | 0 | 0 | 0 | 0 | 3G | 0 | | 8G | 4G | | 4G | | 0 | 0 | 0 | 0 | 4G |
| BARNYARD GRASS | 0 | 7H | 0 | 7H | 9H | 2G | | 2G | 0 | | 0 | | 7G | 8H | 7H | 8H | 9H |
| NUTSEDGE | 0 | 10E | 0 | 0 | 9G | 7G | | 9G | 8G | | 0 | | 0 | 0 | 0 | 0 | 6G |
| GIANT FOXTAIL | 0 | 3G | 0 | 0 | 7G | 0 | | 5G | 2G | | 2G | | 0 | 0 | 0 | 2G | 4H |
| CHEATGRASS | 0 | 9H | 0 | 3G | 5G | 5G | | 4G | 0 | | 0 | | 5G | 8G | 5G | 5G | 9G |
| WILD OATS | 0 | 0 | 0 | 0 | 0 | 3H | | 0 | 0 | | 0 | | 2G | 7H | 2G | 2G | 3C,8G |
| COCKLEBUR | 1C | 2C,7H | 1H | 3C,3H | 3C,3H | 7G | | 3C,5G | 3C,7H | | 1C | | 3G | 9H | 3G | 4H | 3C,6H |
| MORNING GLORY | 0 | 9G | 0 | 7H | 7H | 3C,8H | | 3C,4H | 9G | | 2C | | 0 | 6G | 0 | 5G | 9G |
| VELVETLEAF | 0 | 2H | 0 | 2C,2G | 3H | 3H | | 2C,2H | 6H | | 2G | | 5G | 8H | 6H | 0 | 9G |
| SORGHUM | 9G | 9H | 2C,7H | 5C,9G | 3C,9H | 3C,8H | | 2C | 5G | | 2C,3G | | 9H | 10H | 3C,9H | 3C,9H | 3C,9H |

| | CMPD 22 | | CMPD 23 | | CMPD 24 | | CMPD 25 | |
|---|---|---|---|---|---|---|---|---|
| RATE = KG/HA | 0.01 | 0.05 | 0.01 | 0.05 | 0.01 | 0.05 | 0.01 | 0.05 |
| POSTEMERGENCE | | | | | | | | |
| CORN | 2G | 3C,9H | 2C,3G | 9H | 0 | 4G | 0 | 0 |
| WHEAT | 3G | 4G | 0 | 3G | 0 | 3G | 0 | 2G |
| BARLEY | 2G | 4G | 2G | 3G | 0 | 0 | 0 | 0 |
| RICE | 4G | 2C,8G | 9C | 4C,8G | 1C | 4C,8G | 4H | 3G |
| SOYBEAN | 3C,9G | 4C,9G | 9C | 5C,9G | 4C,9G | 4C,9G | 9C | 8G |
| COTTON | 3C,9G | 4C,9G | 9C | 10C | 4C,9G | 4C,9G | 9C | 9C |
| SUGAR BEETS | 9C | 10C | 10C | 10C | 10C | 9C | 4G | 10C |
| CRABGRASS | 0 | 3G | 0 | 0 | 0 | 5H | 0 | 0 |
| BARNYARD GRASS | 3C,5G | 3C,8H | 3C,7H | 3C,7H | 0 | 0 | 0 | 2H |
| NUTSEDGE | 9C | 10C | 10C | 0 | 0 | 2C,5G | 9C | 9C |
| GIANT FOXTAIL | 0 | 2C,4H | 2C,4H | 3G | 3C,5G | 3C,5G | 0 | 0 |
| CHEATGRASS | 3C,5G | 9C | 9C | 2G | 2C,4G | 2C,4G | 3G | 3G |
| WILD OATS | 0 | 3C,5G | 3C,5G | 2G | 2G | 2G | 0 | 0 |

TABLE A-continued

| | | | | | | | | | |
|---|---|---|---|---|---|---|---|---|---|
| COCKLEBUR | 10C | | 10C | 10C | 10C | 10C | 10C | 9C | 10C |
| MORNING GLORY | 4C,9G | | 10C | 10C | 10C | 10C | 10C | 10C | 10C |
| VELVETLEAF | 4C,9G | 10C | 10C | 10C | 10C | 10C | 5G | 9C | 10C |
| SORGHUM | 7H | 3C,9H | 3G | 3C,8H | 2C,4H | 2C,3G | 2C,6H | 0 | 3C,8G |

PREEMERGENCE

| | | | | | | | | | |
|---|---|---|---|---|---|---|---|---|---|
| CORN | 0 | 3C,7G | 3C,4G | 3C,7G | 1C | 2C,5G | 0 | 2G |
| WHEAT | 0 | 0 | 0 | 0 | 0 | 0 | 0 | 0 |
| BARLEY | 0 | 2C | 0 | 2C,3G | 0 | 1C | 0 | 0 |
| RICE | 7G | 3C,5H | 3C,7H | 8G | 3G | 7G | 0 | 7G |
| SOYBEAN | 1C,1H | 9G | 8H | 9H | 3C,7H | 3C,9H | 0 | 1C |
| COTTON | 0 | 5G | 8H | 9G | 5G | 3C,8G | 0 | 2G |
| SUGAR BEETS | 2G | 3C,7G | 9C | 9G | 4C,9G | 9C | 5G | 8G |
| CRABGRASS | 0 | 2G | 0 | 0 | 0 | 0 | 0 | 0 |
| BARNYARD GRASS | 0 | 7H | 1C | 2H | 0 | 0 | 0 | 4H |
| NUTSEDGE | 0 | 10E | 0 | 0 | 0 | 0 | 5G | 9G |
| GIANT FOXTAIL | 0 | 4G | 0 | 0 | 0 | 0 | 0 | 0 |
| CHEATGRASS | 0 | 8G | 0 | 2G | 0 | 0 | 0 | 3G |
| WILD OATS | 0 | 0 | 0 | 0 | 0 | 0 | 0 | 0 |
| COCKLEBUR | 2G | 7G | 3C,7H | 9H | 3C,8G | 9H | | 1C |
| MORNING GLORY | 2G | 7G | 9G | 9G | 9G | 4C,9G | 5G | 9H |
| VELVETLEAF | 0 | 4H | 7H | 4C,9G | 0 | 2G | 3G | 6H |
| SORGHUM | 8G | 3C,9H | 2C,3G | 8G | 2C,3G | 3C,6G | 3G | 2C,7G |

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sickelpod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xantium pensylvanicum*), moringglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, they sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, moringglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (-) response means no test.

Response ratings are contained in Table B.

TABLE B

| | Compound 1 | | | | | | | | Compound 3 | | | | | | | | Compound 4 | | | | | | | | CMPD 8 | | | |
|---|---|---|---|---|---|---|---|---|---|---|---|---|---|---|---|---|---|---|---|---|---|---|---|---|---|---|---|---|
| | POSTEMERGENCE | | | | PREEMERGENCE | | | | POSTEMERGENCE | | | | PREEMERGENCE | | | | POSTEMERGENCE | | | | PREEMERGENCE | | | | POSTEMERGENCE | | PREEMERGENCE | |
| Rate g/ha | 62 | 16 | 4 | 1 | 250 | 62 | 16 | 4 | 62 | 16 | 4 | 1 | 250 | 62 | 16 | 4 | 62 | 16 | 4 | 1 | 250 | 62 | 16 | 4 | 0001 0004 | 0016 | 0062 | 0250 |
| Corn | 70 | 30 | 0 | 0 | 20 | 20 | 0 | 0 | 20 | 0 | 0 | 0 | 40 | 0 | 0 | 0 | 30 | 0 | 0 | 0 | 60 | 20 | 0 | 0 | 0 20 | 80 | 90 | 90 |
| Wheat | 0 | 0 | 0 | 0 | 20 | 0 | 0 | 0 | 0 | 0 | 0 | 0 | 0 | 0 | 0 | 0 | 0 | 0 | 0 | 0 | 30 | 0 | 0 | 0 | 0 0 | 0 | 0 | 0 |
| Barley | 30 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 | 0 0 | 0 | 0 | 0 |
| Rice | 90 | 30 | 0 | 0 | 90 | 60 | 30 | 0 | 0 | 0 | 0 | 0 | 60 | 40 | 20 | 0 | 0 | 0 | 0 | 0 | 70 | 0 | 0 | 0 | 20 40 | 60 | 80 | 70 |
| Soybean | 70 | 50 | 30 | 0 | 70 | 50 | 30 | 30 | 0 | 0 | 0 | 0 | 20 | 0 | 0 | 0 | 20 | 0 | 0 | 0 | 0 | 0 | 0 | 30 | 40 40 | 40 | 50 | 90 |
| Cotton | 70 | 60 | 30 | 30 | 70 | 50 | 30 | 30 | 0 | 0 | 0 | 0 | 50 | 20 | 0 | 0 | 90 | 40 | 0 | 0 | 100 | 0 | 0 | 0 | 40 80 | 80 | 70 | 100 |
| Sugar beet | 100 | 100 | 90 | 80 | 90 | 90 | 80 | 70 | 70 | 50 | 30 | 30 | 100 | 80 | 70 | 80 | 100 | 90 | 70 | 50 | 90 | 90 | 70 | 50 | 70 80 | 100 | 90 | 100 |
| Rape | 100 | 100 | 100 | 70 | 100 | 80 | 70 | 50 | 100 | 70 | 50 | 50 | 100 | 90 | 80 | 70 | 100 | 70 | 50 | 30 | 100 | 80 | 70 | 50 | | | | |
| Crabgrass | 70 | 50 | 30 | 0 | 100 | 80 | 30 | 0 | 60 | 30 | 0 | 0 | 50 | 30 | 0 | 0 | 70 | 50 | 20 | 0 | 50 | 30 | 0 | 0 | 0 20 | 50 | 0 | 100 |
| Johnsongrass | 60 | 30 | 0 | 0 | 80 | 60 | 30 | 0 | 70 | 30 | 0 | 0 | 90 | 70 | 50 | 30 | 50 | 30 | 0 | 0 | 70 | 50 | 0 | 0 | 0 0 | 0 | 0 | 0 |
| Blackgrass | 70 | 50 | 30 | 0 | 50 | 30 | 0 | 0 | 30 | 0 | 0 | 0 | 70 | 30 | 0 | 0 | 30 | 0 | 0 | 0 | 30 | 0 | 0 | 0 | 0 40 | 30 | 30 | 30 |
| Barnyardgrass | 90 | 70 | 60 | 30 | 80 | 70 | 60 | 0 | 70 | 30 | 30 | 0 | 80 | 60 | 40 | 30 | 90 | 60 | 40 | 0 | 70 | 50 | 30 | 30 | 40 40 | 80 | 80 | 100 |
| Nutsedge | 100 | 100 | 70 | 100 | 100 | 90 | 70 | 50 | 80 | 60 | 50 | 0 | 80 | 60 | 50 | 30 | 100 | 70 | 50 | 30 | 100 | 70 | 50 | 30 | 80 100 | 90 | 100 | 100 |
| Giant Foxtail | 90 | 60 | 30 | 0 | 100 | 90 | 70 | 30 | 80 | 50 | 30 | 30 | 90 | 60 | 30 | 30 | 80 | 50 | 30 | 0 | 70 | 50 | 30 | 0 | 20 60 | 90 | 100 | 100 |
| Green Foxtail | 80 | 50 | 30 | 0 | 100 | 90 | 60 | 40 | 70 | 30 | 30 | 30 | 70 | 30 | 50 | 30 | 70 | 30 | 30 | 0 | 90 | 70 | 50 | 30 | 0 30 | 100 | 100 | 100 |
| Cheatgrass | 70 | 50 | 30 | 0 | 100 | 80 | 60 | 30 | 60 | 30 | 0 | 0 | 80 | 60 | 30 | 50 | 30 | 0 | 0 | 0 | 70 | 30 | 30 | 0 | 30 30 | 50 | 50 | 80 |
| Wild Oats | 20 | 0 | 0 | 0 | 30 | 20 | 0 | 0 | 0 | 0 | 0 | 0 | 0 | 0 | 0 | 0 | 0 | 0 | 0 | 0 | 0 | 0 | 0 | 0 | 0 0 | 0 | 0 | 20 |
| Wild Buckwheat | 90 | 70 | 50 | 30 | 90 | 80 | 70 | 50 | 50 | 50 | 30 | 30 | 100 | 70 | 50 | 30 | 100 | 70 | 50 | 50 | 80 | 60 | 40 | 50 | 30 50 | 0 | 100 | 30 |
| Viola | 90 | 70 | 50 | 30 | 100 | 100 | 80 | 50 | 70 | 70 | 50 | 50 | 90 | 90 | 70 | 50 | 90 | 90 | 70 | 70 | 100 | 90 | 80 | 70 | | 100 | | 100 |
| Lambsquarter | 90 | 70 | 50 | 30 | 100 | 70 | 50 | 50 | 100 | 70 | 70 | 70 | 100 | 50 | 30 | 30 | 100 | 70 | 50 | 30 | 100 | 70 | 50 | 30 | 100 70 | 100 | 100 | 100 |
| Cocklebur | 100 | 70 | 50 | 30 | 90 | 80 | 70 | 50 | 100 | 90 | 70 | 70 | 80 | 50 | 30 | 50 | 100 | 90 | 50 | 40 | 100 | 90 | 80 | 30 | 40 30 | 80 | 80 | 100 |
| Morningglory | 70 | 50 | 30 | 0 | 90 | 70 | 70 | 30 | 90 | 70 | 70 | 70 | 80 | 60 | 60 | 40 | 100 | 90 | 70 | 70 | 90 | 80 | 60 | 40 | 0 30 | 70 | 70 | 100 |
| Teaweed | 80 | 50 | 30 | 0 | 90 | 70 | 50 | 30 | 90 | 70 | 70 | 30 | 80 | 60 | 60 | 40 | 90 | 70 | 50 | 30 | 100 | 70 | 50 | 30 | 0 50 | 100 | 100 | 100 |
| Sicklepod | 90 | 70 | 50 | 30 | 90 | 80 | 50 | 30 | 60 | 30 | 0 | 30 | 80 | 60 | 50 | 50 | 80 | 30 | 30 | 30 | 100 | 70 | 50 | 30 | 30 100 | 90 | 100 | 100 |
| Jimsonweed | 100 | 70 | 50 | 30 | 90 | 70 | 70 | 50 | 90 | 50 | 30 | 30 | 100 | 70 | 60 | 50 | 100 | 70 | 50 | 30 | 100 | 70 | 50 | 50 | 30 100 | 50 | 50 | 100 |
| Velvetleaf | 90 | 60 | 40 | 20 | 90 | 80 | 60 | 40 | 90 | 70 | 50 | 30 | 90 | 70 | 50 | 30 | 100 | 70 | 50 | 50 | 90 | 80 | 70 | 50 | 100 100 | 100 | 100 | 100 |
| Cassia | | | | | | | | | | | | | | | | | | | | | | | | | | | | |
| Rapeseed | | | | | | | | | | | | | | | | | | | | | | | | | | | | |
| Buckwheat | | | | | | | | | | | | | | | | | | | | | | | | | | | | |

| | CMPD 8 | | | | CMPD 22 | | | | | |
|---|---|---|---|---|---|---|---|---|---|---|
| | PREEMERGENCE | | POSTEMERGENCE | | POSTEMERGENCE | | | | PREEMERGENCE | | |
| Rate g/ha | 0004 | 0016 | 0062 | 0250 | 0001 | 0004 | 0016 | 0062 | 0004 | 0016 | 0062 | 0250 |
| Corn | 20 | 50 | 70 | 100 | 0 | 0 | 0 | 60 | 0 | 0 | 20 | 60 |
| Wheat | 0 | 0 | 0 | 0 | 0 | 0 | 0 | 0 | 0 | 0 | 0 | 90 |
| Barley | 0 | 0 | 20 | 0 | 0 | 0 | 0 | 20 | 0 | 0 | 0 | 80 |
| Rice | 0 | 20 | 50 | 100 | 70 | 30 | 0 | 50 | 100 | 30 | 50 | 80 |
| Soybean | 30 | 50 | 70 | 100 | 50 | 50 | 30 | 100 | 60 | 50 | 70 | 80 |
| Cotton | 90 | 100 | 100 | 100 | 70 | 70 | 70 | 90 | 100 | 60 | 70 | 90 |
| Sugar beet | 0 | 20 | 60 | 90 | 0 | 0 | 30 | 70 | 0 | 30 | 60 | 90 |
| Rape | 0 | 40 | 60 | 90 | 0 | 30 | 30 | 70 | 30 | 30 | 70 | 80 |
| Crabgrass | 40 | 90 | 100 | 90 | 0 | 30 | 30 | 50 | 50 | 20 | 50 | 80 |
| Johnsongrass | 50 | 100 | 100 | 100 | 30 | 50 | 60 | 70 | 30 | 60 | 80 | 90 |
| Blackgrass | 90 | 90 | 100 | 100 | 50 | 50 | 70 | 50 | 50 | 30 | 40 | 80 |
| Barnyardgrass | 40 | 100 | 100 | 100 | 50 | 70 | 100 | 100 | 40 | 50 | 100 | 90 |
| Nutsedge | 70 | 100 | 100 | 100 | 30 | 50 | 50 | 50 | 100 | 50 | 50 | 70 |
| Giant Foxtail | 70 | 90 | 100 | 100 | 0 | 30 | 30 | 60 | 0 | 30 | 60 | 90 |
| Green Foxtail | 90 | 100 | 100 | 100 | 30 | 60 | 70 | 60 | 0 | 30 | 30 | 80 |
| Cheatgrass | 70 | 90 | 100 | 100 | 30 | 30 | 50 | 80 | 40 | 30 | 30 | 80 |

TABLE B-continued

| | | | | | | | | | | | | |
|---|---|---|---|---|---|---|---|---|---|---|---|---|
| Wild Oats | 0 | 0 | 0 | 0 | 0 | 0 | 0 | 0 | 0 | 0 | 0 | 30 |
| Wild Buckwheat | 80 | 90 | 100 | 100 | 30 | 50 | 70 | 80 | 70 | 80 | 90 | 100 |
| Viola | | | | | | | | | | | | |
| Lambsquarter | 90 | 100 | 100 | 100 | 30 | 40 | 50 | 70 | 70 | 80 | 90 | 100 |
| Cocklebur | 40 | 50 | 90 | 100 | 70 | 80 | 100 | 100 | 60 | 70 | 80 | 90 |
| Morningglory | 40 | 60 | 90 | 100 | 30 | 80 | 100 | 100 | 70 | 80 | 90 | 100 |
| Teaweed | 30 | 80 | 90 | 100 | 30 | 50 | 70 | 90 | 50 | 70 | 80 | 90 |
| Sicklepod | | | | | | | | | | | | |
| Jimsonweed | 40 | 80 | 100 | 100 | 30 | 50 | 70 | 100 | 50 | 70 | 80 | 90 |
| Velvetleaf | 50 | 90 | 100 | 100 | 50 | 70 | 100 | 100 | 30 | 50 | 70 | 90 |
| Cassia | 0 | 40 | 70 | 100 | 30 | 50 | 80 | 100 | 30 | 50 | 70 | 100 |
| Rapeseed | 40 | 90 | 100 | 100 | 100 | 100 | 100 | 100 | 80 | 90 | 100 | 100 |
| Buckwheat | | | | | | | | | | | | |

TEST C

Sixteen cm diameter Wagner pots, equipped with a stoppered drain opening near the bottom of the side wall, were partially filled with Woodstown sandy loam. About 1500 mls of water were added to each pot to bring the water level to a point 3 cm above the soil surface. Japonica and Indica rice seedlings were transplanted as described in Test E. Also, a number of barnyardgrass (*Echinochola crusgalli*) seeds were added to each pot. At the same time, seedlings or tubers of the following species were transplanted into the muddy soil: water plantain (*Alisma trivale*), Scirpus (*Scirpus mucranatus*), and Cyperus (*Cyperus difformis*). The weed species selected for this test are of economic importance in major rice-growing areas. The chemical treatments were applied directly to the paddy water after being formulated in a nonphytotoxic solvent within hours after transplanting of two additional species: water chestnuts (Eleocharis spp.) and arrowhead (*Sagittaria latifolia*). Shortly after treatment, the drain hole was opened to drop the water level by 2 cm. Water was then added to restore the water level to its original height. The following day the draining and refilling process was repeated. The pots were then maintained in the greenhouse. Rates of application and plant response ratings made 21 days after treatment are summarized in Table C.

In the subsequent tables, LS is used as an abbreviation for leaf stage.

TABLE C

| | CMPD 8 | | |
|---|---|---|---|
| RATE RATE = G/HA | 0004 | 0008 | 0016 |
| SOIL | | | |
| BARNYARD GRASS | 50 | 67 | 70 |
| WATER CHESTNUT | 62 | 77 | 90 |
| ARROWHEAD | 0 | 57 | 80 |
| SCIRPUS (SEDGE) | 37 | 72 | 85 |
| CYPRESS (SEDGE) | 75 | 75 | 95 |
| WATER PLANTAIN | 75 | 55 | 90 |
| RICE JAP EFF | 0 | 0 | 10 |
| RICE INDICA EFF | 0 | 17 | 0 |

TEST D

The soybeans were planted in large 25 cm-diameter pots of soil, 6 to 10 plants per pot. The other plant species were planted in 15 cm-diameter pots of soil. Carn, because of its importance as a rotational crop, was by itself in one container, 3 to 5 plants per pot. The weed species used in this test were all of major economic importance in soybean-growing regions. They were planted 3 to 4 species per pot, each confined to a separate quadrant of the soil surface. The following species were included in the screen:

barnyardgrass: *Echinochloa crus-galli*
giant foxtail: *Setaria faberi*
green foxtail: *Setaris virdis*
johnsongrass: *Sorghum halepense*
fall panicum: *Panicum dichotomiflorum*
purple nutsedge: *Cyperus rotundus*
signalgrass: *Brachiaria platyphylla*
crabgrass: *Digitaria sanguinalis*
velvetleaf: *Abutilon theophrasti*
jimsonweed: *Datura stramonium*
hemp sesbania: *Sesbania exaltata*
sicklepod: *Cassia obtusifolia*
cocklebur: *Xanthium pensylvanicum*
ivyleaf morningglory: *Ipomoea hederacea*
purslane: *Portulaca oleracea*
pigweed: *Amaranthus retroflexus*
lambsquarter: *Chenopodium album*
teaweed: *Sida spinosa*
bindweed: *Convolvulus arvensis*.

For the post-emergence phase of the test, crop and weed species were planted two to three weeks before application so that they were present as young plants at the time of treatment. Plantings for the pre-emergence phase were made on the day before, or on the day of treatment. Approximate planting depths were: corn and soybeans—3 to 4 cm; morningglory, cocklebur and nutsedge—2.5 to 3 cm; velvetleaf, sicklepod and sesbania—2 cm; all other species—0.5 cm.

The test chemicals were dissolved/suspended in a non-phytotoxic solvent in concentrations required to obtain the desirec rate of application. The solutions or suspensions were then applied as soil/foliage sprays to the young plants (post-emergence phase) and to the soil surfaces of the freshly planted containers (pre-emergence phase). Application was made utilizing an automatic spray machine at a spray volume of 500 liters per hectare. Immediately after treatment, the containers were transferred to a greenhouse and subsequently watered on a demand basis, taking care not to wet the foliage of the plants in the post-emergence phase of the test.

TABLE D

| COMPOUND 9 | | | | | |
|---|---|---|---|---|---|
| RATE RATE GM/H | 0002 | 0004 | 0008 | 0016 | 0031 |
| POSTEMERGENCE | | | | | |
| SOYBEAN | 0 | 0 | 0 | 20 | 60 |
| CORN | 0 | 0 | 0 | 50 | 70 |
| VELVETLEAF | 50 | 65 | 90 | 100 | 100 |
| NIGHTSHADE | 0 | 20 | 30 | 75 | 85 |
| JIMSONWEED | 0 | 0 | 20 | 30 | 40 |
| SICKLEPOD | 0 | 0 | 0 | 20 | 50 |
| SESBANIA | 0 | 0 | 0 | 30 | 50 |
| COCKLEBUR | 40 | 85 | 100 | 100 | 100 |
| IVYLEAF M/G | 30 | 65 | 75 | 80 | 95 |
| PIGWEED | 40 | 60 | 75 | 85 | 90 |
| LAMBSQUARTER | 30 | 60 | 85 | 85 | 85 |
| PRICKLY SIDA | 0 | 30 | 50 | 75 | 85 |
| SMARTWEED | 40 | 50 | 80 | 80 | 90 |
| BARNYARDGRASS | 0 | 30 | 50 | 70 | 80 |
| GIANT FOXTAIL | 0 | 0 | 0 | 40 | 65 |
| GREEN FOXTAIL | 0 | 0 | 0 | 40 | 60 |
| JOHNSONGRASS | 0 | 30 | 65 | 80 | 95 |
| FALL PANICUM | 0 | 20 | 40 | 50 | 75 |
| CRABGRASS | 0 | 0 | 0 | 20 | 30 |
| SIGNALGRASS | 0 | 20 | 30 | 50 | 65 |
| NUTSEDGE | 65 | 80 | 90 | 100 | 100 |
| RATE RATE GM/H | 0031 | 0062 | 0125 | 0250 | |
| PREEMERGENCE | | | | | |
| SOYBEAN | 0 | 0 | 25 | 60 | |
| CORN | 0 | 20 | 65 | 90 | |
| VELVETLEAF | 0 | 20 | 80 | 95 | |
| NIGHTSHADE | 50 | 70 | 85 | 95 | |
| JIMSONWEED | 0 | 30 | 70 | 95 | |
| SICKLEPOD | 0 | 0 | 30 | 60 | |
| SESBANIA | 0 | 0 | 40 | 50 | |
| COCKLEBUR | 80 | 75 | 80 | 95 | |
| IVYLEAF M/G | 0 | 0 | 40 | 50 | |
| PIGWEED | 70 | 85 | 100 | 100 | |
| LAMBSQUARTER | 20 | 75 | 95 | 100 | |
| PRICKLY SIDA | 40 | 70 | 80 | 90 | |
| SMARTWEED | 70 | 90 | 90 | 100 | |
| BARNYARDGRASS | 0 | 0 | 40 | 85 | |
| GIANT FOXTAIL | 0 | 0 | 30 | 70 | |
| GREEN FOXTAIL | 0 | 20 | 40 | 70 | |
| JOHNSONGRASS | 85 | 90 | 95 | 95 | |
| FALL PANICUM | 90 | 100 | 100 | 95 | |
| CRABGRASS | 0 | 0 | 20 | 40 | |

TABLE D-continued

COMPOUND 9

| | | | | |
|---|---|---|---|---|
| SIGNALGRASS | 0 | 30 | 70 | 85 |
| NUTSEDGE | 80 | 90 | 100 | 100 |

What is claimed:

1. A compound of Formula I

wherein

J is

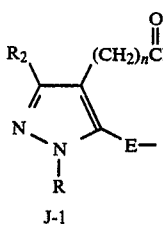 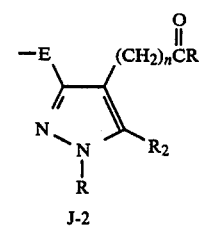

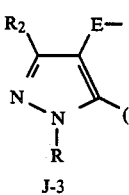 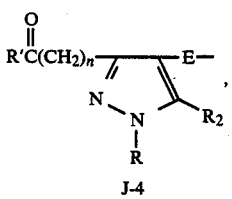

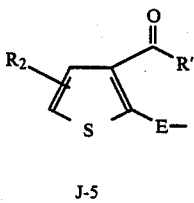 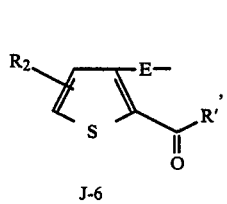

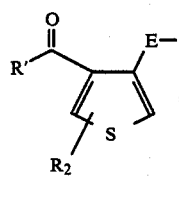 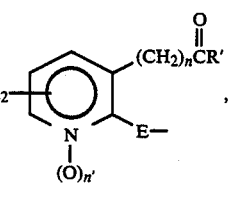

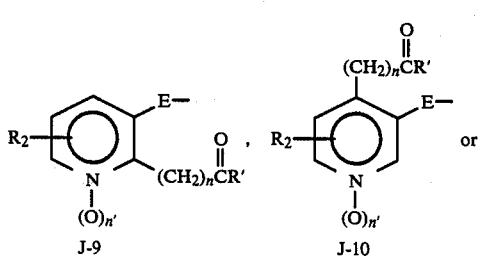

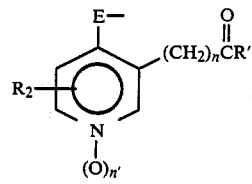

R is H, $C_1-C_3$ alkyl, phenyl, $SO_2NR_aR_b$, $C_1-C_2$ haloalkyl, $C_2-C_4$ alkoxyalkyl, $C_2-C_3$ cyanoalkyl, $C_2-C_4$ alkylthioalkyl, $C_2-C_4$ alkylsulfinylalkyl, $C_2-C_4$ alkylsulfonylalkyl, $CO_2C_1-C_2$ alkyl, $C_1-C_4$ alkylcarbonyl, $C_1-C_2$ alkylsulfonyl, $C_3-C_4$ alkenyl, $C_3-C_4$ alkynyl or $C_1-C_2$ alkyl substituted with $CO_2C_1-C_2$ alkyl;

$R_2$ is H or $CH_3$;

$R_2$ is H, $C_1-C_3$ alkyl, $C_1-C_3$ haloalkyl, halogen, nitro, $C_1-C_3$ alkoxy, $SO_2NR_cR_d$, $C_1-C_3$ alkylthio, $C_1-C_3$ alkylsulfinyl, $C_1-C_3$ alkylsulfonyl, CN, $CO_2R_e$, $C_1-C_3$ haloalkoxy, $C_1-C_3$ haloalkylthio, amino, $C_1-C_2$ alkylamino, di($C_1-C_3$ alkyl)amino or $C_1-C_2$ alkyl substituted with $C_1-C_2$ alkoxy, $C_1-C_2$ haloalkoxy, $C_1-C_2$ alkylthio, $C_1-C_2$ haloalkylthio, CN, OH or SH;

$R_a$ and $R_b$ are independently $C_1-C_2$ alkyl;

$R_c$ is H, $C_1-C_4$ alkyl, $C_2-C_3$ cyanoalkyl, methoxy or ethoxy;

$R_d$ is H, $C_1-C_4$ alkyl or $C_3-C_4$ alkenyl; or $R_c$ and $R_d$ may be taken together as $-(CH_2)_3-$, $-(CH_2)_4-$, $-(CH_2)_5-$ or $-CH_2CH_2OCH_2CH_2-$;

$R_e$ is $C_1-C_4$ alkyl, $C_3-C_4$ alkenyl, $C_3-C_4$ alkynyl, $C_2-C_4$ haloalkyl, $C_1-C_2$ cyanoalkyl, $C_5-C_6$ cycloalkyl, $C_4-C_7$ cycloalkylalkyl or $C_2-C_4$ alkoxyalkyl;

R' is $C_1-C_5$ alkyl, $C_1-C_5$ haloalkyl, $C_1-C_5$ alkyl substituted with one or two $R_3$ groups, $C_2-C_5$ alkenyl, $C_2-C_5$ haloalkenyl, $C_3-C_5$ alkenyl substituted with one or two $R_3$ groups, $C_3-C_5$ alkynyl, $C_3-C_5$ haloalkynyl, $C_3-C_5$ alkynyl substituted with one or two $R_3$ groups, $C_3-C_5$ cycloalkyl, $C_3-C_5$ halocycloalkyl, $C_3-C_5$ cycloalkyl substituted with one or two $R_4$ groups, $C_4-C_7$ cycloalkylalkyl, $C_4-C_7$ halocycloalkylalkyl, $C_4-C_7$ cycloalkylalkyl substituted with one or two $R_4$ groups, phenyl or benzyl;

$R_3$ is $C_1-C_3$ alkoxy, $C_1-C_3$ alkylthio, $C_1-C_3$ haloalkoxy, $C_1-C_3$ alkylsulfinyl, $C_1-C_3$ alkylsulfonyl, CN, $NO_2$, OH, $OR_5$ or di-($C_1-C_3$ alkyl)amino;

$R_4$ is $C_1-C_3$ alkyl, $C_1-C_3$ alkoxy, $C_1-C_3$ haloalkoxy, CN, $NO_2$, OH, $OR_5$ or di-($C_1-C_3$ alkyl)amino;

$R_5$ is $SO_2CH_3$, $Si(CH_3)_3$, $C_2-C_3$ alkylcarbonyl or $CO_2C_1-C_2$ alkyl;

E is a single bond or $CH_2$;

W is O;

n is 0 or 1;

n' is 0 or 1;

A is

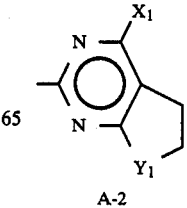 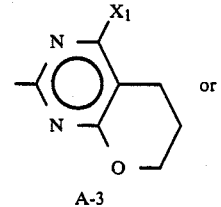 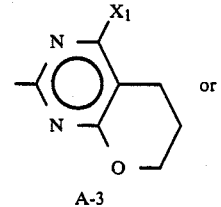

-continued

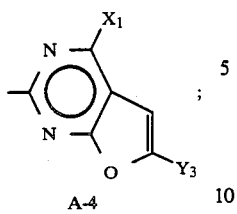

$Y_1$ is O or $CH_2$;
$X_1$ is $CH_3$, $OCH_3$, $OC_2H_5$ or $OCF_2H$; and
$Y_3$ is H or $CH_3$;
and their agriculturally suitable salts; provided that
(a) when J is J-1, J-2, J-3 or J-4 then R' is other than $C_3-C_5$ cycloalkyl or phenyl;
(b) when J is J-5, J-6 or J-7 wherein E is a single bond, then R' is other than $C_1-C_5$ alkyl, $C_3-C_5$ alkenyl, phenyl, benzyl, cyclopentyl or $C_4-C_7$ cycloalkylalkyl; and
(c) when J is J-5, J-6 or J-7 and E is $CH_2$, then R' is other than $C_1-C_5$ alkyl.

2. Compounds of claim 1 where E is a single bond.
3. Compounds of claim 1 where E is $CH_2$.
4. Compounds of claim 2 where
$R_2$ is H, $C_1-C_3$ alkyl, halogen, $C_1-C_3$ alkyl substituted with 1 to 3 halogen atoms selected from 1 to 3Cl, 1 to 3F or 1Br, $OCH_3$, $SO_2NHCH_3$, $SO_2N(CH_3)_2$, $S(O)_nCH_3$, $CO_2CH_3$, $CO_2CH_2CH_3$, $OCF_2H$, $CH_2OCH_3$ or $CH_2CN$; and
R is H, $C_1-C_3$ alkyl, phenyl, $CH_2CF_3$ or $CH_2CH=CH_2$.

5. Compounds of claim 4 where
R' is $C_1-C_4$ alkyl, $C_1-C_3$ alkyl substituted with 1 to 3 halogen atoms selected from 1 to 3Cl, 1 to 3F or 1Br, $C_2-C_4$ alkoxyalkyl, $C_2-C_4$ alkylthioalkyl, $C_2-C_4$ cyanoalkyl, $C_2-C_4$ alkenyl, $C_2-C_3$ alkenyl substituted with 1 to 3 halogen atoms selected from 1 to 3Cl, 1 to 3F or 1Br, $C_3-C_4$ alkynyl, $C_3-C_5$ cycloalkyl, $C_3-C_5$ cycloalkyl substituted with 1 to 3 halogen atoms selected from 1 to 3Cl, 1 to 3F or 1Br or cyclopropylmethyl.

6. Compounds of claim 5 where
n is O.

7. Compounds of claim 6 where
$R_1$ is H;
$R_2$ is H, Cl, Br, $OCH_3$ or $CH_3$; and
R' is $C_1-C_3$ alkyl, $C_1-C_3$ alkyl substituted with 1 to 3F, $C_2-C_3$ alkoxyalkyl, $C_2-C_3$ alkylthioalkyl, $C_2-C_3$ cyanoalkyl, $C_2-C_3$ alkenyl, propargyl, $C_3-C_5$ cycloalkyl or cyclopropylmethyl.

8. Compounds of claim 7 where J is J-1.
9. Compounds of claim 8 where R' is $C_1-C_3$ alkyl.
10. Compounds of claim 8 where R' is $C_1-C_3$ alkyl substituted with 1 to 3F, $C_2-C_3$ alkoxyalkyl, $C_2-C_3$ alkylthioalkyl, $C_2-C_3$ cyanoalkyl, $C_2-C_3$ alkenyl, propargyl, $C_3-C_5$ cyclo alkyl or cyclopropylmethyl.

11. Compounds of claim 3 where
R is H, $C_1-C_3$ alkyl, phenyl, $CH_2CF_3$ or $CH_2CH_2=CH_2$;
$R_2$ is H, Cl, Br, $OCH_3$ or $CH_3$;
R' is $C_1-C_3$ alkyl, $C_1-C_3$ alkyl substituted with 1 to 3F, $C_2-C_3$ alkoxyalkyl, $C_2-C_3$ alkylthioalkyl, $C_2-C_3$ cyanoalkyl, $C_2-C_3$ alkenyl, propargyl, $C_3-C_5$ cycloalkyl or cyclopropylmethyl; and
n is O.

12. Compounds of claim 1 where
J is J-1, J-2, J-3 or J-4; and
R' is $C_1-C_5$ haloalkyl, $C_1-C_5$ alkyl substituted with one or two $R_3$ groups, $C_2-C_5$ alkenyl, $C_2-C_5$ haloalkenyl, $C_3-C_5$ alkenyl substituted with one or two $R_3$ groups, $C_3-C_5$ alkynyl, $C_3-C_5$ haloalkynyl, $C_3-C_5$ alkynyl substituted with one or two $R_3$ groups, $C_3-C_5$ cycloalkyl, $C_3-C_5$ halocycloalkyl, $C_3-C_5$ cycloalkyl substituted with one or two $R_4$ groups, $C_4-C_7$ cycloalkylalkyl substituted with one or two $R_4$ groups, phenyl or benzyl.

13. An agriculturally suitable composition for controlling the growth of undesired vegetation comprising an effective amount of the compound of claim 1 and at least one of the following: surfactant, solid or liquid diluent.

14. An agriculturally suitable composition for controlling the growth of undesired vegetation comprising an effective amount of the compound of claim 2 and at least one of the following: surfactant, solid or liquid diluent.

15. An agriculturally suitable composition for controlling the growth of undesired vegetation comprising an effective amount of the compound of claim 3 and at least one of the following: surfactant, solid or liquid diluent.

16. An agriculturally suitable composition for controlling the growth of undesired vegetation comprising an effective amount of the compound of claim 4 and at least one of the following: surfactant, solid or liquid diluent.

17. An agriculturally suitable composition for controlling the growth of undesired vegetation comprising an effective amount of the compound of claim 5 and at least one of the following: surfactant, solid or liquid diluent.

18. An agriculturally suitable composition for controlling the growth of undesired vegetation comprising an effective amount of the compound of claim 6 and at least one of the following: surfactant, solid or liquid diluent.

19. An agriculturally suitable composition for controlling the growth of undesired vegetation comprising an effective amount of the compound of claim 7 and at least one of the following: surfactant, solid or liquid diluent.

20. An agriculturally suitable composition for controlling the growth of undesired vegetation comprising an effective amount of the compound of claim 8 and at least one of the following: surfactant, solid or liquid diluent.

21. An agriculturally suitable composition for controlling the growth of undesired vegetation comprising an effective amount of the compound of claim 9 and at least one of the following: surfactant, solid or liquid diluent.

22. An agriculturally suitable composition for controlling the growth of undesired vegetation comprising an effective amount of the compound of claim 10 and at least one of the following: surfactant, solid or liquid diluent.

23. An agriculturally suitable composition for controlling the growth of undesired vegetation comprising an effective amount of the compound of claim 11 and at least one of the following: surfactant, solid or liquid diluent.

24. An agriculturally suitable composition for controlling the growth of undesired vegetation comprising an effective amount of the compound of claim 12 and at least one of the following: surfactant, solid or liquid diluent.

25. A method for controlling the growth of undesired vegetation which comprises applying to the locus to be protected an effective amount of a compound of claim 1.

26. A method for controlling the growth of undesired vegetation which comprises applying to the locus to be protected an effective amount of a compound of claim 2.

27. A method for controlling the growth of undesired vegetation which comprises applying to the locus to be protected an effective amount of a compound of claim 3.

28. A method for controlling the growth of undesired vegetation which comprises applying to the locus to be protected an effective amount of a compound of claim 4.

29. A method for controlling the growth of undesired vegetation which comprises applying to the locus to be protected an effective amount of a compound of claim 5.

30. A method for controlling the growth of undesired vegetation which comprises applying to the locus to be protected an effective amount of a compound of claim 6.

31. A method for controlling the growth of undesired vegetation which comprises applying to the locus to be protected an effective amount of a compound of claim 7.

32. A method for controlling the growth of undesired vegetation which comprises applying to the locus to be protected an effective amount of a compound of claim 8.

33. A method for controlling the growth of undesired vegetation which comprises applying to the locus to be protected an effective amount of a compound of claim 9.

34. A method for controlling the growth of undesired vegetation which comprises applying to the locus to be protected an effective amount of a compound of claim 10.

35. A method for controlling the growth of undesired vegetation which comprises applying to the locus to be protected an effective amount of a compound of claim 11.

36. A method for controlling the growth of undesired vegetation which comprises applying to the locus to be protected an effective amount of a compound of claim 12.

* * * * *

UNITED STATES PATENT AND TRADEMARK OFFICE
CERTIFICATE OF CORRECTION

PATENT NO. : 4,778,512
DATED : October 18, 1988
INVENTOR(S) : Barry A. Wexler

It is certified that error appears in the above—identified patent and that said Letters Patent is hereby corrected as shown below:

Claim 1, Column 134 at line 19, delete "$R_2$ is H or $CH_3$;" and substitute therefore "$R_1$ is H or $CH_3$" and at line 25, delete "$C_1 \propto C_2$" and substitute therefore -- $C_1$-$C_2$ --.

Signed and Sealed this

Twenty-first Day of March, 1989

Attest:

DONALD J. QUIGG

Attesting Officer      Commissioner of Patents and Trademarks